(12) United States Patent
Adam et al.

(10) Patent No.: US 6,544,985 B2
(45) Date of Patent: Apr. 8, 2003

(54) DIHYDRO-BENZO [B][1,4]DIAZEPIN-2-ONE DERIVATIVES

(75) Inventors: Geo Adam, Schopfheim (DE); Erwin Goetschi, Reinach (CH); Vincent Mutel, Brunstatt (FR); Juergen Wichmann, Steinen (DE); Thomas Johannes Woltering, Weil am Rhein (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/115,826

(22) Filed: Apr. 3, 2002

(65) Prior Publication Data

US 2002/0193367 A1 Dec. 19, 2002

(30) Foreign Application Priority Data

Apr. 12, 2001 (EP) .............................. 01109125

(51) Int. Cl.⁷ ................... C07D 243/12; C07D 403/14; C07D 403/10; A61K 31/5513; A61P 25/00
(52) U.S. Cl. ....................... 514/221; 540/517
(58) Field of Search ........................... 514/221; 540/517

(56) References Cited

U.S. PATENT DOCUMENTS 6,407,094 B1 * 6/2002 Adam et al. ............. 514/221

FOREIGN PATENT DOCUMENTS

| WO | WO 01/10846 | 2/2001 |
| WO | WO 01/29011 | 4/2001 |
| WO | WO 01/29012 | 4/2001 |

OTHER PUBLICATIONS

F. D. Bellamy, Tetrahedron Lett., vol. 25, pp. 839–842 (1984).
Achmatowicz Jr. et al., Tetrahedron Lett., vol. 27, pp. 1973–1996 (1971).
J. Heterocycl. Chem., vol. 25, pp. 1003–1005 (1998).
Hunt et al., Aust. J. Chem., vol. 36, pp. 2317–2325 (1983).
Cheng et al., Biochem. Pharmacol., vol. 22, pp. 3099–3108 (1973).

* cited by examiner

*Primary Examiner*—Bruck Kifle
(74) *Attorney, Agent, or Firm*—George W. Johnston; Patricia S. Rocha-Tramaloni

(57) ABSTRACT

This invention is a dihydro-benzo[b][1,4]diazepin-2-one derivative of the formula

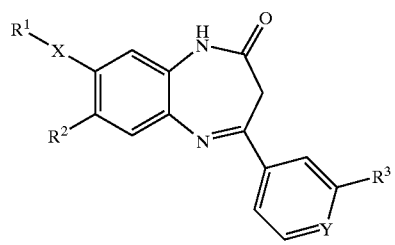

wherein $R^1$, $R^2$, $R^3$, X and Y are as defined in the specification. The invention includes pharmaceutical compositions containing these compounds, a process for their preparation, their use in preparation of pharmaceutical compositions and administration of an effective amount of the compounds for the treatment or prevention of acute and/or chronic neurological disorders to a patient in need of such treatment.

17 Claims, No Drawings

DIHYDRO-BENZO [B][1,4]DIAZEPIN-2-ONE DERIVATIVES

FIELD OF INVENTION

This invention is a dihydro-benzo[b][1,4]diazepin-2-one derivative of the formula

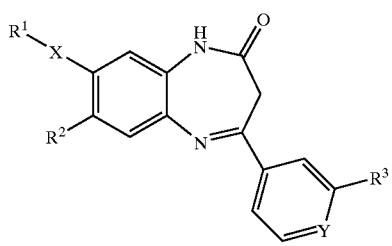

The compounds of formula I are metabotropic glutamate receptor antagonists.

BACKGROUND

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

SUMMARY

The present invention is a compound of formula I

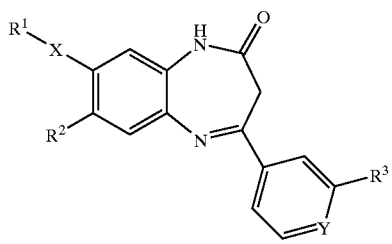

wherein

X is a single bond or an ethynediyl group; wherein when X is a single bond,
$R^1$ is selected from the group consisting of cyano,
halogen,
lower alkyl,
$C_3$–$C_6$-cycloalkyl,
lower alkoxy,
fluoro-lower alkoxy,
fluoro-lower alkyl,
unsubstituted pyrrol-1-yl, and pyrrol-1-yl substituted by between one and three substituents selected from the group consisting of
fluoro, chloro, cyano, —$(CH_2)_{1-4}$-hydroxy, fluoro-lower alkyl, lower alkyl, —$(CH_2)_n$-lower alkoxy, —$(CH_2)_n$—C(O)O—R", —$(CH_2)_{1-4}$—NR'R", hydroxy-lower alkoxy, and —$(CH_2)_n$—CONR'R", unsubstituted phenyl, and phenyl substituted by one or two substituents selected from the group consisting of halogen, lower alkyl, fluoro-lower alkyl, lower alkoxy, fluoro-lower alkoxy and cyano;
when X is an ethynediyl group,
$R^1$ is unsubstituted phenyl, or phenyl substituted by between one and three substituents
selected from the group consisting of halogen, lower alkyl, fluoro-lower alkyl,
$C_3$–$C_6$-cycloalkyl, lower alkoxy and fluoro-lower alkoxy;
$R^2$ is -selected from the group consisting of NR'R", fluoro-lower alkoxy,
unsubstituted 3-oxo-piperazin-1-yl, pyrrolidin-1-yl or piperidin-1-yl, and 3-oxo-piperazin-1-yl, pyrrolidin-1-yl or piperidin-1-yl substituted by R";
R' is selected from the group consisting of hydrogen,
lower alkyl,
$C_3$–$C_6$-cycloalkyl,
fluoro-lower alkyl and
2-lower alkoxy lower alkyl;
R" is selected from the group consisting of hydrogen,
lower alkyl,
$C_3$–$C_6$-cycloalkyl,
fluoro-lower alkyl,
2-lower alkoxy lower alkyl,
—$(CH_2)_{2-4}$-di-lower alkylamino,
—$(CH_2)_{2-4}$-morpholinyl,
$(CH_2)_{2-4}$-pyrrolidinyl,
—$(CH2)_{2-4}$-piperidinyl and
3-hydroxy-lower alkyl;
Y is —CH= or =N—;
$R^3$ is selected from the group consisting of halogen,
lower alkyl,
fluoro-lower alkyl,
lower alkoxy,
cyano,
—$(CH_2)_n$—C(O)—OR",
—$(CH_2)_n$—C(O)—NR'R",
unsubstituted five-membered aromatic heterocycle, and a five-membered aromatic heterocycle, substituted by halogen, fluoro-lower alkyl, fluoro-lower alkoxy, cyano, —$(CH_2)_n$—NR'R", —$(CH_2)_n$—C(O)—OR", —$(CH_2)_n$—C(O)—NR'R", —$(CH_2)_n$—$SO_2$—NR'R" lower alkyl, or lower alkyl substituted by a substituent selected from the group consisting of fluoro, hydroxy, lower alkoxy, cyano and carbamoyloxy; and
n is 0, 1, 2, 3 or 4;
or a pharmaceutically acceptable addition salt thereof.

It has surprisingly been found that the compounds of formula I are metabotropic glutamate receptor antagonists. Compounds of formula I are distinguished by valuable therapeutic properties.

Objects of the present invention are: compounds of formula I or a pharmaceutically acceptable salt thereof; pharmaceutically active substances and their manufacture the use of a compound of the invention in the control or prevention of illnesses as described above; and the production of pharmaceutical compositions containing a therapeutically effective amount of the compound of formula I in a pharmaceutically acceptable carrier.

The compounds of formula I can also be used in form of their prodrugs. Examples are esters, N-oxides, phosphate esters, glycoamide esters, glyceride conjugates and the like. The prodrugs may add to the value of the present compounds advantages in absorption, pharmacokinetics in distribution and transport to the brain.

All tautomeric forms of the compounds of the invention are also embraced herewith.

DETAILED DESCRIPTION

Preferred are compounds of formula I wherein X is a single bond. Exemplarly preferred are compounds, wherein $R^1$ is trifluoromethyl, and especially those wherein $R^3$ is cyano, for example the following compounds:

4-(4-oxo-8-pyrrolidin-1-yl-7-trifluoromethyl-4,5-dihydro-3H-benzo[b][1,4]diazepin-2-yl)-pyridine-2-carbonitrile, 4-[8-(cyclopropylmethyl-methyl-amino)-4-oxo-7-trifluoromethyl-4,5-dihydro-3H-benzo[b][1,4]diazepin-2-yl]-pyridine-2-carbonitrile, 4-[8-(cyclopropylmethyl-amino)-4-oxo-7-trifluoromethyl-4,5-dihydro-3H-benzo[b][1,4]diazepin-2-yl]-pyridine-2-carbonitrile, 4-[4-oxo-8-(2,2,2-trifluoro-ethoxy)-7-trifluoromethyl-4,5-dihydro-3H-benzo[b][1,4]diazepin-2-yl]-pyridine-2-carbonitrile, and 4-[8-(isopropyl-methyl-amino)-4-oxo-7-trifluoromethyl-4,5-dihydro-3H-benzo [b][1,4]diazepin-2-yl]-pyridine-2-carbonitrile.

Further preferred are compounds, wherein X is a single bond, $R^1$ is trifluoromethyl and $R^3$ is an unsubstituted five-member aromatic heterocycle or a substituted five-membered aromatic heterocycle, substituted by halogen, fluoro-lower alkyl, fluoro-lower alkoxy, cyano, —(CH$_2$)$_n$—NR'R", —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, unsubstituted lower alkyl or lower alkyl substituted by fluoro, hydroxy, lower alkoxy, cyano or carbamoyloxy. Examples of such compounds are the following:

7-dimethylamino-4-[3-(3-methyl-isoxazol-5-yl)-phenyl]-8-trifluoromethyl-1,3-dihydro-benzo[b][1,4]diazepin-2-one, 7-dimethylamino-4-[3-(2-methyl-2H-pyrazol-3-yl)-phenyl]-8-trifluoromethyl-1,3-dihydro-benzo [b][1,4]diazepin-2-one, 7-dimethylamino-4-(3-imidazol-1-yl-phenyl)-8-trifluoromethyl-1,3-dihydro-benzo[b][1,4]diazepin-2-one, 4-[3-(3-methyl-isoxazol-5-yl)-phenyl]-7-(methyl-propyl-amino)-8-trifluoromethyl-1,3-dihydro-benzo [b][1,4] diazepin-2-one, 7-(isobutyl-methyl-amino)-4-[3-(3-methyl-isoxazol-5-yl)-phenyl]-8-trifluoromethyl-1,3-dihydro-benzo[b][1,4] diazepin-2-one, 7-(isopropyl-methyl-amino)-4-[3-(3-methyl-isoxazol-5-yl)-phenyl]-8-trifluoromethyl-1,3-dihydro-benzo[b][1,4] diazepin-2-one, 7-(isobutyl-methyl-amino)-4-(3-{5-[(isopropyl-methyl-amino)-methyl]-[1,2,3]triazol-1-yl}-phenyl)-8-trifluoromethyl-1,3-dihydro-benzo[b][1,4]diazepin-2-one, 7-(isopropyl-methyl-amino)-4-[3-(5-pyrrolidin-1-ylmethyl-[1,2,3]triazol-1-yl)-phenyl]-8-trifluoromethyl-1,3-dihydro-benzo [b][1,4]diazepin-2-one, 7-(methyl-propyl-amino)-4-(3-[1,2,3]triazol-1-yl-phenyl)-8-trifluoromethyl-1,3-dihydro-benzo[b][1,4]diazepin-2-one, 7-(isobutyl-methyl-amino)-4-(3-[1,2,3]triazol-1-yl-phenyl)-8-trifluoromethyl-1,3-dihydro-benzo[b][1,4]diazepin-2-one, 4-(3-imidazol-1-yl-phenyl)-7-isobutylamino-8-trifluoromethyl-1,3-dihydro-benzo[b][1,4]diazepin-2-one, 7-dimethylamino-4-[3-(4-hydroxymethyl-thiazol-2-yl)-phenyl]-8-trifluoromethyl-1,3-dihydro-benzo[b][1,4] diazepin-2-one, 7-dimethylamino-4-[3-(4-hydroxymethyl-oxazol-2-yl)-phenyl]-8-trifluoromethyl-1,3-dihydro-benzo[b][1,4] diazepin-2-one, 4-[3-(4-hydroxymethyl-thiazol-2-yl)-phenyl]-7-(methyl-propyl-amino)-8-trifluoromethyl-1,3-dihydro-benzo[b][1,4]diazepin-2-one, and 4-[3-(5-hydroxymethyl-[1,3,4]thiadiazol-2-yl)-phenyl]-7-(methyl-propyl-amino)-8-trifluoromethyl-1,3-dihydro-benzo[b][1,4]diazepin-2-one.

Also preferred are compounds, wherein X is a single bond, and $R^1$ is chloro, for example the following compounds:

8-chloro-7-isobutylamino-4-[3-(3-methyl-isoxazol-5-yl)-phenyl]-1,3-dihydro-benzo[b][1,4]diazepin-2-one, 8-chloro-7-(methyl-propyl-amino)-4-[3-(5-pyrrolidin-1-ylmethyl-[1,2,3]triazol-1-yl)-phenyl]-1,3-dihydro-benzo [b][1,4]diazepin-2-one, 8-chloro-7-(isopropyl-methyl-amino)-4-[3-(5-pyrrolidin-1-ylmethyl-[1,2,3]triazol-1-yl)-phenyl]-1,3-dihydro-benzo [b][1,4]diazepin-2-one, 8-chloro-7-(isobutyl-methyl-amino)-4-[3-(5-pyrrolidin-1-ylmethyl-[1,2,3]triazol-1-yl)-phenyl]-1,3-dihydro-benzo [b][1,4]diazepin-2-one, 8-chloro-4-[3-(5-dimethylaminomethyl-[1,2,3]triazol- 1-yl)-phenyl]-7-(isobutyl-methyl-amino)-1,3-dihydro-benzo [b][1,4]diazepin-2-one, 4-[3-(5-azetidin-1-ylmethyl-[1,2,3]triazol-1-yl)-phenyl]-8-chloro-7-(isopropyl-methyl-amino)-1,3-dihydro-benzo [b][1,4]diazepin-2-one,4-[3-(5-azetidin-1-ylmethyl-[1,2,3]triazol-1-yl)-phenyl]-8-chloro-7-(isobutyl-methyl-amino)-1,3-dihydro-benzo [b][1,4]diazepin-2-one,8-chloro-7-(isobutyl-methyl-amino)-4-[3-(5-piperidin-1-ylmethyl-[1,2,3]triazol-1-yl)-phenyl]-1,3-dihydro-benzo [b][1,4]diazepin-2-one,8-chloro-7-(isopropyl-methyl-amino)-4-(3-{5-[(isopropyl-methyl-amino)-methyl]-[1,2,3]triazol-1-yl}-phenyl)-1,3-dihydro-benzo [b][1,4] diazepin-2-one,8-chloro-4-(3-{5-[-(isobutyl-methyl-amino)-methyl]-[1,2,3]triazol-1-yl}-phenyl)-7-(isopropyl-methyl-amino)-1,3-dihydro-benzo[b][1,4] diazepin-2-one,8-chloro-7-isopropylamino-4-[3-(3-methyl-isoxazol-5-yl)-phenyl]-1,3-dihydro-benzo[b][1,4] diazepin-2-one,8-chloro-7-(isobutyl-methyl-amino)-4-(3-[1,2,3]triazol-1-yl-phenyl)-1,3-dihydro-benzo[b][1,4] diazepin-2-one,8-chloro-4-(3-imidazol-1-yl-phenyl)-7-isobutylamino-1,3-dihydro-benzo[b][1,4]diazepin-2-one, 8-chloro-7-(ethyl-methyl-amino)-4-[3-(4-hydroxymethyl-thiazol-2-yl)-phenyl]-1,3-dihydro-benzo [b][1,4]diazepin-2-one8-chloro-4-[3-(4-hydroxymethylthiazol-2-yl)-phenyl]-7-(methyl-propyl-amino)-1,3-dihydro-benzo [b][1,4]diazepin-2-one 8-chloro-4-[3-(4-hydroxymethyl-thiazol-2-yl)-phenyl]-7-(isopropyl-methyl-amino)-1,3-dihydro-benzo[b][1,4]diazepin-2-one 8-chloro-4-[3-(4-hydroxymethyl-thiazol-2-yl)-phenyl]-7-(isobutyl-methyl-amino)-1,3-dihydro-benzo[b][1,4]diazepin-2-one 8-chloro-7-(ethyl-methyl-amino)-4-[3-(4-hydroxymethyl-oxazol-2-yl)-phenyl]-1,3-dihydro-benzo[b][1,4]diazepin-2-one 8-chloro-4-[3-(4-hydroxymethyl-oxazol-2-yl)-phenyl]-7-(methyl-propyl-amino)-1,3-dihydro-benzo [b][1,4]diazepin-2-one 8-chloro-4-[3-(4-hydroxymethyl-oxazol-2-yl)-phenyl]-7-(isopropyl-methyl-amino)-1,3-dihydro-benzo[b][1,4]diazepin-2-one, and 8-chloro-4-[3-(4-hydroxymethyl-oxazol-2-yl)-phenyl]-7-(isobutyl-methyl-amino)-1,3-dihydro-benzo[b][1,4]diazepin-2-one.

Further preferred are compounds, wherein X is a single bond and $R^1$ is cyano. Examples of such compounds are the following:

8-diethylamino-2-[3-(3-methyl-isoxazol-5-yl)-phenyl]-4-oxo-4,5-dihydro-3H-benzo[b][1,4]diazepin-7-carbonitrile, and 2-[3-(3-methyl-isoxazol-5-yl)-phenyl]-4-oxo-8-piperidin-1-yl-4,5-dihydro-3H-benzo[b][1,4]diazepine-7-carbonitrile.

Also, preferred are further those compounds of formula I, wherein $R^3$ is an unsubstituted five-membered aromatic heterocycle, or a five-membered heterocycle substituted by halogen, fluoro-lower alkyl, fluoro-lower alkoxy, cyano, —(CH$_2$)$_n$—NR'R", —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, unsubstituted lower alkyl, or lower alkyl substituted by fluoro, hydroxy, lower alkoxy, cyano or carbamoyloxy.

Especially preferred are those compounds of formula I, wherein $R^3$ is an unsubstituted or substituted five-membered aromatic heterocycle selected from the group consisting of thiazolyl, oxazolyl, isoxazolyl, imidazolyl, 2H-pyrazolyl, [1,2,3 triazolyl, [1,2,4]triazolyl, [1,3,4]thiadiazolyl and [1,3,4]oxadiazolyl. Examples of such compounds are the following:

7-dimethylamino-8-phenylethynyl-4-(3-[1,2,3]triazol-1-yl-phenyl)-1,3-dihydro-benzo[b][1,4]diazepin-2-one, 8-(2-fluoro-phenyl)-4-(3-[1,2,3]triazol-1-yl-phenyl)-7-(2,2,2-trifluoro-ethoxy)-1,3-dihydro-benzo[b][1,4]diazepin-2-one, 7-(ethyl-methyl-amino)-8-methyl-4-[3-(3-methyl-isoxazol-5-yl)-phenyl]-1,3-dihydro-benzo[b][1,4]diazepin-2-one, 7-dimethylamino-8-methyl-4-[3-(3-methyl-isoxazol-5-yl)-phenyl)-]-1,3-dihydro-benzo[b][1,4]diazepin-2-one, 7-(isobutyl-methyl-amino)-8-methyl-4-[3-(3-methyl-isoxazol-5-yl)-phenyl]-1,3-dihydro-benzo [b][1,4]diazepin-2-one, 7-(isobutyl-methyl-amino)-8-methyl-4-[3-(5-pyrrolidin-1-ylmethyl-[1,2,3]triazol-1-yl)-phenyl]-1,3-dihydro-benzo[b][1,4]diazepin-2-one, and 4-(3-{5-[(cyclopropylmethyl-amino)-methyl]-[1,2,3]triazol-1-yl}-phenyl) (isobutyl-methyl-amino)-8-methyl-1,3-dihydro-benzo [b][1,4 ]diazepin-2-one.

Additionally, preferred are compounds of formula I, wherein $R^2$ is —N(CH$_3$)$_2$ or pyrrolidine. Also preferred are compounds, wherein $R^2$ is isopropyl-amino, isopropyl-methyl-amino, isobutyl-amino or isobutyl-methyl-amino.

Also, preferred compounds of formula I in the scope of the present invention are those, wherein $R^3$ is cyano or an unsubstituted five-membered aromatic heterocycle, or a five-member aromatic heterocycle substituted by —CH$_2$OH or —CH$_2$N(CH$_3$)$_2$.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" embraces fluorine, chlorine, bromine and iodine.

The term "fluoro-lower alkyl" means a lower alkyl residue, wherein at least one hydrogen—atom is replaced by fluoro.

The term "fluoro-lower alkoxy" denotes a lower alkoxy residue in the sense of the definition herein before, wherein at least one hydrogen—atom is replaced by fluoro.

The term "$C_3$–$C_6$-cycloalkyl" means a cycloalkyl group containing 3 to 6 carbon atoms, such as cyclopropyl, cyclobutyl, cyclopentyl or cyclohexyl.

The term "lower alkylthio" denotes a lower alkyl residue in the sense of the foregoing definition bound via a sulfur atom, for example methylsulfanyl.

The expression "five-membered aromatic heterocycle" embraces furane, thiophene, thiazole, pyrrole, imidazole, pyrazole, oxazole, isoxazole, triazole, oxadiazole, thiadiazole and tetrazole. Preferred five-membered aromatic heterocycles are 1,2,3-triazole, 1,2,4-triazole, isoxazole, 1,3-oxazole, 1,3-thiazole, 1,3,4-oxadiazole or imidazole.

Substituted" means that a group is substituted with at least one, preferably one or two substituents independently selected from the specified group. The term "unsubstituted" in this document is consistent with the generally accepted usage of this term.

The term "pharmaceutically acceptable addition salt" refers to any salt derived from a pharmaceutically acceptable inorganic or organic acid or base.

The compounds of formula I and their pharmaceutically acceptable salts can be manufactured according to methods, which process comprises reacting a compound of formula II

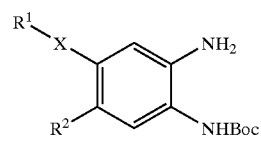

II with a compound of formula IV or IVa

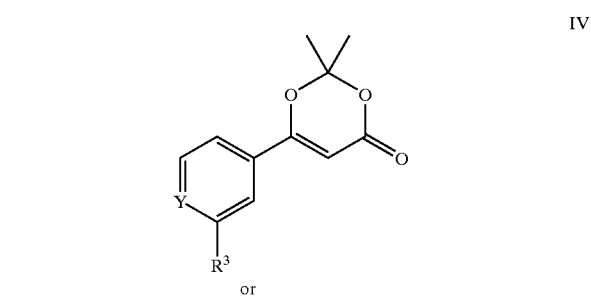

IV or

-continued

IVa

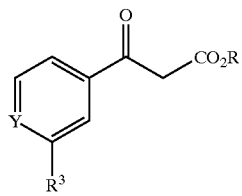

wherein R is alkyl, preferably ethyl or butyl, forming a compound of formula III

III

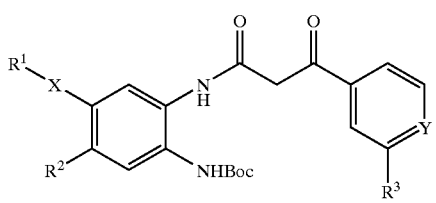

then deprotecting the amino group and cyclizing, forming a compound of formula

I

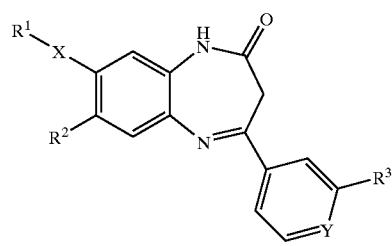

wherein $R^1$, $R^2$, $R^3$, X and Y are as described above. A pharmaceutically acceptable addition salt is formed as described above by reacting the compound with a pharmaceutically acceptable organic or inorganic acid or base.

Scheme A

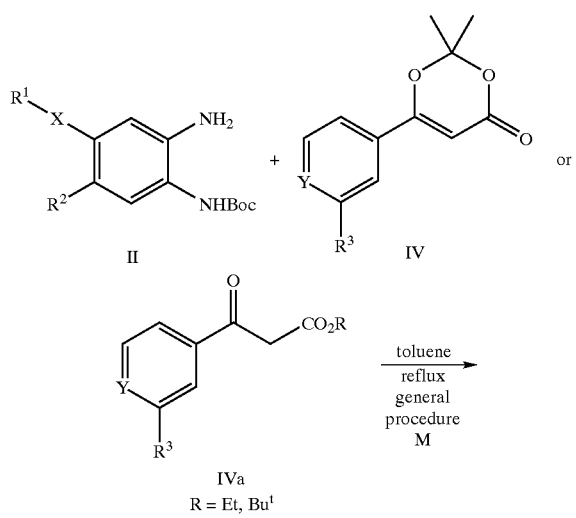

-continued

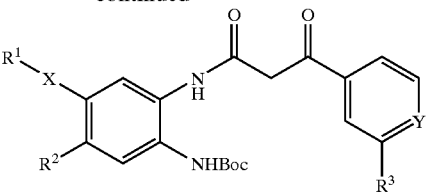

According to scheme A, compounds of formula I, in which X, Y, $R^1$, $R^2$ and $R^3$ are as described above, can be prepared from compounds of formula II via an acylation-deprotection-cyclization sequence:

For example reacting compounds of formula II with a dioxinone IV, in which Y and $R^3$ are as described above, in an inert solvent such as toluene or xylene at elevated temperatures, preferably between 80° C. and 160° C. gives rise to compounds of formula III.

Alternatively, compounds of formula III can also be prepared by for example reaction of a compound of formula II with a β-ketoester (formula IVa), in which Y and $R^3$ are as described above using the same conditions as described for the reaction with the dioxinones.

Afterwards, cleaving the BOC protecting group in compounds of formula III and concomitant cyclization of the deprotected compound yields the desired compounds of formula I. Any other suitable amino protecting group, such as e.g. Fmoc or benzyloxycarbonyl (Z), can be alternatively used instead of the BOC group.

The deprotection-cyclization step can be carried out by treating the compounds of formula III with for example a Bronsted acid such as trifluoroacetic acid in an inert solvent such as dichloromethane (DCM). The reaction is preferably carried out at temperatures between 0° C. and 50° C. It may be advantageous to use also anisole or 1,3-dimethoxybenzene as a carbocation scavenger in the reaction mixture.

Scheme B

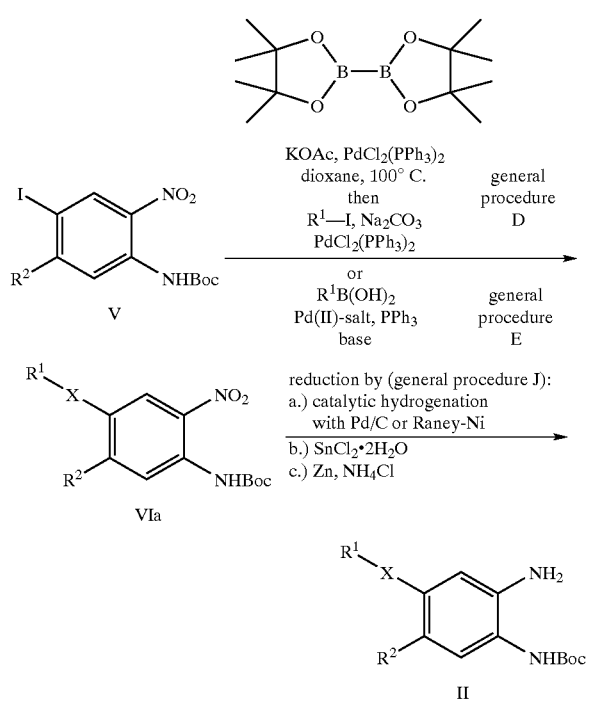

Scheme C

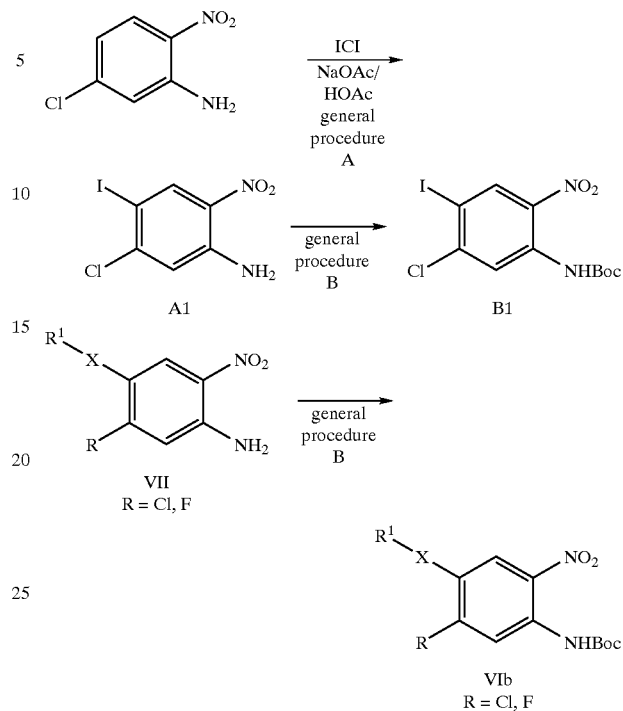

GP B, method a: diphosgene, EtOAc, 77° C.; then t-BuOH
GP B, method b: Boc₂O, Cs₂CO₃, 2-butanone, 52° C.
GP B, method c: i) Boc₂O, DMAP, THF; ii) TFA, DCM, 0° C.

According to scheme B, compounds of formula II in which $R^1$ is phenyl optionally substituted as described above for compounds where X is a single bond and $R^2$ is as described above, can be prepared by different routes depending on the nature of $R^1$ from the iodo-compounds of formula V, in which $R^2$ is as described above. As shown in scheme B, the key step is a coupling reaction of Suzuki-type to produce compounds of the formula VIa.

Compounds of formula II, in which $R^1$, $R^2$ and X are as described above can be prepared according to scheme B, by reducing the nitro group in compounds of formula VIa to the amino group. The reduction can for example be carried out using hydrogen gas in presence of a suitable catalyst like for example Raney-Nickel or Palladium on carbon. Another possible reduction method is using stannous (II) chloride (SnCl₂.2H₂O) in ethanol at temperatures between 70° C. and 80° C. (as described in *Tetrahedron Lett.* 1984, 25, 839), or alternatively in polar aprotic solvents, like DMF, DMA or NMP and the like, optionally in the presence of bases, like for example pyridine or triethylamine and the like, at temperatures between 0° C. and 80° C. Another suitable method is using zinc-powder in the presence of ammonium chloride in protic solvents like for example water or ethanol at temperatures between 20° C. and 80° C. The exact conditions for the respective compounds of formula II can be found in the experimental part.

Compounds of formula V, in which $R^2$ is as described above, can be prepared by different routes depending on the individual residue $R^2$:

As shown in scheme C, compound B1 can be prepared from the commercially available 5-chloro-2-nitroaniline by iodination to give the synthetic intermediate A1, which in turn can be protected to yield the compound B1.

The iodination step can be carried out by for example using iodine monochloride in acetic acid in the presence of sodium acetate. The reaction can be for example carried out at temperatures between 20° C. and 80° C.

The protection of the amino function can be applied to a number of commercially available starting materials or compounds synthesized by anyone skilled in the art to produce the corresponding 2-nitroanilines with the formula VII, in which X is a single bond and $R^1$ is as described above. This transformation leads to the key intermediates of the formula VIb, and the exact conditions for the respective compounds used in this invention can be found in the experimental part.

One possibility for the protection of the amino function is for example reacting compounds of formula VII with di-tert.-butyl-carbonate in the presence of a base such as cesium carbonate. The reaction can be carried out in polar solvents such as acetone or butanone and the like at temperatures between 20° C. and 60° C.

Alternatively, the protection of the amino group can be achieved by preparing the intermediate isocyanate by treatment of compounds of the formula VII with diphosgene, preferably in aprotic solvents such as ethyl acetate or 1,4-dioxane at temperatures from 0° C. to 100° C., and subsequent treatment of the isocyanate with tert.butanol in solvents such as dichloromethane or 1,2-dichloroethane and the like at temperatures between 20° C. and 85° C. to give the desired compounds of formula VIb.

Another suitable method to achieve this protection step is the intermediate formation of a di-BOC compound by treatment of compounds of the formula VII with di-tert.-butyl-carbonate in the presence of DMAP in an aprotic solvent such as tetrahydrofuran and the like, followed by selective removal of a single BOC-group by treatment with a Bronsted-acid, like e.g. TFA, in aprotic solvents such as dichloromethane, chloroform or 1,2-dichloroethane at temperatures between 0° C. and 20° C. to give the desired compounds of formula VIb.

According to scheme D, compounds of formula VII in which $R^1$ is pyrrol-1-yl optionally substituted as described above, X is a single bond and R is chloride, can be prepared from known 5-chloro-2-nitro-1,4-phenylenediamine [CAS-No. 26196-45-2] by selective condensation of the 4-amino-group with a suitable substituted 2,5-dimethoxytetrahydrofuran with the formula VIII, as described in *J. Heterocycl. Chem.* 1988, 25, 1003.

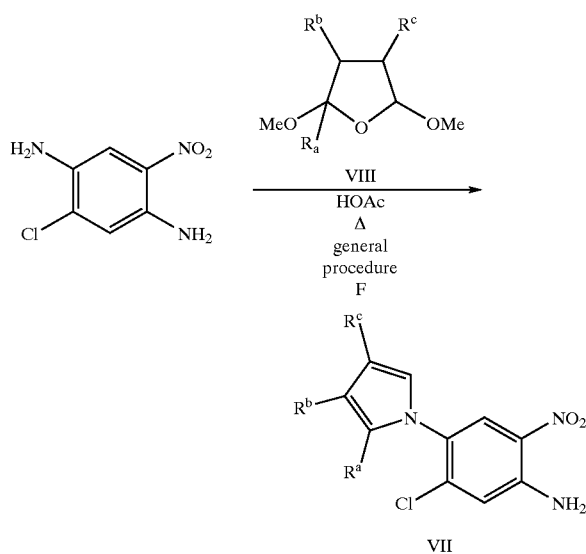

The reaction is preferably carried out in acidic media, like for example acetic acid or propionic acid and the like, at temperatures between 40° C. to 100° C. The exact conditions for the respective compounds can be found in the experimental part.

The corresponding substituted 2,5-dimethoxytetrahydrofurans with the formula VIII, in which $R^a$, $R^b$ and $R^c$ are selected from the group consisting of fluoro, chloro, cyano, —$(CH_2)_{1-4}$-hydroxy, fluoro-lower alkyl, lower alkyl, —$(CH_2)_n$-lower alkoxy, —$(CH_2)_n$—C(O)O—R'', —$(CH_2)_{1-4}$—NR'R'', hydroxy-lower alkoxy, and —$(CH_2)_n$—CONR'R'', are either commercially available, or synthesized from the suitable substituted furan, as shown in scheme E. The corresponding substituents can optionally be protected with suitable protecting groups, known to someone skilled in the art, or alternatively can be introduced after the pyrrol ring synthesis. The two-step sequence consists of reacting the furan with bromine in MeOH at low temperature, like for example −35° C., followed by treatment with base, like for example triethylamine and the like or potassium carbonate or sodium hydrogen carbonate and the like. The resulting 2,5-dimethoxydihydrofuran with the formula VIII, in which $R^a$, $R^b$ and $R^c$ are as described above, can be reduced by catalytic hydrogenation, preferably in MeOH with catalysts like for example Palladium on carbon or Raney-Nickel and the like, to produce the desired 2,5-dimethoxytetrahydrofurans with the formula VIII. An example for this sequence can be found in *Tetrahedron* 1971, 27, 1973–1996.

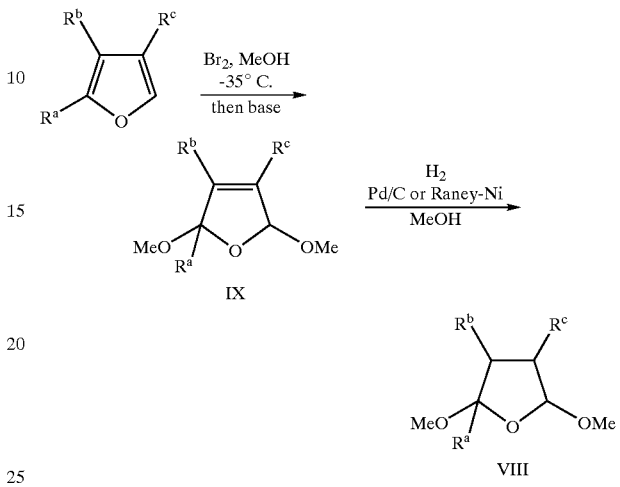

The exact conditions for the individual compounds to be synthesized can be found in the experimental part.

As shown in scheme F, compounds of formula VIc, in which $R^2$ is attached via a nitrogen-atom and is as described above, can be prepared from the intermediate compounds with the formula VIb—which individual synthesis can be found in the experimental part—by a nucleophilic substitution reaction with the respective amines in the presence of a suitable base.

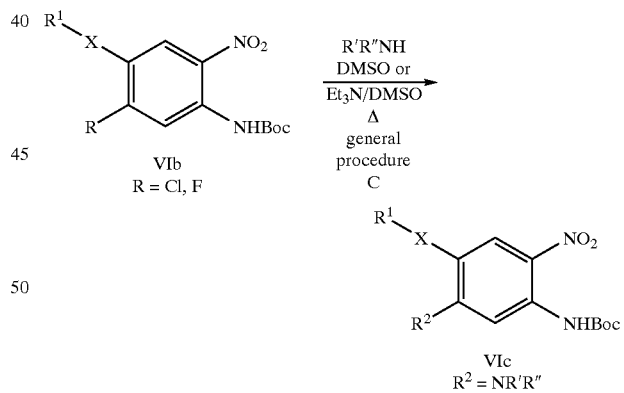

The reaction is preferably carried out in a polar, aprotic solvent such as dimethyl formamide, N-methyl-pyrrolidone or dimethyl sulfoxide and the like. The base can be selected from the sterically hindered amines such as triethylamine or Hunig's base, alkoxides such as sodium methoxide and tert.-butoxide, or hydrides such as sodium hydride. The reaction can be performed at temperatures between 20° C. and 110° C., depending on the individual compounds to be synthesized.

Scheme G

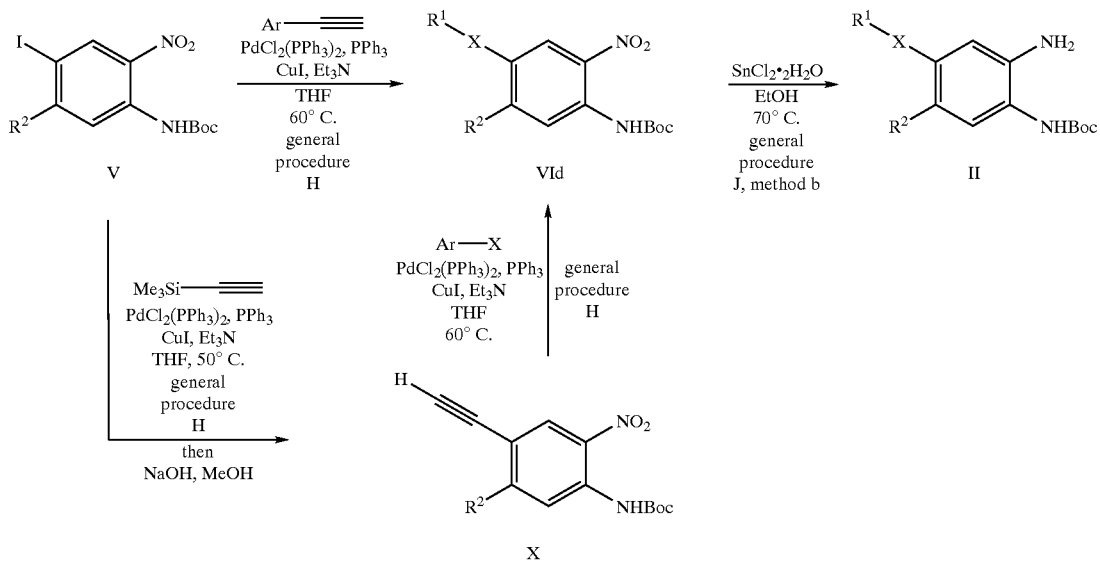

According to scheme G, compounds of formula II in which $R^1$ is as described above for compounds where X is an ethynediyl group can be prepared by different routes from the iodo-compounds V, depending on the nature of $R^1$ and $R^2$. As shown in scheme G, the transformation can for example be carried out by directly attaching the $R^1$-alkynediyl-substituent to a compound of formula V via a Sonogashira-type coupling to produce compounds of the formula VId followed by the reduction of the nitro group or by two stepwise Sonogashira-type couplings, in which first trimethylsilyl-acetylene is coupled to a compound of formula V to yield, after desilylation with sodium hydroxide in methanol, the intermediate X which then can be transformed via a second Sonogashira-type coupling with the appropriate reactant $R^1$—I, $R^1$—Br or $R^1$—OSO$_2$CF$_3$ into compounds of the formula VId and reduction of the nitro group leads to the desired compounds of formula II.

The exact conditions for the respective compounds can be found in the experimental part.

Scheme H

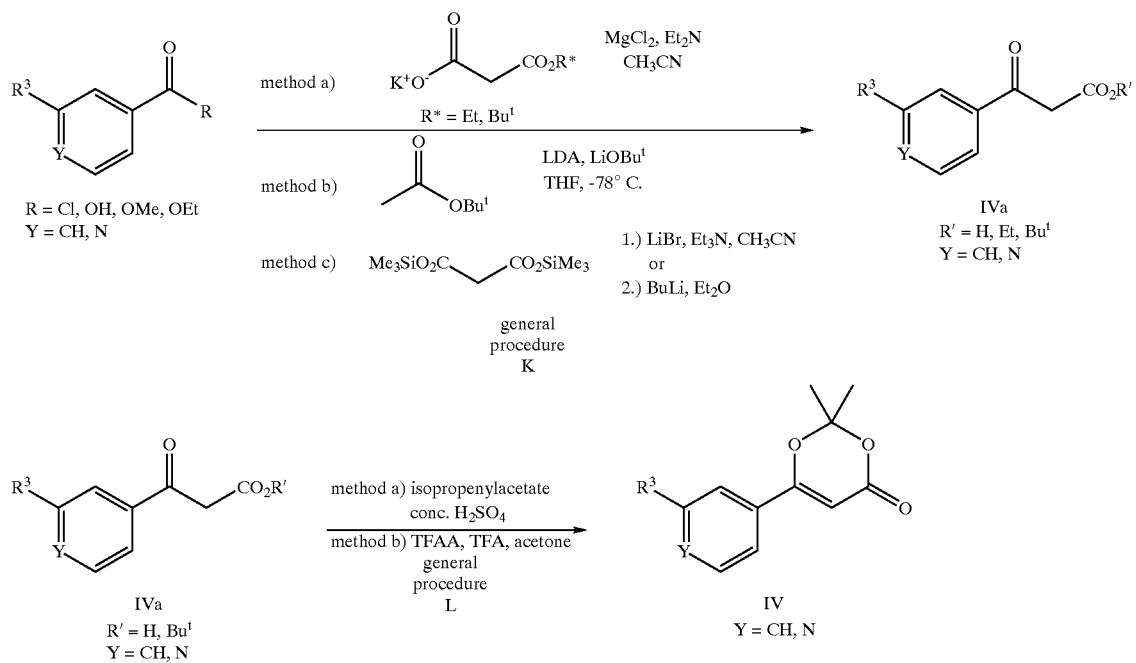

According to Scheme H, the dioxinones and 9-keto esters building blocks with the formula IV and IVa can be prepared by methods known to someone skilled in the art from the corresponding carboxylic acid derivatives R³—COR, i.e. free acids, methyl or ethyl esters and acid chlorides. The exact conditions for the corresponding compounds can be found in the experimental part.

The pharmaceutically acceptable salts can be manufactured readily according to known methods, taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The compounds of formula I and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of formula I or pharmaceutically acceptable salts thereof can be used as pharmaceutical compositions, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I or pharmaceutically acceptable salts thereof can be processed with pharmaceutically acceptable and therapeutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a therapeutically effective amount of a compound of formula I or a pharmaceutically acceptable salt thereof and a therapeutically inert, i.e., pharmaceutically acceptable, excipient are also an object of the present invention, as is a process for the production of such pharmaceutical compositions which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The present invention includes the use of compounds of formula I and of pharmaceutically acceptable salts thereof for the production of pharmaceutical compositions, especially for the control or prevention of acute and/or chronic neurological disorders of the aforementioned kind.

The compounds of the present invention are group II mGlu receptor antagonists. The compounds show $K_i$ values, as measured in the assay described below, of 10 $\mu$M or less, typically 1 $\mu$M or less, and ideally of 0.3 $\mu$M or less.

In Table I below some specific $K_i$ values of preferred compounds of the invention are presented. These values were obtained by indirect measurement of the affinity of the compounds for the recombinant rat mGluR2 expressed in CHO cells using a displacement binding assay with 3H-LY354740.

TABLE I

| Compound | $K_i$ mGlu2 ($\mu$M) |
| --- | --- |
| 3-(8-Dimethylamino-4-oxo-7-phenylethynyl-4,5-dihydro-3H-benzo[b][1,4]diazepin-2-yl)-benzonitrile | 0.030 |
| 8-(2,3-Difluoro-phenyl)-7-dimethylamino-4-(3-[1,2,3]triazol-1-yl-phenyl)-1,3-dihydro-benzo[b][1,4]diazepin-2-one | 0.070 |
| 8-Chloro-7-[(2-methoxy-ethyl)-methyl-amino]-4-[3-(3-methyl-isoxazol-5-yl)-phenyl]-1,3-dihydro-benzo[b][1,4]diazepin-2-one | 0.025 |
| 8-Chloro-7-dimethylamino-4-[3-(2-methyl-2H-pyrazol-3-yl)-phenyl]-1,3-dihydro-benzo[b][1,4]diazepin-2-one | 0.023 |
| 8-Chloro-7-dimethylamino-4-[3-(4-hydroxymethyl-thiazol-2-yl)-phenyl]-1,3-dihydro-benzo[b][1,4]diazepin-2-one | 0.030 |
| 8-(2-Fluoro-phenyl)-4-[3-(3-methyl-isoxazol-5-yl)-phenyl]-7-(2,2,2-trifluoro-ethoxy)-1,3-dihydro-benzo[b][1,4]diazepin-2-one | 0.03 |
| 8-Chloro-7-dimethylamino-4-[3-(4-hydroxymethyl-oxazol-2-yl)-phenyl]-1,3-dihydro-benzo[b][1,4]diazepin-2-one | 0.039 |
| 8-Chloro-7-(methyl-propyl-amino)-4-[3-(5-hydroxymethyl-[1,2,3]triazol-1-yl)-phenyl]-1,3-dihydro-benzo[b][1,4]diazepin-2-one | 0.030 |
| 8-Chloro-7-(diethyl-amino)-4-[3-(5-hydroxymethyl-[1,2,3]triazol-1-yl)-phenyl]-1,3-dihydro-benzo[b][1,4]diazepin-2-one | 0.044 |
| 8-Chloro-4-[3-(5-hydroxymethyl-1,2,3]triazol-1-yl)-phenyl]-7-pyrrolidin-1-yl-1,3-dihydro-benzo[b][1,4]diazepin-2-one | 0.019 |
| 8-Chloro-7-(cyclopropyl-methyl-amino)-4-[3-(5-hydroxymethyl-[1,2,3]triazol-1-yl)-phenyl]-1,3-dihydro-benzo[b][1,4]diazepin-2-one | 0.16 |

TABLE I-continued

| Compound | $K_i$ mGlu2 (µM) |
|---|---|
| 8-Chloro-7-dimethylamino-4-(3-pyrazol-1-yl-phenyl)-1,3-dihydro-benzo[b][1,4]diazepin-2-one | 0.11 |
| 7-Dimethylamino-4-[3-(3-morpholin-4-ylmethyl-isoxazol-5-yl)-phenyl]-8-trifluoromethyl-1,3-dihydro-benzo[b][1,4]diazepin-2-one | 0.125 |
| 7-Dimethylamino-4-[3-(2-methylsulfanyl-imidazol-1-yl)-phenyl]-8-trifluoromethyl-1,3-dihydro-benzo[b][1,4]diazepin-2-one | 0.019 |
| 4-[8-(Cyclopropylmethyl-methyl-amino)-4-oxo-7-trifluoromethyl-4,5-dihydro-3H-benzo[b][1,4]diazepin-2-yl]-pyridine-2-carbonitrile | 0.005 |
| 4-[3-(5-Cyclopropylaminomethyl-[1,2,3]triazol-1-yl)-phenyl]-7-dimethylamino-8-trifluoromethyl-1,3-dihydro-benzo[b][1,4]diazepin-2-one | 0.049 |
| 4-[4-Oxo-8-(2,2,2-trifluoro-ethoxy)-7-trifluoromethyl-4,5-dihydro-3H-benzo[b][1,4]diazepin-2-yl]-pyridine-2-carbonitrile | 0.004 |
| 3-[7-Methyl-8-(methyl-propyl-amino)-4-oxo-4,5-dihydro-3H-benzo[b][1,4]diazepin-2-yl]-benzonitrile | 0.025 |
| 8-Chloro-4-[3-(5-hydroxymethyl-[1,2,3]triazol-1-yl)-phenyl]-7-(isobutyl-methyl-amino)-1,3-dihydro-benzo[b][1,4]diazepin-2-one | 0.02 |
| 8-Diethylamino-2-[3-(3-methyl-isoxazol-5-yl)-phenyl]-4-oxo-4,5-dihydro-3H-benzo[b][1,4]diazepine-7-carbonitrile | 0.009 |
| 4-[3-(5-Azetidin-1-ylmethyl-[1,2,3]triazol-1-yl)-phenyl]-8-chloro-7-(methyl-propyl-amino)-1,3-dihydro-benzo[b][1,4]diazepin-2-one | 0.015 |
| 8-Chloro-4-[3-(5-hydroxymethyl-[1,2,4]triazol-1-yl)-phenyl]-7-(isobutyl-methyl-amino)-1,3-dihydro-benzo[b][1,4]diazepin-2-one | 0.089 |
| 7-(Methyl-propyl-amino)-4-(3-[1,2,4]triazol-1-yl-phenyl)-8-trifluoromethyl-1,3-dihydro-benzo[b][1,4]diazepin-2-one | 0.027 |
| 7-(Isobutyl-methyl-amino)-4-(3-[1,2,4]triazol-1-yl-phenyl)-8-trifluoromethyl-1,3-dihydro-benzo[b][1,4]diazepin-2-one | 0.012 |
| 8-Chloro-4-[3-(4-hydroxymethyl-thiazol-2-yl)-phenyl]-7-(isobutyl-methyl-amino)-1,3-dihydro-benzo[b][1,4]diazepin-2-one | 0.003 |
| 8-Chloro-7-dimethylamino-4-[3-(2-ethylamino-thiazol-4-yl)-phenyl]-1,3-dihydro-benzo[b][1,4]diazepin-2-one | 0.48 |
| 7-Dimethylamino-4-[3-(5-hydroxymethyl-[1,3,4]thiadiazol-2-yl)-phenyl]-8-trifluoromethyl-1,3-dihydro-benzo[b][1,4]diazepin-2-one | 0.017 |
| 7-Dimethylamino-4-[3-(2-methyl-5-propyl-oxazol-4-yl)-phenyl]-8-trifluoromethyl-1,3-dihydro-benzo[b][1,4]diazepin-2-one | 0.046 |
| 4-[3-(5-Hydroxymethyl-[1,3,4]thiadiazol-2-yl)-phenyl]-7-(methyl-propyl-amino)-8-trifluoromethyl-1,3-dihydro-benzo[b][1,4]diazepin-2-one | 0.008 |

[$^3$H]-LY354740 Binding on mGlu2 Transfected CHO Cell Membranes

Transfection and Cell Culture cDNA encoding the rat mGlu2 receptor protein in pBluescript II was obtained from Prof. S. Nakanishi (Kyoto, Japan), and subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco BRL (Basel, Switzerland). Selection was made in the presence of G-418 (1000 ug/ml final). Clones were identified by reverse transcription of 5 µg total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM (NH4)$_2$SO$_4$, 2 mM MgCl$_2$, 25 units/ml Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[$^3$H]-LY354740 Binding

After thawing, the membranes were resuspended in cold 50 mM Tris-HCl buffer containing 2 mM MgCl$_2$ and 2 mM CaCl$_2$, (pH 7) (binding buffer). The final concentration of the membranes in the assays was 25 pg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/C glass fiber filters and washed 5 times with cold binding buffer. Non specific binding was measured in the presence of 10 µM DCG IV. After transfer of the filters into plastic vials containing 10 ml of Ultima-gold scintillation fluid (Packard, Zürich, Switzerland), the radioactivity was measured by liquid scintillation in a Tri-Carb 2500 TR counter (Packard, Zürich, Switzerland).

Data Analysis

The inhibition curves were fitted with a four parameter logistic equation giving IC$_{50}$ values, and Hill coefficients and the K$_i$ values were calculated using the Cheng and Prusoff equation (Cheng, Y. and Prusoff, W. H., *Biochem. Pharmacol.* 1973, 22, 3099–3108). A small K$_i$ value expresses high affinity of the compound towards the receptor.

EXAMPLES

Unless stated to the contrary, all of the examples given below were prepared and characterized as described.

General Procedure A

Preparation of 4-iodo-2-nitroanilines by iodination of 2-nitroanilines [According to Wilson, J. Gerald; Hunt, Frederick C. *Aust. J. Chem.* 1983, 36, 2317–25]

To a stirred solution of the 2-nitroaniline (1.0 mol) in HOAc (500 mL) containing anhydrous NaOAc (93–103 g, 1.125–1.25 mol), iodine monochloride (59–66 mL, 1.125–1.25 mol) in HOAc (300 mL) was added over 60 min. The reaction mixture was heated to the given temperature until thin layer chromatography (tlc) indicated complete conversion of the starting material, stirred for another 30 min at 23° C., then diluted slowly with H$_2$O (1000 mL) which caused the separation of the crystalline product. Stirring was continued for 1 h and the product was filtered off, washed free of HOAc and dried in vacuum at 60° C.

Example A1

5-Chloro-4-iodo-2-nitro-phenylamine

MS (EI) 298 (M$^+$) and 300 [(M+2)$^+$]; mp 202–203° C. (dec.).

General Procedure B

Preparation of (2-nitro-phenyl)-carbamic acid tert.-butyl esters from 2-nitroanilines Method a (from 2-nitroanilines): To a solution of diphosgene (4.1 mL, 34.1 mmol) in EtOAc (40 mL) at 0° C. was added a solution of the 2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 2-nitrophenylisocyanate as a yellow solid. This material was refluxed in a mixture of excess tert.-BuOH in $CH_2Cl_2$ for 2.5 h. Removal of the solvent left an orange solid which was purified by silica gel column chromatography with hexane/EtOAc to give the (2-nitro-phenyl)-carbamic acid tert.-butyl ester as a yellow solid.

Method b (from 2-nitroanilines): To a mixture of the 2-nitroaniline (142 mmol) and cesium carbonate (55.5 g, 170 mmol) in 2-butanone (740 mL) was dropwise added a solution of $Boc_2O$ (37.8 g, 173 mmol) in 2-butanone (170 mL) and the resulting mixture was stirred at 50° C. to 80° C. until tlc indicated complete conversion. The solvent was removed in vacuum, the residue was treated with a mixture of $H_2O$ (240 mL) and MeOH (240 mL) and extracted with hexane (3×500 mL). The combined hexane layer was washed with brine (200 mL) and all aqueous layers were reextracted with hexane (300 mL). All combined hexane layers were dried over $MgSO_4$, filtered and the solvent was removed in vacuum to give an orange solid, which was purified by silica gel column chromatography with hexane/EtOAc to give the (2-nitro-phenyl)-carbamic acid tert.-butyl ester as a yellow solid.

Method c (from 2-nitroanilines): To a solution of the 2-nitroaniline (550 mmol) and DMAP (1.22 g, 10 mmol) in THF (1000 mL) at 23° C. was dropwise added within 70 min a solution of $Boc_2O$ (246 g, 1128 mmol) in THF (500 mL) and stirring was continued at 23° C. for 75 min. The entire mixture was evaporated to dryness and dried at HV to leave a dark brown solid. This material was dissolved in DCM (1100 mL), cooled to 0° C. and TFA (84 mL, 1100 mmol) was added dropwise. The mixture was stirred at 0° C. for 2 h, poured into icecold sat. $NaHCO_3$-sol., extracted with DCM, washed with brine and dried over $MgSO_4$. Removal of the solvent in vacuum left a dark brown solid which was coated on silica gel and purified by silica gel column chromatography with hexane/EtOAc to give the (2-nitro-phenyl)-carbamic acid tert.-butyl ester as a yellow solid.

Method d (from 2-nitroacetanilides): To a solution of the 2-nitroacetanilide (100 mmol) and DMAP (122 mg, 1 mmol) in THF (100 mL) at 23° C. was dropwise added within 15 min a solution of $Boc_2O$ (22.92 g, 105 mmol) in THF (100 mL) and stirring was continued at 23° C. until tlc indicated completed conversion. The entire mixture was evaporated to dryness and dried at HV to leave a yellow to dark brown solid. This material was dissolved in THF (200 mL) and 25% $NH_4OH$ (77 mL, 500 mmol) was added dropwise. The mixture was stirred at 23° C. until tlc indicated complete conversion, poured into 1N HCl-sol., extracted with EtOAc, washed the organic layer with sat. $NaHCO_3$-sol. and brine, dried over MgSO4. Removal of the solvent in vacuum left an yellow to brown solid which was generally pure enough for further transformation or—if necessary—coated on silica gel and purified by silica gel column chromatography with hexane/EtOAc to give the (2-nitro-phenyl)-carbamic acid tert.-butyl ester as a yellow solid.

Example B1

(5-Chloro-4-iodo-2-nitro-phenyl)-carbamic acid tert.-butyl ester

The title compound was prepared via the isocyanate from 5-chloro-4-iodo-2-nitro-phenylamine (Example A1) (7.0 g, 23.45 mmol) with diphosgene (2.12 mL, 17.6 mmol) in EtOAc (30 mL), followed by treatment with tert.-BuOH (100 mL) in $CH_2Cl_2$ (100 mL) according to the general procedure B (method a). Obtained as a yellow solid (7.1 g, 76%).

MS (EI) 398 ($M^+$) and 400 [$(M+2)^+$]; mp 82–84° C.

Example B2

(4,5-Dichloro-2-nitro-phenyl)-carbamic acid tert.-butyl ester

The title compound was prepared via the di-Boc-compound from commercially available 4,5-dichloro-2-nitroaniline (15 g, 72.5 mmol) and $Boc_2O$ (32.4 g, 148.5 mmol), followed by treatment-with 2 eq. TFA in $CH_2Cl_2$ according to the general procedure B (method c). Obtained as a brown solid (21.63 g, 97%).

MS (ISN) 305 [$(M-H)^-$]; mp 68–73° C.

Example B3

(5-Fluoro-2-nitro-4-trifluoromethyl-phenyl)-carbamic acid tert.-butyl ester

The title compound was prepared via the di-Boc-compound from 5-fluoro-2-nitro-4-trifluoromethyl-phenylamine; prepared from commercially available 4-amino-2-fluorobenzotrifluoride by acetylation with $Ac_2O$ in toluene at 23° C., nitration with 100% nitric acid from 10–23° C. and deacetylation with 2N NaOH in THF at 50° C.] (5.21 g, 23.2 mmol) and $Boc_2O$ (10.63 g, 48.7 mmol), followed by treatment with 2 eq. TFA in $CH_2Cl_2$ according to the general procedure B (method c). Obtained as a light yellow solid (6.33 g, 84%).

MS (ISN) 323 [(M–H)–]; mp 104° C.

Example B4

[4-Iodo-2-nitro-5-(2,2,2-trifluoro-ethoxy)-phenyl]-carbamic acid tert.-butyl ester The title compound was prepared via the di-Boc-compound from 4-iodo-2-nitro-5-(2,2,2-trifluoro-ethoxy)-phenylamine [prepared by stirring 5-chloro-4-iodo-2-nitro-phenylamine (Example A1) (8.95 g, 30 mmol), 2,2,2-trifluoroethanol (30 mL) and KOH (4.36 g, 66 mmol) in DMSO (60 mL) at 23° C. for 35 days.] (10.41 g, 29 mmol) and $Boc_2O$ (12.87 g, 59 mmol), followed by treatment with 2 eq. TFA in $CH_2Cl_2$ according to the general procedure B (method c). Obtained as a yellow solid (13.34 g, 100%).

MS (ISN) 461 [$(M-H)^-$].

Example B5

(5-Chloro-2-nitro-4-trifluoromethyl-phenyl)-carbamic acid tert.-butyl ester

The title compound was prepared via the di-Boc-compound from commercially available 5-chloro-2-nitro-4-trifluoromethyl-phenylamine [CAS-No. 35375-74-7] (22.61 g, 94 mmol) and $Boc_2O$ (42.06 g, 193 mmol), followed by treatment with 2 eq. TFA in $CH_2Cl_2$ according to the general procedure B (method c). Obtained as a yellow solid (31.82 g, 99%).

MS (ISN) 339.1 [$(M-H)^-$] and 341 [$(M+2-H)^-$]; mp 113–115° C.

Example B6

(5-Chloro-4-fluoro-2-nitro-phenyl)-carbamic acid tert.-butyl ester

The title compound was prepared via the di-Boc-compound from commercially available 3'-chloro-4'-fluoro- 6'-nitroacetanilide [CAS-No. 81962-58-5] (59 g, 254 mmol), and Boc$_2$O (58.13 g, 266 mmol), followed by treatment with NH$_4$OH (25%, 77.5 mL, 507 mmol) according to the general procedure B (method d). Obtained as a yellow solid (73.53 g, 100%).

MS (ISN) 289 [(M−H)$^-$] and 291 [(M+2−H)$^-$]; mp 73–74° C.

Example B7

[2-Nitro-5-(2,2,2-trifluoro-ethoxy)-4-trifluoromethyl-phenyl]-carbamic acid tert.-butyl ester The title compound was prepared via the di-Boc-compound from 4-iodo-2-nitro-5-(2,2,2-trifluoro-ethoxy)-phenylamine [prepared by stirring 5-chloro-4-iodo-2-nitro-phenylamine (Example A1), 2,2,2-trifluoroethanol and KOH in DMSO at 23° C. for 32.5 days.] and Boc$_2$O, followed by treatment with 2 eq. TFA in CH$_2$Cl$_2$ according to the general procedure B (method c). Obtained as a yellow solid (18.955 g).

MS (ISN) 403 [(M−H)$^-$].

Example B8

(5-Chloro-4-methyl-2-nitro-phenyl)-carbamic acid tert-butyl ester

The title compound was prepared via the di-Boc compound from commercially available 5-chloro-4-methyl-2-nitroaniline (10.0 g, 53.6 mmol) and Boc$_2$O (23.9 g, 109 mmol), followed by treatment with 2 eq. TFA in CH$_2$Cl$_2$ according to the general procedure B (method c). Obtained by column chromatography (toluene/ethylacetate 19:1) as a yellow solid (14.6 g, 95%).

MS (ISN) 285.1 [(M−H)$^-$].

Example B9

(4-Cyano-5-fluoro-2-nitro-phenyl)-carbamic acid tert-butyl ester

The title compound was prepared via the di-Boc compound from 4-cyano-5-fluoro-2-nitroaniline (24.9 g, 137 mmol) [Ohmori et al. J. Med. Chem. 1994,37, 467–475] and Boc$_2$O (61.5 g, 282 mmol), followed by treatment with 2 eq. TFA in CH$_2$Cl$_2$ according to the general procedure B (method c). Obtained by column chromatography (hexane/ethylacetate 4:1) as a light yellow solid (14.5 g, 39%).

MS (ISN) 280.1 [(M−H)$^-$].

General Procedure C

Preparation of 5-N-substituted-(2-nitro-phenyl)-carbamic acid tert.-butyl esters (5-Chloro or -fluoro-2-nitro-phenyl)-carbamic acid tert.-butyl ester was stirred with the desired amine optionally with DMSO, DMF, DMA, NMP or THF and/or DIPEA or Et$_3$N at temperatures from 23° C. to 130° C. until tlc indicated complete disappearance of the chloride or fluoride. The reaction was cooled to 23° C. poured into ice-water, the precipitate was filtered off, washed with water and dried in vacuum. In cases were the product did not precipitate, the mixture was extracted with EtOAc, washed with water and brine, dried over Na$_2$SO$_4$. Filtration and removal of the solvent in vacuum left a crude product, which was—if necessary—purified by silica gel column chromatography with hexane/EtOAc to give the pure title compound.

Example C1

(4-Chloro-5-dimethylamino-2-nitro-phenyl)-carbamic acid tert.-butyl ester

The title compound was prepared from (4,5-dichloro-2-nitro-phenyl)-carbamic acid tert.-butyl ester (Example B2) (3.0 g, 9.77 mmol) and dimethylamine (5.6 N in EtOH, 8.7 mL, 48.8 mmol) in DMSO (35 mL) at 23° C. according to the general procedure C. Obtained as a yellow solid (2.81 g).

MS (ISP) 316 [(M+H)$^+$] and 318 [(M+2+H)$^+$]; mp 136–138° C.

Example C2

(5-Dimethylamino-4-iodo-2-nitro-phenyl)-carbamic acid tert.-butyl ester

The title compound was prepared from (5-chloro-4-iodo-2-nitro-phenyl)-carbamic acid tert.-butyl ester (Example B1) (399 mg, 1 mmol) and dimethylamine (5.6 N in EtOH, 0.36 mL, 2 mmol) in THF (3 mL) at 65° C. for 18 h in a sealed tube according to the general procedure C. Obtained as a yellow solid (386 mg).

MS (EI) 407 (M+); mp 120–122° C.

Example C3

{4-Chloro-5-[(2-methoxy-ethyl)-methyl-amino]-2-nitro-phenyl}-carbamic acid tert.-butyl ester The title compound was prepared from (4,5-dichloro-2-nitro-phenyl)-carbamic acid tert.-butyl ester (Example B2) (3.07 g, 10 mmol), N-(2-methoxyethyl)methylamine (2.43 mL, 23 mmol) and Et$_3$N (4.2 mL, 30 mmol) in DMSO (20 mL) at 23° C. according to the general procedure C. Obtained as a brown oil (3.57 g).

MS (ISP) 360 [(M+H)$^+$] and 362 [(M+2+H)$^+$].

Example C4

(5-Dimethylamino-2-nitro-4-trifluoromethyl-phenyl)-carbamic acid tert.-butyl ester The title compound was prepared from (5-fluoro-2-nitro-4-trifluoromethyl-phenyl)-carbamic acid tert.-butyl ester (Example B3) (1.62 g, 5.0 mmol) and dimethylamine (5.6 N in EtOH, 4.47 mL, 25.0 mmol) in DMSO (10 mL) at 23° C. according to the general procedure C. Obtained as a yellow solid (1.48 g).

MS (ISN) 348 [(M−H)$^-$]; mp 110° C.

Example C5

[4-Chloro-5-(ethyl-methyl-amino)-2-nitro-phenyl]-carbamic acid tert-butyl ester

The title compound was prepared from (4,5-dichloro-2-nitro-phenyl)-carbamic acid tert.-butyl ester (Example B2) (3.0 g, 9.77 mmol) and N-ethyl-methylamine (2.89 g, 48.8 mmol) in DMSO (35 mL) at RT according to the general procedure C. Obtained as a pale brown solid (3.21 g).

MS (ISP) 330.3 [(M+H)$^+$]; mp 94° C.

Example C6

[4-Chloro-5-(methyl-propyl-amino)-2-nitro-phenyl]-carbamic acid tert-butyl ester The title compound was prepared from (4,5-dichloro-2-nitro-phenyl)-carbamic acid tert.-butyl ester (Example B2)

(3.0 g, 9.77 mmol) and N-methyl-propyl-amine (2.50 g, 34.2 mmol) in DMSO (30 mL) at RT according to the general procedure C. Obtained as a pale brown solid (3.58 g).

MS (ISP) 344.3 [(M+H)$^+$]; mp 68° C.

Example C7

[4-Chloro-5-(diethyl-amino)-2-nitro-phenyl]-carbamic acid tert-butyl ester

The title compound was prepared from (4,5-dichloro-2-nitro-phenyl)-carbamic acid tert.-butyl ester (Example B2) (3.0 g, 9.77 mmol) and diethyl-amine (3.57 g, 48.8 mmol) in DMSO (35 mL) at 60° C. according to the general procedure C. Obtained as a yellow solid (2.63 g).

MS (ISP) 344.3 [(M+H)$^+$]; mp 95° C.

Example C8

(4-Chloro-2-nitro-5-pyrrolidin-1-yl-phenyl)-carbamic acid tert.-butyl ester

The title compound was prepared from (4,5-dichloro-2-nitro-phenyl)-carbamic acid tert.-butyl ester (Example B2) and pyrrolidine in DMSO at 23° C. according to the general procedure C. Obtained as a yellow solid (6.65 g).

MS (ISP) 342 [(M+H)$^+$] and 344 [(M+2+H)$^+$]; mp 157–158° C.

Example C9

4-Chloro-5-(cyclopropyl-methyl-amino)-2-nitro-phenyl]-carbamic acid tert.-butyl ester The title compound was prepared from (4,5-dichloro-2-nitro-phenyl)-carbamic acid tert.-butyl ester (Example B2) (3.07 g, 10 mmol) and cyclopropyl-methyl-amine hydrochloride (3.22 g, 30 mmol) and Et$_3$N (6.97 mL, 50 mmol) in DMSO (30 mL) at 23° C. according to the general procedure C. Obtained as a yellow solid (3.25 g).

MS (ISP) 342.2 [(M+H)$^+$] and 344 (M+2+H)$^+$]; mp 104–106° C.

Example C10

(2-Nitro-5-pyrrolidin-1-yl-4-trifluoromethyl-phenyl)-carbamic acid tert.-butyl ester The title compound was prepared from (5-chloro-2-nitro-4-trifluoromethyl-phenyl)-carbamic acid tert.-butyl ester (Example B5) (6.81 g, 20 mmol) and pyrrolidine (8.27 mL, 100 mmol) in DMSO (70 mL) at 23° C. according to the general procedure C. Obtained as a yellow solid (7.35 g).

MS (ISN) 374 [(M–H)$^-$]; mp 138–141° C.

Example C11

(5-Dimethylamino-4-fluoro-2-nitro-phenyl)-carbamic acid tert.-butyl ester

The title compound was prepared from (5-chloro-4-fluoro-2-nitro-phenyl)-carbamic acid tert.-butyl ester (Example B6) (4.94 g, 17 mmol) and Me$_2$NH (40% in H$_2$O, 7.9M, 10.9 mL, 86 mmol) in DMSO (35 mL) at 23° C. according to the general procedure C. Obtained as a yellow solid (4.93 g).

MS (ISP) 303 [(M+H)$^+$]; mp 144–148° C.

Example C12

(4-Chloro-2-nitro-5-piperidin-1-yl-phenyl)-carbamic acid tert.-butyl ester

The title compound was prepared from (4,5-dichloro-2-nitro-phenyl)-carbamic acid tert.-butyl ester (Example B2) and piperidine in DMSO at 23° C. according to the general procedure C. Obtained as a yellow solid (1.173 g).

MS (ISP) 356 [(M+H)$^+$] and 358 [(M+2+H)$^+$]; mp 132–133° C.

Example C13

(4-Fluoro-2-nitro-5-pyrrolidin-1-yl-phenyl)-carbamic acid tert.-butyl ester

The title compound was prepared from (5-chloro-4-fluoro-2-nitro-phenyl)-carbamic acid tert.-butyl ester (Example B6) (5.81 g, 20 mmol) and pyrrolidine (8.27 mL, 100 mmol) in DMSO (40 mL) at 23° C. according to the general procedure C. Obtained as a yellow solid (6.42 g).

MS (ISP) 326 [(M+H)$^+$]; mp 188–193° C.

Example C14

(5-Azetidin-1-yl-4-chloro-2-nitro-phenyl)-carbamic acid tert.-butyl ester

The title compound was prepared from (4,5-dichloro-2-nitro-phenyl)-carbamic acid tert.-butyl ester (Example B2) (6.14 g, 20 mmol), azetidine (2.33 mL, 34 mmol) and Et$_3$N (8.4 mL, 60 mmol) in DMSO (40 mL) at 23° C. according to the general procedure C. Obtained as an orange solid (5.85 g).

MS (EI) 327 (M$^+$) and 329 [(M+2)$^+$].

Example C15

(5-Azetidin-1-yl-2-nitro-4-trifluoromethyl-phenyl)-carbamic acid tert.-butyl ester The title compound was prepared from (5-chloro-2-nitro-4-trifluoromethyl-phenyl)-carbamic acid tert.-butyl ester (Example B5), azetidine and Et$_3$N in DMSO at 23° C. according to the general procedure C. Obtained as a yellow solid (6.925 g).

MS (ISN) 360 [(M–H)$^-$].

Example C16

[5-(Cyclopropylmethyl-methyl-amino)-2-nitro-4-trifluoromethyl-phenyl]-carbamic acid tert.-butyl ester The title compound was prepared from (5-chloro-2-nitro-4-trifluoromethyl-phenyl)-carbamic acid tert.-butyl ester (Example B5) (5.11 g 15 mmol), cyclopropylmethyl-methyl-amine hydrochloride (5.47 g, 45 mmol) and Et$_3$N (10.5 mL, 75 mmol) in DMSO (50 mL) at 23° C. according to the general procedure C. Obtained as a yellow solid (5.73 g).

MS (ISN) 388 [(M–H)$^-$]; mp 51° C.

Example C17

[5-(Cyclopropyl-methyl-amino)-2-nitro-4-trifluoromethyl-phenyl]-carbamic acid tert.-butyl ester The title compound was prepared from (5-chloro-2-nitro-4-trifluoromethyl-phenyl)-carbamic acid tert.-butyl ester (Example B5) (3.40 g, 10 mmol) and cyclopropyl-methyl-amine hydrochloride (3.22 g, 30 mmol) and Et$_3$N (6.97 mL, 50 mmol) in DMSO (50 mL) at 23° C. according to the general procedure C. Obtained as a yellow solid (3.74 g).

MS (ISP) 374.2 [(M+H)$^+$].

Example C18

(2-Dimethylamino-2'-fluoro-5-nitro-biphenyl-4-yl)-carbamic acid tert.-butyl ester The title compound was prepared from (2-chloro-2'-fluoro-5-nitro-biphenyl-4-yl)-carbamic acid tert.-butyl ester (Example D3) (9.568 g, ca. 26 mmol) and $Me_2NH$ (60% in $H_2O$, 12 mL) in DMSO (87 mL) at 23° C. according to the general procedure C. Obtained as a yellow solid (4.54 g).
MS (ISP) 376.3 [(M+H)$^+$].

Example C19

(5-Dimethylamino-4-methyl-2-nitro-phenyl)-carbamic acid tert-butyl ester

The title compound was prepared from (5-chloro-4-methyl-2-nitro-phenyl)-carbamic acid tert-butyl ester (Example B8) (3.5 g, 12.2 mmol) and dimethylamine (11 ml, 33% in EtOH, 61.0 mmol) in DMSO (35 mL) at 50° C. according to the general procedure C. Obtained as a yellow solid (3.50 g, 97%).
MS (ISP) 296.3 [(M+H)$^+$].

Example C20

(4-Cyano-5-dimethylamino-2-nitro-phenyl)-carbamic acid tert-butyl ester

The title compound was prepared from (4-cyano-5-fluoro-2-nitro-phenyl)-carbamic acid tert-butyl ester (Example B9) (2.0 g, 7.11 mmol) and dimethylamine (6.3 ml, 33% in EtOH, 35.0 mmol) in DMSO (30 mL) at RT according to the general procedure C. Obtained as a yellow solid (1.87 g, 86%).
MS (ISP) 307.3 [(M+H)$^+$].

Example C21

[4-Methyl-5-(methyl-propyl-amino)-2-nitro-phenyl]-carbamic acid tert-butyl ester The title compound was prepared from (5-chloro-4-methyl-2-nitro-phenyl)-carbamic acid tert-butyl ester (Example B8) (3.5 g, 12.2 mmol) and N-methylpropylamine (6.5 ml, 61.0 mmol) in DMSO (35 mL) at 55° C. according to the general procedure C. Obtained as a yellow oil (3.89 g, 98%).
MS (ISP) 324.4 [(M+H)$^+$].

Example C22

[5-(Ethyl-methyl-amino)-4-methyl-2-nitro-phenyl]-carbamic acid tert-butyl ester

The title compound was prepared from (5-chloro-4-methyl-2-nitro-phenyl)-carbamic acid tert-butyl ester (Example B8) (3.5 g, 12.2 mmol) and N-ethylmethylamine (5.5 ml, 61.0 mmol) in DMSO (35 mL) at 55° C. according to the general procedure C. Obtained as a yellow solid (3.58 g, 95%).
MS (ISP) 310.3 [(M+H)$^+$].

Example C23

[4-Chloro-5-(isopropyl-methyl-amino)-2-nitro-phenyl]-carbamic acid tert-butyl ester The title compound was prepared from (4,5-dichloro-2-nitro-phenyl)-carbamic acid tert.-butyl ester (Example B2) (5.0 g, 16.3 mmol) and N-isopropyl-methylamine (5.95 g, 81.4 mmol) in DMSO (50 mL) at 75° C. according to the general procedure C. Obtained as a yellow solid (4.07 g, 73%).
MS (ISP) 344.3 [(M+H)$^+$].

Example C24

[4-Chloro-5-(isobutyl-methyl-amino)-2-nitro-phenyl]-carbamic acid tert-butyl ester The title compound was prepared from (4,5-dichloro-2-nitro-phenyl)-carbamic acid tert.-butyl ester (Example B2) (5.0 g, 16.3 mmol) and N-isobutyl-methylamine (7.09 g, 81.4 mmol) in DMSO (50 mL) at RT according to the general procedure C. Obtained as a brown oil (5.79 g, 99%).
MS (ISP) 358.2 [(M+H)$^+$].

Example C25

(4-Cyano-2-nitro-5-pyrrolidin-1-yl-phenyl)-carbamic acid tert-butyl ester

The title compound was prepared from (4-cyano-5-fluoro-2-nitro-phenyl)-carbamic acid tert-butyl ester (Example B9) (2.0 g, 7.11 mmol) and pyrrolidine (2.94 ml, 35.6 mmol) in DMSO (30 mL) at RT according to the general procedure C. Obtained as a yellow solid (1.97 g, 83%).
MS (ISP) 331.2 [(M–H)$^-$].

Example C26

[4-Cyano-5-(methyl-propyl-amino)-2-nitro-phenyl]-carbamic acid tert-butyl ester

The title compound was prepared from (4-cyano-5-fluoro-2-nitro-phenyl)-carbamic acid tert-butyl ester (Example B9) (1.95 g, 6.93 mmol) and N-methyl-propylamine (3.72 ml, 34.7 mmol) in DMSO (20 mL) at RT according to the general procedure C. Obtained as a yellow solid (1.75 g, 75%).
MS (ISP) 333.3 [(M–H)$^-$].

Example C27

(4-Cyano-5-diethylamino-2-nitro-phenyl)-carbamic acid tert-butyl ester

The title compound was prepared from (4-cyano-5-fluoro-2-nitro-phenyl)-carbamic acid tert-butyl ester (Example B9) (1.95 g, 6.93 mmol) and N,N-diethylamine (3.60 ml, 34.7 mmol) in DMSO (20 mL) at RT according to the general procedure C. Obtained as a yellow solid (1.78 g, 77%).
MS (ISP) 333.2 [(M–H)$^-$].

Example C28

[4-Cyano-5-(isopropyl-methyl-amino)-2-nitro-phenyl]-carbamic acid tert-butyl ester The title compound was prepared from (4-cyano-5-fluoro-2-nitro-phenyl)-carbamic acid tert-butyl ester (Example B9) (1.95 g, 6.93 mmol) and N-isopropyl-N-methylamine (3.60 ml, 34.7 mmol) in DMSO (30 mL) at RT according to the general procedure C. Obtained as a yellow solid (1.84 g, 79%).
MS (ISP) 333.3 [(M–H)$^-$].

Example C29

[4-Cyano-5-(isobutyl-methyl-amino)-2-nitro-phenyl]-carbamic acid tert-butyl ester The title compound was prepared from (4-cyano-5-fluoro-2-nitro-phenyl)-carbamic acid tert-butyl ester (Example B9) (1.95 g, 6.93 mmol) and N-isobutyl-N-methylamine (3.02 g, 34.7 mmol) in DMSO (20 mL) at RT according to the general procedure C. Obtained as a yellow solid (1.87 g, 77%).

MS (ISP) 347.4 [(M–H)⁻].

Example C30

(4-Cyano-2-nitro-5-piperidin-1-yl-phenyl)-carbamic acid tert-butyl ester

The title compound was prepared from (4-cyano-5-fluoro-2-nitro-phenyl)-carbamic acid tert-butyl ester (Example B9) (2.0 g, 7.11 mmol) and piperidine (3.51 ml, 35.6 mmol) in DMSO (20 mL) at RT according to the general procedure C. Obtained as a yellow solid (1.94 g, 79%).

MS (ISP) 345.3 [(M–H)⁻].

Example C31

(4-Chloro-5-isobutylamino-2-nitro-phenyl)-carbamic acid tert-butyl ester

The title compound was prepared from (4,5-dichloro-2-nitro-phenyl)-carbamic acid tert.-butyl ester (Example B2) (3.0 g, 9.77 mmol) and isobutylamine (3.57 g, 48.8 mmol) in DMSO (20 mL) at 55° C. according to the general procedure C. Obtained as a brown solid (2.26 g, 67%).

MS (ISP) 344.2 [(M+H)⁺].

Example C32

[5-(Methyl-propyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example B5) (4.00 g, 11.7 mmol), N-methyl-propyl-amine (1.89 ml, 17.6 mmol) and triethylamine (5.73 ml, 41.1 mmol) in DMSO (30 mL) at RT according to the general procedure C.

Obtained as a yellow solid (4.04 g, 91%).
MS (ISP) 378.3 [(M+H)⁺].

Example C33

[5-(Isobutyl-methyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example B5) (4.00 g, 11.7 mmol), N-isobutyl-methyl-amine (1.54 g, 17.6 mmol) and triethylamine (5.73 ml, 41.1 mmol) in DMSO (30 mL) at RT according to the general procedure C. Obtained as a yellow solid (4.18 g, 91%).

MS (ISP) 390.3 [(M–H)⁻].

Example C34

[5-(Isopropyl-methyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example B5) (4.00 g, 11.7 mmol), N-isopropyl-methyl-amine (3.67 ml, 35.2 mmol) and triethylamine (5.73 ml, 41.1 mmol) in DMSO (30 mL) at 50° C. according to the general procedure C. Obtained as a yellow solid (3.27 g, 74%).

MS (ISP) 376.3 [(M–H)⁻].

Example C35

[5-(Isobutyl-methyl-amino)-4-methyl-2-nitro-phenyl]-carbamic acid tert-butyl ester The title compound was prepared from (5-chloro-4-methyl-2-nitro-phenyl)-carbamic acid tert-butyl ester (Example B8) (3.01 g, 10.5 mmol) and N-isobutyl-methylamine (4.56 g, 52.3 mmol) in DMSO (30 mL) at 55° C. according to the general procedure C. Obtained as a yellow oil (1.84 g, 52%).

MS (ISP) 336.3 [(M–H)⁻].

Example C36

(4-Methyl-2-nitro-5-pyrrolidin-1-yl-phenyl)-carbamic acid tert-butyl ester

The title compound was prepared from (5-chloro-4-methyl-2-nitro-phenyl)-carbamic acid tert-butyl ester (Example B8) (3.01 g, 10.5 mmol) and pyrrolidine (4.33 ml, 52.3 mmol) in DMSO (30 mL) at 55° C. according to the general procedure C. Obtained as a yellow solid (3.27 g, 97%).

MS (ISP) 320.3 [(M–H)⁻]; mp 145° C.

Example C37

(4-Chloro-5-isopropylamino-2-nitro-phenyl)-carbamic acid tert-butyl ester

The title compound was prepared from (4,5-dichloro-2-nitro-phenyl)-carbamic acid tert.-butyl ester (Example B2) (5.0 g, 16.3 mmol) and isopropylamine (7.0 ml, 81.4 mmol) in DMSO (35 mL) at 55° C. according to the general procedure C. Obtained as a brown solid (3.95 g, 73%).

MS (ISP) 330.2 [(M+H)⁺].

Example C38

(5-Isobutylamino-2-nitro-4-trifluoromethyl-phenyl)-carbamic acid tert-butyl ester The title compound was prepared from (5-chloro-2-nitro-4-trifluoromethyl-phenyl)-carbamic acid tert-butyl ester (Example B5) (5.00 g, 14.7 mmol), isobutyl-amine (7.36 mL, 73.4 mmol) in DMSO (35 mL) at RT according to the general procedure C. Obtained as a yellow solid (5.39 g, 97%).

MS (ISP) 376.3 [(M–H)⁻].

General Procedure D

Preparation of (4-aryl-2-nitro-phenyl)-carbamic acid tert.-butyl esters by Direct Suzuki-coupling of (4-iodo-2-nitro-phenyl)-carbamic acid tert.-butyl esters with arylboronic acids A mixture of the (4-iodo-2-nitro-phenyl)-carbamic acid tert.-butyl ester (3.0 mmol), the arylboronic acid (4.5 mmol) and PdCl₂(PPh₃)₂ (2 mol %) was refluxed in 1,4-dioxane (25 mL) and 2M Na₂CO₃-sol. (7.5 mL) [or alternatively with 1M NaHCO₃-sol. (7.5 mL), LiCl (6.0 mmol) and (Ph₃P)₄Pd (3 mol %) in DME (30 mL); also possible with Et₃N (9.0 mmol), Pd(OAc)₂ (3 mol %), PPh₃ (6 mol %) in DMF (10 mL) at 100° C.] until tlc indicated complete conversion of the iodide. The mixture was transferred into a separating funnel, H₂O (25 mL) was added and the product was extracted with ether or EtOAc (3×30 mL). The combined organic layers were washed with brine (50 mL) and dried over Na₂SO₄. Removal of the solvent left a brown residue, which was purified by silica gel column chromatography with cyclohexane/ether or cyclohexane/EtOAc to give the title compound.

Example D1

(2-Dimethylamino-2',3'-difluoro-5-nitro-biphenyl-4-yl)-carbamic acid tert.-butyl ester The title compound was prepared from (5-dimethylamino-4-iodo-2-nitro-phenyl)-carbamic acid tert.-butyl ester (Example C2) and 2,3-difluorophenylboronic acid according to the general procedure D. Obtained as a yellow solid (3.096 g).

MS (ISN) 392 [(M−H)⁻].

Example D2

[2'-Fluoro-5-nitro-2-(2,2,2-trifluoro-ethoxy)-biphenyl-4-yl]-carbamic acid tert.-butyl ester The title compound was prepared from [4-iodo-2-nitro-5-(2,2,2-trifluoro-ethoxy)-phenyl]-carbamic acid tert.-butyl ester (Example B4) and 2-fluorophenylboronic acid according to the general procedure D. Obtained as a yellow solid (1.39 g).

MS (ISP) 491 [(M+H)⁺]; mp 73–75° C.

Example D3

(2-Chloro-2'-fluoro-5-nitro-biphenyl-4-yl)-carbamic acid tert.-butyl ester

The title compound was prepared from (5-chloro-4-iodo-2-nitro-phenyl)-carbamic acid tert.-butyl ester (Example 1) (30 g, 75.3 mmol) and 2-fluorophenylboronic acid (13.82 g, 98.8 mmol) according to the general procedure D. Obtained as a yellow gum (1.39 g).

MS (ISN) 365.0 [(M−H)⁻].

General Procedure E

Preparation of (4-aryl-2-nitro-phenyl)-carbamic acid tert.-butyl esters by Suzuki-coupling of (4-iodo-2-nitro-phenyl)-carbamic acid tert.-butyl esters with bis(pinacolato)diboron and Subsequent Reaction with aryl halides A mixture of the (4-iodo-2-nitro-phenyl)-carbamic acid tert.-butyl ester (2.0 mmol), bis(pinacolato)diboron (2.2 mmol), KOAc (6.0 mmol) and PdCl₂(PPh₃)₂ (3 mol %) in 1,4-dioxane (25 mL) was stirred at 100° C. until tlc indicated complete conversion of the iodide [cf. *Tetr. Lett.* 1997, 38, 3841–3844]. After addition of the aryl halide (4.0 mmol), PdCl₂(PPh₃)₂ (3 mol %) and 2M Na₂CO₃-sol. (7.5 mL) the mixture was stirred at 100° C. until tlc indicated complete conversion of the intermediate boronic ester. The mixture was transferred into a separating funnel, H₂O (30 mL) was added and the product was extracted with ether or EtOAc (3×50 mL). The combined organic layers were washed with brine (100 mL) and dried over Na₂SO₄. Removal of the solvent left a brown residue, which was purified by silica gel column chromatography with cyclohexane/ether or cyclohexane/EtOAc to give the title compound.

General Procedure F

Preparation of 5-chloro-2-nitro-4-pyrrol-1-yl-phenylamines by condensation of 5-chloro-2-nitro-1,4-phenylenediamine with 2,5-dimethoxytetrahydrofurans [cf. *J. Heterocycl. Chem.* 1988, 25, 1003–1005]

A mixture of the 5-chloro-2-nitro-1,4-phenylenediamine (4.69 g, 25 mmol), the 2,5-dimethoxytetrahydrofuran (26–32.5 mmol) in HOAc (150 mL) was stirred at 60–120° C. until tlc indicated complete conversion of the phenylenediamine. After cooling to 23° C., the mixture was poured into brine (500 mL) and extracted with EtOAc (3×200 mL). The combined organic layers were washed with brine (300 mL) and dried over MgSO₄. Removal of the solvent left a brown residue, which was purified by silica gel column chromatography with cyclohexane/EtOAc to give the title compound.

General Procedure G

Preparation of 2,5-dimethoxydihydrofurans by bromination of furans in MeOH [cf. *Tetrahedron* 1971, 27, 1973–1996]

To a solution of the furan (177.5 mmol) in a mixture of anhydrous ether (54 mL) and abs. MeOH (79 mL) kept at −35° C. bromine (10.0 mL, 195 mmol) in MeOH (105 mL) was added gradually with stirring. The reaction mixture was stirred for 30 min, saturated with gaseous NH₃ to pH 8, and allowed to warm up to 23° C. Poured into ice-water, extracted with ether (3×400 mL), washed with brine, dried over Na₂SO₄. Evaporation of the solvent left a yellow liquid, which was purified by vacuum distillation to give the title compound.

General Procedure H

Preparation of (4-alkynyl-2-nitro-phenyl)-carbamic acid tert.-butyl esters by Sonogashira-coupling of (4-iodo-2-nitro-phenyl)-carbamic acid tert.-butyl esters with acetylenic compounds; also Sonogashira-coupling of (4-ethynyl-2-nitro-phenyl)-carbamic acid tert.-butyl esters with aryl halides:

A mixture of the halide (3.0–4.5 mmol), acetylenic compound (3.0–4.5 mmol), Et3N (13.5 mmol), PdCl₂(PPh₃)₂ (5 mol %) and PPh3 (2.5 mol %) in THF (12 mL) [with very insoluble material DMF (up to 12 mL) could be added] was stirred for 20 min at 23° C. while being purged with Argon. CuI (1.2 mol %) was added and stirring was continued at 60° C. under Argon atmosphere until tlc indicated complete conversion of the minor component [cf. *J. Org. Chem.* 1998, 63, 8551]. The mixture was transferred into a separating funnel, 5% citric acid (50 mL) was added and the product was extracted with EtOAc (2×100 mL). The combined organic layers were washed with sat. NaHCO₃-sol. (50 mL) and brine (50 mL), followed by drying over MgSO₄. Removal of the solvent left a yellow residue, which was purified by silica gel column chromatography with hexane/EtOAc and/or triturated with hexane or aqueous EtOH to give the title compound.

Example H1

(5-Hydroxymethyl-2-nitro-4-phenylethynyl-phenyl)-carbamic acid tert.-butyl ester The title compound was prepared from (5-dimethylamino-4-iodo-2-nitro-phenyl)-carbamic acid tert.-butyl ester (Example C2) (386 mg, 0.97 mmol) and phenylacetylene (149 mg, 1.46 mmol) according to the general procedure H. Obtained as an orange solid (370 mg).

MS (EI) 381 (M+); mp 141–149° C.

General Procedure J

Preparation of the (2-amino-phenyl)-carbamic acid tert.-butyl esters by reduction of (2-nitro-phenyl)-carbamic acid tert.-butyl esters Method a: Catalytic hydrogenation A mixture of the nitro compound (1.0 mmol) in MeOH or EtOH and THF (1:1 ca. 20 mL) [or solely EtOAc for aromatic chlorides] and 10% Palladium on carbon (20 mg), Raney-Ni (20 mg) or 5% Platinum on carbon was stirred vigorously at 23° C. under hydrogen atmosphere until tlc indicated complete conversion. The catalyst was filtered off, washed thoroughly with MeOH or EtOH and THF (1:1) [or EtOAc], the solvent was removed in vacuum to give the title compound, which was generally pure enough for further transformations, but could be crystallized from hot hexane if necessary.

Method b: Reduction with $SnCl_2.2H_2O$

A mixture of the nitro compound (1.0 mmol) and $SnCl_2.2H_2O$ (5.0 mmol) was either stirred in EtOH (30 mL) at 70–80° C. or alternatively in pyridine (3 mL) and DMF (12 mL) at 23° C. under Argon atmosphere until tlc indicated complete conversion [cf. *Tetr. Lett.* 1984, 25, 839]. The reaction mixture was brought to pH 8 by addition of sat. $NaHCO_3$-sol. and extracted with EtOAc (2×100 mL). The combined organic layer were washed with brine and dried over $Na_2SO_4$. Removal of the solvent left a yellow solid, which—if necessary—can be purified by silica gel column chromatography.

Method c: Reduction with Zn and $NH_4Cl$

To a mixture of the nitro compound (1.0 mmol) in EtOH/THF/sat. $NH_4Cl$-sol. (1:1:1, 30 mL) was added Zinc dust (3.0 mmol) and the mixture was stirred at 70° C. under Argon atmosphere until tlc indicated complete conversion. Aqueous workup as described in method b.

Example J1

(2-Amino-4-chloro-5-dimethylamino-phenyl)-carbamic acid tert.-butyl ester

The title compound was prepared from (4-chloro-5-dimethylamino-2-nitro-phenyl)-carbamic acid tert.-butyl ester (Example C1) (2.76 g, 8.74 mmol) by reduction with $SnCl_2.2H_2O$ according to the general procedure J (method b). Obtained as an orange solid (2.3 g).

MS (ISP) 286 [(M+H)$^+$] and 288 [(M+2+H)$^+$]; mp 96–101° C.

Example J2

(2-Amino-5-dimethylamino-4-phenylethynyl-phenyl)-carbamic acid tert.-butyl ester The title compound was prepared from (5-dimethylamino-2-nitro-4-phenylethynyl-phenyl)-carbamic acid tert.-butyl ester (Example H1) by reduction with $SnCl_2.2H_2O$ according to the general procedure J (method b). Obtained as a brown solid (1.927 g).

MS (ISP) 352 [(M+H)$^+$].

Example J3

(5-Amino-2-dimethylamino-2',3'-difluoro-biphenyl-4-yl)-carbamic acid tert.-butyl ester The title compound was prepared from (2-dimethylamino-2',3'-difluoro-5-nitro-biphenyl-4-yl)-carbamic acid tert.-butyl ester (Example D1) by reduction with $SnCl_2.2H_2O$ according to the general procedure J (method b). Obtained as an orange solid (2.206 g).

MS (ISP) 364 [(M+H)$^+$].

Example J4

{2-Amino-4-chloro-5-[(2-methoxy-ethyl)-methyl-amino]-phenyl}-carbamic acid tert.-butyl ester The title compound was prepared from {4-chloro-5-[(2-methoxy-ethyl)-methyl-amino]-2-nitro-phenyl}-carbamic acid tert.-butyl ester (Example C3) (3.46 g, 9.62 mmol) by reduction with $SnCl_2.2H_2O$ according to the general procedure J (method b). Obtained as a yellow solid (2.25 g).

MS (ISP) 330 [(M+H)$^+$] and 332 [(M+2+H)$^+$]; mp 112° C.

Example J5

[5-Amino-2'-fluoro-2-(2,2,2-trifluoro-ethoxy)-biphenyl-4-yl]-carbamic acid tert.-butyl ester The title compound was prepared from [2'-fluoro-5-nitro-2-(2,2,2-trifluoro-ethoxy)-biphenyl-4-yl]-carbamic acid tert.-butyl ester (Example D2) by hydrogenation with 10% Pd/C according to the general procedure J (method a). Obtained as a grey solid (1.17 g).

MS (ISP) 401 [(M+H)$^+$].

Example J6

(2-Amino-5-dimethylamino-4-trifluoromethyl-phenyl)-carbamic acid tert.-butyl ester The title compound was prepared from (5-dimethylamino-2-nitro-4-trifluoromethyl-phenyl)-carbamic acid tert.-butyl ester (Example C4) by hydrogenation with 10% Pd/C according to the general procedure J (method a). Obtained as an amorphous yellow substance (1.34 g).

MS (ISP) 320 [(M+H)$^+$].

Example J7

[2-Amino-4-chloro-5-(ethyl-methyl-amino)-phenyl]-carbamic acid tert-butyl ester

The title compound was prepared from [4-chloro-5-(ethyl-methyl-amino)-2-nitro-phenyl]-carbamic acid tert-butyl ester (Example C5) (3.0 g, 9.09 mmol) by reduction with $SnCl_2.2H_2O$ according to the general procedure J (method b). Obtained as a pale brown solid (2.64 g).

MS (ISP) 300.3 [(M+H)$^-$]; mp 81° C.

Example J8

[2-Amino-4-chloro-5-(methyl-propyl-amino)-phenyl]-carbamic acid tert-butyl ester The title compound was prepared from [4-chloro-5-(methyl-propyl-amino)-2-nitro-phenyl]-carbamic acid tert-butyl ester (Example C6) (3.15 g, 9.16 mmol) by reduction with $SnCl_2.2H_2O$ according to the general procedure J (method b). Obtained as a pale brown solid (2.58 g).

MS (ISP) 314.3 [(M+H)$^+$]; mp 92° C.

Example J9

[2-Amino-4-chloro-5-(diethyl-amino)-phenyl]-carbamic acid tert-butyl ester

The title compound was prepared from [4-chloro-5-(diethyl-amino)-2-nitro-phenyl]-carbamic acid tert-butyl ester (Example C7) (2.25 g, 6.54 mmol) by reduction with SnCl$_2$.2H$_2$O according to the general procedure J (method b). Obtained as an orange solid (1.55 g).

MS (ISP) 314.3 [(M+H)$^+$]; mp 110° C.

Example J10

(2-Amino-4-chloro-5-pyrrolidin-1-yl-phenyl)-carbamic acid tert.-butyl ester

The title compound was prepared from (4-chloro-2-nitro-5-pyrrolidin-1-yl-phenyl)-carbamic acid tert.-butyl ester (Example C8) by reduction with SnCl$_2$.2H$_2$O according to the general procedure J (method b). Obtained as a red solid (4.80 g).

MS (ISP) 312 [(M+H)$^+$] and 314 [(M+2+H)$^+$]; mp 136–138° C.

Example J11

[2-Amino-4-chloro-5-(cyclopropyl-methyl-amino)-phenyl]-carbamic acid tert.-butyl ester The title compound was prepared from [4-chloro-5-(cyclopropyl-methyl-amino)-2-nitro-phenyl]-carbamic acid tert.-butyl ester (Example C9) (3.2 g, 9.36 mmol) by reduction with SnCl$_2$.2H$_2$O according to the general procedure J (method b). Obtained as brown solid (2.00 g).

MS (ISP) 312 [(M+H)$^+$] and 314 [(M+2+H)$^+$].

Example J12

(2-Amino-5-pyrrolidin-1-yl-4-trifluoromethyl-phenyl)-carbamic acid tert.-butyl ester The title compound was prepared from (2-nitro-5-pyrrolidin-1-yl-4-trifluoromethyl-phenyl)-carbamic acid tert.-butyl ester (Example C10) (7.35 g, 19.75 mmol) by hydrogenation with 10% Pd/C according to the general procedure J (method a). Obtained as a light orange solid (6.75 g).

MS (ISP) 346 [(M+H)$^+$]; mp 101–103° C.

Example J13

(2-Amino-5-dimethylamino-4-fluoro-phenyl)-carbamic acid tert.-butyl ester

The title compound was prepared from (5-dimethylamino-4-fluoro-2-nitro-phenyl)-carbamic acid tert.-butyl ester (Example C11) (4.88 g, 16 mmol) by hydrogenation with 10% Pd/C according to the general procedure J (method a). Obtained as a green solid (4.55 g).

MS (ISP) 270 [(M+H)$^+$]; mp 120–123° C.

Example J14

(2-Amino-4-chloro-5-piperidin-1-yl-phenyl)-carbamic acid tert.-butyl ester

The title compound was prepared from (4-chloro-2-nitro-5-piperidin-1-yl-phenyl)-carbamic acid tert.-butyl ester (Example C12) by reduction with SnCl$_2$.2H$_2$O according to the general procedure J (method b). Obtained as light brown solid (747 mg).

MS (ISP) 326 [(M+H)$^+$] and 328 [(M+2+H)$^-$]; mp 149–151° C.

Example J15

(2-Amino-4-fluoro-5-pyrrolidin-1-yl-phenyl)-carbamic acid tert.-butyl ester

The title compound was prepared from (4-fluoro-2-nitro-5-pyrrolidin-1-yl-phenyl)-carbamic acid tert.-butyl ester (Example C13) (6.37 g, 20 mmol) by hydrogenation with 10% Pd/C according to the general procedure J (method a). Obtained as a grey solid (5.92 g).

MS (ISP) 296 [(M+H)$^+$]; mp 75–76° C.

Example J16

(2-Amino-5-azetidin-1-yl-4-chloro-phenyl)-carbamic acid tert.-butyl ester

The title compound was prepared from (5-azetidin-1-yl-4-chloro-2-nitro-phenyl)-carbamic acid tert.-butyl ester (Example C14) by hydrogenation with 5% Pt/C according to the general procedure J (method a). Obtained as a white solid (3.664 g).

MS (ISP) 298 [(M+H)$^{30}$] and 300 [(M+2+H)$^+$]; mp 176–179° C.

Example J17

(2-Amino-5-azetidin-1-yl-4-trifluoromethyl-phenyl)-carbamic acid tert.-butyl ester The title compound was prepared from (5-azetidin-1-yl-2-nitro-4-trifluoromethyl-phenyl)-carbamic acid tert.-butyl ester (Example C15) by hydrogenation with 5% Pt/C according to the general procedure J (method a).

Obtained as a white solid (5.173 g).

MS (ISP) 332 [(M+H)$^+$]; mp 166–167° C.

Example J18

[2-Amino-5-(cyclopropylmethyl-methyl-amino)-4-trifluoromethyl-phenyl]-carbamic acid tert.-butyl ester The title compound was prepared from [5-(cyclopropylmethyl-methyl-amino)-2-nitro-4-trifluoromethyl-phenyl]-carbamic acid tert.-butyl ester (Example C16) (5.66 g, 14.5 mmol) by reduction with SnCl$_2$.2H$_2$O according to the general procedure J (method b). Obtained as yellow solid (4.7 g).

MS (ISP) 360 [(M+H)$^+$]; mp 56° C.

Example J19

[2-Amino-5-(cyclopropyl-methyl-amino)-4-trifluoromethyl-phenyl]-carbamic acid tert.-butyl ester The title compound was prepared from [5-(cyclopropyl-methyl-amino)-2-nitro-4-trifluoromethyl-phenyl]-carbamic acid tert.-butyl ester (Example C17) (3.74 g, 9.96 mmol) by reduction with SnCl$_2$.2H$_2$O according to the general procedure J (method b). Obtained as an orange semisolid (2.00 g).

MS (ISP) 346.4 [(M+H)$^+$].

Example J20

(5-Amino-2-dimethylamino-2'-fluoro-biphenyl-4-yl)-carbamic acid tert.-butyl ester The title compound was prepared from (2-dimethylamino-2'-fluoro-5-nitro-biphenyl-4-yl)-carbamic acid tert.-butyl ester (Example C18) (4.54 g, 12.1 mmol) by hydrogenation with 10% Pd/C according to the general procedure J (method a). Obtained as a light brown solid (3.324 g).

MS (ISP) 346.4 [(M+H)$^+$].

Example J21

[2-Amino-5-(2,2,2-trifluoro-ethoxy)-4-trifluoromethyl-phenyl]-carbamic acid tert.-butyl ester The title compound was prepared from [2-nitro-5-(2,2,2-trifluoro-ethoxy)-4-trifluoromethyl-phenyl]-carbamic acid tert.-butyl ester (Example B7) by hydrogenation with 5% Pt/C according to the general procedure J (method a). Obtained as a yellow solid (17.374 g).

MS (ISP) 375 [(M+H)$^+$].

Example J22

(2-Amino-5-dimethylamino-4-methyl-phenyl)-carbamic acid tert-butyl ester

The title compound was prepared from (5-dimethylamino-4-methyl-2-nitro-phenyl)-carbamic acid tert-butyl ester (Example C19) (3.22 g, 10.9 mmol) by hydrogenation with 10% Pd/C according to the general procedure J (method a). Obtained as a gray solid (2.05 g, 58%).

MS (ISP) 266.3 [(M+H)$^+$]; mp 78° C.

Example J23

(2-Amino-4-cyano-5-dimethylamino-phenyl)-carbamic acid tert-butyl ester

The title compound was prepared from (4-cyano-5-dimethylamino-2-nitro-phenyl)-carbamic acid tert-butyl ester (Example C20) (3.9 g, 12.7 mmol) by reduction with SnCl$_2$.2H$_2$O according to the general procedure J (method b). Obtained as a pale brown solid (2.05 g, 58%).

MS (ISP) 277.2 [(M+H)$^-$]; mp 120° C.

Example J24

[2-Amino-4-methyl-5-(methyl-propyl-amino)-phenyl]-carbamic acid tert-butyl ester The title compound was prepared from [4-methyl-5-(methyl-propyl-amino)-2-nitro-phenyl]-carbamic acid tert-butyl ester (Example C21) (3.59 g, 11.1 mmol) by hydrogenation with 10% Pd/C according to the general procedure J (method a). Obtained as a purple solid (3.23 g, 99%).

MS (ISP) 294.4 [(M+H)$^+$].

Example J25

[2-Amino-5-(ethyl-methyl-amino)-4-methyl-phenyl]-carbamic acid tert-butyl ester

The title compound was prepared from [5-(ethyl-methyl-amino)-4-methyl-2-nitro-phenyl]-carbamic acid tert-butyl ester (Example C22) (3.28 g, 10.6 mmol) by hydrogenation with 10% Pd/C according to the general procedure J (method a). Obtained as a purple solid (2.94 g, 99%).

MS (ISP) 280.3 [(M+H)$^+$].

Example J26

(2-Amino-4-chloro-5-(isopropyl-methyl-amino)-phenyl)-carbamic acid tert-butyl ester The title compound was prepared from [4-chloro-5-(isopropyl-methyl-amino)-2-nitro-phenyl]-carbamic acid tert-butyl ester (Example C23) (4.07 g, 11.8 mmol) by reduction with SnCl$_2$.2H$_2$O according to the general procedure J (method b). Obtained as a pale brown solid (3.08 g, 83%).

MS (ISP) 314.3 [(M+H)$^+$]; mp 116° C.

Example J27

[2-Amino-4-chloro-5-(isobutyl-methyl-amino)-phenyl]-carbamic acid tert-butyl ester The title compound was prepared from [4-chloro-5-(isobutyl-methyl-amino)-2-nitro-phenyl]-carbamic acid tert-butyl ester (Example C24) (5.55 g, 15.5 mmol) by reduction with SnCl$_2$.2H$_2$O according to the general procedure J (method b). Obtained as a pale brown solid (3.98 g, 78%).

MS (ISP) 328.3 [(M+H)$^+$].

Example J28

(2-Amino-4-cyano-5-pyrrolidin-1-yl-phenyl)-carbamic acid tert-butyl ester

The title compound was prepared from (4-cyano-2-nitro-5-pyrrolidin-1-yl-phenyl)-carbamic acid tert-butyl ester (Example C25) (1.82 g, 5.48 mmol) by reduction with SnCl$_2$.2H$_2$O according to the general procedure J (method b). Obtained as a pale brown solid (1.27 g, 77%).

MS (ISP) 303.2 [(M+H)$^+$].

Example J29

[2-Amino-4-cyano-5-(methyl-propyl-amino)-phenyl]-carbamic acid tert-butyl ester

The title compound was prepared from [4-cyano-5-(methyl-propyl-amino)-2-nitro-phenyl]-carbamic acid tert-butyl ester (Example C26) (1.64 g, 4.90 mmol) by reduction with SnCl$_2$.2H$_2$O according to the general procedure J (method b). Obtained as a dark red oil (1.24 g, 83%).

MS (ISP) 305.3 [(M+H)$^+$].

Example J30

(2-Amino-4-cyano-5-diethylamino-phenyl)-carbamic acid tert-butyl ester

The title compound was prepared from (4-cyano-5-diethylamino-2-nitro-phenyl)-carbamic acid tert-butyl ester (Example C27) (1.66 g, 4.96 mmol) by reduction with SnCl$_2$.2H$_2$O according to the general procedure J (method b). Obtained as an off-white solid (1.38 g, 91%).

MS (ISP) 305.3 [(M+H)$^+$]; mp 151° C.

Example J31

[2-Amino-4-cyano-5-(isopropyl-methyl-amino)-phenyl]-carbamic acid tert-butyl ester The title compound was prepared from [4-cyano-5-(isopropyl-methyl-amino)-2-nitro-phenyl]-carbamic acid tert-butyl ester (Example C28) (1.73 g, 5.17 mmol) by reduction with SnCl$_2$.2H$_2$O according to the general procedure J (method b). Obtained as an off-white solid (1.56 g, 99%).

MS (ISP) 305.3 [(M+H)$^+$]; mp 77° C.

Example J32

[2-Amino-4-cyano-5-(isobutyl-methyl-amino)-phenyl]-carbamic acid tert-butyl ester The title compound was prepared from [4-cyano-5-(isobutyl-methyl-amino)-2-nitro-phenyl]-carbamic acid tert-butyl ester (Example C29) (1.76 g, 5.05 mmol) by reduction with SnCl$_2$.2H$_2$O according to the general procedure J (method b). Obtained as a light brown solid (1.55 g, 96%).

MS (ISP) 319.5 [(M+H)$^+$]; mp 88° C.

Example J33

(2-Amino-4-cyano-5-piperidin-1-yl-phenyl)-carbamic acid tert-butyl ester

The title compound was prepared from (4-cyano-2-nitro-5-piperidin-1-yl-phenyl)-carbamic acid tert-butyl ester (Example C30) (2.08 g, 5.71 mmol) by reduction with SnCl$_2$.2H$_2$O according to the general procedure J (method b). Obtained as an off-white solid (1.67 g, 99%).

MS (ISP) 317.2 [(M+H)$^+$]; mp 86° C.

Example J34

(2-Amino-4-chloro-5-isobutylamino-phenyl)-carbamic acid tert-butyl ester

The title compound was prepared from (4-chloro-5-isobutylamino-2-nitro-phenyl)-carbamic acid tert-butyl ester (Example C31) (1.93 g, 5.61 mmol) by reduction with SnCl$_2$.2H$_2$O according to the general procedure J (method b). Obtained as a brown solid (1.30 g, 74%).

MS (ISP) 314.3 [(M+H)$^+$].

Example J35

[2-Amino-5-(methyl-propyl-amino)-4-trifluoromethyl-phenyl]-carbamic acid tert-butyl ester The title compound was prepared from [5-(methyl-propyl-amino)-2-nitro-4-trifluoromethyl-phenyl]-carbamic acid tert-butyl ester (Example C32) (3.78 g, 10.0 mmol) by hydrogenation with 10% Pd/C according to the general procedure J (method a). Obtained as a red oil (3.40 g, 98%).

MS (ISP) 248.4 [(M+H)$^+$].

Example J36

[2-Amino-5-(isobutyl-methyl-amino)-4-trifluoromethyl-phenyl]-carbamic acid tert-butyl ester The title compound was prepared from [5-(isobutyl-methyl-amino)-2-nitro-4-trifluoromethyl-phenyl]-carbamic acid tert-butyl ester (Example C33) (3.88 g, 9.91 mmol) by hydrogenation with 10% Pd/C according to the general procedure J (method a). Obtained as a orange oil (2.70 g, 75%).

MS (ISP) 362.3 [(M+H)$^+$].

Example J37

[2-Amino-5-(isopropyl-methyl-amino)-4-trifluoromethyl-phenyl]-carbamic acid tert-butyl ester The title compound was prepared from [5-(isopropyl-methyl-amino)-2-nitro-4-trifluoromethyl-phenyl]-carbamic acid tert-butyl ester (Example C34) (2.98 g, 7.90 mmol) by hydrogenation with 10% Pd/C according to the general procedure J (method a). Obtained as a orange oil (2.42 g, 88%).

MS (ISP) 348.5 [(M+H)$^+$].

Example J38

[2-Amino-5-(isobutyl-methyl-amino)-4-methyl-phenyl]-carbamic acid tert-butyl ester The title compound was prepared from [5-(isobutyl-methyl-amino)-4-methyl-2-nitro-phenyl]-carbamic acid tert-butyl ester (Example C35) (1.48 g, 4.39 mmol) by hydrogenation with 10% Pd/C according to the general procedure J (method a). Obtained as a white solid (1.08 g, 80%).

MS (ISP) 308.3 [(M+H)$^+$]; mp 71° C.

Example J39

(2-Amino-4-methyl-5-pyrrolidin-1-yl-phenyl)-carbamic acid tert-butyl ester

The title compound was prepared from (4-methyl-2-nitro-5-pyrrolidin-1-yl-phenyl)-carbamic acid tert-butyl ester (Example C36) (3.27 g, 10.2 mmol) by hydrogenation with 10% Pd/C according to the general procedure J (method a). Obtained as a pale brown solid (2.48 g, 83%).

MS (ISP) 292.3 [(M+H)$^+$]; mp 115° C.

Example J40

(2-Amino-4-chloro-5-isopropylamino-phenyl)-carbamic acid tert-butyl ester

The title compound was prepared from (4-chloro-5-isopropylamino-2-nitro-phenyl)-carbamic acid tert-butyl ester (Example C37) (3.75 g, 11.3 mmol) by reduction with SnCl$_2$.2H$_2$O according to the general procedure J (method b). Obtained as a brown solid (2.90 g, 86%).

MS (ISP) 303.3 [(M+H)$^+$].

Example J41

[2-Amino-5-(isobutyl-amino)-4-trifluoromethyl-phenyl]-carbamic acid tert-butyl ester The title compound was prepared from [5-(isobutyl-amino)-2-nitro-4-trifluoromethyl-phenyl]-carbamic acid tert-butyl ester (Example C38) (5.28 g, 13.99 mmol) by hydrogenation with 10% Pd/C according to the general procedure J (method a). Obtained as a pale yellow solid (3.69 g, 76%).

MS (ISP) 348.5 [(M+H)$^+$]; mp 141° C.

The following examples relate to the preparation of the ethyl or tert.-butyl 3-aryl-3-oxo-propionates (formula IVa), which serve as building blocks in the synthesis of the target compounds (Synthetic Scheme H):

General Procedure K

Method a) Preparation of ethyl or tert.-butyl 3-aryl-3-oxo-propionates

The ethyl or tert.-butyl 3-aryl-3-oxo-propionates were prepared from the aryl acid chlorides and ethyl or tert.-butyl malonate potassium salt [CAS-no. 6148-64-7 and 75486-33-8] with Et$_3$N and MgCl$_2$ in CH$_3$CN at 0° C. to 23° C. according to *Synthesis* 1993, 290. If the free aryl carboxylic acid was employed in this reaction, it was activated by treatment with ethyl chloroformate and Et$_3$N in THF/CH$_3$CN at 0° C. prior to reaction with the malonate salt.

Method b) Preparation of tert.-butyl 3-aryl-3-oxo-propionates

The tert.-butyl 3-aryl-3-oxo-propionates were alternatively prepared from the methyl or ethyl aryl esters by treatment with lithium tert.-butyl acetate [prepared by treatment of tert.-butyl acetate with lithium diisopropylamide in THF at −78° C.] in the presence of lithium tert.-butoxide according to *Synthesis* 1985, 45. If the product contained residual starting material after workup, thus could be removed by selective saponification with LiOH in THF/MeOH/$H_2O$ at 23° C.

Method c) Preparation of 3-aryl-3-oxo-propionic acids

The 3-aryl-3-oxo-propionic acids were prepared from the aryl acid chlorides and bis(trimethylsilyl)malonate with $Et_3N$ and LiBr in $CH_3CN$ at 0° C. according to *Synth. Commun.* 1985, 15, 1039 (method c1) or with n-BuLi in ether at −60° C. to 0° C. according to *Synthesis* 1979, 787 (method c2).

Example K1

3-Oxo-3-(3-[1,2,3]triazol-1-yl-phenyl)-propionic acid ethyl ester

The title compound was prepared from 3-[1,2,3]triazol-1-yl-benzoic acid, prepared by refluxing of methyl 3-azidobenzoate [CAS-No. 93066-93-41] in trimethylsilyl-acetylene, followed by saponification with aqueous NaOH in refluxing EtOH] by activation with ethyl chloroformate/$Et_3N$ and reaction with ethyl malonate potassium salt with $Et_3N$ and $MgCl_2$ in $CH_3CN$ according to general procedure K (method a). Obtained as a light yellow solid (2.22 g).

MS (EI) 259 ($M^+$); mp 72–74° C.

Example K2

3-(3-Cyano-phenyl)-3-oxo-propionic acid tert.-butyl ester

The title compound was prepared from methyl 3-cyanobenzoate [CAS-No. 13531-48-1] by treatment with lithium tert.-butyl acetate according to general procedure K (method b). Obtained as a light brown oily semisolid.

MS (EI) 245 ($M^+$).

Example K3

3-(2-Cyano-pyridin-4-yl)-3-oxo-propionic acid tert.-butyl ester

The title compound was prepared from 2-cyano-isonicotinic acid ethyl ester [CAS-No. 58481-14-4] by treatment with lithium tert.-butyl acetate according to general procedure K (method b). Obtained as a light brown solid (7.70 g).

MS (ISN) 245 [(M−H)$^-$].

Example K4

3-[3-(3-Methyl-isoxazol-5-yl)-phenyl]-3-oxo-propionic acid tert.-butyl ester

The title compound was prepared from ethyl 3-(3-methyl-isoxazol-5-yl)-benzoate [prepared by reaction of ethyl 3-ethynylbenzoate [CAS-No. 178742-95–5] with a mixture of NCS, acetaldoxime, $Et_3N$ and cat. amount of pyridine in $CHCl_3$ at 50° C. according to *Tetrahedron* 1984, 40, 2985–2988] by treatment with lithium tert.-butyl acetate according to general procedure K (method b). Obtained as a yellow solid (2.54 g).

MS (ISP) 302 [(M+H)$^+$]; mp 50–56° C.

Example K5

(RS)-3-Oxo-3-{3-[5-(tetrahydro-pyran-2-yloxymethyl)-[1,2,3]triazol-1-yl]-phenyl}-propionic acid tert.-butyl ester The title compound was prepared from (RS)-3-[5-(tetrahydro-pyran-2-yloxymethyl)-[1,2,3]triazol-1-yl]-benzoic acid methyl ester [prepared by the following sequence: i.) methyl 3-azidobenzoate [CAS-No. 93066-93-4] (15.55 g, 88 mmol) and (RS)-tert.-butyl-dimethyl-[3-(tetrahydro-pyran-2-yloxy)-prop-1-ynyl]-silane [CAS-No. 135294-85-8] (33.50 g, 132 mmol) were heated to 60° C. for 10 days; ii.) The obtained material (48.2 g, ca. 88 mmol) was stirred in TBAF (300 mL, 1M in THF) at 70° C. for 6 days and subsequently refluxed in 1N HCl (400 mL) for 2 h; iii.) The obtained material (16.15 g, 74 mmol) was stirred in MeOH (400 mL) and conc. H2SO4 (30 mL) at 23° C. for 11 days. iv.) Part of the obtained material (4.60 g, 19.7 mmol) was reacted with 3,4-dihydro-2H-pyran (2.67 mL, 29.5 mmol) and cat. amount p-TsOH.$H_2O$ in DCM (38 mL) at 23° C. for 20 h.] (6.20 g, 19.5 mmol) by treatment with lithium tert.-butyl acetate according to general procedure K (method b). Obtained as a yellow oil (8.47 g).

MS (ISP) 402 [(M+H)$^+$].

Example K6

3-[2-(3-Methyl-isoxazol-5-yl)-pyridin-4-yl]-3-oxo-propionic acid tert.-butyl ester The title compound was prepared from 2-(3-methyl-isoxazol-5-yl)-isonicotinic acid methyl ester [prepared by i.) reaction of 2-iodo-isonicotinic acid methyl ester [CAS-No. 134579-47-8] with trimethylsilylacetylene according to general procedure H; ii.) desilylation by reaction with cat. $K_2CO3$ in MeOH at 0° C. for 4 h; iii.) cycloadditon with a mixture of NCS, acetaldoxime, $Et_3N$ and cat. amount of pyridine in $CHCl_3$ at 50° C. according to *Tetrahedron* 1984, 40, 2985-2988] by treatment with lithium tert.-butyl acetate according to general procedure K (method b). Obtained as a brown solid (5.17 g).

MS (EI) 302 ($M^+$); mp 59–67° C.

Example K7

3-[3-(2-Methyl-2H-pyrazol-3-yl)-phenyl]-3-oxo-propionic acid tert.-butyl ester

The title compound was prepared from 3-(2-methyl-2H-pyrazol-3-yl)-benzoic acid methyl ester [prepared by i.) reaction of 1-(3-bromo-phenyl)-3-dimethylamino-propenone [CAS-No. 163852–04-8] with methylhydrazine in EtOH at 23° C. for 2.5 days; ii.) chromatographic separation of the obtained isomers; iii.) treatment of the clean isomer with n-BuLi in THF at −78° C. for 1 h, followed by quenching with a stream of $CO_2$ and subsequent esterification with MeOH and conc. $H_2SO_4$ at 23° C. for 48 h.] by treatment with lithium tert.-butyl acetate according to general procedure K (method b). Obtained as a yellow oil (5.96 g).

MS (EI) 300 ($M^+$).

Example K8

3-[3-(5-Dimethylaminomethyl-[1,2,3]triazol-1-yl)-phenyl]-3-oxo-propionic acid tert.-butyl ester The title compound was prepared from 3-(5-dimethylaminomethyl -[1,2,3]triazol-1-yl)-benzoic acid methyl ester [prepared from methyl 3-azidobenzoate following the synthetic steps i.) to iii.) as described in the preparation of Example K5 and reacting the obtained product with $SOCl_2$ in THF at 0 to 23° C. for 1 h, followed by addition of dimethylamine (7.9 M in $H_2O$) and stirring at 23 to 70° C. for 1 h.] (2.14 g, 8.22 mmol) by treatment with lithium tert.-butyl acetate according to general procedure K (method b). Obtained as a yellow oil (2.90 g).

MS (ISP) 345 [(M+H)$^+$].

Example K9

3-[3-(3-Methoxymethyl-isoxazol-5-yl)-phenyl]-3-oxo-propionic acid tert.-butyl ester

The title compound was prepared from methyl 3-(3-methoxymethyl-isoxazol-5-yl)-benzoate [prepared by reaction of ethyl 3-ethynylbenzoate [CAS-No. 178742-95-5] with a mixture of NCS, 2-methoxyacetaldoxime [CAS-No. 71494-93-4], Et$_3$N and cat. amount of pyridine in CHCl$_3$ at 50° C. according to *Tetrahedron* 1984, 40, 2985–2988] by treatment with lithium tert.-butyl acetate according to general procedure K (method b). Obtained as a light yellow liquid (1.548 g).

MS (EI) 331 (M$^+$).

Example K10

(RS)-3-Oxo-3{3-[4-(tetrahydro-pyran-2-yloxymethyl)-thiazol-2-yl]-phenyl}-propionic acid tert.-butyl ester

The title compound was prepared from (RS)-3-[4-(tetrahydro-pyran-2-yloxymethyl)-thiazol-2-yl]-benzoic acid methyl ester [prepared by the following sequence: i.) A mixture of 3-thiocarbamoyl-benzoic acid methyl ester [CAS-No. 106748-27-0] (7.8 g), 1,3-dichloro-2-propanone (8.4 g) and sodium bicarbonate (8.4 g) in 1,4-dioxane (180 mL) was heated to 60° C. for 24 h. The reaction mixture was cooled to 20° C. and added to a stirred solution of sodium methoxide (5.4 g) in methanol (200 mL). Stirring was continued for 0.5 h. The mixture was poured into ice-cold 2N HCl (200 mL) and the product was extracted with ethyl acetate. The organic layer was washed with brine, dried over sodium sulfate and evaporated in vacuum. The residue was crystallized from dichloromethane/hexane to give 3-(4-hydroxymethyl-thiazol-2-yl)-benzoic acid methyl ester (7.5 g) as light-brown crystals, 115–117 °C. ii.) A mixture of this material (7.5 g), dihydropyrane (4.1 mL) and p-toluenesulfonic acid hydrate (0.19 g) in ethyl acetate (50 mL) was stirred at 20 ° C. for 1 h. The solution was diluted with ethyl acetate, washed with 5% sodium bicarbonate solution and with brine, dried over sodium sulfate and evaporated in vacuum. The residual oil was purified by chromatography on silica gel using ethyl acetate/hexane (1:2) as eluent to give (RS)-3-[4-(tetrahydro-pyran-2-yloxymethyl)-thiazol-2-yl]-benzoic acid methyl ester (9.6 g) as a pale-yellow oil.] (3.5 g, 11 mmol) by treatment with lithium tert.-butyl acetate according to general procedure K (method b). Obtained as a pale yellow oil (3.8 g).

MS (ISP) 418.2 [(M+H)$^+$].

Example K11

(RS)-3-Oxo-3-{3-[4-(tetrahydro-pyran-2-yloxymethyl)-oxazol-2-yl]-phenyl}-propionic acid tert-butyl ester

The title compound was prepared from (RS)-3-[4-(tetrahydro-pyran-2-yloxymethyl)-oxazol-2-yl]-benzoic acid methyl ester [prepared by the following sequence: i.) A mixture of 3-carbamoyl-benzoic acid methyl ester [CAS-No. 106748-24-7] (17.9 g) and 1,3-dichloro-2-propanone (14.0 g) was heated to 140° C. for 1.5 h. The mixture was cooled to 20° C. and conc. sulfuric acid (12 mL) was carefully added. The mixture was stirred for 10 min. and then poured into ice-water. The product was extracted with ethyl acetate and the organic layer was washed with brine, dried over sodium sulfate and evaporated in vacuum. The residue was chromatographed on silica gel using ethyl acetate/hexane (1:1) as eluent to give 3-(4-chloromethyl-oxazol-2-yl)-benzoic acid methyl ester (11.8 g) as a pale-yellow oil. MS (ISP) 252.2 [(M+H)$^+$]. ii.) A solution of this material (7.6 g) and lithium hydroxide monohydrate (5.0 g) in DMSO (30 mL) was heated to 60° C. for 7 h. The cooled reaction mixture was poured into ice-water and the mixture was extracted with diethyl ether. The aqueous layer was acidified to pH 1 by the addition of 6N HCl and the precipitate formed was collected by filtration and crystallized from dichloromethane/hexane. The pale-yellow crystals (5.5 g) were dissolved in DMSO (25 mL), and after the addition of N,N,N',N'-tetramethyl-guanidine (4.4 mL) and methyl iodide (2.2 mL), the mixture was stirred at 20° C. for 1 h. Ethyl acetate was added and the mixture was washed successively with water, 1N HCl and brine. The organic layer was dried over sodium sulfate and evaporated in vacuum. The residue was chromatographed on silica gel using ethyl acetate/hexane (1:1) as eluent and the purified product was crystallized from diethyl ether/hexane to give 3-(4-hydroxymethyl-oxazol-2-yl)-benzoic acid methyl ester (2.1 g) as white crystals, mp 118–119° C. iii.) A mixture of this material (2.1 g), dihydropyrane (1.2 mL) and p-toluenesulfonic acid hydrate (0.1 g) in ethyl acetate (15 mL) was stirred at 20° C. for 1 h. The solution was diluted with ethyl acetate, washed with 5% sodium bicarbonate solution and with brine, dried over sodium sulfate and evaporated in vacuum. The residual oil was purified by chromatography on silica gel using ethyl acetate/hexane (1:2) as eluent to give (RS)-3-[4-(tetrahydro-pyran-2-yloxymethyl)-oxazol-2-yl]-benzoic acid methyl ester (3.5 g) as a pale-yellow oil.] (3.5 g, 11 mmol) by treatment with lithium tert.-butyl acetate according to general procedure K (method b). Obtained as a pale yellow oil (3.8 g).

MS (ISP) 402.5 [(M+H)$^+$].

Example K12

(RS)-3-Oxo-3-{3-[3-(tetrahydro-pyran-2-yloxymethyl)-isoxazol-5-yl]-phenyl}-propionic acid tert.-butyl ester

The title compound was prepared from (RS)-3-[3-(tetrahydro-pyran-2-yloxymethyl)-isoxazol-5-yl]-benzoic acid methyl ester [prepared by the following sequence: i.) 4-(3-bromo-phenyl)-2,4-dioxo-butyric acid ethyl ester [CAS-No. 151646-31-0] (7.55 g, 23 mmol) and hydroxylamine hydrochloride (4.74 g, 68 mmol) were refluxed in EtOH for 1 h; ii.) The obtained ester (5.94 g, 20 mmol) was reduced with LiAlH$_4$ (761 mg, 20 mmol) in THF at –10° C. for 1 h; iii.) The obtained alcohol (4.90 g, 19 mmol) was reacted with 3,4-dihydro-2H-pyran and cat. amount p-TsOH.H$_2$O in DCM at 23° C. for 20 h. iv.) The obtained THP-ether (5.24 g, 15 mmol) was treated with n-BuLi at –78° C. for 45 min, followed by a stream of CO$_2$. v.) The obtained crude acid was stirred in MeOH (90 mL) and conc. H$_2$SO$_4$ (6.5 mL) at 50° C. for 12 h. vi.) The obtained material (2.01 g, 8.62 mmol) was reacted with 3,4-dihydro-2H-pyran (1.17 mL, 12.9 mmol) and cat. amount p-TsOH.H$_2$O in DCM (17 mL) at 23° C. for 5 h.] (2.44 g, 7.7 mmol) by treatment with lithium tert.-butyl acetate according to general procedure K (method b). Obtained as a yellow oil (3.06 g).

MS (ISP) 402 [(M+H)$^+$].

Example K13

(RS)-3-{3-[3-Methyl-4-(tetrahydro-pyran-2-yloxymethyl)-isoxazol-5-yl]-phenyl}-3-oxo-propionic acid tert.-butyl ester

The title compound was prepared from (RS)-3-[3-methyl-4-(tetrahydro-pyran -2-yloxymethyl)-isoxazol-5-yl]- benzoic acid methyl ester [prepared by the following sequence: i.) (3-bromo-phenyl)-3-oxo-propionic acid ethyl ester [CAS-No. 21575-91-7], pyrrolidine and TMSOTf in benzene were refluxed for 16 h (Org. Synth. 53, 59); ii.) The obtained 3-(3-bromo-phenyl)-3-pyrrolidin-1-yl-acrylic acid ethyl ester was reacted with nitroethane, $POCl_3$ and $Et_3N$ at 23° C.; iii.) The obtained 5-(3-bromo-phenyl)-3-methyl-isoxazole-4-carboxylic acid ethyl ester was reduced with $LiAlH_4$ in THF at −10° C. for 1 h iv.) The obtained [5-(3-bromo-phenyl)-3-methyl-isoxazol-4-yl]-methanol was reacted with 3,4-dihydro-2H-pyran and cat. amount p-TsOH.$H_2O$ in DCM at 23° C. for 20 h. iv.) The obtained THP-ether was treated with n-BuLi at −78° C. for 45 min, followed by a stream of $CO_2$. v.) The obtained crude acid was stirred in MeOH and conc. $H_2SO_4$ at 50° C. for 18 h. vi.) The obtained 3-(4-hydroxymethyl-3-methyl-isoxazol-5-yl)-benzoic acid methyl ester was reacted with 3,4-dihydro-2H-pyran and cat. amount p-TsOH.$H_2O$ in DCM at 23° C. for 1 h.] by treatment with lithium tert.-butyl acetate according to general procedure K (method b). Obtained as a light yellow oil (972 mg).

MS (EI) 416 [(M+H)$^+$].

Example K14

(RS)-3-{3-[2-Methyl-5-(tetrahydro-pyran-2-yloxymethyl)-2H-pyrazol-3-yl]-phenyl}-3-oxo-propionic acid tert.-butyl ester The title compound was prepared from (RS)-3-[2-methyl-5-(tetrahydro-pyran-2-yloxymethyl)-2H-pyrazol-3-yl]-benzoic acid methyl ester [prepared by the following sequence: i.) 4-(3-bromo-phenyl)-2,4-dioxo-butyric acid ethyl ester [CAS-No. 151646-31-0] (6.135 g, 21 mmol), $MeNHNH_2$ (1.296 mL, 25 mmol) and HCl (4M in dioxane, 6.25 mL, 25 mol) in EtOH (35 mL) were refluxed for 1.5 h; ii.) The obtained 5-(3-bromo-phenyl)-1-methyl-1H-pyrazole-3-carboxylic acid ethyl ester (7.02 g, 22.7 mmol) was reduced with $LiAlH_4$ (862 mg, 22.7 mmol) in THF (60 mL) at −10° C. for 1 h; iii.) The obtained [5-(3-bromo-phenyl)-1-methyl-1H-pyrazol-3-yl]-methanol (6.34 g, 24 mmol) was reacted with 3,4-dihydro-2H-pyran (3.25 mL, 36 mmol) and cat. amount p-TsOH.$H_2O$ in DCM (50 mL) at 23° C. for 23 h. iv.) The obtained (RS)-[5-(3-bromo-phenyl)-1-methyl-3-(tetrahydro-pyran-2-yloxymethyl)-1H-pyrazole (8.64 g, 25 mmol) was treated with n-BuLi at −78° C. for 45 min, followed by a stream of $CO_2$. v.) The obtained crude acid was stirred in MeOH (90 mL) and conc. $H_2SO_4$ (6.5 mL) at 50° C. for 5 h. vi.) The obtained 3-(5-hydroxymethyl-2-methyl-2H-pyrazol-3-yl)-benzoic acid methyl ester (3.41 g, 13.85 mmol) was reacted with 3,4-dihydro-2H-pyran (1.75 mL, 20.77 mmol) and cat. amount p-TsOH.$H_2O$ in DCM (28 mL) at 23° C. for 18 h.] (3.93 g, 11.9 mmol) by treatment with lithium tert.-butyl acetate according to general procedure K (method b). Obtained as a yellow oil (4.90 g).

MS (ISP) 415 [(M+H)$^+$].

Example K15

(RS)-3-Oxo-3-{3-[5-(tetrahydro-pyran-2-yloxymethyl)-isoxazol-3-yl]-phenyl}-propionic acid tert.-butyl ester The title compound was prepared from (RS)-3-[5-(tetrahydro-pyran-2-yloxymethyl)-isoxazol-3-yl]-benzoic acid methyl ester [prepared from (Z)-3-(hydroxyimino-methyl)-benzoic acid methyl ester [CAS-No. 91186-80-0] by treatment with NCS, cat. amount pyridine in $CHCl_3$ followed by addition of (RS)-tetrahydro-2-(2-propynyloxy)-2H-pyran and slow addition of $Et_3N$ in $CHCl_3$ at 23°C.] by treatment with lithium tert.-butyl acetate according to general procedure K (method b). Obtained as a yellow oil (3.00 g).

MS (ISN) 400.5 [(M−H)$^-$].

Example K16

3-Oxo-3-(3-pyrazol-1-yl-phenyl)-propionic acid tert.-butyl ester

The title compound was prepared from 3-pyrazol-1-yl-benzoic acid methyl ester [CAS-No. 168618-35-7] by treatment with lithium tert.-butyl acetate according to general procedure K (method b). Obtained as a yellow oil (5.00 g).

MS (EI) 286 (M$^+$).

Example K17

(RS)-3-Oxo-3-{3-[4-(tetrahydro-pyran-2-yloxymethyl)-pyrazol-1-yl]-phenyl}-propionic acid tert.-butyl ester The title compound was prepared from (RS)-3-[4-(tetrahydro-pyran-2-yloxymethyl)-pyrazol-1-yl]-benzoic acid methyl ester [prepared by the following sequence: i.) A mixture of 3-hydrazino-benzoic acid methyl ester hydrochloride [CAS-No. 167626-26-8] (15.14 g, 75 mmol), 2-cyano-3-ethoxy-acrylic acid benzyl ester [CAS-No. 32016-27-6] (17.36 g, 75 mmol) and $Et_3N$ (10.5 mL, 75 mmol) in isopropanol (115 mL) was refluxed for 1.5 h. ii.) The obtained 5-amino-1-(3-methoxycarbonyl-phenyl)-1H-pyrazole-4-carboxylic acid benzyl ester (26.0 g, 74 mmol) was refluxed with isopentyl nitrite (30 mL, 225 mmol; 10 mL) in THF (200 mL) for 22 h. iii.) The obtained 1-(3-methoxycarbonyl-phenyl)-1H-pyrazole-4-carboxylic acid benzyl ester (18.98 g, 56 mmol) was hydrogenated in the presence of Pd/C (10% Pd/C, 600 mg, 1 mol %) in EtOAc (350 mL) and THF (250 mL) at 23° C. for 16 h. iv.) The obtained 1-(3-methoxycarbonyl-phenyl)-1H-pyrazole-4-carboxylic acid (13.70 g, 55.6 mmol) was reduced with $BH_3.SMe_2$ (28.46 mL, 278.2 mmol) in THF (364 mL) at 5 to 23° C. for 16 h. v.) The obtained 3-(4-hydroxymethyl-pyrazol-1-yl)-benzoic acid methyl ester (10.66 g, 45.9 mmol) was reacted with 3,4-dihydro-2H-pyran (6.24 mL, 68.9 mmol) and cat. amount p-TsOH.$H_2O$ in DCM (91 mL) at 23° C. for 22 h.] (14.18 g, 44.8 mmol) by treatment with lithium tert.-butyl acetate according to general procedure K (method b). Obtained as a yellow oil (15.87 g).

MS (ISN) 399 [(M−H)$^-$].

Example K18

(RS)-3-Oxo-3-{3-[4-(tetrahydro-pyran-2-yloxymethyl)-isoxazol-3-yl]-phenyl}-propionic acid tert.-butyl ester The title compound was prepared from (RS)-3-[4-(tetrahydro-pyran-2-yloxymethyl)-isoxazol-3-yl]-benzoic acid methyl ester [prepared by the following sequence: i.) (Z)-3-(hydroxyimino-methyl)-benzoic acid methyl ester [CAS-No. 91186-80-0] was treated with NCS, cat. amount pyridine in $CHCl_3$ followed by addition of (E)-3-pyrrolidin-1-yl-acrylic acid tert.-butyl ester [CAS-No. 340257-76-3] and slow addition of $Et_3N$ in $CHCl_3$ at 23° C. ii.) The obtained 3-(3-methoxycarbonyl-phenyl)-isoxazole-4-carboxylic acid tert.-butyl ester was stirred in formic acid at 50° C. for 18 h. iii.) The obtained 3-(3-methoxycarbonyl-phenyl)-isoxazole-4-carboxylic acid was reduced with $BH_3.SMe_2$ in THF at 5 to 23° C. for 16 h. iv.) The obtained 3-(4-hydroxymethyl-isoxazol-3-yl)-benzoic acid methyl ester was reacted with 3,4-dihydro-2H-pyran and cat. amount p-TsOH.$H_2O$ in DCM at 23° C. for 1 h.] by treatment with lithium tert.-butyl acetate according to general procedure K (method b). Obtained as a yellow oil (1.817 g).

MS (ISN) 400 [(M–H)⁻].

Example K19

(RS)-3-{3-[2-Methyl-4-(tetrahydro-pyran-2-yloxymethyl)-2H-pyrazol-3-yl]-phenyl}-3-oxo-propionic acid tert.-butyl ester The title compound was prepared from (RS)-3-[2-methyl-4-(tetrahydro-pyran -2-yloxymethyl)-2H-pyrazol-3-yl]-benzoic acid methyl ester [prepared by the following sequence: i.) 3-bromobenzoyl chloride and 3-isopropylamino -acrylic acid methyl ester [CAS-No. 89895-40-9] were reacted in toluene and $Et_3N$ according to *Synthesis* 1982, 318. ii.) The obtained 2-(3-bromo-benzoyl)-3-isopropylamino-acrylic acid methyl ester was reacted with methylhydrazine in ether at 23° C. according to *Synthesis* 1982, 318. iii.) The obtained 5-(3-bromo-phenyl)-1-methyl-1H-pyrazole-4-carboxylic acid methyl ester was reduced with $LiAlH_4$ in THF at –10° C. for 1 h. iv.) The obtained [5-(3-bromo-phenyl)-1-methyl-1H-pyrazol-4-yl]-methanol was reacted with 3)4-dihydro-2H-pyran and cat. amount p-TsOH.$H_2O$ in DCM at 23° C. for 20 h. v.) The obtained (RS)-5-(3-bromo-phenyl)-1-methyl-4-(tetrahydro-pyran-2-yloxymethyl)-1H-pyrazole was treated with n-BuLi at –78° C. for 45 min, followed by a stream of $CO_2$. vi.) The obtained crude acid was stirred in MeOH and conc. $H_2SO_4$ at 50° C. for 18 h. vii.) The obtained 3-(4-methoxymethyl-2-methyl-2H-pyrazol-3-yl)-benzoic acid methyl ester was reacted with 1M $BBr_3$-sol. in DCM at –78 to 23° C. for 1 h. viii.) The obtained crude bromide was reacted with KOAc in DMF at 60° C. for 30 min. ix.) The obtained crude acetate was reacted with NaOMe-sol. In MeOH at 23° C. for 20 min. x.) The obtained 3-(4-hydroxymethyl-2-methyl-2H-pyrazol-3-yl) -benzoic acid methyl ester was reacted with 3,4-dihydro-2H-pyran and cat. amount p-TsOH.$H_2O$ in DCM at 23° C. for 1 h.] by treatment with lithium tert.-butyl acetate according to general procedure K (method b). Obtained as a yellow solid (11.106 g).

MS (ISN) 413 [(M–H)⁻.

Example K20

(RS)-3-Oxo-3-(3-{2-2-(tetrahydro-pyran-2-yloxy)-ethyl]-2H-pyrazol-3-yl}-phenyl) -propionic acid tert.-butyl ester The title compound was prepared from (RS)-3-{2-[2-(tetrahydro-pyran-2-yloxy)-ethyl]-2H-pyrazol-3-yl}-benzoic acid methyl ester [prepared by i.) reaction of 1-(3-bromo-phenyl)-3-dimethylamino-propenone [CAS-No. 163852-04-8] with 2-hydroxy-ethylhydrazine in EtOH at 23° C. for 2.5 days. ii.) The obtained mixture of pyrazoles (12.36 g, 35.19 mmol) was reacted with 3,4-dihydro-2H-pyran (4.79 mL, 52.8 mmol) and cat. amount p-TsOH.$H_2O$ in DCM (70 mL) at 23° C. for 20 h iii.) chromatographic separation of the obtained isomers. iv.) treatment of the clean isomer (7.35 g, 73.7 mmol) was treated with n-BuLi (13.08 mL, 20.9 mmol) in THF (42 mL) at –78° C. for 45 min, followed by a stream of $CO_2$. v.) The obtained (RS)-3-{2-[2-(tetrahydro -pyran-2-yloxy)-ethyl]-2H-pyrazol-3-yl}-benzoic acid was reacted (4.56 g, 14.1 mmol) was reacted with $KHCO_3$ (2.89 g, 28.8 mmol) and MeI (0.99 mL, 15.9 mmol) in DMF (29 mL) at 23° C. for 2 h.] (2.96 g, 8.96 mmol) by treatment with lithium tert.-butyl acetate according to general procedure K (method b). Obtained as a yellow oil (3.00 g).

S (ISP) 415 [(M+H)⁺].

Example K21

(RS)-3-Oxo-3-(3-{5-[2-(tetrahydro-pyran-2-yloxy)-ethyl]- [1,2,3 triazol-1-yl}-phenyl)-propionic acid tert.-butyl ester The title compound was prepared from (RS)-3-{5-[2-(tetrahydro-pyran-2-yloxy)-ethyl]-[1,2,3]triazol-1-yl}-benzoic acid methyl ester [prepared by the following sequence: i.) methyl 3-azidobenzoate [CAS-No. 93066-93-4] and (RS)-tert.-butyl-dimethyl-[4-(tetrahydro-pyran-2-yloxy)-but-1-ynyl]-silane [CAS-No. 198411-20-0) were heated to 60° C. for 10 days; ii.) The obtained material was stirred in TBAF (1M in THF) at 70° C. for 6 days and subsequently refluxed in 1N HCl for 2 h; iii.) The obtained 3-[5-(2-hydroxy -ethyl)-[1,2,3]triazol-1-yl]-benzoic acid was stirred in MeOH and conc. $H_2SO_4$ at 23° C. for 11 days. iv.) The obtained 3-[5-(2-hydroxy-ethyl)-[1,2,3]triazol-1-yl]-benzoic acid methyl ester was reacted with 3,4-dihydro-2H-pyran and cat. amount p-TsOH.$H_2O$ in DCM at 23° C. for 20 h.] by treatment with lithium tert.-butyl acetate according to general procedure K (method b). Obtained as a yellow oil (6.748 g).

MS (ISP) 416 [(M+H)⁺].

Example K22

(RS)-3-Oxo-3-{3- [5-(tetrahydro-pyran-2-yloxymethyl)-pyrazol-1-yl]-phenyl}-propionic acid ethyl ester The title compound was prepared from (RS)-3-[5-(tetrahydro-pyran-2-yloxymethyl)-pyrazol-1-yl]-benzoic acid [prepared by the following sequence: i.) A mixture of 3-hydrazino-benzoic acid [CAS-No. 38235-71-1], 4-dimethylamino-2-oxo-but-3-enoic acid ethyl ester [CAS-No. 67751-14-8] in acetic acid was refluxed for 15.5 h. ii.) The obtained 2-(3-carboxy-phenyl)-2H -pyrazole-3-carboxylic acid ethyl ester was stirred DMF-di-tert.-butyl acetal in toluene at 80° C. for 45 h. iii.) The obtained 2-(3-tert.-butoxycarbonyl-phenyl) -2H-pyrazole-3-carboxylic acid ethyl ester was saponified with 3N NaOH in THF at 0–23° C. for 16 h. iv.) The obtained 2-(3-tert.-butoxy-carbonyl -phenyl)-2H-pyrazole-3-carboxylic acid was reduced with $BH_3.SMe_2$ in THF at 5 to 23° C. for 18 h. v.) The obtained 3-(5-hydroxymethyl-pyrazol-1-yl) -benzoic acid tert-butyl ester (3.188 g, 11.62 mmol) was stirred in formic acid (22 mL) at 50° C. for 5 h. vi.) The obtained crude acid was stirred in MeOH (50 mL) and $SOCl_2$ (1.54 mL, 21.25 mmol) at 23° C. for 6.5 h. vii.) The obtained 3-(5-hydroxymethyl-pyrazol-1-yl)-benzoic acid methyl ester (2.84 g, 12.2 mmol) was reacted with 3,4-dihydro-2H-pyran (1.66 mL, 18.3 mmol) and cat. amount p-TsOH.$H_2O$ in DCM (25 mL) at 23° C. for 3 days. viii.) The obtained (RS)-3-[5-(tetrahydro-pyran-2-yloxymethyl )-pyrazol-1-yl]-benzoic acid methyl ester (2.926 g, 9.25 mmol) was saponified with 6N NaOH (5 mL) in THF (20 mL) at 23° C. for 3 h.] (1.90 g, 6.3 mmol) by activation with $ClCO_2Et$ (0.63 mL, 6.6 mmol) and Et₃N (1 mL, 7.0 mmol) in THF (9 mL)/CH₃CN (7 mL) at 0° C. for 2 h, followed by reaction with mono-ethyl malonate potassium salt (2.15 g, 12.6 mmol), MgCl₂ (1.5 g, 15.8 mmol) and Et₃N (2.9 mL, 20.8 mmol) at 0–23° C. for 2 days according to general procedure K (method a). Obtained as a light yellow oil (1.124 g).

MS (ISP) 373.4 [(M+H)⁺].

Example K23

3-Oxo-3-(3-[1,2,3]triazol-1-yl-phenyl)-propionic acid tert.-butyl ester

The title compound was prepared from 3-[1,2,3]triazol-1-yl-benzoic acid [prepared by refluxing of methyl 3-azidobenzoate [CAS-No. 93066-93-4] in trimethylsilyl-acetylene, followed by saponification with aqueous NaOH in refluxing EtOH] (10.0 g, 52.86 mmol) by activation with ethyl chloroformate/Et₃N and reaction with mono tert.-butyl malonate potassium salt with Et₃N and MgCl₂ in CH₃CN according to general procedure K (method a). Obtained as an orange oil (11.55 g).

MS (ISP) 288 [(M+H)⁺].

Example K24

(RS)-3-Oxo-3-{3-[5-(tetrahydro-pyran-2-yloxymethyl)-[1,2,4]triazol-1-yl]-phenyl}-propionic acid tert.-butyl ester The title compound was prepared from (RS)-3-[5-(tetrahydro-pyran-2-yloxymethyl )-[1,2,4]triazol-1-yl]-benzoic acid methyl ester [prepared by the following sequence: i.) methyl 3-(1H-1,2,4-triazol-1-yl)-benzoate, [CAS-No. 167626-27-9] (39.4 g, 194 mmol) was heated in 36% formaldehyde-water (250 ml) in an autoclave for 41 h at 150° C. Cristallisation from water and ethyl acetate/hexane (1:1) yielded a light brown solid (24.3 g, 54%) mp 164° C.; ii.) The obtained material (24.3 g, 104 mmol) was reacted with 3,4-dihydro-2H-pyran (29.3 mL, 320 mmol) and cat. amount p-TsOH.H₂O in dichloromethane (360 mL)/THF (300 ml) at 23° C. for 20 h. Purification by column chromatography on silica gel (toluene/ethyl acetate 1:1) gave a light brown oil.] (16.6 g, 52.3 mmol) by treatment with lithium tert.-butyl acetate according to general procedure K (method b). Obtained as a light yellow oil (14.3 g, 68%).

MS (ISP) 400.4 [(M−H)⁻].

Example K25

3-Oxo-3-(3-[1,2,4]triazol-1-yl-phenyl)-propionic acid tert-butyl ester

The title compound was prepared from methyl 3-[1,2,4]triazol-1-yl-benzoate [CAS-No. 167626-27-9] by treatment with lithium tert.-butyl acetate according to general procedure K (method b). Obtained as an orange liquid (2.41 g).

MS (EI) 287 (M⁺).

Example K26

3-(3-Imidazol-1-yl-phenyl)-3-oxo-propionic acid tert-butyl ester

The title compound was prepared from methyl 3-(1H-imidazol-1-yl)benzoate [prepared from 3-(1H-imidazol-1-yl)benzoic acid (J. Med. Chem. 1987, 30, 1342; CAS-No. [108035-47-8] by refluxing in conc. H₂SO₄/MeOH ] by treatment with lithium tert.-butyl acetate according to general procedure K (method b). Obtained as an orange-brown oil.

MS (ISP) 287 [(M+H)⁺].

Example K27

3-oxo-3-[3-[4-(tetrahydro-pyran-2-yloxymethyl)-thiazol-2-yl]-phenyl]-propionic acid tert-butyl ester 3-(4-Hydroxymethyl-thiazol-2-yl)-benzoic acid methyl ester A mixture of 3-thiocarbamoyl-benzoic acid methyl ester (7.8 g), 1,3-dichloro-2-propanone (8.4 g) and NaHCO₃ (8.4 g) in 1,4-dioxane (180 mL) was heated to 60° C. for 24 h. The reaction mixture was cooled to 20° C. and added to a stirred solution of NaOMe (5.4 g) in MeOH (200 mL). Stirring was continued for 0.5 h. The mixture was poured into ice-cold 2N HCl (200 mL) and the product was extracted with AcOEt. The organic layer was washed with brine, dried and evaporated in vacuum. The residue was crystallized from CH₂Cl₂/hexane to give 3-(4-hydroxymethyl-thiazol-2-yl)-benzoic acid methyl ester (7.5 g) as light-brown crystals, mp 115–117° C.

3-[4-(Tetrahydro-pyran-2-yloxymethyl)-thiazol-2-yl]-benzoic acid methyl ester

A mixture of the material prepared in a) (7.5 g), dihydropyrane (4.1 mL) and p-toluenesulfonic acid hydrate (0.19 g) in AcOEt (50 mL) was stirred at 20° C. for 1 h. The solution was diluted with AcOEt, washed with 5% NaHCO₃ solution and with brine, dried over Na₂SO₄ and evaporated in vacuo. The residual oil was purified by chromatography on silica gel using AcOEt/hexane (1:2) as eluent to give 3-[4-(tetrahydro-pyran-2-yloxymethyl)-thiazol-2-yl]-benzoic acid methyl ester (9.6 g) as a pale-yellow oil.

3-Oxo-3-[3-[4-(tetrahydro-pyran-2-yloxymethyl)-thiazol-2-yl]-phenyl]-propionic acid tert-butyl ester A sample of the material prepared in b) (3.3 g) was treated with lithium tert.-butyl acetate according to the general procedure K (method b) to give 3-oxo-3-[3-[4-(tetrahydro-pyran-2-yloxymethyl)-thiazol-2-yl]-phenyl]-propionic acid tert-butyl ester (3.25 g) as a pale-yellow oil, MS (ISP) 418.2 [(M+H)⁺].

Example K28

3-Oxo-3-[3-(2-bromo-1,1-dimethoxy-ethyl)-phenyl]-propionic acid tert-butyl ester 3-(2-Bromo-1,1-dimethoxy-ethyl)-benzoic acid methyl ester A mixture of 3-(2-bromo-acetyl)-benzoic acid [CAS-No 62423-73-8](2.43 g), 4-toluenesulfonic acid hydrate (0.38 g) and trimethyl orthoformiate (5.5 ml) in MeOH (40 mL) was heated at reflux for 20 h. The cooled solution was diluted with AcOEt (0.15 mL), washed with 5% NaHCO₃ solution and with brine, dried and evaporated in vacuum to give 3-(2-bromo-1,1-dimethoxy-ethyl)-benzoic acid methyl ester (3.0 g) as a pale-yellow oil.

3-Oxo-3-[3-(2-bromo-1,1-dimethoxy-ethyl)-phenyl]-propionic acid tert-butyl ester 3-(2-Bromo-1,1-dimethoxy-ethyl)-benzoic acid methyl ester (3.9 g) was treated with lithium tert.-butyl acetate according to the general procedure K (method b) to give 3-oxo-3-[3-(2-bromo-1,1-dimethoxy-ethyl)-phenyl]-propionic acid tert-butyl ester (2.8 g) as a yellow oil.

Example K29

3-Oxo-3-[3-(2-methyl-oxazol-4-yl)-phenyl]-propionic acid tert-butyl ester 3-(2-Methyl-oxazol-4-yl)-benzoic acid A mixture of 3-(2-bromo-acetyl)-benzoic acid (2.43 g) and acetamide (1.77 g) was heated with stirring to 130° C. for 40 min. The mixture was cooled and diluted with $H_2O$ (30 mL) and the precipitate formed was collected by filtration to give 3-(2-methyl-oxazol-4-yl)-benzoic acid (1.51 g) as brown solid.

3-(2-Methyl-oxazol-4-yl)-benzoic acid methyl ester

A solution of 3-(2-methyl-oxazol-4-yl)-benzoic acid (1.42 g) in a mixture of MeOH (30 mL) and 4NHCl/$Et_2O$ (6 mL) was heated to 40° C. for 4 h. The solution was evaporated in vacuum and the residual oil was stirred with $H_2O$ (30 mL), the pH of the mixture being set to about 6 by the addition of sat. $NaHCO_3$ solution. The precipitate was isolated by filtration to give 3-(2-methyl-oxazol-4-yl)-benzoic acid methyl ester (1.18 g) as light-brown solid,

MS (ISP) 218.2 [(M+H)$^+$].

3-Oxo-3-[3-(2-methyl-oxazol-4-yl)-phenyl]-propionic acid tert-butyl ester 3-(2-Methyl-oxazol-4-yl)-benzoic acid methyl ester (1.02 g) was treated with lithium tert.-butyl acetate according to the general procedure K (method b) to give crude 3-oxo-3-(3-(2-methyl-oxazol-4-yl)-phenyl]-propionic acid tert-butyl ester (1.50 g) as a pale-yellow oil.

Example K30

3-Oxo-3-{3-[5-(tetrahydro-1pyran-2-yloxymethyl)-[1,3,4]thiadiazol-2-yl]-phenyl}-propionic acid tert-butyl ester 3-(N'-tert-butoxycarbonyl-hydrazinocarbothioyl)-benzoic acid methyl ester A mixture of 3-(N'-tert-butoxycarbonyl-hydrazinocarbonyl)-benzoic acid methyl ester (1.47 g) and Lawesson reagent (1.62 g) in toluene (30 mL) was heated to 70° C. for 1.5 h. The mixture was concentrated in vacuum and then subjected to chromato-graphy on silica gel using AcOEt/hexane (1:2) as eluent to give 3-(N'-tert-butoxy-carbonyl-hydrazinocarbothioyl)-benzoic acid methyl ester (1.31 g) as a yellow solid, MS (ISP) 328.3 [(M+NH$_4$)$^+$].

3-Hydrazinothiocarbonyl-benzoic acid methyl ester trifluoroacetate

A solution of 3-(N'-tert-butoxy-carbonyl-hydrazinocarbothioyl)-benzoic acid methyl ester (0.93 g) in TFA (9 mL)/anisole (2 mL) was stirred at 0° C. for 1 h. The solvents were evaporated in vacuum to give crude 3-hydrazinothiocarbonyl-benzoic acid methyl ester trifluoroacetate (0.98 g) as a crystallizing oil.

3-(5-Hydroxymethyl-[1,3,4]thiadiazol-2-yl)-benzoic acid methyl ester

A mixture of 3-hydrazinothiocarbonyl-benzoic acid methyl ester trifluoroacetate (0.49 g) and 2-chloro-acetimidic acid ethyl ester hydrochloride (0.47 g) in EtOH (6 mL) was heated to 80° C. for 2.5 h. The mixture was diluted with AcOEt and washed with 1N HCl and with brine. The organic layer was dried and evaporated. The residual oil (0.8 g) was dissolved in MeOH (5 mL), MeONa (0.08 g) was added and the solution was heated to 65° C. for 0.5 h. The mixture was diluted with AcOEt and washed with 1N HCl and with brine. The organic layer was dried and evaporated and the residue was crystallized from AcOEt/hexane to give 3-(5-hydroxymethyl-[1,3,4]thiadiazol-2-yl) -benzoic acid methyl ester (0.15 g) as a white solid, MS (ISP) 251.2 [(M+H)$^+$].

3-[5-(Tetrahydro-pyran-2-yloxymethyl)-[1,3,4 thiadiazol-2-yl]-benzoic acid methyl ester A mixture of 3-(5-hydroxymethyl-1,3,4]thiadiazol-2-yl)-benzoic acid methyl ester (7.8 g), dihydropyrane (5.6 mL) and p-toluenesulfonic acid hydrate (0.59 g) in AcOEt (80 mL) was stirred at 20° C. for 1 h. The solution was diluted with AcOEt, washed with 5% $NaHCO_3$ solution and with brine, dried and evaporated in vacuum. The residual oil was purified by chromatography on silica gel using AcOEt/hexane (1:2) as eluent to give 3-[5-(tetrahydro-pyran-2-yloxymethyl)-[1,3,4]thiadiazol-2-yl]-benzoic acid methyl ester (5.85 g) as a pale-yellow oil.

3-Oxo-3-{3-5-(tetrahydro-pyran-2-yloxymethyl)-[1,3,4]thiadiazol-2-yl]1-phenyl}-propionic acid tert-butyl ester 3-[5-(Tetrahydro-pyran-2-yloxymethyl)-[1,3,4] thiadiazol-2-yl]-benzoic acid methyl ester (5.85 g) was treated with lithium tert.-butyl acetate according to general procedure K (method b) to give crude 3-oxo-3-{3-[5-(tetrahydro-pyran-2-yloxymethyl)-[1,3,4]thiadiazol-2-yl]-phenyl}-propionic acid tert-butyl ester (8.9 g) as a pale-yellow oil.

Example K31

3-Oxo-3-(3-{5-[2-(tetrahydro-pyran-2-yloxy)-ethyl]-[1,3,4]thiadiazol-2-yl}-phenyl)-propionic acid tert-butyl ester 3-[5-(2-Hydroxy-ethyl)-[1,3,4]thiadiazol-2-yl]-benzoic acid methyl ester A mixture of 3-hydrazinothiocarbonyl-benzoic acid methyl ester trifluoroacetate (0.45 g) and 3-hydroxy-propionimidic acid ethyl ester hydrochloride (0.35 g) in pyridine (5 mL) was heated to 100° C. for 1.5 h. The mixture was diluted with AcOEt and washed with lN HCl and with brine. The organic layer was dried and evaporated and the residual oil was chromatography on silica gel using AcOEt/hexane (1:1) as eluent to give 3-[5-(2-hydroxy-ethyl)-[1,3, 4]thiadiazol-2-yl]-benzoic acid methyl ester (0.37 g) as a white solid, MS (ISP) 265.3 [(M+H)$^+$].

3-{5-[2-(Tetrahydro-pyran-2-yloxy)-ethyl]-[1,3,4] thiadiazol-2-yl}-benzoic acid methyl ester A mixture of 3-[5-(2-hydroxy-ethyl)-[1,3,4]thiadiazol-2-yl]-benzoic acid methyl ester (1.86 g), dihydropyrane (0.95 mL) and p-toluenesulfonic acid hydrate (0.13 g) in AcOEt (25 mL) was stirred at 20° C. for 1 h. The solution was diluted with AcOEt, washed with 5% $NaHCO_3$ solution and with brine, dried and evaporated in vacuum. The residual oil was purified by chromatography on silica gel using AcOEt/hexane (1:2) as eluent to give 3-{5-[2-(tetrahydro-pyran-2-yloxy)-ethyl]-[1,3,4]thiadiazol-2-yl]-benzoic acid methyl ester (1.60 g) as a pale-yellow oil.

3-Oxo-3-(3-{5-[2-(tetrahydro-pyran-2-yloxy)-ethyl]-[1,3,4thiadiazol-2-yl}-phenyl)-propionic acid tert-butyl ester 3-(5-[2-(Tetrahydro-pyran-2-yloxy)-ethyl]-[1,3,4]thiadiazol-2-yl}-benzoic acid methyl ester (1.60 g) was treated with lithium tert.-butyl acetate according to general procedure K (method b) to give 3-oxo-3-(3-{5-[2-(tetrahydro-pyran-2-yloxy)-ethyl]-[1,3,4]thiadiazol-2-yl}-phenyl)-propionic acid tert-butyl ester (2.1 g) as a pale-yellow oil.

Example K32

3-Oxo-3-{3-[5-(tetrahydro-pyran-2-yloxymethyl)-[1,3,4]oxadiazol-2-yl]-phenyl}-propionic acid tert-butyl ester 3-(5-Hydroxymethyl-1 1,3,4]oxadiazol-2-yl)-benzoic acid methyl ester A mixture of 3-hydrazinocarbonyl-benzoic acid methyl (0.97 g) and 2-chloro-acetimidic acid ethyl ester hydrochloride (0.95 g) in EtOH (20 mL) was heated to 80° C. for 1 h. The mixture was diluted with AcOEt and washed with 1N HCl and with brine. The organic layer was dried and evaporated and the residual oil (1.1 g) was dissolved in DMF (4 mL). Upon addition of AcOK (0.59 g) and KI (0.07 g), the mixture was stirred at 100° C. for 0.5 h. After cooling to 20° C., MeOH (10 mL) and NaOMe (0.14 g) were added and stirring was continued for 0.5 h at 65° C. The mixture was diluted with AcOEt and washed with 1N HCl and with brine. The organic layer was dried and evaporated and the residue was crystallized from AcOEt/hexane to give 3-(5-hydroxymethyl-[1,3,4]oxadiazol-2-yl)-benzoic acid methyl ester (0.72 g) as a white solid, MS (ISP) 235.3 [(M+H)⁺].

3-[5-(Tetrahydro-pyran-2-yloxymethyl)-[1,3,4]thiadiazol-2-yl]-benzoic acid methyl ester A mixture of 3-(5-hydroxymethyl-[1,3,4]oxadiazol-2-yl)-benzoic acid methyl ester (9.8 g), dihydropyrane (7.7 mL) and p-toluenesulfonic acid hydrate (0.80 g) in AcOEt (100 mL) was stirred at 20° C. for 1 h. The solution was diluted with AcOEt, washed with 5% NaHCO3 solution and with brine, dried and evaporated. The residual oil was purified by chromatography on silica gel using AcOEt/hexane (1:2) as eluent to give 3-[5-(tetrahydro-pyran-2-yloxymethyl)-[1,3,4]thiadiazol-2-yl]-benzoic acid methyl ester (12.6 g) as a pale-yellow oil.

3-Oxo-3-{3-[5-(tetrahydro-pyran-2-yloxymethyl)-[1,3,4]oxadiazol-2-yl]-phenyl}-propionic acid tert-butyl ester 3-[5-(tetrahydro-pyran-2-yloxymethyl )-[1,3,4]thiadiazol-2-yl]-benzoic acid methyl ester (12.6 g) was treated with lithium tert.-butyl acetate according to general procedure K (method b) to give crude 3-oxo-3-{3-[5-(tetrahydro-pyran-2-yloxymethyl)-[1,3,4]oxadiazol-2-yl]-phenyl}-propionic acid tert-butyl ester (17.0 g) as a pale-yellow oil.

Example K33

3-Oxo-3-(3-{5-[2-(tetrahydro-pyran-2-yloxy)-ethyl]-[1,3,4]oxadiazol-2-yl}-phenyl)-propionic acid tert-butyl ester 3-[5-(2-Hydroxy-ethyl)-[1,3,4]oxadiazol-2-yl]-benzoic acid methyl ester A mixture of crude 3-hydrazinocarbonyl-benzoic acid methyl (2.90 g) and 3-hydroxy-propionimidic acid ethyl ester hydrochloride (2.76 g) in pyridine (10 mL) was heated to 100° C. for 2 h. The mixture was diluted with AcOEt and washed with 1N HCl and with brine. The organic layer was dried and evaporated and the residual oil was crystallized from Et₂O to give 3-[5-(2-hydroxy-ethyl)-[1,3,4]oxadiazol-2-yl]-benzoic acid methyl ester (2.5 g) as a white solid, MS (ISP) 249.1 [(M+H)⁺].

3-{5-[2-(Tetrahydro-pyran-2-yloxy)-ethyl]-[1,3,4]thiadiazol-2-yl}-benzoic acid methyl ester A mixture of 3-[5-(2-hydroxy-ethyl)-[1,3,4]oxadiazol-2-yl]-benzoic acid methyl ester (7.45 g), dihydropyrane (4.1 mL) and p-toluenesulfonic acid hydrate (0.57 g) in AcOEt (80 mL) was stirred at 20° C. for 2 h. The solution was diluted with AcOEt, washed with 5% NaHCO₃ solution and with brine, dried and evaporated in vacuum. The residual oil was purified by chromatography on silica gel using AcOEt/hexane (1:2) as eluent to give 3-{5-[2-(tetrahydro-pyran-2-yloxy)-ethyl]-[1,3,4]thiadiazol-2-yl}-benzoic acid methyl ester (8.2 g) as a pale-yellow oil.

3-Oxo-3-(3-{5-[2-(tetrahydro-pyran-2-yloxy)-ethyl]-[1,3,4]oxadiazol-2-yl}-phenyl)-propionic acid tert-butyl ester 3-{5-[2-(Tetrahydro-pyran-2-yloxy)-ethyl]-[1,3,4]thiadiazol-2-yl}-benzoic acid methyl ester (8.2 g) was treated with lithium tert.-butyl acetate according to the general procedure K (method b) to give crude 3-oxo-3-(3-{5-[2-(tetrahydro-pyran-2-yloxy)-ethyl]-[1,3,4]oxadiazol-2-yl}-phenyl)-propionic acid tert-butyl ester (11.6 g) as a pale-yellow oil.

Example K34

3-(3-Oxazol-4-yl-phenyl)-3-oxo-propionic acid tert-butyl ester

3-Oxazol-4-yl-benzoic acid methyl ester

A mixture of 3-(2-bromo-acetyl)-benzoic acid (1.94 g) and formamide (1.08 g) was heated with stirring to 130° C. for 3 h. The mixture was partitioned between AcOEt and brine, the organic layer was dried and evaporated and the residual oil was dissolved in a mixture of MeOH (30 mL) and 4NHCl/Et₂O (8 mL). After being kept at 20° C. for 18 h, the solution was concentrated in vacuum, diluted with AcOEt, washed with sat. NaHCO₃ solution and brine, dried and evaporated. The residue was chromatographed on silica gel using AcOEt/hexane (1:3) as eluent to give 3-oxazol-4-yl-benzoic acid methyl ester (0.85 g) as off-white solid, MS (ISP) 204.1 [(M+H)⁺].

3-(3-Oxazol-4-yl-phenyl)-3-oxo-propionic acid tert-butyl ester

3-Oxazol-4-yl-benzoic acid methyl ester (0.85 g) was treated with lithium tert.-butyl acetate according to the general procedure K (method b) to give crude 3-(3-oxazol-4-yl-phenyl)-3-oxo-propionic acid tert-butyl ester (1.46 g) as a pale-yellow oil.

Example K35

3-Oxo-³-(3-thiazol-4-yl-phenyl)-propionic acid tert-butyl ester

3-Thiazol-4-yl-benzoic acid methyl ester

A solution of 3-(2-bromo-acetyl)-benzoic acid (1.22 g) and thioformamide (0.46 g) in EtOH (5 mL) was heated to 80° C. for 1 h. The mixture was partitioned between AcOEt and brine and the organic layer was dried and evaporated. The residual oil was dissolved in a mixture of MeOH (20 mL) and 4NHCl/Et2O (5 mL). After being kept at 20° C. for 18 h, the solution was concentrated in vacuum, diluted with AcOEt, washed with sat. NaHCO$_3$ solution and brine, dried and evaporated. The residue was chromatographed on silica gel using AcOEt/hexane (1:3) as eluent to give 3-thiazol-4-yl-benzoic acid methyl ester (0.98 g) as off-white solid, MS (ISP) 220.2 [(M+H)$^+$].

3-Oxo-3-(3-thiazol-4-yl-phenyl)-propionic acid tert-butyl ester

3-Thiazol-4-yl-benzoic acid methyl ester (0.91 g) was treated with lithium tert.-butyl acetate according to the general procedure K (method b) to give crude 3-oxo-3-(3-thiazol-4-yl-phenyl)-propionic acid tert-butyl ester (1.54 g) as a pale-yellow oil.

Example K36

3-[3-(5-Methyl-oxazol-4-yl)-phenyl]-3-oxo-propionic acid tert-butyl ester 3-tert-Butoxycarbonylacetyl-benzoic acid methyl ester Dimethyl isophthalate (67.9 g) was treated with lithium tert.-butyl acetate according to general procedure K (method b) to give crude 3-tert-butoxycarbonylacetyl-benzoic acid methyl ester (74.5 g) as a pale-yellow oil.

3-Propionyl-benzoic acid methyl ester

To a stirred solution of 3-tert-butoxycarbonylacetyl-benzoic acid methyl ester (11.1 g) and MeI (2.2 mL) in DMF (40 mL) was added portionwise at 0° C. NaH (55% dispersion in mineral oil, 1.4 g). Stirring was continued at 0° C. for 15 min and at 20° C. for 30 min. The mixture was partitioned between AcOEt and brine, the pH being set to 7 by the addition of 3N HCl. The organic layer was dried and evaporated. The residue was stirred in a mixture of CH$_2$Cl$_2$ (30 mL) and TFA (30 mL) for 40 min at 20° C. After the evaporation of the solvents, the solution of the residue in AcOEt was extracted with ice-cold sat. Na$_2$CO$_3$ solution and the aqueous extracts were immediately acidified with 3N HCl and extracted with AcOEt. The solvent of this extract was evaporated and the residue heated in a mixture of toluene (40 mL) and 3N HCl (3 mL) to 100° C. for 1 h. The cooled mixture was diluted with AcOEt, washed with sat. NaHCO$_3$ and brine, dried and evaporated to give 3-propionyl-benzoic acid methyl ester (3.87 g) as white solid, MS (ISP) 193.2 [(M+H)$^+$].

rac-3-(2-Bromo-propionyl)-benzoic acid methyl ester

A mixture of 3-propionyl-benzoic acid methyl ester (3.6 g) and CuBr$_2$ (7.45 g) in AcOEt (45 mL) was heated at reflux for 2 h. Unsoluble material was filtered off from the cooled mixture and the clear solution was washed with brine, dried and evaporated to give crude rac-3-(2-bromo-propionyl)-benzoic acid methyl ester (5.0 g) as pale-yellow oil.

3-(5-Methyl-oxazol-4-yl)-benzoic acid methyl ester rac-3-(2-Bromo-propionyl)-benzoic acid methyl ester (5.42 g) and formamide (3.6 ml) were heated together to 130° C. for 5 h. The mixture was partitioned between AcOEt and brine, the organic layer was dried and evaporated and the residual oil was chromatographed on silica gel using AcOEt/hexane (1:4) as eluent to give 3-(5-methyl-oxazol-4-yl)-benzoic acid methyl ester (2.52 g) as white solid.

3-[3-(5-Methyl-oxazol-4-yl)-phenyl]-3-oxo-propionic acid tert-butyl ester 3-(5-methyl-oxazol-4-yl)-benzoic acid methyl ester (0.87 g) was treated with lithium tert.-butyl acetate according to the general procedure K (method b) to give crude 3-[3-(5-methyl-oxazol-4-yl)-phenyl]-3-oxo-propionic acid tert-butyl ester (1.46 g) as a pale-yellow oil.

Example K37

3-[3-(2-Methyl-5-propyl-oxazol-4-yl)-phenyl]-3-oxo-propionic acid tert-butyl ester 3-Pent-4-enoyl-benzoic acid methyl ester To a stirred solution of 3-tert-butoxycarbonylacetyl-benzoic acid methyl ester (11.1 g) and allyl bromide (3.0 mL) in DMF (40 mL) was added portionwise at 0° C. NaH (55% dispersion in mineral oil, 1.44 g). Stirring was continued at 0° C. for 20 min and at 20° C. for 30 min. The mixture was partitioned between AcOEt and brine, the pH being set to 7 by the addition of 3N HCl. The organic layer was dried and evaporated. The residual oil was stirred in a mixture of CH$_2$Cl$_2$ (30 mL) and TFA (30 mL) for 40 min at 20° C. The solvents were evaporated. The solution of the residue in AcOEt was extracted with ice-cold sat. Na$_2$CO$_3$ solution and the aqueous extracts were immediately acidified with 3N HCl and extracted with AcOEt. The solvent of this extract was evaporated and the residue heated in a mixture of toluene (40 mL) and 3N HCl (2 mL) to 100° C. for 1 h. The cooled mixture was diluted with AcOEt, washed with sat. NaHCO$_3$ and brine, dried and evaporated to give 3-pent-4-enoyl-benzoic acid methyl ester (5.11 g) as a pale-yellow oil, MS (ISP) 236.2 [(M+NH4)$^+$].

rac-3-(2-Bromo-pentanoyl)-benzoic acid methyl ester

A sample of 3-pent-4-enoyl-benzoic acid methyl ester (3.93 g) was hydrogenated in AcOEt (50 mL) in the presence of 5% Pd-C (190 mg) for 30 min at 20° C. The catalyst was filtered off, CuBr$_2$ (4.44 g) was added to the solution and the mixture was heated at reflux for 1 h. Unsoluble material was filtered off from the cooled mixture and the clear solution was washed with 1N HCl and brine, dried and evaporated to give crude rac-3-(2-bromo-pentanoyl)-benzoic acid methyl ester (3.6 g) as pale-yellow oil.

3-(2-Methyl-5-propyl-oxazol-4-yl)-benzoic acid methyl ester

A sample of rac-3-(2-bromo-pentanoyl)-benzoic acid methyl ester (1.50 g) and acetamide (0.89 g) were heated together to 130° C. for 15 h. The mixture was partitioned between AcOEt and brine, the organic layer was dried and evaporated and the residual oil was chromatographed on silica gel using AcOEt/hexane (1:3) as eluent to give 3-(2-methyl-5-propyl-oxazol-4-yl)-benzoic acid methyl ester (0.47 g) as a light-yellow oil.

3-[3-(2-Methyl-5-propyl-oxazol-4-yl)-phenyl]-3-oxo-propionic acid tert-butyl ester 3-(2-Methyl-5-propyl-oxazol-4-yl)-benzoic acid methyl ester (0.47 g) was treated with lithium tert.-butyl acetate according to the general procedure K (method b) to give crude 3-[3-(2-methyl-5-propyl-oxazol-4-yl)-phenyl]-3-oxo-propionic acid tert-butyl ester (0.58 g) as a light-brown oil.

Example K38

3-[3-(5-Methyl-thiazol-4-yl)-phenyl]-3-oxo-propionic acid tert-butyl ester 3-(5-Methyl-thiazol-4-yl)-benzoic acid methyl ester A solution of crude rac-3-(2-bromo-propionyl)-benzoic acid methyl ester (2.71 g) and thioformamide (1.83 g) in EtOH (20 ml) was heated at reflux for 1 h. The mixture was partitioned between AcOEt and brine, the organic layer was dried and evaporated and the residual oil was chromatographed on silica gel using AcOEt/hexane (1:4) as eluent to give 3-(5-methyl-thiazol-4-yl)-benzoic acid methyl ester (2.41 g) as white solid.

3-[3-(5-Methyl-thiazol-4-yl)-phenyl]-3-oxo-propionic acid tert-butyl ester

A sample of 3-(5-methyl-thiazol-4-yl)-benzoic acid methyl ester (1.05 g) was treated with lithium tert.-butyl acetate according to the general procedure K (method b) to give crude 3-[3-(5-methyl-thiazol-4-yl)-phenyl]-3-oxo-propionic acid tert-butyl ester (1.9 g) as a pale-yellow oil.

Example K39

3-[3-(2,5-Dimethyl-thiazol-4-yl)-phenyl]-3-oxo-propionic acid tert-butyl ester 3-(2,5-Dimethyl-thiazol-4-yl)-benzoic acid methyl ester A mixture of rac-3-(2-bromo-propionyl)-benzoic acid methyl ester (6.78 g) and thioacetamide (5.63 g) was heated to 130° C. for 20 min. The mixture was partitioned between AcOEt and H$_2$O, the organic layer was dried and evaporated and the residual oil was chromatographed on silica gel using AcOEt/hexane (1:4) as eluent to give 3-(2,5-dimethyl-thiazol-4-yl)-benzoic acid methyl ester (4.97 g) as yellow oil.

3-[3-(2,5-Dimethyl-thiazol-4-yl)-phenyl]-3-oxo-propionic acid tert-butyl ester

A sample of 3-(2,5-dimethyl-thiazol-4-yl)-benzoic acid methyl ester (0.99 g) was treated with lithium tert.-butyl acetate according to the general procedure K (method b) to give 3-[3-(2,5-dimethyl-thiazol-4-yl)-phenyl]-3-oxo-propionic acid tert-butyl ester (1.12 g) as a pale-yellow oil.

Example K40

3-Oxo-3-[3-[5-methyl-4-(tetrahydro-pyran-2-yloxymethyl)-thiazol-4-yl]-phenyl]- propionic acid tert-butyl ester 3-(2-Hydroxymethyl-5-methyl-thiazol-4-yl)-benzoic acid methyl ester A solution of rac-3-(2-bromo-propionyl)-benzoic acid methyl ester (2.71 g) and 2-(tert.-butylcarbonyloxy) thioacetamide (2.1 g) in EtOH (20 mL) was heated at reflux for 6 h. The mixture was partitioned between AcOEt and brine, and the organic layer was dried and evaporated. A solution of the residual oil and NaOMe (0.54 g) in MeOH (20 mL) was stirred at 60° C. for 1 h. The solution was diluted with AcOEt, washed with 1N HCl and brine, dried and evaporated to give 3-(2-hydroxymethyl-5-methyl-thiazol-4-yl)-benzoic acid methyl ester (1.17 g) as white crystals, MS (ISP) 264.1 [(M+H)$^+$].

3-[5-Methyl-4-(tetrahydro-pyran-2-yloxymethyl)-thiazol-4-yl]-benzoic acid methyl ester A mixture of 3-(2-hydroxymethyl-5-methyl-thiazol-4-yl)-benzoic acid methyl ester (1.05 g), dihydropyrane (0.73 mL) and p-toluenesulfonic acid hydrate (0.07 g) in AcOEt (10 mL) was stirred at 20° C. for 1 h. The solution was diluted with AcOEt, washed with 5% NaHCO$_3$ solution and with brine, dried and evaporated. The residual oil was purified by chromatography on silica gel using AcOEt/hexane (1:3) as eluent to give 3-[5-methyl-4-(tetrahydro-pyran-2-yloxymethyl)-thiazol-4-yl]-benzoic acid methyl ester (1.45 g) as a pale-yellow oil.

3-Oxo-3-[3-[5-methyl-4-(tetrahydro-pyran-2-yloxymethyl)-thiazol-4-yl]-phenyl]-propionic acid tert-butyl ester 3-[5-Methyl-4-(tetrahydro-pyran-2-yloxymethyl)-thiazol-4-yl]-benzoic acid methyl ester (1.45 g) was treated with lithium tert.-butyl acetate according to the general procedure K (method b) to give crude 3-oxo-3-[3-[5-methyl-4-(tetrahydro-pyran-2-yloxymethyl)-thiazol-4-yl]-phenyl]-propionic acid tert-butyl ester (2.13 g) as a pale-yellow oil.

Example K41

3-Oxo-3-[3-[5-propyl-4-(tetrahydro-pyran-2-yloxymethyl)-thiazol-2-yl]-phenyl]-propionic acid tert-butyl ester 3-(2- Hydroxymethyl-5-methyl-thiazol-4-yl)-benzoic acid methyl ester A sample of rac-3-(2-bromo-pentanoyl)-benzoic acid methyl ester (0.60 g) and and 2-(tert.-butylcarbonyloxy) thioacetamide (0.36 g) in EtOH (4 mL) was heated at reflux for 5 h. The mixture was partitioned between AcOEt and 5% NaHCO$_3$ solution, the organic layer was washed with brine, dried and evaporated. A solution of the residual oil and of NaOMe (0.13 g) in MeOH (10 mL) was stirred at 60° C. for 30 min. The solution was diluted with AcOEt, washed with 1N HCl and brine, dried and evaporated to give 3-(2-hydroxymethyl-5-methyl-thiazol-4-yl)-benzoic acid methyl ester (0.44 g) as an oil.

3-[5-Propyl-4-(tetrahydro-pyran-2-yloxymethyl)-thiazol-2-yl]-benzoic acid methyl ester 3-(2-hydroxymethyl-5-methyl-thiazol-4-yl)-benzoic acid methyl ester (0.38 g), dihydropyrane (0.73 mL) and p-toluenesulfonic acid hydrate (0.07 g) in AcOEt (10 mL) was stirred at 20° C. for 1 h. The solution was diluted with AcOEt, washed with 5% NaHCO$_3$ solution and brine, dried and evaporated. The residual oil was purified by chromatography on silica gel using AcOEt/hexane (1:3) as eluent to give 3-[5-propyl-4-(tetrahydro-pyran-2-yloxymethyl)-thiazol-2-yl]-benzoic acid methyl ester (0.36 g) as a pale-yellow oil.

3-Oxo-3-[3-[5-propyl-4-(tetrahydro-pyran-2-yloxymethyl)-thiazol-2-yl]-phenyl]-propionic acid tert-butyl ester 3-[5-Propyl-4-(tetrahydro-pyran-2-yloxymethyl)-thiazol-2-yl]-benzoic acid methyl ester (0.34 g) was treated with lithium tert.-butyl acetate according to the general procedure K (method b) to give crude 3-oxo-3-[3-[5-propyl-4-(tetrahydro-pyran-2-yloxymethyl)-thiazol-2-yl]-phenyl]-propionic acid tert-butyl ester (0.42 g) as a pale-yellow oil.

Example K42

3-Oxo-3-[3-[2-methyl-5-(tetrahydro-pyran-2-yloxymethyl)-thiazol-4-yl]-phenyl]-propionic acid tert-butyl ester 3-(5-Bromomethyl-2-methyl-thiazol-4-yl)-benzoic acid methyl ester A mixture of 3-(2,5-dimethyl-thiazol-4-yl)-benzoic acid methyl ester (3.96 g), N-bromosuccinimid (3.13 g) and α,α'-bis(isobutyronitrile) (0.02 g) in CCl$_4$ (60 mL) was heated at reflux for 30 min. The cooled mixture was filtered and the solvent was evaporated to give crude 3-(5-bromomethyl-2-methyl-thiazol-4-yl)-benzoic acid methyl ester (6.2 g) as an oil.

3-(5-Hydroxymethyl-2-methyl-thiazol-4-yl)-benzoic acid methyl ester 3-(5-bromomethyl-2-methyl-thiazol-4-yl)-benzoic acid methyl ester was stirred in DMF (16 mL) together with KOAc (2.35 g) at 20° C. for 20 min. MeOH (32 mL) and naOMe (0.86 g) were added and stirring was continued at 50° C. for 30 min. The mixture was partitioned between AcOEt and brine and the organic layer was dried and evaporated. The residual oil was chromatographed on silica gel using AcOEt/hexane (1:1) as eluent to give 3-(5-hydroxymethyl-2-methyl-thiazol-4-yl)-benzoic acid methyl ester (2.93 g) as a white solid.

3-[2-Methyl-5-(tetrahydro-pyran-2-yloxymethyl)-thiazol-4-yl]-benzoic acid methyl ester 3-(5-Hydroxymethyl-2-methyl-thiazol-4-yl)-benzoic acid methyl ester (0.38 g), dihydropyrane (2.01 mL) and p-toluenesulfonic acid hydrate (0.21 g) in AcOEt (25 mL) was stirred at 20° C. for 1 h. The solution was diluted AcOEt, washed with 5% NaHCO$_3$ solution and with brine, dried and evaporated. The residual oil was purified by chromatography on silica gel using AcOEt/hexane (1:3) as eluent to give 3-[2-methyl-5-(tetrahydro-pyran-2-yloxymethyl)-thiazol-4-yl]-benzoic acid methyl ester (3.8 g) as a pale-yellow oil.

3-Oxo-3-[3-[2-methyl-5-(tetrahydro-pyran-2-yloxymethyl)-thiazol-4-yl]-phenyl]-propionic acid tert-butyl ester 3-[2-Methyl-5-(tetrahydro-pyran-2-yloxymethyl)-thiazol-4-yl]-benzoic acid methyl ester was treated with lithium tert.-butyl acetate according to the general procedure K (method b) to give crude 3-oxo-3-[3-[2-methyl-5-(tetrahydro-pyran-2-yloxymethyl)-thiazol-4-yl]-phenyl]-propionic acid tert-butyl ester (5.45 g) as a pale-yellow oil.

Example K43

3-Oxo-3-{[5-(tetrahydro-pyran-2-yloxymethyl)-thiazol-4-yl]-phenyl}-propionic acid tert-butyl ester 3-(5-Bromomethyl-thiazol-4-yl)-benzoic acid methyl ester A mixture of 3-(5-methyl-thiazol-4-yl)-benzoic acid methyl ester (2.40 g), N-bromosuccinimid (2.01 g) and α,α'-bis(isobutyronitrile) (0.02 g) in CCl$_4$ (40 mL) was heated at reflux for 30 min. The cooled mixture was filtered and the solvent was evaporated to give crude 3-(5-bromomethyl-thiazol-4-yl)-benzoic acid methyl ester (3.36 g) as an oil.

3-(5-Hydroxymethyl-thiazol-4-yl)-benzoic acid methyl ester 3-(5-Bromomethyl-thiazol-4-yl)-benzoic acid methyl ester was stirred in DMF (10 mL) together with KOAc (1.52 g) at 20° C. for 30 min. MeOH (20 mL) and NaOMe (0.84 g) were added and stirring was continued at 50° C. for 30 min. The mixture was partitioned between AcOEt and brine and the organic layer was dried and evaporated. The residual oil was chromatographed on silica gel using AcOEt/hexane (1:2) as eluent to give 3-(5-hydroxymethyl-thiazol-4-yl)-benzoic acid methyl ester (1.43 g) as a white solid.

3-[5-(Tetrahydro-pyran-2-yloxymethyl)-thiazol-4-yl]-benzoic acid methyl ester 3-(5-Hydroxymethyl-thiazol-4-yl)-benzoic acid methyl ester (1.25 g), dihydropyrane (0.84 mL) and p-toluenesulfonic acid hydrate (0.10 g) in AcOEt (12 mL) was stirred at 20° C. for 3 h. The solution was diluted AcOEt, washed with 5% NaHCO$_3$ solution and with brine, dried and evaporated. The residual oil was purified by chromatography on silica gel using AcOEt/hexane (1:3) as eluent to give 3-[5-(tetrahydro-pyran-2-yloxymethyl)-thiazol-4-yl]-benzoic acid methyl ester (1.60 g) as a pale-yellow oil.

3-Oxo-3-{[5-(tetrahydro-pyran-2-yloxymethyl)-thiazol-4-yl]-phenyl}-propionic acid tert-butyl ester 3-[5-(Tetrahydro-pyran-2-yloxymethyl)-thiazol-4-yl]-benzoic acid methyl ester was treated with lithium tert.-butyl acetate according to the general procedure K (method b) to give crude 3-oxo-3-{[5-(tetrahydro-pyran-2-yloxymethyl)-thiazol-4-yl]-phenyl}-propionic acid tert-butyl ester (2.3 g) as a pale-yellow oil.

Example K44

3-[3-(2-Isopropyl-3H-imidazol-4-yl)-phenyl]-3-oxo-propionic acid tert-butyl ester 3-Dihydroxyacetyl-benzoic acid methyl ester A mixture of 3-(2-bromo-acetyl)-benzoic acid (2.43 g), DMSO (17 mL) and 48% HBr (3.4 mL) was heated to 55° C. for 30 min. The mixture was partitioned between AcOEt and H$_2$O and the organic layer was washed with brine, dried and evaporated to give 3-dihydroxyacetyl-benzoic acid methyl ester (1.06 g) as a white solid.

3-(2-Isopropyl-3H-imidazol-4-yl)-benzoic acid methyl ester

A solution of 3-dihydroxyacetyl-benzoic acid methyl ester (0.36 g) and 2-methyl-propionaldehyde (0.24 mL) in 5% aqueous NH$_3$ (6 mL) was heated to 100° C. for 1 h. The mixture was evaporated in vacuum and the solution of the residue in a mixture of MeOH (10 mL) and 4NHCl/Et$_2$O (2 mL) was heated to 40° C. for 18 h. The solution was concentrated in vacuum, diluted with AcOEt, washed with sat. Na$_2$CO$_3$ solution and brine, dried and evaporated. The residue was chromatographed on silica gel using AcOEt as eluent to give 3-(2-isopropyl-3H-imidazol-4-yl)-benzoic acid methyl ester (0.37 g) as a pale-yellow oil.

3-[3-(2-Isopropyl-3H-imidazol-4-yl)-phenyl]-3-oxo-propionic acid tert-butyl ester 3-(2-Isopropyl-3H-imidazol-4-yl)-benzoic acid methyl ester was treated with lithium tert.-butyl acetate according to the general procedure K (method b) to give crude 3-[3-(2-isopropyl-3H-imidazol-4-yl)-phenyl]-3-oxo-propionic acid tert-butyl ester (0.25 g) as a pale-yellow oil.

The following examples relate to the preparation of the 6-aryl-2,2-dimethyl-[1,3]dioxin-4-ones (formula IV), which serve as building blocks in the synthesis of the target compounds (Synthetic Scheme H):

General Procedure L

Preparation of 6-aryl-2,2-dimethyl-[1,3]dioxin-4-ones

Method a)

The 6-aryl-2,2-dimethyl-[1,3]dioxin-4-ones were prepared from 3-aryl-3-oxo-propionic acids and catalytic amount of conc. $H_2SO_4$ or trifluoroacetic acid (TFA) in isopropenyl acetate at 23° C. according to *Chem. Pharm. Bull.* 1983, 31, 1896. The final products were purified by silica gel column chromatography with hexane/EtOAc.

Method b)

The 6-aryl-2,2-dimethyl-[1,3]dioxin-4-ones were prepared from the tert.-butyl 3-aryl-3-oxo-propionates by treatment with trifluoroacetic anhydride (TFAA) in a mixture of TFA and acetone at 23° C. according to *Tetrahedron Lett.* 1998, 39, 2253. The final products were if necessary purified by silica gel column chromatography with hexane/EtOAc.

Example L1

3-(2,2-Dimethyl-6-oxo-6H-[1,3]dioxin-4-yl)-benzonitrile

The 3-(3-cyano-phenyl)-3-oxo-propionic acid was prepared from 3-cyanobenzoyl chloride (828 mg, 5 mmol) and bis(trimethylsilyl)malonate (2.56 mL, 10 mmol) with n-BuLi (1.6M in hexane, 6.25 mL) in ether at −60° C. to 0° C. according to general procedure M (method c2). The crude material (1.04 g) was transformed into the title compound by stirring in isopropenyl acetate and TFA according to general procedure L (method a). Obtained as a light yellow solid (0.8 g).

MS (EI) 229 (M$^+$); mp 138° C. (dec.).

Example L2

4-(2,2-Dimethyl-6-oxo-6H-[1,3]dioxin-4-yl)-pyridine-2-carbonitrile

The title compound was prepared from 3-(2-cyano-pyridin-4-yl)-3-oxo-propionic acid tert.-butyl ester (Example M10) by stirring in TFA/acetone with TFAA according to general procedure L (method b). Obtained as a brown solid (3.30 g).

MS (EI) 230 (M$^+$); mp 132° C. (dec.).

Example L3

6-(3-Imidazol-1-yl-phenyl)-2,2-dimethyl-[1,3]dioxin-4-one

The 3-(3-imidazol-1-yl-phenyl)-3-oxo-propionic acid was prepared from 3-(1H-imidazol-1-yl)benzoyl chloride hydrochloride [prepared by treatment of 3-(1H-imidazol-1-yl)-benzoic acid (*J. Med. Chem.* 1987, 30, 1342; CAS-No. [108035-47-8] with $SOCl_2$) and bis(trimethylsilyl)malonate with $Et_3N$ and LiBr in $CH_3CN$ at 0° C. according to general procedure K (method c1). The crude material was transformed into the title compound by stirring in isopropenyl acetate and conc. $H_2SO_4$ according to general procedure L (method a). Obtained as an orange semisolid (617 mg).

MS (EI) 270 (M$^+$).

Example L4

2,2-Dimethyl-6-(3-[1,2,3]triazol-1-yl-phenyl)-[1,3]dioxin-4-one

The title compound was prepared from 3-oxo-3-(3-[1,2,3]triazol-1-yl -phenyl)-propionic acid tert.-butyl ester (Example K23) by stirring in TFA/acetone with TFAA according to general procedure L (method b). Obtained as a beige solid (7.80 g).

MS (EI) 271 (M$^+$); mp 144–147° C. (dec.).

General procedure M

Preparation of {2-[3-aryl-3-oxo-propionylamino]-phenyl}-carbamic acid tert.-butyl ester by reaction of (2-amino-phenyl)-carbamic acid tert.-butyl esters with ethyl or tert.-butyl 3-aryl-3-oxo-propionates or 6-aryl-2,2-dimethyl-[1,3]dioxin-4-ones A mixture of the (2-amino-phenyl)-carbamic acid tert.-butyl ester or (1.0–1.2 mmol) and (1.0–1.5 mmol) of the ethyl or tert.-butyl 3-aryl-3-oxo-propionate or 6-aryl-2,2-dimethyl-[1,3]dioxin-4-one was heated in toluene (4–8 mL) to 80° C. to 120° C. until tlc indicated complete consumption of the minor component. The solution was allowed to cool to 23° C., whereupon the product generally crystallized (in cases where crystallization failed to appear it was induced by addition of hexane or ether, alternatively the reaction mixture was directly subjected to silica gel column chromatography). The solid was filtered off, washed with ether or mixtures of ether/hexane and dried in vacuum to give the {2-[3-aryl-3-oxo-propionylamino]-phenyl}-carbamic acid tert.-butyl esters, which was used directly in the following step or—if necessary—was purified by recrystallization or by silica gel column chromatography.

Example M1

{4-Chloro-2-[3-(3-cyano-phenyl)-3-oxo-propionylamino]-5-dimethylamino-phenyl}-carbamic acid tert.-butyl ester The title compound was prepared from (2-amino-4-chloro-5-dimethylamino-phenyl)-carbamic acid tert.-butyl ester (Example J1) (0.5 mmol) and 3-(3-cyano-phenyl)-3-oxo-propionic acid ethyl ester [CAS-No. 62088-13-5; prepared from 3-cyanobenzoyl chloride according to general procedure K, method a] (0.55 mmol) according to the general procedure M. Obtained as a white solid (160 mg).

MS (ISP) 457 [(M+H)$^+$]; mp 159–163° C.

Example M2

{4-Chloro-5-dimethylamino-2-[3-oxo-3-(3-[1,2,3]triazol-1-yl-phenyl)-propionylamino]-phenyl}-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-oxo-3-(3-[1,2,3]triazol-1-yl-phenyl)-propionic acid ethyl ester (Example K1) (150 mg, 0.58 mmol) according to the general procedure M. Obtained as a beige solid (160 mg).

MS (ISP) 499 [(M+H)$^+$] and 501 [(M+2+H)$^+$]; mp 136–137° C.

Example M3

(RS)-[4-Chloro-5-dimethylamino-2-(3-oxo-3-{3-[5-(tetrahydro-pyran-2-yloxymethyl)-[1,2,3]triazol-1-yl]-phenyl}-propionylamino)-phenyl]-carbamic acid tert.-butyl ester The title compound was prepared from (2-amino-4-chloro-5-dimethylamino-phenyl)-carbamic acid tert.-butyl ester (Example J1) (143 mg, 0.5 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (250 mg, 0.62 mmol) according to the general procedure M. Obtained as a yellow oil (257 mg).

MS (ISP) 613 [(M+H)$^+$] and 615 [(M+2+H)$^+$].

Example M4

{2-[3-(3-Cyano-phenyl)-3-oxo-propionylamino]-5-dimethylamino-4-phenylethynyl-phenyl}-carbamic acid tert.-butyl ester The title compound was prepared from (2-amino-4-chloro-5-dimethylamino-phenyl)-carbamic acid tert.-butyl ester (Example J2) and 3-(2,2-dimethyl-6-oxo-6H-[1,3]dioxin-4-yl)-benzonitrile (Example L1) according to the general procedure M. Obtained as an orange solid (108 mg).

MS (ISP) 523 [(M+H)$^+$].

Example M5

{5-Dimethylamino-2-[3-oxo-3-(3-[1,2,3]triazol-1-yl-phenyl)-propionylamino]-4-phenylethynyl-phenyl}-carbamic acid tert.-butyl ester The title compound was prepared from (2-amino-4-chloro-5-dimethylamino-phenyl)-carbamic acid tert.-butyl ester (Example J2) and 3-oxo-3-(3-[1,2,3]triazol-1-yl-phenyl)-propionic acid ethyl ester (Example K1) according to the general procedure M. Obtained as an orange solid (148 mg).

MS (ISP) 565 [(M+H)$^+$].

Example M6

(4-Chloro-5-dimethylamino-2-{3-[3-(3-methyl-isoxazol-5-yl)-phenyl]-3-oxo-propionylamino}-phenyl)-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-[3-(3-methyl-isoxazol-5-yl)-phenyl]-3-oxo-propionic acid tert.-butyl ester (Example K4) (450 mg, 0.75 mmol) according to the general procedure M. Obtained as a white solid (136 mg).

S (ISP) 513 [(M+H)$^+$] and 515 [(M+2+H)$^+$]; mp 109–114° C.

Example M7

(RS)-[2-Dimethylamino-2',3'-difluoro-5-(3-oxo-3-{3-[5-(tetrahydro-pyran-2-yloxymethyl)-[1,2,3]triazol-1-yl]-phenyl}-propionylamino)-biphenyl-4-yl]-carbamic acid tert.-butyl ester The title compound was prepared from (5-amino-2-dimethylamino-2',3'-difluoro-biphenyl-4-yl)-carbamic acid tert.-butyl ester (Example J3) and (RS)-3-oxo-3-{3-[5-(tetrahydro-pyran-2-yloxymethyl)-[1,2,3]triazol-1-yl]-phenyl}-propionic acid tert-butyl ester (Example K5) according to the general procedure M. Obtained as a yellow solid (253 mg).

MS (ISP) 691 [(M+H)$^+$].

Example M8

{2-Dimethylamino-2',3'-difluoro-5-[3-oxo-3-(3-[1,2,3]triazol-1-yl-phenyl)-propionylamino]-biphenyl-4-yl}-carbamic acid tert.-butyl ester The title compound was prepared from (5-amino-2-dimethylamino-2',3'-difluoro-biphenyl-4-yl)-carbamic acid tert.-butyl ester (Example J3) and 3-oxo-3-(3-[1,2,3]triazol-1-yl-phenyl)-propionic acid ethyl ester (Example K1) according to the general procedure M. Obtained as a yellow solid (253 mg).

MS (ISP) 577 [(M+H)$^+$].

Example M9

{5-[3-(3-Cyano-phenyl)-3-oxo-propionylamino]-2-dimethylamino-2',3'-difluoro-biphenyl-4-yl}-carbamic acid tert.-butyl ester The title compound was prepared from (5-amino-2-dimethylamino-2',3'-difluoro-biphenyl-4-yl)-carbamic acid tert.-butyl ester (Example J3) 3-(2,2-dimethyl-6-oxo-6H-[1,3]dioxin-4-yl)-benzonitrile (Example L1) according to the general procedure M. Obtained as a yellow solid (145 mg).

MS (ISP) 535 [(M+H)$^+$].

Example M10

(4-Chloro-5-dimethylamino-2-{3-[2-(3-methyl-isoxazol-5-yl)-pyridin-4-yl]-3-oxo-propionylamino}-phenyl)-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-[2-(3-methyl-isoxazol-5-yl)-pyridin-4-yl]-3-oxo-propionic acid tert.-butyl ester (Example K6) (170 mg, 0.56 mmol) according to the general procedure M. Obtained as a brown solid (206 mg).

MS (ISP) 514 [(M+H)$^+$] and 516 [(M+2+H)$^+$]; mp 181–183° C.

Example M11

(4-Chloro-5-[(2-methoxy-ethyl)-methyl-amino]-2-{3-[3-(3-methyl-isoxazol-5-yl)-phenyl]-3-oxo-propionylamino}-phenyl)-carbamic acid tert.-butyl ester The title compound was prepared from {2-amino-4-chloro-5-[(2-methoxy-ethyl)-methyl-amino]-phenyl}-carbamic acid tert.-butyl ester (Example J4) (165 mg, 0.5 mmol) and 3-[3-(3-methyl-isoxazol-5-yl)-phenyl]-3-oxo-propionic acid tert.-butyl ester (Example K4) (165 mg, 0.55 mmol) according to the general procedure M. Obtained as an amorphous yellow substance (207 mg).

MS (ISP) 557 [(M+H)$^+$] and 559 [(M+2+H)$^+$].

Example M12

(4-Chloro-5-[(2-methoxy-ethyl)-methyl-amino]-2-{3-[2-(3-methyl-isoxazol-5-yl)-pyridin-4-yl]-3-oxo-propionylamino}-phenyl)-carbamic acid tert.-butyl ester The title compound was prepared from {2-amino-4-chloro-5-[(2-methoxy-ethyl)-methyl-amino]-phenyl}- carbamic acid tert.-butyl ester (Example J4) (165 mg, 0.5 mmol) and 3-[2-(3-methyl-isoxazol-5-yl)-pyridin-4-yl]-3-oxo-propionic acid tert.-butyl ester (Example K6) (151 mg, 0.5 mmol) according to the general procedure M. Obtained as a yellow solid (190 mg).

MS (ISP) 558 [(M+H)$^+$] and 560 [(M+2+H)$^+$]; mp 148° C.

Example M13

(RS)-[4-Chloro-5-[(2-methoxy-ethyl)-methyl-amino]-2-(3-oxo-3-{3-[5-(tetrahydro-pyran-2-yloxymethyl)-[1,2,3]triazol-1-yl]-phenyl}-propionylamino)-phenyl]-carbamic acid tert.-butyl ester The title compound was prepared from {2-amino-4-chloro-5-[(2-methoxy-ethyl)-methyl-amino]-phenyl}-carbamic acid tert.-butyl ester (Example J4) (165 mg, 0.5 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (200 mg, 0.5 mmol) according to the general procedure M. Obtained as an amorphous yellow substance (160 mg).

MS (ISP) 657 [(M+H)$^+$] and 659 [(M+2+H)$^+$].

Example M14

{4-Chloro-5-[(2-methoxy-ethyl)-methyl-amino]-2-[3-oxo-3-(3-[1,2,3]triazol-1-yl-phenyl)-propionylamino]-phenyl}-carbamic acid tert.-butyl ester The title compound was prepared from {2-amino-4-chloro-5-[(2-methoxy-ethyl)-methyl-amino]-phenyl}-carbamic acid tert.-butyl ester (Example J4) (165 mg, 0.5 mmol) and 3-oxo-3-(3-[1,2,3]triazol-1-yl-phenyl)-propionic acid ethyl ester (Example K1) (165 mg, 0.5 mmol) according to the general procedure M. Obtained as an amorphous yellow substance (167 mg).

MS (ISP) 543 [(M+H)$^+$] and 545 [(M+2+H)$^+$].

Example M15

{4-Chloro-2-[3-(2-cyano-pyridin-4-yl)-3-oxo-propionylamino]-5-dimethylamino-phenyl}-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-(2-cyano-pyridin-4-yl)-3-oxo-propionic acid tert.-butyl ester (Example K3) (123 mg, 0.5 mmol) according to the general procedure M. Obtained as a yellow solid (155 mg).

MS (ISP) 458 [(M+H)$^+$] and 460 [(M+2+H)$^+$]; mp 110° C.

Example M16

(4-Chloro-5-dimethylamino-2-{3-[3-(2-methyl-2H-pyrazol-3-yl)-phenyl]-3-oxo-propionylamino}-phenyl)-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-[3-(2-methyl-2H-pyrazol-3-yl)-phenyl]-3-oxo-propionic acid tert.-butyl ester (Example K7) (180 mg, 0.6 mmol) according to the general procedure M. Obtained as an amorphous yellow substance (160 mg).

MS (ISP) 512 [(M+H)$^+$] and 514 [(M+2+H)$^+$]).

Example M17

(RS)-[5-Dimethylamino-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) (160 mg, 0.5 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (201 mg, 0.5 mmol) according to the general procedure M. Obtained as an amorphous yellow substance (247 mg).

MS (ISP) 647 [(M+H)$^+$].

Example M18

(5-Dimethylamino-2-{3-[3-(3-methyl-isoxazol-5-yl)-phenyl]-3-oxo-propionylamino}-4-trifluoromethyl-phenyl)-carbamic acid tert.-butyl ester The title compound was prepared from (2-amino-5-dimethylamino-4-trifluoromethyl-phenyl)-carbamic acid tert.-butyl ester (Example J6) (160 mg, 0.5 mmol) and 3-[3-(3-methyl-isoxazol-5-yl)-phenyl]-3-oxo-propionic acid tert.-butyl ester (Example K4) (151 mg, 0.5 mmol) according to the general procedure M. Obtained as an amorphous yellow substance (94 mg).

S (ISP) 547 [(M+H)$^+$].

Example M19

(4-Chloro-5-dimethylamino-2-{3-[3-(5-dimethylaminomethyl-[1,2,3]triazol-1-yl)-phenyl]-3-oxo-propionylamino}-phenyl)-carbamic acid tert.-butyl ester The title compound was prepared from (2-amino-4-chloro-5-dimethylamino-phenyl)-carbamic acid tert.-butyl ester (Example J1) (143 mg, 0.5 mmol) and 3-[3-(5-dimethylaminomethyl-[1,2,3]triazol-1-yl)-phenyl]-3-oxo-propionic acid tert.-butyl ester (Example K8) (172 mg, 0.5 mmol) according to the general procedure M. Obtained as an amorphous yellow substance (176 mg).

MS (ISP) 556 [(M+H)$^+$] and 558 [(M+2+H)$^+$].

Example M20

(4-Chloro-5-dimethylamino-2-{3-[3-(3-methoxymethyl-isoxazol-5-yl)-phenyl]-3-oxo-propionylamino}-phenyl)-carbamic acid tert.-butyl ester The title compound was prepared from (2-amino-4-chloro-5-dimethylamino-phenyl)-carbamic acid tert.-butyl ester (Example J1) and 3-[3-(3-methoxymethyl-isoxazol-5-yl)-phenyl]-3-oxo-propionic acid tert.-butyl ester (Example K9) according to the general procedure M. Obtained as a yellow solid (205 mg).

MS (ISP) 543 [(M+H)$^+$] and 545 [(M+2+H)$^+$].

Example M21

{2-[3-(2-Cyano-pyridin-4-yl)-3-oxo-propionylamino]-5-dimethylamino-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) (319 mg, 1.0 mmol) and 3-(2-cyano-pyridin-4-yl)-3-oxo-propionic acid tert.-butyl ester (Example K3) (246 mg, 1.0 mmol) according to the general procedure M. Obtained as an amorphous yellow substance (297 mg).

MS (ISP) 492 [(M+H)$^+$].

Example M22

[2'-Fluoro-5-[3-(3-imidazol-1-yl-phenyl)-3-oxo-propionylamino]-2-(2,2,2-trifluoro-ethoxy)-biphenyl-4-yl]-carbamic acid tert.-butyl ester The title compound was prepared from [5-amino-2'-fluoro-2-(2,2,2-trifluoro-ethoxy)-biphenyl-4-yl]-carbamic acid tert.-butyl ester (Example J5) (200 mg, 0.5 mmol) and 6-(3-imidazol-1-yl-phenyl)-2,2-dimethyl-[1,3]dioxin-4-one (Example L3) (160 mg, 0.5 mmol) according to the general procedure M. Obtained as an amorphous brown substance (167 mg).

MS (ISP) 492 [(M+H)$^+$].

Example M23

[2'-Fluoro-5-{3-[3-(3-methyl-isoxazol-5-yl)-phenyl]-3-oxo-propionylamino}-2-(2,2,2-trifluoro-ethoxy)-biphenyl-4-yl]-carbamic acid tert.-butyl ester The title compound was prepared from [5-amino-2'-fluoro-2-(2,2,2-trifluoro-ethoxy)-biphenyl-4-yl]-carbamic acid tert.-butyl ester (Example J5) (200 mg, 0.5 mmol) and 3-[3-(3-methyl-isoxazol-5-yl)-phenyl]-3-oxo-propionic acid tert.-butyl ester (Example K4) (160 mg, 0.53 mmol) according to the general procedure M. Obtained as a white solid (40 mg).

MS (ISN) 626 [(M–H)$^-$]; mp 121–123° C.

Example M24

[2'-Fluoro-5-[3-oxo-3-(3-[1,2,3]triazol-1-yl-phenyl)-propionylamino]-2-(2,2,2-trifluoro-ethoxy)-biphenyl-4-yl]-carbamic acid tert.-butyl ester The title compound was prepared from [5-amino-2'-fluoro-2-(2,2,2-trifluoro-ethoxy)-biphenyl-4-yl]-carbamic acid tert.-butyl ester (Example J5) (200 mg, 0.5 mmol) and 3-oxo-3-(3-[1,2,3]triazol-1-yl-phenyl)-propionic acid ethyl ester (Example K1) (150 mg, 0.57 mmol) according to the general procedure M. Obtained as a light yellow solid (110 mg).

MS (ISP) 614 [(M+H)$^+$]; mp 54–56° C.

Example M25

(RS)-[2'-Fluoro-5-(3-oxo-3-{3-[5-(tetrahydro-pyran-2-yloxymethyl)-[1,2,3]triazol-1-yl]-phenyl}-propionylamino)-2-(2,2,2-trifluoro-ethoxy)-biphenyl-4-yl]-carbamic acid tert.-butyl ester The title compound was prepared from [5-amino-2'-fluoro-2-(2,2,2-trifluoro-ethoxy)-biphenyl-4-yl]-carbamic acid tert.-butyl ester (Example J5) (200 mg, 0.5 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (220 mg, 0.55 mmol) according to the general procedure M. Obtained as a yellow oil(100 mg).

Example M26

(RS)-[4-Chloro-5-(ethyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-chloro-5-(ethyl-methyl-amino)-phenyl]-carbamic acid tert-butyl ester (Example J7) (300 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a yellow foam (500 mg).

MS (ISP) 627.1 [(M+H)$^+$].

Example M27

(RS)-[4-Chloro-5-(methyl-propyl-amino)-2-(3-oxo-3-{3-[5-(tetrahydro-pyran-2-yloxymethyl)-[1,2,3]triazol-1-yl -phenyl}-propionylamino)-phenyl]-carbamic acid tert-butyl ester The title compound was prepared from [2-amino-4-chloro-5-(methyl-propyl-amino)-phenyl]-carbamic acid tert-butyl ester (Example J8) (310 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a yellow foam (410 mg).

MS (ISP) 641.3 [(M+H)$^+$].

Example M28

(RS)-[4-Chloro-5-(diethyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-chloro-5-(diethyl-amino)-phenyl]-carbamic acid tert-butyl ester (Example J9) (310 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a yellow foam (530 mg).

MS (ISP) 641.3 [(M+H)$^+$].

Example M29

(RS)-[4-Chloro-5-dimethylamino-2-(3-oxo-3-{3-[3-(tetrahydro-pyran-2-yloxymethyl)-isoxazol-5-yl]-phenyl -propionylamino)-phenyl}-carbamic acid tert.-butyl ester The title compound was prepared from (2-amino-4-chloro-5-dimethylamino-phenyl)-carbamic acid tert.-butyl ester (Example J1) (143 mg, 0.5 mmol) and (RS)-3-oxo-3-{3-[3-(tetrahydro-pyran-2-yloxymethyl)-isoxazol-5-yl]-phenyl}-propionic acid tert-butyl ester (Example K12) (201 mg, 0.5 mmol) according to the general procedure M. Obtained as a yellow foam (530 mg).

MS (ISP) 613.1 [(M+H)$^+$] and 615 [(M+2+H)$^+$].

Example M30

(RS)-[4-Chloro-2-(3-oxo-3-{3-[5-(tetrahydro-pyran-2-yloxymethyl)-[1,2,3]triazol-1-yl]-phenyl}-propionylamino)-5-pyrrolidin-1-yl-phenyl]-carbamic acid tert.-butyl ester The title compound was prepared from (2-amino-4-chloro-5-pyrrolidin-1-yl-phenyl)-carbamic acid tert.-butyl ester (Example J10) and (RS)-3-oxo-3-{3-[5-(tetrahydro-pyran-2-yloxymethyl)-[1,2,3]triazol-1-yl]-phenyl}-propionic acid tert.-butyl ester (Example K5) according to the general procedure M. Obtained as a yellow foam (228 mg).

MS (ISP) 639 [(M+H)$^+$] and 641 [(M+2+H)$^+$].

Example M31

(5-Dimethylamino-2-{3-[3-(2-methyl-2H-pyrazol-3-yl)-phenyl]-3-oxo-propionylamino}-4-trifluoromethyl-phenyl)-carbamic acid tert.-butyl ester The title compound was prepared from (2-amino-5-dimethylamino-4-trifluoromethyl-phenyl)-carbamic acid tert.-butyl ester (Example J6) (160 mg, 0.5 mmol) and 3-[3-(2-methyl-2H-pyrazol-3-yl)-phenyl]-3-oxo-propionic acid tert.-butyl ester (Example K7) (150 mg, 0.5 mmol) according to the general procedure M. Obtained as a yellow foam (90 mg).

MS (ISP) 546.2 [(M+H)$^+$].

Example M32

(RS)-[4-Chloro-5-dimethylamino-2-(3-{3-[3-methyl-4-(tetrahydro-pyran-2-yloxymethyl)-isoxazol-5-yl]-phenyl}-3-oxo-propionylamino)-phenyl]-carbamic acid tert.-butyl ester The title compound was prepared from (2-amino-4-chloro-5-dimethylamino-phenyl)-carbamic acid tert.-butyl ester (Example J1) and (RS)-3-{3-[3-methyl-4-(tetrahydro-pyran-2-yloxymethyl)-isoxazol-5-yl]-phenyl}-3-oxo-propionic acid tert.-butyl ester (Example K13) according to the general procedure M. Obtained as a light yellow solid (187 mg).

MS (ISN) 626 [(M−H)$^-$] and 628 [(M+2−H)$^-$].

Example M33

(RS)-[4-Chloro-5(cyclopropyl-methyl-amino)-2-(3-oxo-3-{3-[5-(tetrahydro-pyran-2-yloxymethyl)-[1,2,3]triazol-1-yl]-phenyl}propionylamino)-phenyl]-carbamic acid tert-butyl ester The title compound was prepared from [2-amino-4-chloro-5-(cyclopropyl-methyl-amino)-phenyl]-carbamic acid tert.-butyl ester (Example J11) (156 mg, 0.5 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (250 mg, 0.62 mmol) according to the general procedure M. Obtained as a yellow solid (215 mg).

MS (ISN) 637.1 [(M−H)$^-$] and 639 [(M+2−H)$^-$]; mp 47–49° C.

Example M34

(5-Dimethylamino-2-{3-[3-(5-dimethylaminomethyl-1,2,3]triazol-1-yl)-phenyl]-3-oxo-propionylamino}-4-trifluoromethyl-phenyl)-carbamic acid tert.-butyl ester The title compound was prepared from (2-amino-5-dimethylamino-4-trifluoromethyl-phenyl)-carbamic acid tert.-butyl ester (Example J6) (160 mg, 0.5 mmol) and 3-[3-(5-dimethylaminomethyl-[1,2,3]triazol-1-yl)-phenyl]-3-oxo-propionic acid tert.-butyl ester (Example K8) (172 mg, 0.5 mmol) according to the general procedure M. Obtained as an amorphous yellow substance (195 mg).

MS (ISN) 588 [(M−H)$^-$].

Example M35

(RS)-[4-Chloro-5-dimethylamino2-(3-{3-[2-methyl-5o(tetrahydro-pyran-2-yloxymethyl)-2H-pyrazol-3-yl]phenyl}-3-oxo-propionylamino)-phenyl]-carbamic acid tert.-butyl ester The title compound was prepared from (2-amino-4-chloro-5-dimethylamino-phenyl)-carbamic acid tert.-butyl ester (Example J1) (200 mg, 0.7 mmol) and (RS)-3-{3-[2-methyl-5-(tetrahydro-pyran-2-yloxymethyl)-2H-pyrazol-3-yl]-phenyl}-3-oxo-propionic acid tert.-butyl ester (Example K14) (290 mg, 0.7 mmol) according to the general procedure M. Obtained as an amorphous yellow substance (329 mg).

MS (ISN) 624.0 [(M−H)$^-$] and 626 [(M+2−H)$^-$].

Example M36

{2-[3-(2-Cyano-pyridin-4-yl)-3-oxo-propionylamino]-5-pyrrolidin-1-yl-4-trifluoromethyl-phenyl}-carbamic acid tert.-butyl ester The title compound was prepared from (2-amino-5-pyrrolidin-1-yl-4-trifluoromethyl-phenyl)-carbamic acid tert.-butyl ester (Example J12) (173 mg, 0.5 mmol) and 3-(2-cyano-pyridin-4-yl)-3-oxo-propionic acid tert.-butyl ester (Example K3) (150 mg, 0.61 mmol) according to the general procedure M. Obtained as a yellow solid (140 mg).

MS (ISP) 518 [(M+H)$^+$].

Example M37

(RS)-[2-(3-Oxo-3-{3-[5-(tetrahydro-pyran-2-yloxymethyl)-[1,2,3]triazol-1-yl]-phenyl}-propionylamino)-5-pyrrolidin-1-yl-4-trifluoromethyl-phenyl]-carbamic acid tert.-butyl ester The title compound was prepared from (2-amino-5-pyrrolidin-1-yl-4-trifluoromethyl-phenyl)-carbamic acid tert.-butyl ester (Example J12) (173 mg, 0.5 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (250 mg, 0.62 mmol) according to the general procedure M. Obtained as an orange foam (168 mg).

MS (ISP) 673 [(M+H)$^+$].

Example M38

(RS)-[5-Dimethylamino-4-fluoro-2-(3-oxo-3-{3-[5-(tetrahydro-pyran-2-yloxymethyl)-[1,2,3]triazol-1-yl]-phenyl}-propionylamino)-phenyl]-carbamic acid tert.-butyl ester The title compound was prepared from (2-amino-5-dimethylamino-4-fluoro-phenyl)-carbamic acid tert.-butyl ester (Example J13) (269 mg, 1.0 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (401 mg, 1.0 mmol) according to the general procedure M. Obtained as a yellow amorphous substance (417 mg).

MS (ISN) 595 [(M−H)$^-$].

Example M39

(5-Dimethylamino-2-{3-[3-(5-dimethylaminomethyl-[1,2,3]triazol-1-yl)-phenyl]-3-oxo-propionylamino}-4-fluoro-phenyl)-carbamic acid tert.-butyl ester The title compound was prepared from (2-amino-5-dimethylamino-4-fluoro-phenyl)-carbamic acid tert.-butyl ester (Example J13) (269 mg, 1.0 mmol) and 3-[3-(5-dimethylaminomethyl-[1,2,3]triazol-1-yl)-phenyl]-3-oxo-propionic acid tert.-butyl ester (Example K8) (344 mg, 1.0 mmol) according to the general procedure M. Obtained as a yellow amorphous substance (211 mg).

MS (ISN) 538 [(M−H)$^-$].

Example M40

(RS)-[5-Dimethylamino-4-fluoro-2-(3-oxo-3-{3-[3-(tetrahydro-pyran-2-yloxymethyl)-isoxazol-5-yl]-phenyl}-propionylamino)-phenyl]-carbamic acid tert.-butyl ester The title compound was prepared from (2-amino-5-dimethylamino-4-fluoro-phenyl)-carbamic acid tert.-butyl ester (Example J13) (269 mg, 1.0 mmol) and (RS)-3-oxo-3-{3-[3-(tetrahydro-pyran-2-yloxymethyl)-isoxazol-5-yl]-phenyl}-propionic acid tert.-butyl ester (Example K12) (401 mg, 1.0 mmol) according to the general procedure M. Obtained as a yellow amorphous substance (360 mg).

MS (ISN) 595 [(M−H)⁻].

Example M41

(RS)-[5-Dimethylamino-2-(3-oxo-3-{3-[3-(tetrahydro-pyran-2-yloxymethyl)-isoxazol-5-yl]-phenyl}-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) (565 mg, 1.77 mmol) and (RS)-3-oxo-3-{3-[3-(tetrahydro-pyran-2-yloxymethyl)-isoxazol-5-yl]-phenyl}-propionic acid tert.-butyl ester (Example K12) (710 mg, 1.77 mmol) according to the general procedure M. Obtained as a yellow amorphous substance (721 mg).

MS (ISN) 645 [(M−H)⁻].

Example M42

(RS)-[5-Dimethylamino-4-fluoro-2-(3-oxo-3-{3-[3-(tetrahydro-pyran-2-yloxymethyl)-isoxazol-5-yl]-phenyl}-propionylamino)-phenyl]-carbamic acid tert.-butyl ester The title compound was prepared from (2-amino-5-dimethylamino-4-fluoro-phenyl)-carbamic acid tert.-butyl ester (Example J13) (269 mg, 1.0 mmol) and 3-[3-(3-methyl-isoxazol-5-yl)-phenyl]-3-oxo-propionic acid tert.-butyl ester (Example K4) (301 mg, 1.0 mmol) according to the general procedure M. Obtained as a yellow amorphous substance (273 mg).

MS (ISP) 497 [(M+H)⁺].

Example M43

(RS)-[4-Chloro-5-dimethylamino-2-(3-oxo-3-{3-[5-(tetrahydro-pyran-2-yloxymethyl)-isoxazol-3-yl]-phenyl}-propionylamino)-phenyl]-carbamic acid tert.-butyl ester The title compound was prepared from (2-amino-4-chloro-5-dimethylamino-phenyl)-carbamic acid tert.-butyl ester (Example J1) and (RS)-3-oxo-3-{3-[5-(tetrahydro-pyran-2-yloxymethyl)-isoxazol-3-yl]-phenyl}-propionic acid tert.-butyl ester (Example K15) according to the general procedure M. Obtained as a yellow foam (232 mg).

MS (ISN) 611.1 [(M−H)⁻] and 613 [(M+2−H)⁻].

Example M44

(RS)-[4-Chloro-2-(3-oxo-3-{3-[5-(tetrahydro-pyran-2-yloxymethyl)-[1,2,3]triazol-1-yl]-phenyl}-propionylamino)-5-piperidin-1-yl-phenyl]-carbamic acid tert.-butyl ester The title compound was prepared from (2-amino-4-chloro-5-piperidin-1-yl-phenyl)-carbamic acid tert.-butyl ester (Example J14) and (RS)-3-oxo-3-{3-[5-(tetrahydro-pyran-2-yloxymethyl)-[1,2,3]triazol-1-yl]-phenyl}-propionic acid tert.-butyl ester (Example K5) according to the general procedure M. Obtained as a yellow foam (257 mg).

MS (ISP) 653.2 [(M+H)⁺] and 655 [(M+2+H)⁺].

Example M45

(RS)-[5-Dimethylamino-2-(3-oxo-3-{3-[5-(tetrahydro-pyran-2-yloxymethyl)-isoxazol-3-yl]-phenyl}-propionylamino)-4-trifluoromethyl-phenyl]-carbamic acid tert.-butyl ester The title compound was prepared from (2-amino-5-dimethylamino-4-trifluoro-methyl-phenyl)-carbamic acid tert.-butyl ester (Example J6) and (RS)-3-oxo-3-{3-[5-(tetrahydro-pyran-2-yloxymethyl)-isoxazol-3-yl]-phenyl}-propionic acid tert.-butyl ester (Example K15) according to the general procedure M. Obtained as a light yellow foam (224 mg).

MS (ISP) 647.2 [(M+H)⁺].

Example M46

{4-Chloro-5-dimethylamino-2-[3-oxo-3-(3-pyrazol-1-yl-phenyl)-propionylamino]-phenyl}-carbamic acid tert.-butyl ester The title compound was prepared from (2-amino-4-chloro-5-dimethylamino-phenyl)-carbamic acid tert.-butyl ester (Example J1) and 3-oxo-3-(3-pyrazol-1-yl-phenyl)-propionic acid tert.-butyl ester (Example K16) according to the general procedure M. Obtained as a light yellow solid (135 mg).

MS (ISP) 498 [(M+H)⁺] and 500 [(M+2+H)⁺]; mp 148–149° C.

Example M47

{2-[3-(2-Cyano-pyridin-4-yl)-3-oxo-propionylamino]-4-fluoro-5-pyrrolidin-1-yl-phenyl}-carbamic acid tert.-butyl ester The title compound was prepared from (2-amino-4-fluoro-5-pyrrolidin-1-yl-phenyl)-carbamic acid tert.-butyl ester (Example J15) and 3-(2-cyano-pyridin-4-yl)-3-oxo-propionic acid tert.-butyl ester (Example K3) according to the general procedure M. Obtained as a yellow solid (196 mg).

MS (ISP) 468 [(M+H)⁺]; mp 231° C. (dec.).

Example M48

(4-Fluoro-2-{3-[3-(3-methyl-isoxazol-5-yl)-phenyl]-3-oxo-propionylamino}-5-pyrrolidin-1-yl-phenyl)-carbamic acid tert.-butyl ester The title compound was prepared from (2-amino-4-fluoro-5-pyrrolidin-1-yl-phenyl)-carbamic acid tert.-butyl ester (Example J15) and 3-[3-(3-methyl-isoxazol-5-yl)-phenyl]-3-oxo-propionic acid tert.-butyl ester (Example K4) according to the general procedure M. Obtained as a light yellow solid (126 mg).

MS (ISP) 468 [(M+H)⁺]; mp 186° C.

Example M49

(RS)-[4-Fluoro-2-(3-oxo-3-{3-[5-(tetrahydro-pyran-2-yloxymethyl)-1,2,3]triazol-1-yl]-phenyl}-propionylamino)-5-pyrrolidin-1-yl-phenyl]-carbamic acid tert.-butyl ester The title compound was prepared from (2-amino-4-fluoro-5-pyrrolidin-1-yl-phenyl)-carbamic acid tert.-butyl ester (Example J15) and (RS)-3-oxo-3-{3-[5-(tetrahydro-pyran-2-yloxymethyl)-[1,2,3]triazol-1-yl]-phenyl}-propionic acid tert.-butyl ester (Example K5) according to the general procedure M. Obtained as an orange viscous oil (268 mg).

MS (ISP) 623 [(M+H)⁺].

Example M50

{5-Azetidin-1-yl-4-chloro-2-[3-(2-cyano-pyridin-4-yl)-3-oxo-propionylamino]-phenyl}-carbamic acid tert.-butyl ester The title compound was prepared from (2-amino-5-azetidin-1-yl-4-chloro-phenyl)-carbamic acid tert.-butyl ester (Example J16) and 3-(2-cyano-pyridin-4-yl)-3-oxo-propionic acid tert.-butyl ester (Example K3) according to the general procedure M. Obtained as a yellow solid (142 mg).

MS (ISP) 470 [(M+H)⁺] and 472 [(M+2+H)⁺]; mp 168° C. (dec.).

Example M51

(RS)-[2-(3-Oxo-3-{3-[5-(tetrahydro-pyran-2-yloxymethyl)-isoxazol-3-yl]-phenyl}-propionylamino)-5-pyrrolidin-1-yl-4-trifluoromethyl-phenyl]-carbamic acid tert.-butyl ester The title compound was prepared from (2-amino-5-pyrrolidin-1-yl-4-trifluoromethyl-phenyl)-carbamic acid tert.-butyl ester (Example J12) and (RS)-3-oxo-3-{3-[5-(tetrahydro-pyran-2-yloxymethyl)-isoxazol-3-yl]-phenyl}-propionic acid tert.-butyl ester (Example K15) according to the general procedure M. Obtained as a yellow foam (522 mg).

MS (ISN) 671.2 [(M−H)⁻].

Example M52

{5-Azetidin-1-yl-2-[3-(2-cyano-pyridin-4-yl)-3-oxo-propionylamino]-4-trifluoromethyl-phenyl}-carbamic acid tert.-butyl ester The title compound was prepared from (2-amino-5-azetidin-1-yl-4-trifluoromethyl-phenyl)-carbamic acid tert.-butyl ester (Example J17) and 3-(2-cyano-pyridin-4-yl)-3-oxo-propionic acid tert.-butyl ester (Example K3) according to the general procedure M. Obtained as a light yellow solid (131 mg).

MS (ISP) 470 [(M+H)⁺]; mp 166–167° C.

Example M53

(5-Azetidin-1-yl-2-{3-[3-(3-methyl-isoxazol-5-yl)-phenyl]-3-oxo-propionylamino}-4-trifluoromethyl-phenyl)-carbamic acid tert.-butyl ester The title compound was prepared from (2-amino-5-azetidin-1-yl-4-trifluoromethyl-phenyl)-carbamic acid tert.-butyl ester (Example J17) and 3-[3-(3-methyl-isoxazol-5-yl)-phenyl]-3-oxo-propionic acid tert.-butyl ester (Example K4) according to the general procedure M. Obtained as a light yellow foam (218 mg).

MS (ISN) 557.2 [(M−H)⁻]; mp 83–84° C.

Example M54

(RS)-[5-Azetidin-1-yl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester The title compound was prepared from (2-amino-5-azetidin-1-yl-4-trifluoromethyl-phenyl)-carbamic acid tert.-butyl ester (Example J17) and (RS)-3-oxo-3-{3-[5-(tetrahydro-pyran-2-yloxymethyl)-[1,2,3]triazol-1-yl]-phenyl}-propionic acid tert.-butyl ester (Example K5) according to the general procedure M. Obtained as a yellow foam (450 mg).

MS (ISN) 657.1 [(M−H)⁻]; mp 76–77° C.

Example M55

{5-Dimethylamino-2-[3-oxo-3-(3-pyrazol-1-yl-phenyl)-propionylamino]-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) (319 mg, 1.0 mmol) and 3-oxo-3-(3-pyrazol-1-yl-phenyl)-propionic acid tert.-butyl ester (Example K16) (286 mg, 1.0 mmol) according to the general procedure M. Obtained as a yellow amorphous substance (485 mg).

MS (ISN) 530 [(M−H)⁻].

Example M56

{5-Dimethylamino-2-[3-oxo-3-(3-[1,2,4]triazol-4-yl-phenyl)-propionylamino]-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) (383 mg, 1.2 mmol) and 3-oxo-3-(3-[1,2,4]triazol-4-yl-phenyl)-propionic acid ethyl ester [CAS-No. 335255-97-5] (259 mg, 1.0 mmol) according to the general procedure M. Obtained as a yellow solid (290 mg).

MS (ISP) 533.3 [(M+H)⁺]; mp 58–62° C.

Example M57

{5-Dimethylamino-2-[3-(3-imidazol-1-yl-phenyl)-3-oxo-propionylamino]-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) and 6-(3-imidazol-1-yl-phenyl)-2,2-dimethyl-[1,3]dioxin-4-one (Example L3) according to the general procedure M. Obtained as an orange oil (238 mg).

MS (ISP) 432 [(M+H)⁺].

Example M58

(RS)-[4-Chloro-5-dimethylamino-2-(3-oxo-3-{3-[4-(tetrahydro-pyran-2-yloxymethyl)-pyrazol-1-yl]-phenyl}-propionylamino)-phenyl]-carbamic acid tert.-butyl ester The title compound was prepared from (2-amino-4-chloro-5-dimethylamino-phenyl)-carbamic acid tert.-butyl ester (Example J1) (429 mg, 1.5 mmol) and (RS)-3-oxo-3-{3-[4-(tetrahydro-pyran-2-yloxymethyl)-pyrazol-1-yl]-phenyl}-propionic acid tert.-butyl ester (Example K17) (601 mg, 1.5 mmol) according to the general procedure M. Obtained as a yellow amorphous substance (710 mg).

MS (ISN) 610 [(M−H)⁻] and 612 [(M+2−H)⁻].

Example M59

(RS)-[5-Dimethylamino-2-(3-oxo-3-{3-[4-(tetrahydro-pyran-2-yloxymethyl)-pyrazol-1-yl]-phenyl}-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) (479 mg, 1.5 mmol) and (RS)-3-oxo-3-{3-[4-(tetrahydro-pyran-2-yloxymethyl)-pyrazol-1-yl]-phenyl}-propionic acid tert.-butyl ester (Example K17) (601 mg, 1.5 mmol) according to the general procedure M. Obtained as a pink amorphous substance (641 mg).

MS (ISN) 644 [(M−H)⁻].

Example M60

(RS)-[5-Dimethylamino-2-(3-{3-[3-methyl-4-(tetrahydro-pyran-2-yloxymethyl)-isoxazol-5-yl]-phenyl}-3-oxo-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) and (RS)-3-{3-[3-methyl-4-(tetrahydro-pyran-2-yloxymethyl)-isoxazol-5-yl]-phenyl}-3-oxo-propionic acid tert.-butyl ester (Example K13) according to the general procedure M. Obtained as a red oil (424 mg).

MS (ISN) 626 [(M−H)⁻].

Example M61

(RS)-[5-Dimethylamino-2-(3-oxo-3-{3-14-(tetrahydro-pyran-2-yloxymethyl)-isoxazol-3-yl]-phenyl}-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) and (RS)-3-oxo-3-{3-[4-(tetrahydro-pyran-2-yloxymethyl)-isoxazol-3-yl]-phenyl}-propionic acid tert.-butyl ester (Example K18) according to the general procedure M. Obtained as a light yellow solid (145 mg).

MS (ISP) 647 [(M+H)⁺].

Example M62

(RS)-(5-Dimethylamino-2-{3-[3-(2-methylsulfanyl-imidazol-1-yl)-phenyl]-3-oxo-propionylamino}-4-trifluoromethyl-phenyl)-carbamic acid tert.-butyl ester The title compound was prepared from (2-amino-5-dimethylamino-4-trifluoromethyl-phenyl)-carbamic acid tert.-butyl ester (Example J6) (319 mg, 1.0 mmol) and 3-[3-(2-methylsulfanyl-imidazol-1-yl)-phenyl]-3-oxo-propionic acid tert.-butyl ester [CAS-No. 335256-01-4] (432 mg, 1.3 mmol) according to the general procedure M. Obtained as a light brown amorphous substance (493 mg).

MS (ISP) 333.2 [(M+H)⁺].

Example M63

(RS)-[5-Dimethylamino-2-(3-{3-[2-methyl-4-(tetrahydro-pyran-2-yloxymethyl)-2H-pyrazol-3-yl]-phenyl}-3-oxo-propionylamino)-4-trifluoromethyl-phenyl]-carbamic acid tert.-butyl ester The title compound was prepared from (2-amino-5-dimethylamino-4-trifluoromethyl-phenyl)-carbamic acid tert.-butyl ester (Example J6) and (RS)-3-{3-[2-methyl-4-(tetrahydro-pyran-2-yloxymethyl)-2H-pyrazol-3-yl]-phenyl}-3-oxo-propionic acid tert.-butyl ester (Example K19) according to the general procedure M. Obtained as a light red solid (576 mg).

MS (ISN) 658 [(M−H)⁻].

Example M64

{4-Chloro-5-dimethylamino-2-[3-oxo-3-(3-[1,2,4]triazol-1-yl-phenyl)-propionylamino]-phenyl}-carbamic acid tert.-butyl ester The title compound was prepared from (2-amino-4-chloro-5-dimethylamino-phenyl)-carbamic acid tert.-butyl ester (Example J1) and 3-oxo-3-(3-[1,2,4]triazol-1-yl-phenyl)-propionic acid tert.-butyl ester [CAS-No. 335255-88-4] according to the general procedure M. Obtained as a light yellow solid (427 mg).

MS (ISN) 497 [(M−H)⁻] and 499 [(M+2−H)⁻].

Example M65

{5-Dimethylamino-2-[3-oxo-3-(3-[1,2,4]triazol-1-yl-phenyl)-propionylamino]-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) and 3-oxo-3-(3-[1,2,4]triazol-1-yl-phenyl)-propionic acid tert.-butyl ester [CAS-No. 335255-88-4] according to the general procedure M. Obtained as a light red solid (502 mg).

MS (ISN) 531 [(M−H)⁻].

Example M66

{2-[3-(3-Cyano-phenyl)-3-oxo-propionylamino]-5-dimethylamino-4-trifluoromethyl-phenyl}-carbamic acid tert.-butyl ester The title compound was prepared from (2-amino-5-dimethylamino-4-trifluoromethyl-phenyl)-carbamic acid tert.-butyl ester (Example J6) (320 mg, 1.0 mmol) and 3-(2,2-dimethyl-6-oxo-6H-[1,3]dioxin-4-yl)-benzonitrile (Example L1) (275 mg, 1.2 mmol) according to the general procedure M. Obtained as a red viscous oil (196 mg).

MS (ISN) 489.1 [(M−H)⁻].

Example M67

(RS)-[5-(Cyclopropylmethyl-methyl-amino)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester The title compound was prepared from [2-amino-5-(cyclopropylmethyl-methyl-amino)-4-trifluoromethyl-phenyl]-carbamic acid tert.-butyl ester (Example J18) (719 mg, 2.0 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (803 mg, 2.0 mmol) according to the general procedure M. Obtained as a yellow amorphous substance (985 mg).

MS (ISP) 687 [(M+H)⁺].

Example M68

[2-[3-(2-Cyano-pyridin-4-yl)-3-oxo-propionylamino]-5-(cyclopropylmethyl-methyl-amino)-4-trifluoromethyl-phenyl]-carbamic acid tert.-butyl ester The title compound was prepared from [2-amino-5-(cyclopropylmethyl-methyl-amino)-4-trifluoromethylphenyl]-carbamic acid tert.-butyl ester (Example J18) (180 mg, 0.5 mmol) and 3-(2-cyano-pyridin-4-yl)-3-oxo-propionic acid tert.-butyl ester (Example K3) (123 mg, 0.5 mmol) according to the general procedure M. Obtained as a yellow amorphous substance (206 mg).

MS (ISP) 532 [(M+H)$^+$].

Example M69

(RS)-{5-Dimethylamino-2-[3-oxo-3-(3-{2-[2-(tetrahydro-pyran-2-yloxy)-ethyl]-2H-pyrazol-3-yl}-phenyl)-propionylamino]-4-trifluoromethyl-phenyl}-carbamic acid tert.-butyl ester The title compound was prepared from (2-amino-5-dimethylamino-4-trifluoro-methyl-phenyl)-carbamic acid tert.-butyl ester (Example J6) (639 mg, 2.0 mmol) and (RS)-3-oxo-3-(3-{2-[2-(tetrahydro-pyran-2-yloxy)-ethyl]-2H-pyrazol-3-yl}-phenyl)-propionic acid tert.-butyl ester (Example K20) (829 mg, 2.0 mmol) according to the general procedure M. Obtained as a pink amorphous substance (272 mg).

MS (ISN) 658 [(M−H)$^-$].

Example M70

[2-[3-(2-Cyano-pyridin-4-yl)-3-oxo-propionylamino]-5-(cyclopropyl-methyl-amino)-4-trifluoromethyl-phenyl]-carbamic acid tert.-butyl ester The title compound was prepared from [2-amino-5-(cyclopropyl-methyl-amino)-4-trifluoromethyl-phenyl]-carbamic acid tert.-butyl ester (Example J19) (259 mg, 0.75 mmol) and 3-(2-cyano-pyridin-4-yl)-3-oxo-propionic acid tert.-butyl ester (Example K3) (192 mg, 0.78 mmol) according to the general procedure M. Obtained as a yellow solid (228 mg).

MS (ISN) 516.2 [(M−H)$^-$]; mp 114–116° C.

Example M71

{2-Dimethylamino-2'-fluoro-5-[3-oxo-3-(3-[1,2,3]triazol-1-yl-phenyl)-propionylamino]-biphenyl-4-yl}-carbamic acid tert.-butyl ester The title compound was prepared from (5-amino-2-dimethylamino-2'-fluoro-biphenyl-4-yl)-carbamic acid tert.-butyl ester (Example J20) (691 mg, 2.0 mmol) and 2,2-dimethyl-6-(3-[1,2,3]triazol-1-yl-phenyl)-[1,3]dioxin-4-one (Example L4) (543 mg, 2.0 mmol) according to the general procedure M. Obtained as a yellow solid (820 mg).

Mp 125–135° C.

Example M72

(RS)-{5-Dimethylamino-2-[3-oxo-3-(3-{5-[2-(tetrahydro-pyran-2-yloxy)-ethyl]-[1,2,3]triazol-1-yl}-phenyl)-propionylamino]-4-trifluoromethyl-phenyl}-carbamic acid tert.-butyl ester The title compound was prepared from (2-amino-5-dimethylamino-4-trifluoro-methyl-phenyl)-carbamic acid tert.-butyl ester (Example J6) and (RS)-3-oxo-3-(3-{5-[2-(tetrahydro-pyran-2-yloxy)-ethyl]-[1,2,3]triazol-1-yl}-phenyl)-propionic acid tert.-butyl ester (Example K21) according to the general procedure M. Obtained as a light red oil (527 mg).

MS (ISP) 577 [(M+H)$^+$].

Example M73

(RS)-[5-Dimethylamino-2-(3-oxo-3-{3-[5-(tetrahydro-pyran-2-yloxymethyl)-pyrazol-1-yl]-phenyl}-propionylamino)-4-trifluoromethyl-phenyl]-carbamic acid tert.-butyl ester The title compound was prepared from (2-amino-5-dimethylamino-4-trifluoro-methyl-phenyl)-carbamic acid tert.-butyl ester (Example J6) and (RS)-3-oxo-3-{3-[5-(tetrahydro-pyran-2-yloxymethyl)-pyrazol-1-yl]-phenyl}-propionic acid ethyl ester (Example K22) according to the general procedure M. Obtained as a brown oil (179 mg).

MS (ISP) 646 [(M+H)$^+$].

Example M74

{5-Dimethylamino-2-[3-oxo-3-(3-[1,2,3]triazol-1-yl-phenyl)-propionylamino]-4-trifluoromethyl-phenyl}-carbamic acid tert.-butyl ester The title compound was prepared from (2-amino-5-dimethylamino-4-trifluoro-methyl-phenyl)-carbamic acid tert.-butyl ester (Example J6) (639 mg, 2.0 mmol) and 2,2-dimethyl-6-(3-[1,2,3]triazol-1-yl-phenyl)-[1,3]dioxin-4-one (Example L4) (543 mg, 2.0 mmol) according to the general procedure M. Obtained as a red solid (915 mg).

MS (ISP) 533.3 [(M+H)$^+$]; mp 79–81° C.

Example M75

[2-[3-(2-Cyano-pyridin-4-yl)-3-oxo-propionylamino]-5-(2,2,2-trifluoro-ethoxy)-4-trifluoromethyl-phenyl]-carbamic acid tert.-butyl ester The title compound was prepared from [2-amino-5-(2,2,2-trifluoro-ethoxy)-4-trifluoromethyl-phenyl]-carbamic acid tert.-butyl ester (Example J21) and 3-(2-cyano-pyridin-4-yl)-3-oxo-propionic acid tert.-butyl ester (Example K3) according to the general procedure M. Obtained as a light brown solid (262 mg).

MS (ISN) 545.0 [(M−H)$^-$]; mp 158° C. (dec.).

Example M76

{2-[3-(3-Cyano-phenyl)-3-oxo-propionylamino]-4-dimethylamino-5-methyl-phenyl}-carbamic acid tert-butyl ester The title compound was prepared from (2-amino-5-dimethylamino-4-methyl-phenyl)-carbamic acid tert-butyl ester (Example J22) (300 mg, 1.0 mmol) and 3-(3-cyano-phenyl)-3-oxo-propionic acid tert-butyl ester (Example K2) (245 mg, 1.0 mmol) according to the general procedure M. Obtained as a light brown foam (250 mg, 57%).

MS (ISP) 437.4 [(M+H)$^+$].

Example M77

(RS)-[5-Dimethylamino-4-methyl-2-(3-oxo-3-{3-[5-(tetrahydro-pyran-2-yloxymethyl)-[1,2,3]triazol-1-yl]phenyl}-propionylamino)-phenyl]-carbamic acid tert-butyl ester The title compound was prepared from (2-amino-5-dimethylamino-4-methyl-phenyl)-carbamic acid tert-butyl ester (Example J22) (265 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5)

(402 mg, 1.0 mmol) according to the general procedure M. Obtained as a yellow foam (420 mg, 71%).

MS (ISP) 593.5 [(M+H)$^+$].

Example M78

{5-Cyano-2-[3-(3-cyano-phenyl)-3-oxo-propionylamino]-4-dimethylamino-phenyl}-carbamic acid tert-butyl ester The title compound was prepared from (2-amino-4-cyano-5-dimethylamino-phenyl)-carbamic acid tert-butyl ester (Example J23) (276 mg, 1.0 mmol) and 3-(3-cyano-phenyl)-3-oxo-propionic acid tert-butyl ester (Example K2) (245 mg, 1.0 mmol) according to the general procedure M. Obtained as a brown foam (290 mg, 65%).

MS (ISP) 448.3 [(M+H)$^+$].

Example M79

[2-[3-(3-Cyano-phenyl)-3-oxo-propionylamino]-5-methyl-4-(methyl-propyl-amino)-phenyl]-carbamic acid tert-butyl ester The title compound was prepared from [2-amino-4-methyl-5-(methyl-propyl-amino)-phenyl]-carbamic acid tert-butyl ester (Example J24) (293 mg, 1.0 mmol) and 3-(3-cyano-phenyl)-3-oxo-propionic acid tert-butyl ester (Example K2) (245 mg, 1.0 mmol) according to the general procedure M. Obtained as a light brown oil (170 mg, 37%).

MS (ISP) 463.3 [(M−H)$^-$].

Example M80

(RS)-[4-Methyl-5-(methyl-propyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-methyl-5-(methyl-propyl-amino)-phenyl]-carbamic acid tert-butyl ester(Example J24) (293 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a yellow foam (350 mg, 56%).

MS (ISP) 621.2 [(M+H)$^+$].

Example M81

(RS)-[5-(Ethyl-methyl-amino)-4-methyl-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-5-(ethyl-methyl-amino)-4-methyl-phenyl]-carbamic acid tert-butyl ester (Example J25) (279 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a yellow foam (400 mg, 66%).

MS (ISP) 607.1 [(M+H)$^+$].

Example M82

(RS)-[4-Cyano-5-dimethylamino-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from (2-amino-4-cyano-5-dimethylamino-phenyl)-carbamic acid tert-butyl ester (Example J23) (276 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a light brown foam (360 mg, 59%).

MS (ISP) 602.1 [(M−H)$^-$].

Example M83

(RS)-[4-Chloro-5-(isopropyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-chloro-5-(isopropyl-methyl-amino)-phenyl]-carbamic acid tert-butyl ester (Example J26) (300 mg, 0.96 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (383 mg, 0.96 mmol) according to the general procedure M. Obtained as a light yellow oil (530 mg, 86%).

MS (ISP) 639.2 [(M−H)$^-$].

Example M84

[4-Methyl-2-{3-[3-(3-methyl-isoxazol-5-yl)-phenyl]-3-oxo-propionylamino}-5-(methyl-propyl-amino)-phenyl]-carbamic acid tert-butyl ester The title compound was prepared from [2-amino-4-methyl-5-(methyl-propyl-amino)-phenyl]-carbamic acid tert-butyl ester(Example J24) (293 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light yellow foam (340 mg, 65%).

MS (ISP) 519.3 [(M−H)$^-$].

Example M85

(4-Cyano-5-dimethylamino-2-{3-[3-(3-methyl-isoxazol-5-yl)-phenyl]-3-oxo-propionylamino}-phenyl)-carbamic acid tert-butyl ester The title compound was prepared from (2-amino-4-cyano-5-dimethylamino-phenyl)-carbamic acid tert-butyl ester (Example J23) (276 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (320 mg, 64%).

MS (ISP) 504.3 [(M+H)$^+$].

Example M86

(5-(Ethyl-methyl-amino)-4-methyl-2-{3-[3-methyl-isoxazol-5-)-phenyl]-3-oxo-propionylamino}-phenyl)-carbamic acid tert-butyl ester The title compound was prepared from [2-amino-5-(ethyl-methyl-amino)-4-methyl-phenyl]-carbamic acid tert-butyl ester (Example J25) (279 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a brown foam (390 mg, 77%).

MS (ISP) 505.3 [(M−H)$^-$].

Example M87

(5-Dimethylamino-4-methyl-2-{3-[3-(3-methyl-isoxazol-5-yl)-phenyl]-3-oxo-propionylamino}-phenyl)-carbamic acid tert-butyl ester The title compound was prepared from (2-amino-5-dimethylamino-4-methyl-phenyl)-carbamic acid tert-butyl ester (Example J22) (265 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a brown foam (330 mg, 67%).

MS (ISP) 491.3 [(M−H)⁻].

Example M88

(RS)-[4-Chloro-5-(isobutyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-chloro-5-(isobutyl-methyl-amino)-phenyl]-carbamic acid tert-butyl ester (Example J27) (328 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light brown foam (330 mg, 50%).

MS (ISP) 655.1 [(M+H)⁺].

Example M89

(4-Chloro-5-(isobutyl-methyl-amino)-2-{3-[3-(3-methyl-isoxazol-5-yl)-phenyl]-3-oxo-propionylamino}-phenyl)-carbamic acid tert-butyl ester The title compound was prepared from [2-amino-4-chloro-5-(isobutyl-methyl-amino)-phenyl]-carbamic acid tert-butyl ester (Example J27) (328 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light yellow foam (360 mg, 65%).

MS (ISP) 555.1 [(M+H)⁺].

Example M90

(RS)-[4-Cyano-2-(3-oxo-3-{3-(5-(tetrahydro-pyran-2-yloxymethyl)-[1,2,3]triazol-1-yl]-phenyl}-propionylamino)-5-pyrrolidin-1-yl-phenyl]-carbamic acid tert-butyl ester The title compound was prepared from (2-amino-4-cyano-5-pyrrolidin-1-yl-phenyl)-carbamic acid tert-butyl ester (Example J28) (302 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light orange foam (380 mg, 60%).

MS (ISP) 630.1 [(M+H)⁺].

Example M91

(4-Cyano-2-{3-[3-(3-methyl-isoxazol-5-yl)-phenyl]-3-oxo-propionylamino}-5-pyrrolidin-1-yl-phenyl)-carbamic acid tert-butyl ester The title compound was prepared from (2-amino-4-cyano-5-pyrrolidin-1-yl-phenyl)-carbamic acid tert-butyl ester (Example J28) (302 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (420 mg, 79%).

MS (ISP) 530.2 [(M+H)⁺].

Example M92

(RS)-[4-Cyano-5-(methyl-propyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-cyano-5-(methyl-propyl-amino)-phenyl]-carbamic acid tert-butyl ester (Example J29) (304 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light red foam (440 mg, 70%).

MS (ISP) 630.1 [(M+H)⁺].

Example M93

[4-Cyano-2-{3-[3-(3-methyl-isoxazol-5-yl)-phenyl]-3-oxo-propionylamino}-5-(methyl-propyl-amino)-phenyl]-carbamic acid tert-butyl ester The title compound was prepared from [2-amino-4-cyano-5-(methyl-propyl-amino)-phenyl]-carbamic acid tert-butyl ester (Example J29) (304 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (370 mg, 70%).

MS (ISP) 532.3 [(M+H)⁺].

Example M94

(4-Cyano-5-diethylamino-2-{3-[3-(3-methyl-isoxazol-5-yl)-phenyl]-3-oxo-1propionylamino}-phenyl)-carbamic acid tert-butyl ester The title compound was prepared from (2-amino-4-cyano-5-diethylamino-phenyl)-carbamic acid tert-butyl ester (Example J30) (304 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (360 mg, 68%).

MS (ISP) 530.2 [(M+H)⁺].

Example M95

(4-Cyano-5-(isopropyl-methyl-amino)-2-{3-[3-(3-methyl-isoxazol-5-yl)-phenyl]-3-oxo-propionylamino}-phenyl)-carbamic acid tert-butyl ester The title compound was prepared from [2-amino-4-cyano-5-(isopropyl-methyl-amino)-phenyl]-carbamic acid tert-butyl ester (Example J31) (304 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (380 mg, 71%).

MS (ISP) 530.2 [(M−H)⁻].

Example M96

(RS)-[4-Cyano-5-(isopropyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-4-cyano-5-(isopropyl-methyl-amino)-phenyl]-carbamic acid tert-butyl ester (Example J31) (304 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a yellow foam (460 mg, 73%).

MS (ISP) 630.1 [(M−H)⁻].

Example M97

(4-Cyano-5-(isobutyl-methyl-amino)-2-{3-[3-(3-methyl-isoxazol-5-yl)-phenyl]-3-oxo-propionylamino}-phenyl)-carbamic acid tert-butyl ester The title compound was prepared from [2-amino-4-cyano-5-(isobutyl-methyl-amino)-phenyl]-carbamic acid tert-butyl ester (Example J32) (318 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (400 mg, 73%).

MS (ISP) 544.3 [(M−H)⁻].

Example M98

(RS)-[4-Cyano-5-(isobutyl-methyl-amino)-2-(3-oxo-3-{3-[5-(tetrahydro-pyran-2-yloxymethyl)-(1,2,3]triazol-1-yl]-phenyl}-propionylamino)-phenyl]-carbamic acid tert-butyl ester The title compound was prepared from [2-amino-4-cyano-5-(isobutyl-methyl-amino)-phenyl]-carbamic acid tert-butyl ester (Example J32) (318 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a yellow foam (470 mg, 73%).

MS (ISP) 644.2 [(M−H)⁻].

Example M99

(4-Cyano-2-{3-[3-(3-methyl-isoxazol-5-yl)-phenyl]-3-oxo-propionylamino}-5-piperidin-1-yl-phenyl)-carbamic acid tert-butyl ester The title compound was prepared from (2-amino-4-cyano-5-piperidin-1-yl-phenyl)-carbamic acid tert-butyl ester (Example J33) (316 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (420 mg, 77%).

MS (ISP) 544.2 [(M+H)⁺].

Example M100

(4-Chloro-5-isobutylamino-2-{3-[3-(3-methyl-isoxazol-5-yl)-phenyl]-3-oxo-propionylamino}-phenyl)-carbamic acid tert-butyl ester The title compound was prepared from (2-amino-4-chloro-5-isobutylamino-phenyl)-carbamic acid tert-butyl ester (Example J34) (314 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as an off-white foam (340 mg, 63%).

MS (ISP) 542.2 [(M+H)⁺].

Example M101

(RS)-[4-Chloro-5-isobutylamino-2-(3-oxo-3-{3-[5-(tetrahydro-pyran-2-yloxymethyl)-1,2,3]triazol-1-yl]-phenyl}-propionylamino)-phenyl]-carbamic acid tert-butyl ester The title compound was prepared from (2-amino-4-chloro-5-isobutylamino-phenyl)-carbamic acid tert-butyl ester (Example J34) (314 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a red oil (180 mg, 28%).

MS (ISP) 640.2 [(M−H)⁻].

Example M102

(RS)-[5-(Methyl-propyl-amino)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester The title compound was prepared from [2-amino-5-(methyl-propyl-amino)-4-trifluoromethyl-phenyl]-carbamic acid tert-butyl ester (Example J35) (380 mg, 1.09 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (439 mg, 1.09 mmol) according to the general procedure M. Obtained as a red foam (150 mg, 20%).

MS (ISP) 675.4 [(M−H)⁻].

Example M103

[2-{3-[3-(3-Methyl-isoxazol-5-yl)-phenyl]-3-oxo-propionylamino}-5-(methyl-propyl-amino)-4-trifluoromethyl-phenyl]-carbamic acid tert-butyl ester The title compound was prepared from [2-amino-5-(methyl-propyl-amino)-4-trifluoromethyl-phenyl]-carbamic acid tert-butyl ester (Example J35) (360 mg, 1.04 mmol) and 3-[3-(3-methyl-isoxazol-5-yl)-phenyl]-3-oxo-propionic acid tert-butyl ester (Example K4) (312 mg, 1.04 mmol) according to the general procedure M. Obtained as a light red foam (270 mg, 45%).

MS (ISP) 573.2 [(M−H)⁻].

Example M104

(RS)-[5-(Isobutyl-methyl-amino)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester The title compound was prepared from [2-amino-5-(isobutyl-methyl-amino)-4-trifluoromethyl-phenyl]-carbamic acid tert-butyl ester (Example J36) (370 mg, 1.02 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (411 mg, 1.02 mmol) according to the general procedure M. Obtained as a light brown foam (520 mg, 74%).

MS (ISP) 687.2 [(M−H)⁻].

Example M105

(5-(Isobutyl-methyl-amino)-2-{3-[3-(3-methyl-isoxazol-5-yl)-phenyl]-3-oxo-propionylamino}-4-trifluoromethyl-phenyl)-carbamic acid tert-butyl ester The title compound was prepared from [2-amino-5-(isobutyl-methyl-amino)-4-trifluoromethyl-phenyl]-carbamic acid tert-butyl ester (Example J36) (360 mg, 1.0 mmol) and 3-[3-(3-methyl-isoxazol-5-yl)-phenyl]-3-oxo-propionic acid tert-butyl ester (Example K4) (302 mg, 1.0 mmol) according to the general procedure M. Obtained as a light brown foam (430 mg, 73%).

MS (ISP) 587.3 [(M−H)⁻].

Example M106

(RS)-[5-(Isopropyl-methyl-amino)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester The title compound was prepared from [2-amino-5-(isopropyl-methyl-amino)-4-trifluoromethyl-phenyl]-carbamic acid tert-butyl ester (Example J37) (340 mg, 0.98 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (393 mg, 0.98 mmol) according to the general procedure M. Obtained as a light yellow foam (510 mg, 77%).

MS (ISP) 673.3 [(M−H)−].

Example M107

(5-(Isopropyl-methyl-amino)-2-{3-[3-(3-methyl-isoxazol-5-yl)-phenyl]-3-oxo-propionylamino}-4-trifluoromethyl-phenyl)-carbamic acid tert-butyl ester The title compound was prepared from [2-amino-5-(isopropyl-methyl-amino)-4-trifluoromethyl-phenyl]-carbamic acid tert-butyl ester (Example J37) (350 mg, 1.01 mmol) and 3-[3-(3-methyl-isoxazol-5-yl)-phenyl]-3-oxo-propionic acid tert-butyl ester (Example K4) (304 mg, 1.01 mmol) according to the general procedure M. Obtained as a light brown foam (380 mg, 66%).

MS (ISP) 573.2 [(M−H)−].

Example M108

(RS)-[5-(Isobutyl-methyl-amino)-4-methyl-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from [2-amino-5-(isobutyl-methyl-amino)-4-methyl-phenyl]-carbamic acid tert-butyl ester (Example J38) (307 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light yellow foam (330 mg, 52%).

MS (ISP) 635.2 [(M+H)+].

Example M109

(5-(Isobutyl-methyl-amino)-4-methyl-2-{3-[3-(3-methyl-isoxazol-5-yl)-phenyl]-3-oxo-propionylamino}-phenyl)-carbamic acid tert-butyl ester The title compound was prepared from [2-amino-5-(isobutyl-methyl-amino)-4-methyl-phenyl]-carbamic acid tert-butyl ester (Example J38) (307 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light yellow foam (330 mg, 62%).

MS (ISP) 535.4 [(M+H)+].

Example M110

(RS)-[4-Methyl-2-(3-oxo-3-{3-[5-(tetrahydro-pyran-2-yloxymethyl)-[1,2,3]triazol-1-yl]-phenyl}-propionylamino)-5-pyrrolidin-1-yl-phenyl]-carbamic acid tert-butyl ester The title compound was prepared from (2-amino-4-methyl-5-pyrrolidin-1-yl-phenyl)-carbamic acid tert-butyl ester acid tert-butyl ester (Example J39) (292 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light yellow foam (410 mg, 66%).

MS (ISP) 619.3 [(M+H)+].

Example M111

(4-Methyl-2-{3-[3-(3-methyl-isoxazol-5-yl)-phenyl]-3-oxo-propionylamino}-5-pyrrolidin-1-yl-phenyl)-carbamic acid tert-butyl ester The title compound was prepared from (2-amino-4-methyl-5-pyrrolidin-1-yl-phenyl)-carbamic acid tert-butyl ester (Example J39) (291 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (330 mg, 64%).

MS (ISP) 517.3 [(M−H)−].

Example M112

(4-Chloro-5-isopropylamino-2-{3-[3-(3-methyl-isoxazol-5-yl)-phenyl]-3-oxo-propionylamino}-phenyl)-carbamic acid tert-butyl ester The title compound was prepared from (2-amino-4-chloro-5-isopropylamino-phenyl)-carbamic acid tert-butyl ester (Example J40) (300 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (169 mg, 32%).

MS (ISP) 525.2 [(M−H)−].

Example M113

(RS)-[4-Chloro-5-isopropylamino-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester The title compound was prepared from (2-amino-4-chloro-5-isopropylamino-phenyl)-carbamic acid tert-butyl ester (Example J40) (300 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (401 mg, 1.0 mmol) according to the general procedure M. Obtained as a light yellow foam (375 mg, 60%).

MS (ISP) 625.1 [(M−H)−].

Example M114

(RS)-[4-Chloro-5-(methyl-propyl-amino)-2-(3-oxo-3-{3-[5-(tetrahydro-pyran-2-yloxymethyl)-[1,2,4]triazol-1-yl]-phenyl}-propionylamino)-phenyl]-carbamic acid tert-butyl ester The title compound was prepared from [2-amino-4-chloro-5-(methyl-propyl-amino)-phenyl]-carbamic acid tert-butyl ester (Example J8) (1.0 g, 3.19 mmol) and (RS)-3-oxo-3-{3-[5-(tetrahydro-pyran-2-yloxymethyl)-[1,2,4]triazol-1-yl]-phenyl}-propionic acid tert-butyl ester (Example K24) (1.28 g, 3.19 mmol) according to the general procedure M. Obtained as a yellow foam (1.48 g).

MS (ISP) 641.3 [(M+H)+].

Example M115

(RS)-[4-Chloro-5-(isobutyl-methyl-amino)-2-(3-oxo-3-{3-[5-(tetrahydro-pyran-2-yloxymethyl)-[1,2,4]triazol-1-yl]-phenyl}-propionylamino)-phenyl]-carbamic acid tert-butyl ester The title compound was prepared from [2-amino-4-chloro-5-(isobutyl-methyl-amino)-phenyl]-carbamic acid tert-butyl ester (Example J24) (1.0 mg, 3.05 mmol) and (RS)-3-oxo-3-{3-[5-(tetrahydro-pyran-2-yloxymethyl)-[1,2,4]triazol-1-yl]-phenyl}-propionic acid tert-butyl ester (Example K24) (1.22 g, 3.05 mmol) according to the general procedure M. Obtained as a light brown foam (620 mg, 31%).

MS (ISP) 655.1 [(M+H)$^+$].

Example M116

(RS)-[5-(Isobutyl-methyl-amino)-4-methyl-2-(3-oxo-3-{3-[5-(tetrahydro-pyran-2-yloxymethyl)-[1,2,4]triazol-1-yl]-phenyl}-propionylamino)-phenyl]-carbamic acid tert-butyl ester The title compound was prepared from [2-amino-5-(isobutyl-methyl-amino)-4-methyl-phenyl]-carbamic acid tert-butyl ester (Example J38) (1.0 g, 3.25 mmol) and (RS)-[3-oxo-3-{3-[5-(tetrahydro-pyran-2-yloxymethyl)-[1,2,4]triazol-1-yl]-phenyl}-propionic acid tert-butyl ester (Example K24) (1.31 g, 3.25 mmol) according to the general procedure M. Obtained as a light yellow foam (970 mg, 47%).

MS (ISP) 635.2 [(M+H)$^+$].

Example M117

{5-(Methyl-propyl-amino)-2-[3-oxo-3-(3-[1,2,4]triazol-1-yl-phenyl)-propionylamino]-4-trifluoromethyl-phenyl}-carbamic acid tert-butyl ester The title compound was prepared from [2-amino-5-(methyl-propyl-amino)-4-trifluoromethyl-phenyl]-carbamic acid tert-butyl ester (Example J35) (347 mg, 1.0 mmol) and 3-oxo-3-(3-[1,2,4]triazol-1-yl-phenyl)-propionic acid tert-butyl ester (Example K25) (287 mg, 1.0 mmol) according to the general procedure M. Obtained as a light yellow foam (320 mg, 57%).

MS (ISP) 561.4 [(M+H)$^+$].

Example M118

{5-(Methyl-propyl-amino)-2-[3-oxo-3-(3-[1,2,3]triazol-1-yl-phenyl)-propionylamino]-4-trifluoromethyl-phenyl}-carbamic acid tert-butyl ester The title compound was prepared from (2-amino-5-(methyl-propyl-amino)-4-trifluoromethyl-phenyl]-carbamic acid tert-butyl ester (Example J35) (347 mg, 1.0 mmol) and 3-oxo-3-(3-[1,2,3]triazol-1-yl-phenyl)-propionic acid tert-butyl ester (Example K23) (287 mg, 1.0 mmol) according to the general procedure M. Obtained as a light brown oil (340 mg, 61%).

MS (ISP) 561.3 [(M+H)$^+$].

Example M119

{5-(Isobutyl-methyl-amino)-2-[3-oxo-3-(3-pyrazol-1-yl-phenyl)-propionylamino]-4-trifluoromethyl-phenyl}-carbamic acid tert-butyl ester The title compound was prepared from [2-amino-5-(isobutyl-methyl-amino)-4-trifluoromethyl-phenyl]-carbamic acid tert-butyl ester (Example J40) (361 mg, 1.0 mmol) and 3-oxo-3-(3-pyrazol-1-yl-phenyl)-propionic acid tert-butyl ester (Example K16) (286 mg, 1.0 mmol) according to the general procedure M. Obtained as a light brown foam (500 mg, 87%).

MS (ISP) 574.2 [(M+H)$^+$].

Example M120

[2-[3-(2-Cyano-pyridin-4-yl)-3-oxo-propionylamino]-5-(isopropyl-methyl-amino)-4-trifluoromethyl-phenyl]-carbamic acid tert-butyl ester The title compound was prepared from [2-amino-5-(isoproyl-methyl-amino)-4-trifluoromethyl-phenyl]-carbamic acid tert-butyl ester (Example J37) (500 mg, 1.44 mmol) and 3-(2-cyano-pyridin-4-yl)-3-oxo-propionic acid tert-butyl ester (Example K3) (355 mg, 1.44 mmol) according to the general procedure M. Obtained as a light orange oil (670 mg, 90%).

MS (ISP) 518.1 [(M−H)$^-$].

Example M121

{4-Chloro-5-(isobutyl-methyl-amino)-2-[3-oxo-3-(3-[1,2,4]triazol-1-yl-phenyl)-propionylamino]-phenyl}-carbamic acid tert-butyl ester The title compound was prepared from [2-amino-4-chloro-5-(isobutyl-methyl-amino)-phenyl]-carbamic acid tert-butyl ester (Example J27) (500 mg, 1.53 mmol) and 3-oxo-3-(3-[1,2,4]triazol-1-yl-phenyl)-propionic acid tert-butyl ester (Example K25) (438 mg, 1.53 mmol) according to the general procedure M. Obtained as a light orange foam (700 mg, 85%).

MS (ISP) 539.2 [(M−H)$^-$].

Example M122

{5-(Isobutyl-methyl-amino)-2-[3-oxo-3-(3-[1,2,4]triazol-1-yl-phenyl)-propionylamino]-4-trifluoromethyl-phenyl}-carbamic acid tert-butyl ester The title compound was prepared from [2-amino-5-(isobutyl-methyl-amino)-4-trifluoromethyl-phenyl]-carbamic acid tert-butyl ester (Example J36) (361 mg, 1.0 mmol) and 3-oxo-3-(3-[1,2,4]triazol-1-yl-phenyl)-propionic acid tert-butyl ester (Example K25) (287 mg, 1.0 mmol) according to the general procedure M. Obtained as a light red foam (490 mg, 85%).

MS (ISP) 575.2 [(M+H)$^+$].

Example M123

{4-Chloro-5-(isobutyl-methyl-amino)-2-[3-oxo-3-(3-[1,2,3]triazol-1-yl-phenyl)-propionylamino]-phenyl}-carbamic acid tert-butyl ester The title compound was prepared from [2-amino-4-chloro-5-(isobutyl-methyl-amino)-phenyl]-carbamic acid tert-butyl ester (Example J27) (328 mg, 1.0 mmol) and 3-oxo-3-(3-[1,2,3]triazol-1-yl-phenyl)-propionic acid tert-butyl ester (Example K23) (287 mg, 1.0 mmol) according to the general procedure M. Obtained as an orange oil (250 mg, 46%).

MS (ISP) 539.2 [(M−H)$^-$].

Example M124

{5-(Isobutyl-methyl-amino)-2-[3-oxo-3-(3-[1,2,3]triazol-1-yl-phenyl)-propionylamino]-4-trifluoromethyl-phenyl}-carbamic acid tert-butyl ester The title compound was prepared from [2-amino-5-(isobutyl-methyl-amino)-4-trifluoromethyl-phenyl]- carbamic acid tert-butyl ester (Example J41) (460 mg, 1.27 mmol) and 3-oxo-3-(3-[1,2,3]triazol-1-yl-phenyl)-propionic acid tert-butyl ester (Example K23) (364 mg, 1.27 mmol) according to the general procedure M. Obtained as a light brown oil (480 mg, 69%).

MS (ISP) 573.1 [(M−H)−].

Example M125

{2-[3-(3-Imidazol-1-yl-phenyl)-3-oxo-propionylamino]-5-isobutylamino-4-trifluoromethyl-phenyl}-carbamic acid tert-butyl ester The title compound was prepared from [2-amino-5-(isobutyl-amino)-4-trifluoromethyl-phenyl]-carbamic acid tert-butyl ester (Example J41) (347 mg, 1.0 mmol) and 3-(3-imidazol-1-yl-phenyl)-3-oxo-propionic acid tert-butyl ester (Example K26) (286 mg, 1.0 mmol) according to the general procedure M. Obtained as a light yellow foam (430 mg, 77%).

MS (ISP) 558.2 [(M−H)−].

Example M126

{4-Chloro-2-[3-(3-imidazol-1-yl-phenyl)-3-oxo-propionylamino]-5-isobutylamino-phenyl}-carbamic acid tert-butyl ester The title compound was prepared from (2-amino-4-chloro-5-isobutylamino-phenyl)-carbamic acid tert-butyl ester (Example J34) (313 mg, 1.0 mmol) and 3-(3-imidazol-1-yl-phenyl)-3-oxo-propionic acid tert-butyl ester (Example K26) (286 mg, 1.0 mmol) according to the general procedure M. Obtained as a light yellow foam (330 mg, 63%).

MS (ISP) 524.1 [(M−H)−].

Example M127

{4-Chloro-5-(isobutyl-amino)-2-[3-oxo-3-(3-[1,2,3]triazol-1-yl-phenyl)-propionylamino]-phenyl}-carbamic acid tert-butyl ester The title compound was prepared from [2-amino-4-chloro-5-(isobutyl-amino)-phenyl]-carbamic acid tert-butyl ester (Example J34) (313 mg, 1.0 mmol) and 3-oxo-3-(3-[1,2,3]triazol-1-yl-phenyl)-propionic acid tert-butyl ester (Example K23) (287 mg, 1.0 mmol) according to the general procedure M. Obtained as a pale brown foam (220 mg, 42%).

MS (ISP) 525.1 [(M−H)−].

Example M128

{5-(Isobutyl-amino)-2-[3-oxo-3-(3-[1,2,3]triazol-1-yl-phenyl)-propionylamino]-4-trifluoromethyl-phenyl}-carbamic acid tert-butyl ester The title compound was prepared from [2-amino-5-(isobutyl-amino)-4-trifluoro-methyl-phenyl]-carbamic acid tert-butyl ester (Example J41) (347 mg, 1.0 mmol) and 3-oxo-3-(3-[1,2,3]triazol-1-yl-phenyl)-propionic acid tert-butyl ester (Example K23) (287 mg, 1.0 mmol) according to the general procedure M. Obtained as a light yellow foam (340 mg, 60%).

MS (ISP) 559.2 [(M−H)−].

Example M129

{4-Chloro-5-(isobutyl-amino)-2-[3-oxo-3-(3-[1,2,4]triazol-1-yl-phenyl)-propionylamino]-phenyl}-carbamic acid tert-butyl ester The title compound was prepared from [2-amino-4-chloro-5-(isobutyl-amino)-phenyl]-carbamic acid tert-butyl ester (Example J34) (313 mg, 1.0 mmol) and 3-oxo-3-(3-[1,2,4]triazol-1-yl-phenyl)-propionic acid tert-butyl ester (Example K25) (287 mg, 1.0 mmol) according to the general procedure M. Obtained as a light yellow foam (390 mg, 74%).

MS (ISP) 525.1 [(M−H)−].

Example M130

{5-(Isobutyl-amino)-2-[3-oxo-3-(3-[1,2,4]triazol-1-yl-phenyl)-propionylamino]-4-trifluoromethyl-phenyl}-carbamic acid tert-butyl ester The title compound was prepared from [2-amino-5-(isobutyl-amino)-4-trifluoromethyl-phenyl]-carbamic acid tert-butyl ester (Example J41) (347 mg, 1.0 mmol) and 3-oxo-3-(3-[1,2,4]triazol-1-yl-phenyl)-propionic acid tert-butyl ester (Example K25) (287 mg, 1.0 mmol) according to the general procedure M. Obtained as a light yellow foam (430 mg, 77%).

MS (ISP) 559.2 [(M+H)+].

General Procedure N

Preparation of 4-aryl-1,3-dihydro-benzo[b][1,4]diazepin-2-ones

A solution or suspension of the {2-[3-aryl-3-oxo-propionylamino]-phenyl}-carbamic acid tert-butyl ester or {2-[3-aryl-3-oxo-propionylamino]-phenyl}-carbamic acid tert-butyl ester (1.0 mmol) in $CH_2Cl_2$ (5 mL) [anisole or 1,3-dimethoxybenzene (5–15 mmol) can be added if necessary] was treated with TFA (0.5–5.0 mL) at 0° C. and stirring was continued at 23° C. until tlc indicated complete consumption of the starting material.

Workup procedure a: The solvent was removed in vacuum, the residue treated with little ether, whereupon it crystallized. The solid was stirred with sat. $NaHCO_3$-sol. or 1M $Na_2CO_3$-sol., filtered, washed with $H_2O$ and ether or mixtures of ether/THF/MeOH and was dried to give the title compound, which if necessary can be purified by crystallization from 1,4-dioxane or by silica gel column chromatography with cyclohexane/EtOAc or EtOAc/EtOH.

Workup procedure b: The reaction mixture was diluted with DCM or EtOAc, washed with sat. $NaHCO_3$-sol. or 1M $Na_2CO_3$-sol., brine and dried over $MgSO_4$ or $Na_2SO_4$. Removal of the solvent in vacuum left a material, which could be triturated with ether or mixtures of ether/THF/MeOH to give the title compound, or which if necessary can be purified by crystallization from 1,4-dioxane or by silica gel column chromatography with cyclohexane/EtOAc or EtOAc/EtOH.

Example 1

3-(7-Chloro-8-dimethylamino-4-oxo-4,5-dihydro-3H-benzo[b][1,4]diazepin-2-yl)-benzonitrile The title compound was prepared from {4-chloro-2-[3-(3-cyano-phenyl)-3-oxo-propionylamino]-5-dimethylamino-phenyl}-carbamic acid tert.-butyl ester (Example M1) by treatment with TFA in $CH_2Cl_2$ according to the general procedure N. Obtained as a yellow solid (85 mg).

MS (ISP) 339 [(M+H)+] and 341 [(M+2+H)+]; mp >250° C.

Example 2

8-Chloro-7-dimethylamino-4-(3-[1,2,3]triazol-1-yl-phenyl)-1,3-dihydro-benzo[b][1,4]diazepin-2-one The title compound was prepared from {4-chloro-5-dimethylamino-2-[3-oxo-3-(3-[1,2,3]triazol-1-yl-phenyl)- propionylamino]-phenyl}-carbamic acid tert.-butyl ester (Example M2) by treatment with TFA in CH$_2$Cl$_2$ according to the general procedure N. Obtained as a light yellow solid (87 mg).

MS (ISP) 381 [(M+H)$^+$] and 383 [(M+2+H)$^+$]; mp 222–225° C.

Example 3

8-Chloro-7-dimethylamino-4-[3-(5-hydroxymethyl-[-1,2,3]triazol-1-yl)-phenyl]-1,3-dihydro-benzo[b][1,4]diazepin-2-one The title compound was prepared from (RS)-[4-chloro-5-dimethylamino-2-(3-oxo-3-{3-[5-(tetrahydro-pyran-2-yloxymethyl)-[1,2,3]triazol-1-yl]-phenyl}-propionyl-amino)-phenyl]-carbamic acid tert.-butyl ester (Example M3) by treatment with TFA in CH$_2$Cl$_2$ according to the general procedure N. Obtained as a beige solid (60 mg).

MS (ISP) 411 [(M+H)$^+$] and 413 [(M+2+H)$^+$]; mp 210–214° C.

Example 4

3-(8-Dimethylamino-4-oxo-7-phenylethynyl-4,5-dihydro-3H-benzo[b][1,4]diazepin-2-yl)-benzonitrile The title compound was prepared from {2-[3-(3-cyano-phenyl)-3-oxo-propionyl-amino]-5-dimethylamino-4-phenylethynyl-phenyl}-carbamic acid tert.-butyl ester (Example M4) by treatment with TFA in CH$_2$Cl$_2$ according to the general procedure N. Obtained as an orange solid (65 mg).

MS (ISP) 405 [(M+H)$^+$]; mp 215–216° C.

Example 5

7-Dimethylamino-8-phenylethynyl-4-(3-[1,2,3]triazol-1-yl-phenyl)-1,3-dihydro-benzo[b][1,4]diazepin-2-one The title compound was prepared from {5-dimethylamino-2-[3-oxo-3-(3-[1,2,3]triazol-1-yl-phenyl)-propionylamino]-4-phenylethynyl-phenyl}-carbamic acid tert.-butyl ester (Example M5) by treatment with TFA in CH$_2$Cl$_2$ according to the general procedure N. Obtained as an orange solid (76 mg).

MS (ISP) 447 [(M+H)$^+$]; mp 185–186° C.

Example 6

8-Chloro-7-dimethylamino-4-[3-(3-methyl-isoxazol-5-yl)-phenyl]-1,3-dihydro-benzo[b][1,4]diazepin-2-one The title compound was prepared from (4-chloro-5-dimethylamino-2-{3-[3-(3-methyl-isoxazol-5-yl)-phenyl]-3-oxo-propionylamino}-phenyl)-carbamic acid tert.-butyl ester (Example M6) by treatment with TFA in CH$_2$Cl$_2$ according to the general procedure N. Obtained as a light yellow solid (68 mg).

MS (EI) 394 (M$^+$) and 396 [(M+2)$^+$]; mp 212–215° C.

Example 7

8-(2,3-Difluoro-phenyl)-7-dimethylamino-4-[3-(5-hydroxymethyl-[1,2,3]triazol-1-yl)-phenyl]-1,3-dihydro-benzo[b][1,4]diazepin-2-one The title compound was prepared from (RS)-[2-dimethylamino-2',3'-difluoro-5-(3-oxo-3-{3-[5-(tetrahydro-pyran-2-yloxymethyl)-[1,2,3]triazol-1-yl]-phenyl}-propionylamino)-biphenyl-4-yl]-carbamic acid tert.-butyl ester (Example M7) by treatment with TFA in CH$_2$Cl$_2$ according to the general procedure N. Obtained as a yellow solid (26 mg).

MS (ISP) 489 [(M+H)$^+$].

Example 8

8-(2,3-Difluoro-phenyl)-7-dimethylamino-4-(3-[1,2,3]triazol-1-yl-phenyl)-1,3-dihydro-benzo[b][1,4]diazepin-2-one The title compound was prepared from {2-dimethylamino-2',3'-difluoro-5-[3-oxo-3-(3-[1,2,3]triazol-1-yl-phenyl)-propionylamino]-biphenyl-4-yl}-carbamic acid tert.-butyl ester (Example M8) by treatment with TFA in CH$_2$Cl$_2$ according to the general procedure N. Obtained as a yellow solid (47 mg).

MS (ISP) 459 [(M+H)$^+$]; mp 197–199° C.

Example 9

3-[7-(2,3-Difluoro-phenyl)-8-dimethylamino-4-oxo-4,5-dihydro-3H-benzo[b][1,4]diazepin-2-yl]-benzonitrile The title compound was prepared from {5-[3-(3-cyano-phenyl)-3-oxo-propionyl-amino]-2-dimethylamino-2',3'-difluoro-biphenyl-4-yl}-carbamic acid tert.-butyl ester (Example M9) by treatment with TFA in CH$_2$Cl$_2$ according to the general procedure N. Obtained as a light yellow solid (75 mg).

MS (ISP) 417 [(M+H)$^+$]; mp 228–229° C.

Example 10

8-Chloro-7-dimethylamino-4-[2-(3-methyl-isoxazol-5-yl)-pyridin-4-yl]-1,3-dihydro-benzo[b][1,4]diazepin-2-one The title compound was prepared from (4-chloro-5-dimethylamino-2-{3-[2-(3-methyl-isoxazol-5-yl)-pyridin-4-yl]-3-oxo-propionylamino}-phenyl)-carbamic acid tert.-butyl ester (Example M10) by treatment with TFA in CH$_2$Cl$_2$ according to the general procedure N. Obtained as a yellow solid (111 mg).

MS (ISP) 396 [(M+H)$^+$] and 398 [(M+H+2)$^+$]; mp >250° C.

Example 11

8-Chloro-7-(2-methoxy-ethyl)-methyl-amino]-4-[3-(3-methyl-isoxazol-5-yl)-phenyl]-1,3-dihydro-benzo[b][1,4]diazepin-2-one The title compound was prepared from (4-chloro-5-[(2-methoxy-ethyl)-methyl-amino]-2-{3-[3-(3-methyl-isoxazol-5-yl)-phenyl]-3-oxo-propionylamino}-phenyl)-carbamic acid tert.-butyl ester (Example M11) by treatment with TFA in CH$_2$Cl$_2$ according to the general procedure N. Obtained as a yellow solid (115 mg).

MS (EI) 438 (M$^+$) and 440 [(M+2)$^+$]; mp 182° C.

Example 12

8-Chloro-7-[(2-methoxy-ethyl)-methyl-amino]-4-[2-(3-methyl-isoxazol-5-yl)-pyridin-4-yl]-1,3-dihydro-benzo[b][1,4]diazepin-2-one The title compound was prepared from (4-chloro-5-[(2-methoxy-ethyl)-methyl-amino]-2-{3-[2-(3-methylisoxazol-5-yl)-pyridin-4-yl]-3-oxo-propionylamino}-phenyl)-carbamic acid tert.-butyl ester (Example M12) by treatment with TFA in CH$_2$Cl$_2$ according to the general procedure N. Obtained as a yellow solid (106 mg).

MS (ISP) 440 [(M+H)$^+$] and 442 [(M+H+2)$^+$]; mp 213° C.

Example 13

8-Chloro-4-[3-(5-hydroxymethyl-[1,2,3]triazol-1-yl)-phenyl]-7-[(2-methoxy-ethyl)-methyl-amino]-1,3-dihydro-benzo[b][1,4]diazepin-2-one The title compound was prepared from (RS)-[4-chloro-5-[(2-methoxy-ethyl)-methyl-amino]-2-(3-oxo-3-{3-[5-(tetrahydro-pyran-2-yloxymethyl)-[1,2,3]triazol-1-yl]-phenyl}-propionylamino)-phenyl]-carbamic acid tert.-butyl ester (Example M13) by treatment with TFA in CH$_2$Cl$_2$ according to the general procedure N. Obtained as a beige solid (50 mg).

MS (ISP) 455 [(M+H)$^+$] and 457 [(M+H+2)$^+$]; mp 185° C.

Example 14

8-Chloro-7-[(2-methoxy-ethyl)-methyl-amino]-4-(3-[1,2,3]triazol-1-yl-phenyl)-1,3-dihydro-benzo[b][1,4]diazepin-2-one The title compound was prepared from {4-chloro-5-[(2-methoxy-ethyl)-methyl-amino]-2-[3-oxo-3-(3-[1,2,3]triazol-1-yl-phenyl)-propionylamino]-phenyl}-carbamic acid tert.-butyl ester (Example M14) by treatment with TFA in CH$_2$Cl$_2$ according to the general procedure N. Obtained as a yellow solid (69 mg).

MS (ISP) 425 [(M+H)$^+$] and 427 [(M+H+2)$^+$]; mp 156° C.

Example 15

4-(7-Chloro-8-dimethylamino-4-oxo-4,5-dihydro-3H-benzo[b][1,4]diazepin-2-yl)-pyridine-2-carbonitrile The title compound was prepared from {4-chloro-2-[3-(2-cyano-pyridin-4-yl)-3-oxo-propionylamino]-5-dimethylamino-phenyl}-carbamic acid tert.-butyl ester (Example M15) by treatment with TFA in CH$_2$Cl$_2$ according to the general procedure N. Obtained as a yellow solid (50 mg).

MS (ISP) 340 [(M+H)$^+$] and 342 [(M+2+H)$^+$]; mp 216° C.

Example 16

8-Chloro-7-dimethylamino-4-[3-(2-methyl-2H-pyrazol-3-yl)-phenyl]-1,3-dihydro-benzo[b][1,4]diazepin-2-one The title compound was prepared from (4-chloro-5-dimethylamino-2-{3-[3-(2-methyl-2H-pyrazol-3-yl)-phenyl]-3-oxo-propionylamino}-phenyl)-carbamic acid tert.-butyl ester (Example M16) by treatment with TFA in CH$_2$Cl$_2$ according to the general procedure N. Obtained as an off-white solid (67 mg).

MS (ISP) 394 [(M+H)$^+$] and 396 [(M+2+H)$^+$]; mp 225° C.

Example 17

7-Dimethylamino-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-dimethylamino-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M17) by treatment with TFA in CH$_2$Cl$_2$ according to the general procedure N. Obtained as an off-white solid (62 mg).

MS (ISP) 445 [(M+H)$^+$]; mp 210° C.

Example 18

7-Dimethylamino-4-[3-(3-methyl-isoxazol-5-yl)-phenyl]-8-trifluoromethyl-1,3-dihydro-benzo[b][1,4]diazepin-2-one The title compound was prepared from (5-dimethylamino-2-{3-[3-(3-methyl-isoxazol-5-yl)-phenyl]-3-oxo-propionylamino}-4-trifluoromethyl-phenyl)-carbamic acid tert.-butyl ester (Example M18) by treatment with TFA in CH$_2$Cl$_2$ according to the general procedure N. Obtained as an off-white solid (28 mg).

MS (ISP) 429 [(M+H)$^+$]; mp 223° C.

Example 19

8-Chloro-7-dimethylamino-4-[3-(4-hydroxymethyl-thiazol-2-yl)-phenyl]-1,3-dihydro-benzo[b][1,4]diazepin-2-one The title compound was prepared from 3-(7-chloro-8-dimethylamino-4-oxo-4,5-dihydro-3H-benzo[b][1,4]diazepin-2-yl)-thiobenzamide {prepared from 3-(7-chloro-8-dimethylamino-4-oxo-4,5-dihydro-3H-benzo[b][1,4]diazepin-2-yl)-benzonitrile (Example 1) as follows: To a solution of hexamethyldisilthiane (0.55 mL, 2.6 mmol) in 1,3-dimethyl-2-imidazolidinone (2.6 mL) was added at 20° C. sodium methoxide (0.13 g, 2.5 mmol). The mixture was stirred for 15 min. and the blue solution formed was then added to a solution of 3-(7-chloro-8-dimethylamino-4-oxo-4,5-dihydro-3H-benzo[b][1,4]diazepin-2-yl)-benzonitrile (Example 1) (0.34 g, 1.0 mmol) in 1,3-dimethyl-2-imidazolidinone (2 mL). The mixture was stirred for 3 h at 20° C. and then poured into water. The precipitate was isolated by filtration and triturated with acetone to give 3-(7-chloro-8-dimethylamino-4-oxo-4,5-dihydro-3H-benzo[b][1,4]diazepin-2-yl)-thiobenzamide (0.35 g) as yellow solid, mp 234° C. dec.MS (ISP) 373.2 [(M+H)$^+$].} (0.71 g, 1.9 mmol), 1,3-dichloro-2-propanone (0.36 g, 2.85 mmol) and sodium bicarbonate (0.24 g, 2.85 mmol) in 1,4-dioxane (15 mL) was heated to 60° C. for 48 h. The clear solution was evaporated in vacuum. The a solution of the residue in 1,4-dioxane (5 mL) was added 2N KOH (3.8 mL) and the mixture was stirred at 20° C. for 1 h. Water (100 mL) was added and the mixture was stirred for 0.5 h.

The precipitate formed was collected by filtration and crystallized from dichloromethane to give the title compound (0.69 g) as pale-yellow solid.

MS (ISP) 427.2[(M+H)$^+$]; mp 134° C. dec.

Example 20

8-Chloro-7-dimethylamino-4-[3-(5-dimethylaminomethyl-[1,2,3]triazol-1-yl)-phenyl]-1,3-dihydro-benzo[b][1,4]diazepin-2-one The title compound was prepared from (4-chloro-5-dimethylamino-2-{3-[3-(5-dimethylaminomethyl-[1,2,3]triazol-1-yl)-phenyl]-3-oxo-propionylamino}-phenyl)-carbamic acid tert.-butyl ester (Example M19) by treatment with TFA in CH$_2$Cl$_2$ according to the general procedure N. Obtained as a beige solid (34 mg).

MS (ISP) 438 [(M+H)⁺] and 440 [(M+2+H)⁺]; mp 145–160° C.

Example 21

8-Chloro-7-dimethylamino-4-[3-(3-methoxymethyl-isoxazol-5-yl)-phenyl]-1,3-dihydro-benzo[b][1,4]diazepin-2-one The title compound was prepared from (4-chloro-5-dimethylamino-2-{3-[3-(3-methoxymethyl-isoxazol-5-yl)-phenyl]-3-oxo-propionylamino}-phenyl)-carbamic acid tert.-butyl ester (Example M20) by treatment with TFA in CH₂Cl₂ according to the general procedure N. Obtained as a light yellow solid (157 mg).

MS (ISP) 425 [(M+H)⁺] and 427 [(M+2+H)⁺]; mp 191° C.

Example 22

4-(8-Dimethylamino-4-oxo-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-dimethylamino-4-trifluoromethyl-phenyl}-carbamic acid tert.-butyl ester (Example M21) by treatment with TFA in CH₂Cl₂ according to the general procedure N. Obtained as a yellow solid (158 mg).

MS (ISP) 374 [(M+H)⁺]; mp 248° C.

Example 23

8-(2-Fluoro-phenyl)-4-(3-imidazol-1-yl-phenyl)-7-(2,2,2-trifluoro-ethoxy)-1,3-dihydro-benzo[b][1,4]diazepin-2-one The title compound was prepared from [2'-fluoro-5-[3-(3-imidazol-1-yl-phenyl)-3-oxo-propionylamino]-2-(2,2,2-trifluoro-ethoxy)-biphenyl-4-yl]-carbamic acid tert.-butyl ester (Example M22) by treatment with TFA in CH₂Cl₂ according to the general procedure N. Obtained as a brown solid (50 mg).

MS (EI) 494 (M+); mp 208–210° C.

Example 24

8-(2-Fluoro-phenyl)-4-[3-(3-methyl-isoxazol-5-yl)-phenyl]7-(2,2,2-trifluoro-ethoxy)-1,3-dihydro-benzo[b][1,4]diazepin-2-one The title compound was prepared from [2'-fluoro-5-{3-[3-(3-methyl-isoxazol-5-yl)-phenyl]-3-oxo-propionylamino}-2-(2,2,2-trifluoro-ethoxy)-biphenyl-4-yl]-carbamic acid tert.-butyl ester (Example M23) by treatment with TFA in CH₂Cl₂ according to the general procedure N. Obtained as a light yellow solid (21 mg).

MS (EI) 509 (M⁺); mp 218–220° C.

Example 25

8-(2-Fluoro-phenyl)-4-(3-[1,2,3]triazol-1-yl-phenyl)-7-(2,2,2-trifluoro-ethoxy)-1,3-dihydro-benzo[b][1,4]diazepin-2-one The title compound was prepared from [2'-fluoro-5-[3-oxo-3-(3-[1,2,3]triazol-1-yl-phenyl)-propionylamino]-2-(2,2,2-trifluoro-ethoxy)-biphenyl-4-yl]-carbamic acid tert.-butyl ester (Example M24) by treatment with TFA in CH₂Cl₂ according to the general procedure N. Obtained as an orange solid (45 mg).

MS (EI) 495 (M⁺).

Example 26

8-(2-Fluoro-phenyl)-4-[3-(5-hydroxymethyl-[1,2,3]triazol-1-yl)-phenyl]-7-(2,2,2-trifluoro-ethoxy)-1,3-dihydro-benzo[b][1,4]diazepin-2-one The title compound was prepared from (RS)-[2'-fluoro-5-(3-oxo-3-{3-[5-(tetrahydro-pyran-2-yloxymethyl)-[1,2,3]triazol-1-yl]-phenyl}-propionylamino)-2-(2,2,2-trifluoro-ethoxy)-biphenyl-4-yl]-carbamic acid tert.-butyl ester (Example M25) by treatment with TFA in CH₂Cl₂ according to the general procedure N. Obtained as an off-white solid (10 mg).

MS (ISP) 526 [(M+H)⁺]; mp 232–234° C.

Example 27

8-Chloro-7-dimethylamino-4-[3-(4-hydroxymethyl-oxazol-2-yl)-phenyl]-1,3-dihydro-benzo[b][1,4]diazepin-2-one The title compound was prepared from (2-amino-4-chloro-5-dimethylamino-phenyl)-carbamic acid tert.-butyl ester (Example J2) (170 mg) and (RS)-3-oxo-3-{3-[4-(tetrahydro-pyran-2-yloxymethyl)-oxazol-2-yl]-phenyl}-propionic acid tert-butyl ester (Example K11) (270 mg) according to the general procedure M. The obtained material was deprotected and cyclized by treatment with TFA in CH₂Cl₂ according to the general procedure N. Obtained as a light yellow solid (110 mg).

MS (ISP) 411.2 [(M+H)⁺]; mp 193–195° C.

Example 28

8-Chloro-7-(ethyl-methyl-amino)-4-[3-(5-hydroxymethyl-[1,2,3]triazol-1-yl)-phenyl]-1,3-dihydro-benzo[b][1,4]diazepin-2-one The title compound was prepared from (RS)-[4-chloro-5-(ethyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M26) (0.5 g, 0.8 mmol) by treatment with TFA in CH₂Cl₂ according to the general procedure N. Obtained as an off-white solid (60 mg).

MS (ISP) 425.4 [(M+H)⁺]; mp 206° C. (dec.).

Example 29

8-Chloro-7-(methyl-propyl-amino)-4-[3-(5-hydroxymethyl-[1,2,3]triazol-1-yl)-phenyl]-1,3-dihydro-benzo[b][1,4]diazepin-2-one The title compound was prepared from (RS)-[4-chloro-5-(methyl-propyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M27) (0.4 g, 0.64 mmol) by treatment with TFA in CH₂Cl₂ according to the general procedure N. Obtained as a pale yellow solid (110 mg).

MS (ISP) 439.3 [(M+H)⁺]; mp 178° C. (dec.).

Example 30

8-Chloro-7-(diethyl-amino)-4-[3-(5-hydroxymethyl-[1,2,3]triazol-1-yl)-phenyl]-1,3-dihydro-benzo[b][1,4]diazepin-2-one The title compound was prepared from (RS)-[4-chloro-5-(diethyl-amino)-2-(3-oxo-3-{3-[5-(tetrahydro-pyran-2- yloxymethyl)-[1,2,3]triazol-1-yl]-phenyl}-propionylamino)-phenyl]-carbamic acid tert-butyl ester (Example M28) (0.53 g, 0.827 mmol) by treatment with TFA in CH$_2$Cl$_2$ according to the general procedure N. Obtained as an off-white solid (210 mg).

MS (ISP) 439.3 [(M+H)$^+$]; mp 208° C. (dec.).

Example 31

8-Chloro-7-dimethylamino-4-[3-(3-hydroxymethyl-isoxazol-5-yl)-phenyl]-1,3-dihydro-benzo[b][1,4]diazepin-2-one The title compound was prepared from (RS)-[4-chloro-5-dimethylamino-2-(3-oxo-3-{3-[3-(tetrahydro-pyran-2-yloxymethyl)-isoxazol-5-yl]-phenyl}-propionylamino)-phenyl]-carbamic acid tert.-butyl ester (Example M29) (81 mg, 0.13 mmol) by treatment with TFA in CH$_2$Cl$_2$ according to the general procedure N. Obtained as a yellow solid (38 mg).

MS (ISP) 411 [(M+H)$^+$] and 413 [(M+2+H)$^+$]; mp 132° C.

Example 32

8-Chloro-4-[3-(5-hydroxymethyl-[1,2,3]triazol-1-yl)-phenyl]-7-pyrrolidin-1-yl-1,3-dihydro-benzo[b][1,4]diazepin-2-one The title compound was prepared from (RS)-[4-chloro-2-(3-oxo-3-{3-[5-(tetrahydro-pyran-2-yloxymethyl)-[1,2,3]triazol-1-yl]-phenyl}-propionylamino)-5-pyrrolidin-1-yl-phenyl]-carbamic acid tert.-butyl ester (Example M30) by treatment with TFA in CH$_2$Cl$_2$ according to the general procedure N. Obtained as a yellow solid (58 mg).

MS (ISP) 437 [(M+H)$^+$] and 439 [(M+2+H)$^+$]; mp 193–197° C.

Example 33

7-Dimethylamino-4-[3-(2-methyl-2H-pyrazol-3-yl)-phenyl]-8-trifluoromethyl-1,3-dihydro-benzo[b][1,4]diazepin-2-one The title compound was prepared from (5-dimethylamino-2-{3-[3-(2-methyl-2H-pyrazol-3-yl)-phenyl]-3-oxo-propionylamino}-4-trifluoromethyl-phenyl)-carbamic acid tert.-butyl ester (Example M31) (78 mg, 0.14 mmol) by treatment with TFA in CH$_2$Cl$_2$ according to the general procedure N. Obtained as an off-white solid (48 mg).

MS (ISP) 428 [(M+H)$^+$]; mp 225° C.

Example 34

4-[7-Chloro-8-(cyclopropyl-methyl-amino)-4-oxo-4,5-dihydro-3H-benzo[b][1,4]diazepin-2-yl]-pyridine-2-carbonitrile The title compound was prepared from [2-amino-4-chloro-5-(cyclopropyl-methyl-amino)-phenyl]-carbamic acid tert.-butyl ester (Example J11) (150 mg, 0.5 mmol) and 3-(2-cyano-pyridin-4-yl)-3-oxo-propionic acid tert.-butyl ester (Example K3) (150 mg, 0.61 mmol) according to the general procedure M. The obtained material was deprotected and cyclized by treatment with TFA in CH$_2$Cl$_2$ according to the general procedure N. Obtained as a yellow solid (69 mg).

MS (ISN) 364.1 [(M–H)$^-$] and 366 [(M+2–H)$^-$]; mp 199–201° C.

Example 35

8-Chloro-7-dimethylamino-4-[3-(4-hydroxymethyl-3-methyl-isoxazol-5-yl)-phenyl]-1,3-dihydro-benzo[b][1,4]diazepin-2-one The title compound was prepared from (RS)-[4-chloro-5-dimethylamino-2-(3-{3-[3-methyl-4-(tetrahydro-pyran-2-yloxymethyl)-isoxazol-5-yl]-phenyl}-3-oxo-propionylamino)-phenyl]-carbamic acid tert.-butyl ester (Example M32) by treatment with TFA in CH$_2$Cl$_2$ according to the general procedure N. Obtained as a yellow solid (60 mg).

MS (ISP) 425 [(M+H)$^+$] and 427 [(M+2+H)$^+$]; mp 232–233° C.

Example 36

8-Chloro-7-(cyclopropyl-methyl-amino)-4-[3-(3-methyl-isoxazol-5-yl)-phenyl]-1,3-dihydro-benzo[b][1,4]diazepin-2-one The title compound was prepared from [2-amino-4-chloro-5-(cyclopropyl-methyl-amino)-phenyl]-carbamic acid tert.-butyl ester (Example J11) (156 mg, 0.5 mmol) and 3-[3-(3-methyl-isoxazol-5-yl)-phenyl]-3-oxo-propionic acid tert.-butyl ester (Example K4) (170 mg, 0.56 mmol) according to the general procedure M. The obtained material was deprotected and cyclized by treatment with TFA in CH$_2$Cl$_2$ according to the general procedure N. Obtained as a yellow solid (49 mg).

MS (ISP) 421.3 [(M+H)$^+$] and 423 [(M+2+H)$^+$]; mp 195–197° C.

Example 37

8-Chloro-7-(cyclopropyl-methyl-amino)-4-[3-(5-hydroxymethyl-[1,2,3]triazol-1-yl)-phenyl]-1,3-dihydro-benzo[b][1,4]diazepin-2-one The title compound was prepared from (RS)-[4-chloro-5-(cyclopropyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert.-butyl ester (Example M33) (200 mg, 0.313 mmol) by treatment with TFA in CH$_2$Cl$_2$ according to the general procedure N. Obtained as a light yellow solid (54 mg).

MS (ISP) 437.3 [(M+H)$^+$] and 439 [(M+2+H)$^+$].

Example 38

7-Dimethylamino-4-[3-(5-dimethylaminomethyl-[1,2,3]triazol-1-yl)-phenyl]-8-trifluoromethyl-1,3-dihydro-benzo[b][1,4]diazepin-2-one The title compound was prepared from (5-dimethylamino-2-{3-[3-(5-dimethyl-aminomethyl-[1,2,3]triazol-1-yl)-phenyl]-3-oxo-propionylamino}-4-trifluoromethyl-phenyl)-carbamic acid tert.-butyl ester (Example M34) (126 mg, 0.214 mmol) by treatment with TFA in CH$_2$Cl$_2$ according to the general procedure N. Obtained as a light yellow solid (23 mg).

MS (ISP) 472 [(M+H)$^+$]; mp 200° C.

Example 39

8-Chloro-7-dimethylamino-4-[3-(5-hydroxymethyl-2-methyl-2H-pyrazol-3-yl)-phenyl]-1,3-dihydro-benzo[b][1,4]diazepin-2-one The title compound was prepared from (RS)-[4-chloro-5-dimethylamino-2-(3-{3-[2-methyl-5-(tetrahydro-pyran-2-yloxymethyl)-2H-pyrazol-3-yl]-phenyl}-3-oxo-propionylamino)-phenyl]-carbamic acid tert.-butyl ester (Example M35) (278 mg, 0.44 mmol) by treatment with TFA in CH$_2$Cl$_2$ according to the general procedure N. Obtained as a light yellow solid (129 mg).

MS (ISP) 424 [(M+H)⁺] and 426 [(M+2+H)⁺]; mp 184° C.

Example 40

4-(4-Oxo-8-pyrrolidin-1-yl-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-pyrrolidin-1-yl-4-trifluoromethyl-phenyl}-carbamic acid tert.-butyl ester (Example M36) by treatment with TFA in CH$_2$Cl$_2$ according to the general procedure N. Obtained as an orange solid (65 mg).

MS (ISP) 400.4 [(M+H)⁺]; mp 188° C. (dec.).

Example 41

4-[3-(5-Hydroxymethyl-[1,2,3]triazol-1-yl)-phenyl]-7-pyrrolidin-1-yl-8-trifluoromethyl-1,3-dihydro-benzo[b][1,4]diazepin-2-one The title compound was prepared from (RS)-[2-(3-oxo-3-{3-[5-(tetrahydro-pyran-2-yloxymethyl)-[1,2,3]triazol-1-yl]-phenyl}-propionylamino)-5-pyrrolidin-1-yl-4-trifluoromethyl-phenyl]-carbamic acid tert.-butyl ester (Example M37) by treatment with TFA in CH$_2$Cl$_2$ according to the general procedure N. Obtained as a light yellow solid (33 mg).

MS (ISP) 471.2 [(M+H)⁺]; mp 134° C.

Example 42

7-Dimethylamino-8-fluoro-4-[3-(5-hydroxymethyl-[1,2,3]triazol-1-yl)-phenyl]-1,3-dihydro-benzo[b][1,4]diazepin-2-one The title compound was prepared from (RS)-[5-dimethylamino-4-fluoro-2-(3-oxo-3-{3-[5-(tetrahydro-pyran-2-yloxymethyl)-[1,2,3]triazol-1-yl]-phenyl}-propionyl-amino)-phenyl]-carbamic acid tert.-butyl ester (Example M38) (375 mg, 0.63 mmol) by treatment with TFA in CH$_2$Cl$_2$ according to the general procedure N. Obtained as a yellow solid (115 mg).

MS (ISP) 395 [(M+H)⁺]; mp 75° C.

Example 43

7-Dimethylamino-4-[3-(5-dimethylaminomethyl-[1,2,3]triazol-1-yl)-phenyl]-8-fluoro-1,3-dihydro-benzo[b][1,4]diazepin-2-one The title compound was prepared from (5-dimethylamino-2-{3-[3-(5-dimethyl-aminomethyl-[1,2,3]triazol-1-yl)-phenyl]-3-oxo-propionylamino}-4-fluoro-phenyl)-carbamic acid tert.-butyl ester (Example M39) (170 mg, 0.32 mmol) by treatment with TFA in CH$_2$Cl$_2$ according to the general procedure N. Obtained as a yellow solid (34 mg).

MS (ISP) 422 [(M+H)⁺]; mp 181° C.

Example 44

7-Dimethylamino-8-fluoro-4-[3-(3-hydroxymethyl-isoxazol-5-yl)-phenyl]-1,3-dihydro-benzo[b][1,4]diazepin-2-one The title compound was prepared from (RS)-[5-dimethylamino-4-fluoro-2-(3-oxo-3-{3-[3-(tetrahydro-pyran-2-yloxymethyl)-isoxazol-5-yl]-phenyl}-propionylamino)-phenyl]-carbamic acid tert.-butyl ester (Example M40) (314 mg, 0.53 mmol) by treatment with TFA in CH$_2$Cl$_2$ according to the general procedure N. Obtained as a yellow solid (95 mg).

MS (ISP) 395 [(M+H)⁺]; mp 187° C.

Example 45

8-Chloro-7-dimethylamino-4-[3-(5-pyrrolidin-1-ylmethyl-[1,2,3]triazol-1-yl)-phenyl]-1,3-dihydro-benzo[b][1,4]diazepin-2-one The title compound was prepared from 8-chloro-7-dimethylamino-4-[3-(5-hydroxy-methyl-[1,2,3]triazol-1-yl)-phenyl]-1,3-dihydro-benzo[b][1,4]diazepin-2-one (Example 3) (123 mg, 0.3 mmol) by treatment with SOCl$_2$ (0.044 mL, 0.6 mmol) in CH$_2$Cl$_2$ (2 mL) from 23° C. to reflux for 15 min, followed by evaporation to dryness. The crude chloride was dissolved in DMF (2 mL) and stirred with cat. amount of NaI and pyrrolidine (0.248 mL, 3.0 mmol) at 23° C. until tlc indicated complete conversion of the chloride. The reaction mixture was taken up in EtOAc, washed with water and brine, dried over Na$_2$SO$_4$. Removal of the solvent in vacuum left a yellow semisolid, which was purified by silica gel column chromatography. Obtained as a yellow solid (101 mg).

MS (ISP) 464 [(M+H)⁺] and 466 [(M+2+H)⁺]; mp 180–182° C.

Example 46

7-Dimethylamino-4-[3-(3-hydroxymethyl-isoxazol-5-yl)-phenyl]-8-trifluoromethyl-1,3-dihydro-benzo[b][1,4]diazepin-2-one The title compound was prepared from (RS)-[5-dimethylamino-2-(3-oxo-3-{3-[3-(tetrahydro-pyran-2-yloxymethyl)-isoxazol-5-yl]-phenyl}-propionylamino)-4-trifluoromethyl-phenyl]-carbamic acid tert.-butyl ester (Example M41) (680 mg, 1.05 mmol) by treatment with TFA in CH$_2$Cl$_2$ according to the general procedure N. Obtained as a yellow solid (294 mg).

MS (ISP) 455 [(M+H)⁺]; mp 219° C.

Example 47

7-Dimethylamino-8-fluoro-4-[3-(3-methyl-isoxazol-5-yl)-phenyl-1,3-dihydro-benzo[b][1,4]diazepin-2-one The title compound was prepared from (5-dimethylamino-4-fluoro-2-{3-[3-(3-methyl-isoxazol-5-yl)-phenyl]-3-oxo-propionylamino}-phenyl)-carbamic acid tert.-butyl ester (Example M42) (233 mg, 0.47 mmol) by treatment with TFA in CH$_2$Cl$_2$ according to the general procedure N. Obtained as a yellow-brown solid (59 mg).

MS (ISP) 379 [(M+H)⁺]; mp 124° C.

Example 48

4-[3-(5-Azetidin-1-ylmethyl-[1,2,3]triazol-1-yl)-phenyl]-8-chloro-7-dimethylamino-1,3-dihydro-benzo[b][1,4]diazepin-2-one The title compound was prepared from 8-chloro-7-dimethylamino-4-[3-(5-hydroxymethyl-[1,2,3]triazol-1-yl)-phenyl]-1,3-dihydro-benzo[b][1,4]diazepin-2-one (Example 3) (123 mg, 0.3 mmol) by treatment with SOCl$_2$ (3 eq.) and trimethylen imine (10 eq.) as described in Example 45. Obtained as a yellow solid (17 mg).

MS (ISP) 450 [(M+H)⁺]; mp 153° C.

Example 49

8-Chloro-7-dimethylamino-4-[3-(5-hydroxymethyl-isoxazol-3-yl)-phenyl]-1,3-dihydro-benzo[b][1,4]diazepin-2-one The title compound was prepared from (RS)-[4-chloro-5-dimethylamino-2-(3-oxo-3-{3-(5-(tetrahydro-pyran-2-yloxymethyl)-isoxazol-3-yl]-phenyl}-propionylamino)-phenyl]-carbamic acid tert.-butyl ester (Example M43) by treatment with TFA in CH$_2$Cl$_2$ according to the general procedure N. Obtained as a yellow solid (113 mg).

MS (ISP) 411.3 [(M+H)⁺] and 413 [(M+2+H)⁺]; mp 211° C. (dec.).

Example 50

8-Chloro-4-[3-(5-hydroxymethyl-[1,2,3]triazol-1-yl)-phenyl]-7-piperidin-1-yl-1,3-dihydro-benzo[b][1,4]diazepin-2-one The title compound was prepared from (RS)-[4-chloro-2-(3-oxo-3-{3-[5-(tetrahydro-pyran-2-yloxymethyl)-[1,2,3]triazol-1-yl]-phenyl}-propionylamino)-5-piperidin-1-yl-phenyl]-carbamic acid tert.-butyl ester (Example M44) by treatment with TFA in CH$_2$Cl$_2$ according to the general procedure N. Obtained as a light yellow solid (99 mg).

MS (ISP) 451.3 [(M+H)⁺] and 453 [(M+2+H)⁺]; mp 246° C. (dec.).

Example 51

7-Dimethylamino-4-[3-(5-hydroxymethyl-isoxazol-3-yl)-phenyl]-8-trifluoromethyl-1,3-dihydro-benzo[b][1,4]diazepin-2-one The title compound was prepared from (RS)-[5-dimethylamino-2-(3-oxo-3-{3-[5-(tetrahydro-pyran-2-yloxymethyl)-isoxazol-3-yl]-phenyl}-propionylamino)-4-trifluoromethyl-phenyl]-carbamic acid tert.-butyl ester (Example M45) by treatment with TFA in CH$_2$Cl$_2$ according to the general procedure N. Obtained as a light yellow solid (103 mg).

MS (ISP) 445.3 [(M+H)⁺]; mp 211° C. (dec.).

Example 52

8-Chloro-7-dimethylamino-4-(3-pyrazol-1-yl-phenyl)-1,3-dihydro-benzo[b][1,4]diazepin-2-one The title compound was prepared from {4-chloro-5-dimethylamino-2-[3-oxo-3-(3-pyrazol-1-yl-phenyl)-propionylamino]-phenyl}-carbamic acid tert.-butyl ester (Example M46) by treatment with TFA in CH$_2$Cl$_2$ according to the general procedure N. Obtained as a yellow solid (75 mg).

MS (ISP) 380 [(M+H)⁺] and 382 [(M+2+H)⁺]; mp 231–234° C.

Example 53

7-Dimethylamino-4-[3-(3-pyrrolidin-1-ylmethyl-isoxazol-5-yl)-phenyl]-8-trifluoromethyl-1,3-dihydro-benzo[b][1,4]diazepin-2-one The title compound was prepared from 7-dimethylamino-4-[3-(3-hydroxymethyl-isoxazol-5-yl)-phenyl]-8-trifluoromethyl-1,3-dihydro-benzo[b][1,4]diazepin-2-one (Example 46) (111 mg, 0.25 mmol) by treatment with SOCl$_2$ (3 eq.) and pyrrolidine (10 eq.) as described in Example 45. Obtained as a yellow solid (28 mg).

MS (ISP) 498 [(M+H)⁺]; mp 160° C.

Example 54

7-Dimethylamino-4-[3-(3-morpholin-4-ylmethyl-isoxazol-5-yl)-phenyl]-8-trifluoromethyl-1,3-dihydro-benzo[b][1,4]diazepin-2-one The title compound was prepared from 7-dimethylamino-4-[3-(3-hydroxymethyl-isoxazol-5-yl)-phenyl]-8-trifluoromethyl-1,3-dihydro-benzo[b][1,4]diazepin-2-one (Example 46) (53 mg, 0.12 mmol) by treatment with SOCl$_2$ (3 eq.) and morpholine (10 eq.) as described in Example 45. Obtained as a yellow solid (33 mg).

MS (ISP) 514 [(M+H)⁺]; mp 165° C.

Example 55

7-Dimethylamino-4-[3-(3-dimethylaminomethyl-isoxazol-5-yl)-phenyl]-8-trifluoromethyl-1,3-dihydro-benzo[b][1,4]diazepin-2-one The title compound was prepared from 7-dimethylamino-4-[3-(3-hydroxymethyl-isoxazol-5-yl)-phenyl]-8-trifluoromethyl-1,3-dihydro-benzo[b][1,4]diazepin-2-one (Example 46) (53 mg, 0.12 mmol) by treatment with SOCl$_2$ (3 eq.) and 40% aqueous Me$_2$NH-sol. (10 eq.) as described in Example 45. Obtained as a light yellow solid (21 mg).

MS (ISP) 472 [(M+H)⁺]; mp 160° C.

Example 56

4-(7-Fluoro-4-oxo-8-pyrrolidin-1-yl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-4-fluoro-5-pyrrolidin-1-yl-phenyl}-carbamic acid tert.-butyl ester (Example M47) by treatment with TFA in CH$_2$Cl$_2$ according to the general procedure N. Obtained as an orange solid (54 mg).

MS (ISP) 350 [(M+H)⁺]; mp 278–279° C.

Example 57

8-Fluoro-4-[3-(3-methyl-isoxazol-5-yl)-phenyl]-7-pyrrolidin-1-yl-1,3-dihydro-benzo[b][1,4]diazepin-2-one The title compound was prepared from (4-fluoro-2-{3-[3-(3-methyl-isoxazol-5-yl)-phenyl]-3-oxo-propionylamino}-5-pyrrolidin-1-yl-phenyl)-carbamic acid tert.-butyl ester (Example M48) by treatment with TFA in CH$_2$Cl$_2$ according to the general procedure N. Obtained as a brown solid (86 mg).

MS (ISP) 405 [(M+H)⁺]; mp 236° C.

Example 58

8-Fluoro-4-[3-(5-hydroxymethyl-[1,2,3]triazol-1-yl)-phenyl]-7-pyrrolidin-1-yl-1,3-dihydro-benzo[b][1,4]diazepin-2-one The title compound was prepared from (RS)-[4-fluoro-2-(3-oxo-3-{3-[5-(tetrahydro-pyran-2-yloxymethyl)-[1,2,3]

triazol-1-yl]-phenyl}-propionylamino)-5-pyrrolidin-1-yl-phenyl]-carbamic acid tert.-butyl ester (Example M49) by treatment with TFA in CH$_2$Cl$_2$ according to the general procedure N. Obtained as an orange solid (72 mg).

MS (ISP) 421 [(M+H)$^+$]; mp 184–185° C.

Example 59

4-(8-Azetidin-1-yl-7-chloro-4-oxo-4,5-dihydro-3H-benzo[b][1,4]diazepin-2-yl)-pyridine-2-carbonitrile The title compound was prepared from {5-azetidin-1-yl-4-chloro-2-[3-(2-cyano-pyridin-4-yl)-3-oxo-propionylamino]-phenyl}-carbamic acid tert.-butyl ester (Example M50) by treatment with TFA in CH$_2$Cl$_2$ according to the general procedure N. Obtained as an orange solid (66 mg).

MS (ISP) 352 [(M+H)$^+$] and 354 [(M+2+H)$^+$]; mp 276° C.

Example 60

4-[3-(5-Hydroxymethyl-isoxazol-3-yl)-phenyl]-7-pyrrolidin-1-yl-8-trifluoromethyl-1,3-dihydro-benzo[b][1,4]diazepin-2-one The title compound was prepared from (RS)-[2-(3-oxo-3-{3-[5-(tetrahydro-pyran-2-yloxymethyl)-isoxazol-3-yl]-phenyl}-propionylamino)-5-pyrrolidin-1-yl-4-trifluoromethyl-phenyl]-carbamic acid tert.-butyl ester (Example M51) by treatment with TFA in CH$_2$Cl$_2$ according to the general procedure N. Obtained as a yellow solid (224 mg).

MS (ISP) 471.2 [(M+H)$^+$]; mp 206–208° C.

Example 61

4-(8-Azetidin-1-yl-4-oxo-7-trifluoromethyl-4,5-dihydro-3H-benzo[b][1,4]diazepin-2-yl)-pyridine-2-carbonitrile The title compound was prepared from {5-azetidin-1-yl-2-[3-(2-cyano-pyridin-4-yl)-3-oxo-propionylamino]-4-trifluoromethyl-phenyl}-carbamic acid tert.-butyl ester (Example M52) by treatment with TFA in CH$_2$Cl$_2$ according to the general procedure N. Obtained as an orange solid (51 mg).

MS (ISN) 384.2 [(M–H)$^-$]; mp 241° C.

Example 62

7-Azetidin-1-yl-4-[3-(3-methyl-isoxazol-5-yl)-phenyl]-8-trifluoromethyl-1,3-dihydro-benzo[b][1,4]diazepin-2-one The title compound was prepared from (5-azetidin-1-yl-2-{3-[3-(3-methyl-isoxazol-5-yl)-phenyl]-3-oxo-propionylamino}-4-trifluoromethyl-phenyl)-carbamic acid tert.-butyl ester (Example M53) by treatment with TFA in CH$_2$Cl$_2$ according to the general procedure N. Obtained as a yellow solid (94 mg).

MS (ISP) 441.3 [(M+H)$^+$]; mp 239° C. (dec.).

Example 63

7-Azetidin-1-yl-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-azetidin-1-yl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M54) by treatment with TFA in CH$_2$Cl$_2$ according to the general procedure N. Obtained as a yellow solid (182 mg).

MS (ISP) 457.4 [(M+H)$^+$]; mp 202° C. (dec.).

Example 64

7-Dimethylamino-4-(3-pyrazol-1-yl-phenyl)-8-trifluoromethyl-1,3-dihydro-benzo[b][1,4]diazepin-2-one The title compound was prepared from {5-dimethylamino-2-[3-oxo-3-(3-pyrazol-1-yl-phenyl)-propionylamino]-4-trifluoromethyl-phenyl}-carbamic acid tert.-butyl ester (Example M55) (438 mg, 0.82 mmol) by treatment with TFA in CH$_2$Cl$_2$ according to the general procedure N. Obtained as a light yellow solid (238 mg).

MS (ISP) 414 [(M+H)$^+$]; mp 176° C.

Example 65

7-Dimethylamino-4-(3-[1,2,4]triazol-4-yl-phenyl)-8-trifluoromethyl-1,3-dihydro-benzo[b][1,4]diazepin-2-one The title compound was prepared from {5-dimethylamino-2-[3-oxo-3-(3-[1,2,4]triazol-4-yl-phenyl)-propionylamino]-4-trifluoromethyl-phenyl}-carbamic acid tert.-butyl ester (Example M56) (280 mg, 0.526 mmol) by treatment with TFA in CH$_2$Cl$_2$ according to the general procedure N. Obtained as a yellow solid (121 mg).

MS (ISP) 415.3 [(M+H)$^+$]; mp 247–250° C.

Example 66

7-Dimethylamino-4-(3-imidazol-1-yl-phenyl)-8-trifluoromethyl-1,3-dihydro-benzo[b][1,4]diazepin-2-one The title compound was prepared from {5-dimethylamino-2-[3-(3-imidazol-1-yl-phenyl)-3-oxo-propionylamino]-4-trifluoromethyl-phenyl}-carbamic acid tert.-butyl ester (Example M57) by treatment with TFA in CH$_2$Cl$_2$ according to the general procedure N. Obtained as a yellow solid (132 mg).

MS (ISP) 414 [(M+H)$^+$]; mp 203–205° C.

Example 67

8-Chloro-7-dimethylamino-4-[3-(4-hydroxymethyl-pyrazol-1-yl)-phenyl]-1,3-dihydro-benzo[b][1,4]diazepin-2-one The title compound was prepared from (RS)-[4-chloro-5-dimethylamino-2-(3-oxo-3-{3-[4-(tetrahydro-pyran-2-yloxymethyl)-pyrazol-1-yl]-phenyl}-propionylamino)-phenyl]-carbamic acid tert.-butyl ester (Example M58) (642 mg, 1.05 mmol) by treatment with TFA in CH$_2$Cl$_2$ according to the general procedure N. Obtained as a yellow solid (365 mg).

MS (ISP) 410 [(M+H)$^+$]; mp 211° C.

Example 68

7-Dimethylamino-4-[3-(4-hydroxymethyl-pyrazol-1-yl)-phenyl]-8-trifluoromethyl-1,3-dihydro-benzo[b][1,4]diazepin-2-one The title compound was prepared from (RS)-[5-dimethylamino-2-(3-oxo-3-{3-[4-(tetrahydro-pyran-2- yloxymethyl)-pyrazol-1-yl]-phenyl}-propionylamino)-4-trifluoromethyl-phenyl]-carbamic acid tert-butyl ester (Example M58) (590 mg, 0.91 mmol) by treatment with TFA in CH$_2$Cl$_2$ according to the general procedure N. Obtained as a light yellow solid (299 mg).

MS (ISP) 444 [(M+H)$^+$]; mp 175° C.

Example 69

7-Dimethylamino-4-[3-(4-hydroxymethyl-3-methyl-isoxazol-5-yl)-phenyl]-8-trifluoromethyl-1,3-dihydro-benzo[b][1,4]diazepin-2-one The title compound was prepared from (RS)-[5-dimethylamino-2-(3–{3-[3-methyl-4-(tetrahydro-pyran-2-yloxymethyl)-isoxazol-5-yl]-phenyl}-3-oxo-propionylamino)-4-trifluoromethyl-phenyl]-carbamic acid tert.-butyl ester (Example M60) by treatment with TFA in CH$_2$Cl$_2$ according to the general procedure N. Obtained as a light yellow solid (64 mg).

MS (ISP) 459 [(M+H)$^+$]; mp 207–208° C.

Example 70

7-Dimethylamino-4-[3-(4-hydroxymethyl-isoxazol-3-yl)-phenyl]-8-trifluoromethyl-1,3-dihydro-benzo[b][1,4]diazepin-2-one The title compound was prepared from (RS)-[5-dimethylamino-2-(3-oxo-3-{3-[4-(tetrahydro-pyran-2-yloxymethyl)-isoxazol-3-yl]-phenyl}-propionylamino)-4-trifluoromethyl-phenyl]-carbamic acid tert.-butyl ester (Example M61) by treatment with TFA in CH$_2$Cl$_2$ according to the general procedure N. Obtained as a light yellow solid (50 mg).

MS (ISP) 445 [(M+H)$^+$]; mp 217–219° C.

Example 71

7-Dimethylamino-4-[3-(2-methylsulfanyl-imidazol-1-yl)-phenyl]-8-trifluoromethyl-1,3-dihydro-benzo[b][1,4]diazepin-2-one The title compound was prepared from (5-dimethylamino-2-{3-[3-(2-methylsulfanyl-imidazol-1-yl)-phenyl]-3-oxo-propionylamino}-4-trifluoromethyl-phenyl)-carbamic acid tert.-butyl ester (Example M62) (450 mg, 0.78 mmol) by treatment with TFA in CH$_2$Cl$_2$ according to the general procedure N. Obtained as a yellow solid (253 mg).

MS (ISP) 460 [(M+H)$^+$]; mp 192° C.

Example 72

7-Dimethylamino-4-[3-(4-hydroxymethyl-2-methyl-2H-pyrazol-3-yl)-phenyl]-8-trifluoromethyl-1,3-dihydro-benzo[b][1,4]diazepin-2-one The title compound was prepared from (RS)-[5-dimethylamino-2-(3-{3-[2-methyl-4-(tetrahydro-pyran-2-yloxymethyl)-2H-pyrazol-3-yl]-phenyl}-3-oxo-propionyl-amino)-4-trifluoromethyl-phenyl]-carbamic acid tert.-butyl ester (Example M63) by treatment with TFA in CH$_2$Cl$_2$ according to the general procedure N. Obtained as a yellow solid (272 mg).

MS (ISP) 458 [(M+H)$^+$]; mp 243–244° C.

Example 73

8-Chloro-7-dimethylamino-4-(3-[1,2,4]triazol-1-yl-phenyl)-1,3-dihydro-benzo[b][1,4]diazepin-2-one The title compound was prepared from {4-Chloro-5-dimethylamino-2-[3-oxo-3-(3-[1,2,4]triazol-1-yl-phenyl)-propionylamino]-phenyl}-carbamic acid tert.-butyl ester (Example M64) by treatment with TFA in CH$_2$Cl$_2$ according to the general procedure N. Obtained as a yellow solid (316 mg).

MS (ISP) 381 [(M+H)$^+$] and 383 [(M+2+H)$^+$]; mp 239–241° C.

Example 74

7-Dimethylamino-4-(3-[1,2,4]triazol-1-yl-phenyl)-8-trifluoromethyl-1,3-dihydro-benzo[b][1,4]diazepin-2-one The title compound was prepared from {5-dimethylamino-2-[3-oxo-3-(3-[1,2,4]triazol-1-yl-phenyl)-propionylamino]-4-trifluoromethyl-phenyl}-carbamic acid tert.-butyl ester (Example M65) by treatment with TFA in CH$_2$Cl$_2$ according to the general procedure N. Obtained as a yellow solid (269 mg).

MS (ISP) 415 [(M+H)$^+$]; mp 228–230° C.

Example 75

3-(8-Dimethylamino-4-oxo-7-trifluoromethyl-4,5-dihydro-3H-benzo[b][1,4]diazepin-2-yl)-benzonitrile The title compound was prepared from {2-[3-(3-cyano-phenyl)-3-oxo-propionyl-amino]-5-dimethylamino-4-trifluoromethyl-phenyl}-carbamic acid tert.-butyl ester (Example M66) (180 mg, 1.0 mmol) by treatment with TFA in CH$_2$Cl$_2$ according to the general procedure N. Obtained as a yellow solid (41 mg).

MS (ISN) 371 [(M−H)$^−$]; mp 224–227° C.

Example 76

7-Dimethylamino-4-(3-{5-[(2,2,2-trifluoro-ethylamino)methyl]-[1,2,3]triazol-1-yl}-phenyl)8-trifluoromethyl-1,3-dihydro-benzo[b][1,4]diazepin-2-one The title compound was prepared from 7-dimethylamino-4-[3-(5-hydroxymethyl-[1,2,3]triazol-1-yl)-phenyl]-8-trifluoromethyl-1,3-dihydro-benzo[b][1,4]diazepin-2-one (Example 17) (133 mg, 0.3 mmol) by treatment with SOCl$_2$ (3 eq.) and 2,2,2-trifluoroethylamine (10 eq.) as described in Example 45. Obtained as a light yellow solid (19 mg).

MS (ISP) 526 [(M+H)$^+$]; mp 168-170° C.

Example 77

7-(Cyclopropylmethyl-methyl-amino)-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-(cyclopropylmethyl-methyl-amino)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M67) (939 mg, 1.37 mmol) by treatment with TFA in CH$_2$Cl$_2$ according to the general procedure N. Obtained as a light yellow solid (544 mg).

MS (ISN) 483 [(M−H)$^−$]; mp 212° C.

Example 78

4-[8-(Cyclopropylmethyl-methyl-amino)-4-oxo-7-trifluoromethyl-4,5-dihydro-3H-benzo[b][1,4]diazepin-2-yl]-pyridine-2-carbonitrile The title compound was prepared from [2-[3-(2-cyano-pyridin-4-yl)-3-oxo-propionylamino]-5-

(cyclopropylmethyl-methyl-amino)-4-trifluoromethyl-phenyl]-carbamic acid tert.-butyl ester (Example M68) (173 mg, 0.33 mmol) by treatment with TFA in CH$_2$Cl$_2$ according to the general procedure N. Obtained as a yellow solid (81 mg).

MS (ISN) 412 [(M–H)$^-$]; mp 155° C.

Example 79

4-[3-(4-Cyclopropylaminomethyl-pyrazol-1-yl)-phenyl]-7-dimethylamino-8-trifluoromethyl-1,3-dihydro-benzo[b][1,4]diazepin-2-one The title compound was prepared from 7-dimethylamino-4-[3-(4-hydroxymethyl-pyrazol-1-yl)-phenyl]-8-trifluoromethyl-1,3-dihydro-benzo[b][1,4]diazepin-2-one (Example 68) (133 mg, 0.3 mmol) by treatment with SOCl$_2$ (3 eq.) and cyclopropyl amine (10 eq.) as described in Example 45. Obtained as a yellow solid (45 mg).

MS (ISP) 483 [(M+H)$^+$]; mp 135° C.

Example 80

4-[3-(5-Cyclopropylaminomethyl-[1,2,3]triazol-1-yl)-phenyl]-7-(cyclopropylmethyl-methyl-amino)-8-trifluoromethyl-1,3-dihydro-benzo[b][1,4]diazepin-2-one The title compound was prepared from 7-(cyclopropylmethyl-methyl-amino)-4-[3-(5-hydroxymethyl-[1,2,3]triazol-1-yl)-phenyl]-8-trifluoromethyl-1,3-dihydro-benzo[b][1,4]diazepin-2-one (Example 78) (145 mg, 0.3 mmol) by treatment with SOCl$_2$ (3 eq.) and cyclopropyl amine (10 eq.) as described in Example 45. Obtained as a yellow solid (97 mg).

MS (ISP) 524 [(M+H)$^+$]; mp 35-46° C.

Example 81

7-Dimethylamino-4-{3-[2-(2-hydroxy-ethyl)-2H-pyrazol-3-yl]-phenyl}-8-trifluoromethyl-1,3-dihydro-benzo[b][1,4]diazepin-2-one The title compound was prepared from (RS)-{5-dimethylamino-2-[3-oxo-3-(3-{2-[2-(tetrahydro-pyran-2-yloxy)-ethyl]-2H-pyrazol-3-yl}-phenyl)-propionylamino]-4-trifluoromethyl-phenyl}-carbamic acid tert.-butyl ester (Example M69) (237 mg, 0.36 mmol) by treatment with TFA in CH$_2$Cl$_2$ according to the general procedure N. Obtained as an off-white solid (48 mg).

MS (ISP) 458 [(M+H)$^+$]; mp 138° C.

Example 82

4-[3-(5-Cyclopropylaminomethyl-[1,2,3]triazol-1-yl)-phenyl]-7-dimethylamino-8-trifluoromethyl-1,3-dihydro-benzo[b][1,4]diazepin-2-one The title compound was prepared from 7-dimethylamino-4-[3-(5-hydroxymethyl-[1,2,3]triazol-1-yl)-phenyl]-8-trifluoromethyl-1,3-dihydro-benzo[b][1,4]diazepin-2-one (Example 17) (444 mg, 1.0 mmol) by treatment with SOCl$_2$ (3 eq.) and cyclopropyl amine (10 eq.) as described in Example 45. Obtained as a yellow solid (248 mg).

Mp 145–148° C.

Example 83

4-[8-(Cyclopropyl-methyl-amino)-4-oxo-7-trifluoromethyl-4,5-dihydro-3H-benzo[b][1,4]diazepin-2-yl]-pyridine-2-carbonitrile The title compound was prepared from [2-[3-(2-cyano-pyridin-4-yl)-3-oxo-propionylamino]-5-(cyclopropyl-methyl-amino)-4-trifluoromethyl-phenyl]-carbamic acid tert.-butyl ester (Example M70) (215 mg, 0.42 mmol) by treatment with TFA in CH$_2$Cl$_2$ according to the general procedure N. Obtained as a yellow solid (87 mg).

MS (ISP) 400.4 [(M+H)$^+$]; mp 200–205° C.

Example 84

7-Dimethylamino-8-(2-fluoro-phenyl)-4-(3-[1,2,3]triazol-1-yl-phenyl)-1,3-dihydro-benzo[b][1,4]diazepin-2-one The title compound was prepared from {2-dimethylamino-2'-fluoro-5-[3-oxo-3-(3-[1,2,3]triazol-1-yl-phenyl)-propionylamino]-biphenyl-4-yl}-carbamic acid tert.-butyl ester (Example M70) (810 mg, 1.45 mmol) by treatment with TFA in CH$_2$Cl$_2$ according to the general procedure N. Obtained as a yellow solid (61 mg).

MS (ISP) 400.4 [(M+H)$^+$]; mp 225–230° C.

Example 85

7-Dimethylamino-4-{3-[5-(2-hydroxy-ethyl)-[1,2,3]triazol-1-yl]-phenyl}-8-trifluoromethyl-1,3-dihydro-benzo[b][1,4]diazepin-2-one The title compound was prepared from (RS)-{5-dimethylamino-2-[3-oxo-3-(3-{5-[2-(tetrahydro-pyran-2-yloxy)-ethyl]-[1,2,3]triazol-1-yl}-phenyl)-propionylamino]-4-trifluoromethyl-phenyl}-carbamic acid tert.-butyl ester (Example M72) by treatment with TFA in CH$_2$Cl$_2$ according to the general procedure N. Obtained as a light yellow solid (179 mg).

MS (ISP) 459 [(M+H)$^+$]; mp 172–175° C.

Example 86

7-Dimethylamino-4-[3-(5-hydroxymethyl-pyrazol-1-yl)-phenyl]-8-trifluoromethyl-1,3-dihydro-benzo[b][1,4]diazepin-2-one The title compound was prepared from (RS)-[5-dimethylamino-2-(3-oxo-3-{3-[5-(tetrahydro-pyran-2yloxymethyl)-pyrazol-1-yl]-phenyl}-propionylamino)-4-trifluoromethyl-phenyl]-carbamic acid tert.-butyl ester (Example M73) by treatment with TFA in CH$_2$Cl$_2$ according to the general procedure N. Obtained as a light yellow solid (109 mg).

MS (ISP) 444 [(M+H)$^+$]; mp 228–229° C.

Example 87

7-Dimethylamino-4-(3-[1,2,3]triazol-1-yl-phenyl)-8-trifluoromethyl-1,3-dihydro-benzo[b][1,4]diazepin-2-one The title compound was prepared from {5-dimethylamino-2-[3-oxo-3-(3-[1,2,3]triazol-1-yl-phenyl)-propionylamino]-4-trifluoromethyl-phenyl}-carbamic acid tert.-butyl ester (Example M74) (905 mg, 1.7 mmol) by treatment with TFA in CH$_2$Cl$_2$ according to the general procedure N. Obtained as a yellow solid (566 mg).

MS (ISN) 413.2 [(M–H)$^-$]; mp 210–212° C.

Example 88

4-[4-Oxo-8-(2,2,2-trifluoro-ethoxy)-7-trifluoromethyl-4,5-dihydro-3H-benzo[b][1,4]diazepin-2-yl]-pyridine-2-carbonitrile The title compound was prepared from [2-[3-(2-cyano-pyridin-4-yl)-3-oxo-propionylamino]-5-(2,2,2-trifluoroethoxy)-4-trifluoromethyl-phenyl]-carbamic acid tert.-butyl ester (Example M75) by treatment with TFA in $CH_2Cl_2$ according to the general procedure N. Obtained as a light yellow solid (100 mg).

MS (EI) 428.2 (M$^+$); mp 252–255° C.

Example 89

3-(8-Dimethylamino-7-methyl-4-oxo-4,5-dihydro-3H-benzo[b][1,4]diazepin-2-yl)-benzonitrile The title compound was prepared from {2-[3-(3-Cyano-phenyl)-3-oxo-propionyl-amino]-4-dimethylamino-5-methyl-phenyl}-carbamic acid tert-butyl ester (Example M76) (0.24 g, 0.55 mmol) by treatment with TFA in $CH_2Cl_2$ according to the general procedure N. Obtained as a pale yellow solid (114 mg, 59%).

MS (ISP) 319.3 [(M+H)$^+$]; mp 257° C.

Example 90

7-Dimethylamino-4-[3-(5-hydroxymethyl-[1,2,3]triazol-1-yl)-phenyl]-8-methyl-1,3-dihydro-benzo[b][1,4]diazepin-2-one The title compound was prepared from (RS)-[5-dimethylamino-4-methyl-2-(3oxo-3-{3-[5-(tetrahydro-pyran-2-yloxymethyl)-[1,2,3]triazol-1-yl]-phenyl}-propionyl-amino)-phenyl]-carbamic acid tert-butyl ester (Example M77) (0.42 g, 0.71 mmol) by treatment with TFA in $CH_2Cl_2$ according to the general procedure N. Obtained as a pale yellow solid (200 mg, 72%).

MS (ISP) 391.3 [(M+H)$^+$]; mp 190° C.

Example 91

2-(3-Cyano-phenyl)-8-dimethylamino-4-oxo-4,5-dihydro-3H-benzo[b][1,4]diazepine-7-carbonitrile The title compound was prepared from {5-cyano-2-[3-(3-cyano-phenyl)-3-oxo-propionylamino]-4-dimethylamino-phenyl}-carbamic acid tert-butyl ester (Example M78) (0.28 g, 0.63 mmol) by treatment with TFA in $CH_2Cl_2$ according to the general procedure N. Obtained as a yellow solid (36 mg, 59%).

MS (ISP) 328.3 [(M–H)$^-$]; mp 251° C.

Example 92

3-[7-Methyl-8-(methyl-propyl-amino)-4-oxo-4,5-dihydro-3H-benzo[b][1,4]diazepin-2-yl]-benzonitrile The title compound was prepared from [2-[3-(3-cyano-phenyl)-3-oxo-propionylamino]-5-methyl-4-(methyl-propyl-amino)-phenyl]-carbamic acid tert-butyl ester (Example M79) (0.17 g, 0.37 mmol) by treatment with TFA in $CH_2Cl_2$ according to the general procedure N. Obtained as a yellow solid (74 mg, 58%).

MS (ISP) 347.4 [(M+H)$^+$]; mp 195° C.

Example 93

4-[3-(5-Hydroxymethyl-[1,2,3]triazol-1-yl)-phenyl]-8-methyl-7-(methyl-propyl-amino)-1,3-dihydro-benzo[b][1,4]diazepin-2-one The title compound was prepared from (RS)-[4-methyl-5-(methyl-propyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M80) (0.42 g, 0.71 mmol) by treatment with TFA in $CH_2Cl_2$ according to the general procedure N. Obtained as a pale yellow solid (200 mg, 72%).

MS (ISP) 419.4 [(M+H)$^+$]; mp 186° C.

Example 94

7-(Ethyl-methyl-amino)-4-[3-(5-hydroxymethyl-[1,2,3]triazol-1-yl)-phenyl]-8-methyl-1,3-dihydro-benzo[b][1,4]diazepin-2-one The title compound was prepared from (RS)-[5-(ethyl-methyl-amino)-4-methyl-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M81) (0.39 g, 0.64 mmol) by treatment with TFA in $CH_2Cl_2$ according to the general procedure N. Obtained as a off-white solid (159 mg, 61%).

MS (ISP) 405.5 [(M+H)$^+$]; mp 207° C.

Example 95

8-Dimethylamino-2-[3-(5-hydroxymethyl-[1,2,3]triazol-1-yl)-phenyl]-4-oxo-4,5-dihydro-3H-benzo[b][1,4]diazepine-7-carbonitrile The title compound was prepared from (RS)-[4-cyano-5-dimethylamino-2-(3-oxo-3-{3-[5(tetrahydro-pyran-2-yloxymethyl)-[1,2,3]triazol-1-yl]-phenyl}-propionylamino)-phenyl]-carbamic acid tert-butyl ester (Example M82) (0.35 g, 0.58 mmol) by treatment with TFA in $CH_2Cl_2$ according to the general procedure N. Obtained as a yellow solid (149 mg, 64%).

MS (ISP) 402.5 [(M+H)$^+$]; mp 234° C.

Example 96

8-Chloro-4-[3-(5-hydroxymethyl-[1,2,3]triazol-1-yl)-phenyl]-7-(isopropyl-methyl-amino)-1,3-dihydro-benzo[b][1,4]diazepin-2-one The title compound was prepared from (RS)-[4-chloro-5-(isopropyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M83) (0.53 g, 0.83 mmol) by treatment with TFA in $CH_2Cl_2$ according to the general procedure N. Obtained as a off-white solid (120 mg, 33%).

MS (ISP) 439.5 [(M+H)$^+$]; mp 207° C.

Example 97

8-Methyl-4-[3-(3-methyl-isoxazol-5-yl)-phenyl]-7-(methyl-propyl-amino)-1,3-dihydro-benzo[b][1,4]diazepin-2-one The title compound was prepared from [4-methyl-2-{3-[3-(3-methyl-isoxazol-5-yl)-phenyl]-3-oxo-propionylamino}-5-(methyl-propyl-amino)-phenyl]-carbamic acid tert-butyl ester (Example M84) (0.33 g, 0.63 mmol) by treatment with TFA in $CH_2Cl_2$ according to the general procedure N. Obtained as a light yellow solid (163 mg, 64%).

MS (ISP) 403.4 [(M+H)$^+$]; mp 194° C.

Example 98

8-Dimethylamino-2-[3-(3-methyl-isoxazol-5-yl)-phenyl]-4-oxo-4,5-dihydro-3H-benzo[b][1,4]diazepine-7-carbonitrile The title compound was prepared from (4-cyano-5-dimethylamino-2-{3-[3-(3-methyl-isoxazol-5-yl)-phenyl]-

3-oxo-propionylamino}-phenyl)-carbamic acid tert-butyl ester (Example M85) (0.31 g, 0.62 mmol) by treatment with TFA in CH$_2$Cl$_2$ according to the general procedure N. Obtained as a light yellow solid (171 mg, 72%).

MS (ISP) 386.3 [(M+H)$^+$]; mp 248° C.

Example 99

7-(Ethyl-methyl-amino)-8-methyl-4-[3-(3-methyl-isoxazol-5-yl)-phenyl]-1,3-dihydro-benzo[b][1,4]diazepin-2-one The title compound was prepared from (5-(ethyl-methyl-amino)-4-methyl-2-{3-[3-(3-methyl-isoxazol-5-yl)-phenyl]-3-oxo-propionylamino}-phenyl)-carbamic acid tert-butyl ester (Example M86) (0.38 g, 0.75 mmol) by treatment with TFA in CH$_2$Cl$_2$ according to the general procedure N. Obtained as a light yellow solid (160 mg, 55%).

MS (ISP) [(M+H)$^+$]; mp 198° C.

Example 100

7-Dimethylamino-8-methyl-4-[3-(3-methyl-isoxazol-5-yl)-phenyl]-1,3-dihydro-benzo[b][1,4]diazepin-2-one The title compound was prepared from (5-dimethylamino-4-methyl-2-{3-[3-(3-methyl-isoxazol-5-yl)-phenyl]-3-oxo-propionylamino}-phenyl)-carbamic acid tert-butyl ester (Example M87) (0.32 g, 0.65 mmol) by treatment with TFA in CH$_2$Cl$_2$ according to the general procedure N. Obtained as a light yellow solid (140 mg, 57%).

MS (ISP) 375.4 [(M+H)$^+$]; mp 204° C.

Example 101

8-Chloro-4-[3-(5-hydroxymethyl-[1,2,3]triazol-1-yl)-phenyl]-7-(isobutyl-methyl-amino)-1,3-dihydro-benzo[b][1,4]diazepin-2-one The title compound was prepared from (RS)-[4-chloro-5-(isobutyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M88) (0.32 g, 0.49 mmol) by treatment with TFA in CH$_2$Cl$_2$ according to the general procedure N. Obtained as an off-white solid (107 mg, 48%).

MS (ISP) 453.4 [(M+H)$^+$]; mp 201° C.

Example 102

8-Chloro-7-(isobutyl-methyl-amino)-4-[3-(3-methyl-isoxazol-5-yl)-phenyl]-1,3-dihydro-benzo[b][1,4]diazepin-2-one The title compound was prepared from (4-chloro-5-(isobutyl-methyl-amino)-2-{3-[3-(3-methyl-isoxazol-5-yl)-phenyl]-3-oxo-propionylamino}-phenyl)-carbamic acid tert-butyl ester (Example M89) (0.35 g, 0.63 mmol) by treatment with TFA in CH$_2$Cl$_2$ according to the general procedure N. Obtained as a light yellow solid (114 mg, 41%).

MS (ISP) 437.4 [(M+H)$^+$]; mp 194° C.

Example 103

2-[3-(5-Hydroxymethyl-[1,2,3]triazol-1-yl)-phenyl]-4-oxo-8-pyrrolidin-1-yl-4,5-dihydro-3H-benzo[b][1,4]diazepine-7-carbonitrile The title compound was prepared from (RS)-[4-cyano-2-(3-oxo-3-{3-[5-tetrahydro-pyran-2-yloxymethyl)-[1,2,3]triazol-1-yl]-phenyl}-propionylamino)-5-pyrrolidin-1-yl-phenyl]-carbamic acid tert-butyl ester (Example M90) (0.37 g, 0.59 mmol) by treatment with TFA in CH$_2$Cl$_2$ according to the general procedure N. Obtained as a yellow solid (140 mg, 56%).

MS (ISP) 428.5 [(M+H)$^+$]; mp 241° C.

Example 104

2-[3-(3-Methyl-isoxazol-5-yl)-phenyl]-4-oxo-8-pyrrolidin-1-yl-4,5-dihydro-3H-benzo[b][1,4]diazepine-7-carbonitrile Prepared from (4-cyano-2-{3-[3-(3-methyl-isoxazol-5-yl)-3-oxo-propionylamino}-5-pyrrolidin-1-yl-phenyl)-carbamic acid tert-butyl ester (Example M91) (0.41 g, 0.77 mmol) by treatment with TFA in CH$_2$Cl$_2$ according to the general procedure N. Obtained as a yellow solid (90 mg, 28%).

MS (ISP) 412.3 [(M+H)$^+$]; mp 267° C.

Example 105

2-[3-(5-Hydroxymethyl-[1,2,3]triazol-1-yl)-phenyl]-8-(methyl-propyl-amino)-4-oxo-4,5-dihydro-3H-benzo[b][1,4]diazepine-7-carbonitrile The title compound was prepared from (RS)-[4-cyano-5-(methyl-propyl-amino)-2-(3-oxo-3-{3-[5-tetrahydro-pyran-2-yloxymethyl)-[1,2,3]triazol-1-yl]-phenyl}-propionylamino)-phenyl]-carbamic acid tert-butyl ester (Example M92) (0.43 g, 0.68 mmol) by treatment with TFA in CH$_2$Cl$_2$ according to the general procedure N. Obtained as a yellow solid (100 mg, 34%).

MS (ISP) 430.5 [(M+H)$^+$]; mp 221° C.

Example 106

2-[3-(3-Methyl-isoxazol-5-yl)-phenyl]-8-(methyl-propyl-amino)-4-oxo-4,5-dihydro-3H-benzo[b][1,4]diazepine-7-carbonitrile The title compound was prepared from [4-cyano-2-{3-[3-(3-methyl-isoxazol-5-yl)-phenyl]-3-oxo-propionylamino}-5-(methyl-propyl-amino)-phenyl]-carbamic acid tert-butyl ester (Example M93) (0.36 g, 0.68 mmol) by treatment with TFA in CH$_2$Cl$_2$ according to the general procedure N. Obtained as a yellow solid (94 mg, 34%).

MS (ISP) 414.4 [(M+H)$^+$]; mp 133° C.

Example 107

8-Diethylamino-2-[3-(3-methyl-isoxazol-5-yl)-phenyl]-4-oxo-4,5-dihydro-3H-benzo[b][1,4]diazepine-7-carbonitrile The title compound was prepared from (4-cyano-5-diethylamino-2-{3-[3-(3-methyl-isoxazol-5-yl)-phenyl]-3-oxo-propionylamino}-phenyl)-carbamic acid tert-butyl ester (Example M94) (0.35 g, 0.66 mmol) by treatment with TFA in CH$_2$Cl$_2$ according to the general procedure N. Obtained as a yellow solid (209 mg, 77%).

MS (ISP) 414.4 [(M+H)$^+$]; mp 191° C.

Example 108

8-(Isopropyl-methyl-amino)-2-[3-(3-methyl-isoxazol-5-yl)-phenyl]-4-oxo-4,5-dihydro-3H-benzo[b][1,4]diazepine-7-carbonitrile The title compound was prepared from (4-cyano-5-(isopropyl-methyl-amino)-2-{3-[3-(3-methyl-isoxazol-5- yl)-phenyl]-3-oxo-propionylamino}-phenyl)-carbamic acid tert-butyl ester (Example M9;) (0.37 g, 0.70 mmol) by treatment with TFA in CH$_2$Cl$_2$ according to the general procedure N. Obtained as a yellow solid (219 mg, 76%).

MS (ISP) 414.4 [(M+H)$^+$]; mp 197° C.

Example 109

2-[3-(5-Hydroxymethyl-[1,2,3]triazol-1-yl)-phenyl]-8-(isopropyl-methyl-amino)-4-oxo-4,5-dihydro-3H-benzo[b][1,4]diazepine-7-carbonitrile The title compound was prepared from (RS)-[4-cyano-5-(isopropyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M96) (0.45 g, 0.71 mmol) by treatment with TFA in CH$_2$Cl$_2$ according to the general procedure N. Obtained as a yellow solid (236 mg, 77%).

MS (ISP) 430.5 [(M+H)]; mp 206° C.

Example 110

8-(Isobutyl-methyl-amino)-2-[3-(3-methyl-isoxazol-5-yl)-phenyl]-4-oxo-4,5-dihydro-3H-benzo[b][1,4]diazepine-7-carbonitrile The title compound was prepared from (4-cyano-5-(isobutyl-methyl-amino)-2-{3-[3-(3-methyl-isoxazol-5yl)-phenyl]-3-oxo-propionylamino}-phenyl)-carbamic acid tert-butyl ester (Example M97) (0.39 g, 0.71 mmol) by treatment with TFA in CH$_2$Cl$_2$ according to the general procedure N. Obtained as a yellow solid (230 mg, 75%).

MS (ISP) 428.5 [(M+H)$^+$]; mp 170° C.

Example 111

2-[3-(5-Hydroxymethyl-[1,2,3]triazol-1-yl)-phenyl]-8-(isobutyl-methyl-amino)-4-oxo-4,5-dihydro-3H-benzo[b][1,4]diazepine-7-carbonitrile The title compound was prepared from (RS)-[4-cyano-5-(isobutyl-methyl-amino)-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M98) (0.46 g, 0.71 mmol) by treatment with TFA in CH$_2$Cl$_2$ according to the general procedure N. Obtained as a yellow solid (180 mg, 57%).

MS (ISP) 444.4 [(M+H)$^+$]; mp 199° C.

Example 112

2-[3-(3-Methyl-isoxazol-5-yl)-phenyl]-4-oxo-8-piperidin-1-yl-4,5-dihydro-3H-benzo[b][1,4]diazepine-7-carbonitrile The title compound was prepared from (4-cyano-2-{3-[3-(3-methyl-isoxazol-5-yl)-phenyl]-3-oxo-propionylamino}-5-piperidin-1-yl-phenyl)-carbamic acid tert-butyl ester (Example M99) (0.41 g, 0.75 mmol) by treatment with TFA in CH$_2$Cl$_2$ according to the general procedure N. Obtained as a yellow solid (226 mg, 70%).

MS (ISP) 426.4 [(M+H)$^+$]; mp 246° C.

Example 113

8-Chloro-7-isobutylamino-4-[3-(3-methyl-isoxazol-5-yl)-phenyl]-1,3-dihydro-[b][1,4]diazepin-2-one The title compound was prepared from (4-chloro-5-isobutylamino-2-{3-[3-(3-methyl-isoxazol-5-yl)-phenyl]-3-oxo-propionylamino}-phenyl)-carbamic acid tert-butyl ester (Example M100) (0.34 g, 0.63 mmol) by treatment with TFA in CH$_2$Cl$_2$ according to the general procedure N. Obtained as a yellow solid (216 mg, 81%).

MS (ISP) 423.3 [(M+H)$^+$]; mp 249° C.

Example 114

8-Chloro-4-[3-(5-hydroxymethyl-1,2,3]triazol-1-yl)-phenyl]-7-isobutylamino-1,3-dihydro-benzo[b][1,4]diazepin-2-one The title compound was prepared from (RS)-[4-chloro-5-isobutylamino-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M101) (0.17 g, 0.27 mmol) by treatment with TFA in CH$_2$Cl$_2$ according to the general procedure N. Obtained as a yellow solid (41 mg, 35%).

MS (ISP) 439.4 [(M+H)$^+$]; mp 214° C.

Example 115

4-[3-(5-Hydroxymethyl-[1,2,3]triazol-1-yl)-phenyl]-7-(methyl-propyl-amino)-8-trifluoromethyl-1,3-dihydro-benzo[b][1,4]diazepin-2-one The title compound was prepared from (RS)-[5-(methyl-propyl-amino)-2-(3-oxo-3-{3-[5-(tetrahydro-pyran-2-yloxymethyl)-[1,2,3]triazol-1-yl]-phenyl}-propionyl-amino)-4-trifluoromethyl-phenyl]-carbamic acid tert-butyl ester (Example M102) (0.15 g, 0.22 mmol) by treatment with TFA in CH$_2$Cl$_2$ according to the general procedure N. Obtained as an off-white solid (31 mg, 30%).

MS (ISP) 473.2 [(M+H)$^+$]; mp 230° C.

Example 116

4-[3-(3-Methyl-isoxazol-5-yl)-phenyl]-7-(methyl-propyl-amino)-8-trifluoromethyl-1,3-dihydro-benzo[b][1,4]diazepin-2-one The title compound was prepared from [2-{3-[3-(3-methyl-isoxazol-5-yl)-phenyl]-3-oxo-propionylamino}-5-(methyl-propyl-amino)-4-trifluoromethyl-phenyl]-carbamic acid tert-butyl ester (Example M103) (0.26 g, 0.45 mmol) by treatment with TFA in CH$_2$Cl$_2$ according to the general procedure N. Obtained as a light yellow solid (127 mg, 61%).

MS (ISP) 457.4 [(M+H)$^+$]; mp 193° C.

Example 117

4-[3-(5-Hydroxymethyl-1,2,3]triazol-1-yl)-phenyl]-7-(isobutyl-methyl-amino)-8-trifluoromethyl-1,3-dihydro-benzo[b][1,4]diazepin-2-one The title compound was prepared from (RS)-[5-(isobutyl-methyl-amino)-2-(3-oxo-3-{3-[5-(tetrahydro-pyran-2-yloxymethyl)-[1,2,3]triazol-1-yl]-phenyl}-propionyl-amino)-4-trifluoromethyl-phenyl]-carbamic acid tert-butyl ester (Example M104) (0.51 g, 0.74 mmol) by treatment with TFA in CH$_2$Cl$_2$ according to the general procedure N. Obtained as an off-white solid (169 mg, 47%).

MS (ISP) 487.3 [(M+H)$^+$]; mp 230° C.

Example 118

7-(Isobutyl-methyl-amino)-4-[3-(3-methyl-isoxazol-5-yl)-phenyl]-8-trifluoromethyl-1,3-dihydro-benzo[b][1,4]diazepin-2-one The title compound was prepared from (5-(isobutyl-methyl-amino)-2-{3-[3-(3-methyl-isoxazol-5-yl)-phenyl]-

3-oxo-propionylamino}-4-trifluoromethyl-phenyl)-carbamic acid tert-butyl ester (Example M105) (0.42 g, 0.71 mmol) by treatment with TFA in $CH_2Cl_2$ according to the general procedure N. Obtained as a yellow solid (161 mg, 48%).

MS (ISP) 471.2 [(M+H)$^+$]; mp 195° C.

Example 119

4-[3-(5-Hydroxymethyl-[1,2,3]triazol-1-yl)-phenyl]-7-(isopropyl-methyl-amino)-8-trifluoromethyl-1,3-dihydro-benzo[b][1,4]diazepin-2-one The title compound was prepared from (RS)-[5-(isopropyl-methyl-amino)-2-(3-oxo-3-{3-[5-(tetrahydro-pyran-2-yloxymethyl)-[1,2,3]triazol-1-yl]-phenyl}-propionyl-amino)-4-trifluoromethyl-phenyl]-carbamic acid tert-butyl ester (Example M106) (0.50 g, 0.74 mmol) by treatment with TFA in $CH_2Cl_2$ according to the general procedure N. Obtained as an off-white solid (156 mg, 45%).

MS (ISP) 473.3 [(M+H)$^+$]; mp 234° C.

Example 120

7-(Isopropyl-methyl-amino)-4-[3-(3-methyl-isoxazol-5-yl)-phenyl]-8-trifluoromethyl-1,3-dihydro-benzo[b][1,4]diazepin-2-one The title compound was prepared from (5-(isopropyl-methyl-amino)-2-{3-[3-(3-methyl-isoxazol-5-yl)-phenyl]-3-oxo-propionylamino}-4-trifluoromethyl-phenyl)-carbamic acid tert-butyl ester (Example M107) (0.37 g, 0.64 mmol) by treatment with TFA in $CH_2Cl_2$ according to the general procedure N. Obtained as a yellow solid (74 mg, 25%).

MS (ISP) 457.4 [(M+H)$^+$]; mp 199° C.

Example 121

8-Chloro-7-(methyl-propyl-amino)-4-[3-(5-pyrrolidin-1-ylmethyl-[1,2,3]triazol-1-yl)-phenyl]-1,3-dihydro-benzo[b][1,4]diazepin-2-one The title compound was prepared from 8-chloro-7-(methyl-propyl-amino)-4-[3-(5-hydroxymethyl-[1,2,3]triazol-1-yl)-phenyl]-1,3-dihydro-benzo[b][1,4]diazepin-2-one (Example 29) (220 mg, 0.50 mmol) by reaction with thionylchloride in dichloromethane and subsequent treatment of the corresponding chloride with pyrrolidine in DMF according to the method described in Example 45. Obtained as a yellow foam (63 mg, 26%).

MS (ISP) 492.3 [(M+H)$^+$].

Example 122

4-[3-(5-Azetidin-1-ylmethyl-[1,2,3]triazol-1-yl)-phenyl]-8-chloro-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,3]triazol-1-yl)-phenyl]-1,3-dihydro-benzo[b][1,4]diazepin-2-one (Example 29) (118 mg, 0.27 mmol) by reaction with thionylchloride in dichloromethane and subsequent treatment of the corresponding chloride with trimethylene-imine in DMF according to the method described in Example 45. Obtained as a light yellow solid (65 mg, 50%).

MS (ISP) 478.3 [(M+H)$^+$]; mp 169° C.

Example 123

8-Chloro-4-[3-(5-diethylaminomethyl-[1,2,3]triazol-1-yl)-phenyl]-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,3]triazol-1-yl)-phenyl]-1,3-dihydro-benzo[b][1,4]diazepin-2-one (Example 29) (219 mg, 0.50 mmol) by reaction with thionylchloride in dichloro-methane and subsequent treatment of the corresponding chloride with diethylamine in DMF according to the method described in Example 45. Obtained as a light yellow solid (123 mg, 50%).

MS (ISP) 494.3 [(M+H)$^+$]; mp 151° C.

Example 124

8-Chloro-4-(3-{5-[(isopropyl-methyl-amino)-methyl]-[1,2,3]triazol-1-yl}-phenyl)-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,3]triazol-1-yl)-phenyl]-1,3-dihydro-benzo[b][1,4]diazepin-2-one (Example 29) (219 mg, 0.50 mmol) by reaction with thionylchloride in dichloromethane and subsequent treatment of the corresponding chloride with N-isopropyl-methylamine in DMF according to the method described in Example 45. Obtained as a light yellow solid (129 mg, 52%).

MS (ISP) 494.3 [(M+H)$^+$]; mp 148° C.

Example 125

8-Chloro-7-(isopropyl-methyl-amino)-4-[3-(5-pyrrolidin-1-ylmethyl-[1,2,3]triazol-1-yl)-phenyl]-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (219 mg, 0.50 mmol) by reaction with thionylchloride in dichloromethane and subsequent treatment of the corresponding chloride with pyrrolidine in DMF according to the method described in Example 45. Obtained as a light yellow solid (157 mg, 64%).

MS (ISP) 492.3 [(M+H)$^+$]; mp 172° C.

Example 126

8-Chloro-7-(isobutyl-methyl-amino)-4-[3-(5-pyrrolidin-1-ylmethyl-[1,2,3]triazol-1-yl)-phenyl]-1,3-dihydro-benzo[b][1,4]diazepin-2-one The title compound was prepared from 8-chloro-4-[3-(5-hydroxymethyl-[1,2,3]triazol-1-yl)-phenyl]-7-(isobutyl-methyl-amino)-1,3-dihydro-benzo[b][1,4]diazepin-2-one (Example101) (226 mg, 0.50 mmol) by reaction with thionylchloride in dichloromethane and subsequent treatment of the corresponding chloride with pyrrolidine in DMF according to the method described in Example 45. Obtained as a light yellow solid (163 mg, 64%).

MS (ISP) 506.3 [(M+H)$^+$]; mp 190° C.

Example 127

8-Chloro-4-[3-(5-dimethylaminomethyl-[1,2,3]triazol-1-yl)-phenyl]-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 99) (219 mg, 0.50 mmol) by reaction with thionylchloride in dichloromethane and subsequent treatment of the corresponding chloride with dimethylamine in DMF according to the method described in Example 45. Obtained as a light brown solid (143 mg, 61%).

MS (ISP) 566.3 [(M+H)+]; mp 225° C.

Example 128

8-Chloro-4-[3-(5-dimethylaminomethyl-[1,2,3]triazol-1-yl)-phenyl]-7-(isobutyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isobutyl-methyl-amino)-1,3-dihydro-benzo[b][1,4]diazepin-2-one (Example 101) (226 mg, 0.50 mmol) by reaction with thionylchloride in dichloromethane and subsequent treatment of the corresponding chloride with dimethylamine in DMF according to the method described in Example 45. Obtained as a light brown solid (134 mg, 56%).

MS (ISP) 480.5 [(M+H)+]; mp 199° C.

Example 129

4-[3-(5-Azetidin-1-ylmethyl-[1,2,3]triazol-1-yl)-phenyl]-8-chloro-7-(isopropyl-methyl-amino)-1,3dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 99) (219 mg, 0.50 mmol) by reaction with thionylchloride in dichloromethane and subsequent treatment of the corresponding chloride with trimethylene-imine in DMF according to the method described in Example 45. Obtained as a light brown solid (102 mg, 43%).

MS (ISP) 478.3 [(M+H)+]; mp 177° C.

Example 130

4-[3-(5-Azetidin-1-ylmethyl-[1,2,3]triazol-1-yl)-phenyl]-8-chloro-7-(isobutyl-methyl-amino)-1,3-dihydro-benzo[b][1,4]diazepin-2-one The title compound was prepared from 8-chloro-4-[3-(5-hydroxymethyl-[1,2,3]triazol-1yl)-phenyl]-7-(isobutyl-methyl-amino)-1,3-dihydro-benzo[b][1,4]diazepin-2-one (Example 101) (220 mg, 0.49 mmol) by reaction with thionylchloride in dichloromethane and subsequent treatment of the corresponding chloride with trimethylene-imine in DMF according to the method described in Example 45. Obtained as a light brown solid (125 mg, 52%).

MS (ISP) 492.3 [(M+H)+]; mp 191° C.

Example 131

8-Chloro-4-[3-(5-methylaminomethyl-[1,2,3]triazol-1-yl)-phenyl-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,3]triazol-1-yl)-phenyl]-1,3-dihydro-benzo[b][1,4]diazepin-2-one (Example 29) (230 mg, 0.52 mmol) by reaction with thionylchloride in dichloromethane and subsequent treatment of the corresponding chloride with methylamine in DMF according to method described in Example 45. Obtained as a light yellow solid (122 mg, 52%).

MS (ISP) 452.4 [(M+H)+]; mp 185° C.

Example 132

4-[3-(5-Hydroxymethyl-[1,2,3]triazol-1-yl)-phenyl]-7-(isobutyl-methyl-amino)-8-methyl-1,3-dihydro-benzo[b][1,4]diazepin-2-one The title compound was prepared from (RS)-[5-(isobutyl-methyl-amino)-4-methyl-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M108) (0.33 g, 0.52 mmol) by treatment with TFA in CH$_2$Cl$_2$ according to the general procedure N. Obtained as a pale brown solid (188 mg, 79%).

MS (ISP) 431.4 [(M–H)−]; mp 198° C.

Example 133

4-[3-(5-Hydroxymethyl-1,2,3]triazol-1-yl)-phenyl]-8-methyl-7-pyrrolidin-1-yl-1,3-dihydro-benzo[b][1,4]diazepin-2-one The title compound was prepared from (RS)-[4-methyl-2-(3-oxo-3-{3-[5-(tetrahydro-pyran-2-yloxymethyl)-[1,2,3]triazol-1-yl]-phenyl}-propionylamino)-5-pyrrolidin-1-yl-phenyl]-carbamic acid tert-butyl ester (Example M110) (0.41 g, 0.66 mmol) by treatment with TFA in CH$_2$Cl$_2$ according to the general procedure N. Obtained as a light yellow solid (239 mg, 86%).

MS (ISP) 417.3 [(M+H)+]; mp 202° C.

Example 134

7-(Isobutyl-methyl-amino)-8-methyl-4-[3-(3-methyl-isoxazol-5-yl)-phenyl]-1,3-dihydro-benzo[b][1,4]diazepin-2-one The title compound was prepared from (5-(isobutyl-methyl-amino)-4-methyl-2-{3-[3-(3-methyl-isoxazol-5-yl)-phenyl]-3-oxo-propionylamino}-phenyl)-carbamic acid tert-butyl ester (Example M109) (0.33 g, 0.62 mmol) by treatment with TFA in CH$_2$Cl$_2$ according to the general procedure N. Obtained as a pale brown solid (136 mg, 53%).

MS (ISP) 417.3 [(M+H)+]; mp 187° C.

Example 135

8-Methyl-4-[3-(3-methyl-isoxazol-5-yl)-phenyl]-7-pyrrolidin-1-yl-1,3-dihydro-benzo[b][1,4]diazepin-2-one The title compound was prepared from (4-methyl-2-{3-[3-(3-methyl-isoxazol-5-yl)-phenyl]-3-oxo-propionylamino}-5-pyrrolidin-1-yl-phenyl)-carbamic acid tert-butyl ester (Example M111) (0.33 g, 0.64 mmol) by treatment with TFA in CH$_2$Cl$_2$ according to the general procedure N. Obtained as an off-white solid (223 mg, 87%).

MS (ISP) 401.5 [(M+H)+]; mp 211° C.

Example 136

4-[3-(5-Dimethylaminomethyl-[1,2,3]triazol-1-yl)-phenyl]-7-(isobutyl-methyl-amino)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-trifluoromethyl-1,3-dihydro-benzo[b][1,4]diazepin-2-one (Example 117) (300 mg, 0.62 mmol) by reaction with thionylchloride in dichloromethane and subsequent treatment of the corresponding chloride with dimethylamine in DMF according to the method described in Example 45. Obtained as a light brown solid (110 mg, 35%).

MS (ISP) 514.3 [(M+H)+]; mp 182° C.

Example 137

8-(Isobutyl-methyl-amino)-4-oxo-2-[3-(5-pyrrolidin-1-ylmethyl-[1,2,3]triazol-1-yl)-phenyl]-4,5-dihydro-3H-benzo[b][1,4]diazepine-7-carbonitrile The title compound was prepared from 2-[3-(5-hydroxymethyl-[1,2,3]triazol-1-yl)-phenyl]8-(isobutylmethyl-amino)-4-oxo-4,5-dihydro-3H-benzo[b][1,4]diazepine-7-carbonitrile (Example 111) (200 mg, 0.45 mmol) by reaction with thionylchloride in dichloromethane and subsequent treatment of the corresponding chloride with pyrrolidine in DMF according to the method described in Example 45. Obtained as a light yellow solid (140 mg, 63%).

MS (ISP) 497.3 [(M+H)+]; mp 174° C.

Example 138

7-(Isobutyl-methyl-amino)-4-[3-(5-pyrrolidin-1-ylmethyl-[1,2,3]triazol-1-yl)-phenyl]-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-trifluoromethyl-1,3-dihydro-benzo[b][1,4]diazepin-2-one (Example 117) (300 mg, 0.62 mmol) by reaction with thionylchloride in dichloromethane and subsequent treatment of the corresponding chloride with pyrrolidine in DMF according to the method described in Example 45. Obtained as a light orange foam (80 mg, 24%).

MS (ISP) 540.5 [(M+H)+].

Example 139

7-(Isobutyl-methyl-amino)-8-methyl-4-[3-(5-pyrrolidin-1-ylmethyl-[1,2,3]triazol-1-yl)-phenyl]-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-methyl-1,3-dihydro-benzo[b][1,4]diazepin-2-one (Example 132) (200 mg, 0.46 mmol) by reaction with thionylchloride in dichloromethane and subsequent treatment of the corresponding chloride with pyrrolidine in DMF according to the method described in Example 45. Obtained as a light yellow solid (50 mg, 22%).

MS (ISP) 486.4 [(M+H)+]; mp 177° C.

Example 140

8-(Isobutyl-methyl-amino)-2-(3-{5-[(isobutyl-methyl-amino)-methyl]-[1,2,3]triazol-1-yl}-phenyl-4-oxo-4,5-dihydro-3H-benzo[b][1,4]diazepine-7-carbonitrile The title compound was prepared from 2-[3-(5-hydroxymethyl-[1,2,3]triazol-1-yl)-phenyl]-8-(isobutyl-methyl-amino)-4-oxo-4,5-dihydro-3H-benzo[b][1,4]diazepine-7-carbonitrile (Example 111) (220 mg, 0.50 mmol) by reaction with thionylchloride in dichloromethane and subsequent treatment of the corresponding chloride with N-isobutyl-methylamine in DMF according to the method described in Example 45. Obtained as a light yellow solid (100 mg, 39%).

MS (ISP) 513.4 [(M+H)+]; mp 169° C.

Example 141

7-(Isobutyl-methyl-amino)-4-(3-{5-[(isopropyl-methyl-amino)-methyl]-[1,2,3]triazol-1yl}-phenyl)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-trifluoromethyl-1,3-dihydro-benzo[b][1,4]diazepin-2-one (Example 117) (260 mg, 0.53 mmol) by reaction with thionylchloride in dichloromethane and subsequent treatment of the corresponding chloride with N-isopropyl-methylamine in DMF according to the method described in Example 45. Obtained as a light brown solid (70 mg, 24%).

MS (ISP) 542.3 [(M+H)+]; mp 157° C.

Example 142

8-Chloro-4-[3-(5-cyclopentylaminomethyl-[1,2,3]triazol-1-yl)-phenyl]-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with cyclopentylamine in DMF according to the method described in Example 45. Obtained as a light yellow solid (170 mg, 67%).

MS (ISP) 506.3 [(M+H)+]; mp 174° C.

Example 143

4-(3-{5-[(Cyclopropylmethyl-amino)-methyl]-[1,2,3]triazol-1-yl}-phenyl)-7-(isobutyl-methyl-amino)-8-methyl-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-methyl-1,3-dihydro-benzo[b][1,4]diazepin-2-one (Example 132) (250 mg, 0.58 mmol) by reaction with thionylchloride in dichloromethane and subsequent treatment of the corresponding chloride with cyclopropylmethylamine in DMF according to the method described in Example 45. Obtained as a light yellow solid (50 mg, 18%).

MS (ISP) 486.4 [(M+H)+]; mp 184° C.

Example 144

8-Chloro-7-(isobutyl-methyl-amino)-4-[3-(5-piperidin-1-ylmethyl-[1,2,3]triazol-1-yl)-phenyl]-1,3-dihydro-benzo[b][1,4]diazepin-2-one The title compound was prepared from 8-chloro-4-[3-(5-hydroxymethyl-[1,2,3]triazol-1-yl)-phenyl]-7-(isobutyl-methyl-amino)-1,3-dihydro-benzo[b][1,4]diazepin-2-one (Example 101) (220 mg, 0.49 mmol) by reaction with thionylchloride in dichloromethane and subsequent treatment of the corresponding chloride with piperidine in DMF according to the method described in Example 45. Obtained as a light brown solid (250 mg, 99%).

MS (ISP) 520.3 [(M+H)+]; mp 169° C.

Example 145

8-Chloro-4-{3-[5-(isopropylamino-methyl)-[1,2,3]triazol-1-yl]-phenyl}-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with isopropylamine in DMF according to the method described in Example 45. Obtained as a light yellow solid (160 mg, 67%).

MS (ISP) 480.3 [(M+H)+]; mp 208° C.

Example 146

8-Chloro-7-(isopropyl-methyl-amino)-4-[3-(5-{[(2-methoxy-ethyl)-methyl-amino]-methyl}-[1,2,3]triazol-1-yl)-phenyl]-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with N-(2-methoxyethyl) methylamine in DMF according to the method described in Example 45. Obtained as a light yellow solid (120 mg, 47%).

MS (ISP) 510.4 [(M+H)+]; mp 119° C.

Example 147

8-Chloro-4-(3-{5-[(cyclopropylmethyl-amino)-methyl]-[1,2,3]triazol-1}-phenyl)-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with aminomethyl-cyclopropane in DMF according to the method described in Example 45. Obtained as a light brown solid (150 mg, 61%).

MS (ISP) 592.2 [(M+H)+]; mp 151° C.

Example 148

8-Chloro-7-(isopropyl-methyl-amino)-4-(3-{5-[(isopropyl-methyl-amino)-methyl]-[1,2,3]triazol-1-yl}-phenyl)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with N-isopropylmethylamine in DMF according to the method described in Example 45. Obtained as a light yellow solid (120 mg, 49%).

MS (ISP) 494.3 [(M+H)+]; mp 180° C.

Example 149

8-Chloro-4-(3-{5-[(isobutyl-methyl-amino)-methyl]-[1,2,3]triazol-1-yl}-phenyl)-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with N-isobutylmethylamine in DMF according to the method described in Example 45. Obtained as a light yellow solid (190 mg, 75%).

MS (ISP) 508.4 [(M+H)+]; mp 182° C.

Example 150

4-[3-(5-Dimethylaminomethyl-[1,2,3]triazol-1-yl)-phenyl]-7-(isopropyl-methyl-amino)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (200 mg, 0.42 mmol) by reaction with thionylchloride in dichloromethane and subsequent treatment of the corresponding chloride with dimethylamine in DMF according to the method described in Example 45. Obtained as an off-white solid (80 mg, 38%).

MS (ISP) 500.4 [(M+H)+]; mp 197° C.

Example 151

7-(Isopropyl-methyl-amino)-4-[3-(5-pyrrolidin-1-ylmethyl-[1,2,3]triazol-1-yl)-phenyl]-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (200 mg, 0.42 mmol) by reaction with thionylchloride in dichloromethane and subsequent treatment of the corresponding chloride with pyrrolidine in DMF according to the method described in Example 45. Obtained as a light brown solid (140 mg, 63%).

MS (ISP) 526.2 [(M+H)+]; mp 175° C.

Example 152

7-(Isopropyl-methyl-amino)-4-(3-{5-[(isopropyl-methyl-amino)-methyl]-[1,2,3]triazol-1-yl}-phenyl)-8-trifluoromethyl-1.3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (220 mg, 0.47 mmol) by reaction with thionylchloride in dichloromethane and subsequent treatment of the corresponding chloride with N-isopropylmethylamine in DMF according to the method described in Example 45. Obtained as a light yellow solid (110 mg, 45%).

MS (ISP) 528.4 [(M+H)+]; mp 182° C.

Example 153

4-(3-{5-[(Cyclopropylmethyl-amino)-methyl]-[1,2,3]triazol-1-yl}-phenyl)-7-(isopropyl-methyl-amino)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (210 mg, 0.44 mmol) by reaction with thionylchloride in dichloromethane and subsequent treatment of the corresponding chloride with aminomethyl-cyclopropane in DMF according to the method described in Example 45. Obtained as a light brown solid (110 mg, 47%).

MS (ISP) 526.2 [(M+H)$^+$]; mp 152° C.

Example 154

8-Chloro-4-[3-(5-cyclopropylaminomethyl-[1,2,3]triazol-1-yl)-phenyl]-7-(isopropyl-methyl-amino)-1,3-dihydro-benzo[b][1,4]diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]diazepin-2-one (Example 96) (220 mg, 0.50 mmol) by reaction with thionylchloride in dichloromethane and subsequent treatment of the corresponding chloride with cyclopropylamine in DMF according to the method described in Example 45. Obtained as a light yellow solid (40 mg, 17%).

MS (ISP) 478.4 [(M+H)$^+$]; mp 144° C.

Example 155

4-{3-[5-(Isopropylamino-methyl)-[1,2,3]triazol-1-yl]-phenyl}-7-(isopropyl-methyl-amino)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (236 mg, 0.50 mmol) by reaction with thionylchloride in dichloromethane and subsequent treatment of the corresponding chloride with isopropylamine in DMF according to the method described in Example 45. Obtained as a light yellow solid (100 mg, 39%).

MS (ISP) 514.4 [(M+H)$^+$]; mp 191° C.

Example 156

8-Chloro-4-{3-[5-(isobutylamino-methyl)-[1,2,3]triazol-1-yl]-phenyl}-7-(isopropyl-methyl-amino)-1,3-dihydro-benzo[b][1,4]-diazepin-2-one The title compound was prepared from 8-chloro-4-[3-(5-hydroxymethyl-[1,2,3]triazol-1-yl)-phenyl]-7-(isopropyl-methyl-amino)-1,3-dihydro-benzo[b][1,4]-diazepin-2-one (Example 96) (220 mg, 0.50 mmol) by reaction with thionylchloride in dichloromethane and subsequent treatment of the corresponding chloride with isobutylamine in DMF according to the method described in Example 45. Obtained as a light yellow solid (160 mg, 65%).

MS (ISP) 494.4 [(M+H)$^+$]; mp 182° C.

Example 157

4-[3-(5-Cyclopropylaminomethyl-[1,2,3]triazol-1-yl)-phenyl]-7-(isopropyl-methyl-amino)-8-trifluoromethyl-1,3-dihydro-benzo[b][1,4]diazepin-2-one The title compound was prepared from 4-[3-(5-hydroxymethyl-[1,2,3]triazol-1-yl)-phenyl]-7-(isopropyl-methyl-amino)-8-trifluoromethyl-1,3-dihydro-benzo[b][1,4]diazepin-2-one (Example 119) (236 mg, 0.50 mmol) by reaction with thionylchloride in dichloromethane and subsequent treatment of the corresponding chloride with cyclopropylamine in DMF according to the method described in Example 45. Obtained as a light yellow solid (70 mg, 27%).

MS (ISP) 512.4 [(M+H)$^+$]; mp 178° C.

Example 158

7-(Isobutyl-methyl-amino)-8-methyl-4-[3-(5-pyrrolidin-1-ylmethyl-[1,2,4]triazol-1-yl)-phenyl]-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-methyl-1,3-dihydro-benzo[b][1,4]diazepin-2-one (Example 132) (180 mg, 0.42 mmol) by reaction with thionylchloride in dichloromethane and subsequent treatment of the corresponding chloride with pyrrolidine in DMF according to the method described in Example 45. Obtained as an off-white solid (106 mg, 52%).

MS (ISP) 486.5 [(M+H)$^+$]; mp 164° C.

Example 159

4-[3-(5-Cyclopropylaminomethyl-[1,2,4]triazol-1-yl)-phenyl]-7-(isobutyl-methyl-amino)-8-methyl-1,3-dihydro-benzo[b][1,4]diazepin-2-one The title compound was prepared from 4-[3-(5-hydroxymethyl-[1,2,3]triazol-1-yl)-phenyl]-7-(isobutyl-methyl-amino)-8-methyl-1,3-dihydro-benzo[b][1,4]diazepin-2-one (Example 132) (180 mg, 0.42 mmol) by reaction with thionylchloride in dichloromethane and subsequent treatment of the corresponding chloride with cyclopropylamine in DMF according to the method described in Example 45. Obtained as a light yellow solid (108 mg, 55%).

MS (ISP) 472.4 [(M+H)$^+$]; mp 114° C.

Example 160

8-Chloro-7-isopropylamino-4-[3-(3-methyl-isoxazol-5-yl)-phenyl]-1,3-dihydro-benzo[b][1,4]diazepin-2-one The title compound was prepared from (4-chloro-5-isopropylamino-2-{3-[3-(3-methyl-isoxazol-5-yl)-phenyl]-3-oxo-propionylamino}-phenyl)-carbamic acid tert-butyl ester (Example M112) (0.16 g, 0.31 mmol) by treatment with TFA in CH$_2$Cl$_2$ according to the general procedure N. Obtained as a pale brown solid (120 mg, 93%).

MS (ISP) 409.4 [(M+H)$^+$]; mp 225° C.

Example 161

8-Chloro-4-[3-(5-hydroxymethyl-[1,2,3]triazol-1-yl)-phenyl]-7-isopropylamino-1,3-dihydro-benzo[b][1,4]diazepin-2-one The title compound was prepared from (RS)-[4-chloro-5-isopropylamino-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M113) (0.37 g, 0.60 mmol) by treatment with TFA in CH$_2$Cl$_2$ according to the general procedure N. Obtained as a light yellow solid (209 mg, 82%).

MS (ISP) 425.4 [(M+H)$^+$]; mp 250° C.

Example 162

8-Chloro-7-(methyl-propyl-amino)-4-[3-(5-hydroxymethyl-[1,2,4]triazol-1-yl)-phenyl]-1,3-dihydro-benzo[b][1,4]diazepin-2-one The title compound was prepared from (RS)-[4-chloro-5-(methyl-propyl-amino)-2-(3-oxo-3-{3-[5-(tetrahydropyran-2-yloxymethyl)-[1,2,4]triazol-1-yl]-phenyl}-propionylamino)-phenyl]-carbamic acid tert-butyl ester (Example M114) (1.47 g, 2.29 mmol) by treatment with TFA in CH$_2$Cl$_2$ according to the general procedure N. Obtained as a pale yellow solid (1.0 g, 99%).

MS (ISP) 439.5 [(M+H)$^+$]; mp 192° C.

Example 163

8-Chloro-4-[3-(5-hydroxymethyl-[1,2,4]triazol-1-yl)-phenyl]-7-(isobutyl-methyl-amino)-1,3-dihydro-benzo[b][1,4]diazepin-2-one The title compound was prepared from (RS)-[4-chloro-5-(isobutyl-methyl-amino)-2-(3-oxo-3-{3-[5-(tetrahydro-pyran-2-yloxymethyl)-[1,2,4]triazol-1-yl]-phenyl}-propionylamino)-phenyl]-carbamic acid tert-butyl ester (Example M115) (0.61 g, 0.93 mmol) by treatment with TFA in CH$_2$Cl$_2$ according to the general procedure N. Obtained as a light brown solid (290 mg, 69%).

MS (ISP) 453.5 [(M+H)$^+$]; mp 195° C.

Example 164

8-Chloro-7-(methyl-propyl-amino)-4-[3-(5-pyrrolidin-1-ylmethyl-[1,2,4]triazol-1-yl)-phenyl]-1,3-dihydro-benzo[b][1,4]diazepin-2-one The title compound was prepared from 8-chloro-7-(methyl-propyl-amino)-4-[3-(5-hydroxymethyl-[1,2,4]triazol-1-yl)-phenyl]-1,3-dihydro-benzo[b][1,4]diazepin-2-one (Example 162) (220 mg, 0.50 mmol) by reaction with thionylchloride in dichloromethane and subsequent treatment of the corresponding chloride with pyrrolidine in DMF according to the method described in Example 45. Obtained as a light yellow solid (114 mg, 46%).

MS (ISP) 492.3 [(M+H)$^+$]; mp 183° C.

Example 165

8-Chloro-7-(isobutyl-methyl-amino)-4-[3-(5-pyrrolidin-1-ylmethyl-[1,2,4]triazol-1-yl)-phenyl]-1,3-dihydro-benzo[b][1,4]diazepin-2-one The title compound was prepared from 8-chloro-4-[3-(5-hydroxymethyl-[1,2,4]triazol-1-yl)-phenyl]-7-(isobutyl-methyl-amino)-1,3-dihydro-benzo[b][1,4]diazepin-2-one (Example 163) (200 mg, 0.44 mmol) by reaction with thionylchloride in dichloromethane and subsequent treatment of the corresponding chloride with pyrrolidine in DMF according to the method described in Example 45. Obtained as a light yellow solid (99 mg, 44%).

MS (ISP) 506.4 [(M+H)$^+$]; mp 164° C.

Example 166

8-Chloro-4-[3-(5-dimethylaminomethyl-[1,2,4]triazol-1-yl)-phenyl]-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,4]triazol-1-yl)-phenyl]-1,3-dihydro-benzo[b][1,4]diazepin-2-one (Example 162) (220 mg, 0.50 mmol) by reaction with thionylchloride in dichloromethane and subsequent treatment of the corresponding chloride with dimethylamine in DMF according to the method described in Example 45. Obtained as a light yellow solid (93 mg, 540%).

MS (ISP) 466.4 [(M+H)$^+$]; mp 170° C.

Example 167

8-Chloro-4-[3-(5-cyclopropylaminomethyl-[1,2,4]triazol-1-yl)-phenyl]-7-(methyl-propyl-amino)-1,3-dihydro-benzo[b][1,4]diazepin-2-one The title compound was prepared from 8-chloro-7-(methyl-propyl-amino)-4-[3-(5-hydroxymethyl-[1,2,4]triazol-1-yl)-phenyl]-1,3-dihydro-benzo[b][1,4]diazepin-2-one (Example 162) (220 mg, 0.50 mmol) by reaction with thionylchloride in dichloromethane and subsequent treatment of the corresponding chloride with cyclopropylamine in DMF according to the method described in Example 45. Obtained as a light yellow solid (95 mg, 40%).

MS (ISP) 478.4 [(M+H)$^+$]; mp 123° C.

Example 168

4-[3-(5-Hydroxymethyl-[1,2,4]triazol-1-yl)-phenyl]-7-(isobutyl-methyl-amino)-8-methyl-1,3-dihydro-benzo[b][1,4]diazepin-2-one Prepared from (RS)-[5-(isobutyl-methyl-amino)-4-methyl-2-(3-oxo-3-{3-[5-(tetrahydro-pyran-2-yloxymethyl)-[1,2,4]triazol-1-yl]-phenyl}-propionylamino)-phenyl]-carbamic acid tert-butyl ester (Example M116) (0.96 g, 1.51 mmol) by treatment with TFA in CH$_2$Cl$_2$ according to the general procedure N. Obtained as a pale brown solid (480 mg, 73%).

MS (ISP) 433.6 [(M+H)$^+$]; mp 191° C.

Example 169

7-(Methyl-propyl-amino)-4-(3-[1,2,4triazol-1-yl-phenyl)-8-trifluoromethyl-1,3-dihydro-benzo[b][1,4]diazepin-2-one The title compound was prepared from {5-(methyl-propyl-amino)-2-[3-oxo-3-(3-[1,2,4]triazol-1-yl-phenyl)-propionylamino]-4-trifluoromethyl-phenyl}-carbamic acid tert-butyl ester (Example M117) (0.31 g, 0.55 mmol) by treatment with TFA in CH$_2$Cl$_2$ according to the general procedure N. Obtained as a light yellow solid (192 mg, 78%).

MS (ISP) 443.4 [(M+H)$^+$]; mp 185° C.

Example 170

7-(Methyl-propyl-amino)-4-(3-[1,2,3]triazol-1-yl-phenyl)-8-trifluoromethyl-1,3-dihydro-benzo[b][1,4]diazepin-2-one The title compound was prepared from {5-(methyl-propyl-amino)-2-[3-oxo-3-(3-[1,2,3]-triazol-1-yl-phenyl)-propionylamino]-4-trifluoromethyl-phenyl}-carbamic acid tert-butyl ester (Example M118) (0.33 g, 0.59 mmol) by treatment with TFA in CH$_2$Cl$_2$ according to the general procedure N. Obtained as a light yellow solid (115 mg, 44%).

MS (ISP) 443.4 [(M+H)$^+$]; mp 147° C.

Example 171

7-(Isobutyl-methyl-amino)-4-(3-pyrazol-1-yl-phenyl)-8-trifluoromethyl-1,3-dihydro-benzo[b][1,4]diazepin-2-one The title compound was prepared from {5-(isobutyl-methyl-amino)-2-[3-oxo-3-(3-pyrazol-1-yl-phenyl)-propionylamino]-4-trifluoromethyl-phenyl}-carbamic acid tert-butyl ester (Example M119) (0.49 g, 0.85 mmol) by treatment with TFA in CH$_2$Cl$_2$ according to the general procedure N. Obtained as a light yellow solid (324 mg, 83%).

MS (ISP) 454.4 [(M–H)$^-$]; mp 182° C.

Example 172

4-[8-(Isopropyl-methyl-amino)-4-oxo-7-trifluoromethyl-4,5-dihydro-3H-benzo[b][1,4]diazepin-2-yl]-pyridine-2-carbonitrile The title compound was prepared from [2-[3-(2-cyano-pyridin-4-yl)-3-oxo-propionylamino]-5-(isopropyl-methyl-amino)-4-trifluoromethyl-phenyl]-carbamic acid tert-butyl ester (Example M120) (0.67 g, 1.29 mmol) by treatment with TFA in CH$_2$Cl$_2$ according to the general procedure N. Obtained as a light yellow solid (210 mg, 41%).

MS (ISP) 400.3 [(M–H)$^-$]; mp 189° C.

Example 173

8-Chloro-7-(isobutyl-methyl-amino)-4-(3-[1,2,4]triazol-1-yl-phenyl)-1,3-dihydro-benzo[b][1,4]diazepin-2-one The title compound was prepared from {4-chloro-5-(isobutyl-methyl-amino)-2-[3-oxo-3-(3-[1,2,4]triazol-1-yl-phenyl)-propionylamino]-phenyl}-carbamic acid tert-butyl ester (Example M121) (0.76 g, 1.41 mmol) by treatment with TFA in CH$_2$Cl$_2$ according to the general procedure N. Obtained as a light orange solid (530 mg, 89%).

MS (ISP) 423.4 [(M+H)$^+$]; mp 213° C.

Example 174

7-(Isobutyl-methyl-amino)-4-(3-[1,2,4]triazol-1-yl-phenyl)-8-trifluoromethyl-1,3-dihydro-benzo[b][1,4]diazepin-2-one Prepared from {5-(isobutyl-methyl-amino)-2-[3-oxo-3-(3-[1,2,4]triazol-1-yl-phenyl)-propionylamino]-4-trifluoromethyl-phenyl}-carbamic acid tert-butyl ester (Example M122) (0.50 g, 0.87 mmol) by treatment with TFA in CH$_2$Cl$_2$ according to the general procedure N. Obtained as a light brown solid (350 mg, 88%).

MS (ISP) 457.5 [(M+H)$^+$]; mp 198° C.

Example 175

8-Chloro-7-(isobutyl-methyl-amino)-4-(3-[1,2,3]triazol-1-yl-phenyl)-1,3-dihydro-benzo[b][1,4]diazepin-2-one The title compound was prepared from {4-chloro-5-(isobutyl-methyl-amino)-2-[3-oxo-3-(3-[1,2,3]triazol-1-yl-phenyl)-propionylamino]-phenyl}-carbamic acid tert-butyl ester (Example M123) (0.17 g, 0.31 mmol) by treatment with TFA in CH$_2$Cl$_2$ according to the general procedure N. Obtained as a light yellow solid (100 mg, 75%).

MS (ISP) 423.5 [(M+H)$^+$]; mp 85° C.

Example 176

7-(Isobutyl-methyl-amino)-4-(3-[1,2,3]triazol-1-yl-phenyl)-8-trifluoromethyl-1,3-dihydro-benzo[b][1,4]diazepin-2-one The title compound was prepared from {5-(isobutyl-methyl-amino)-2-[3-oxo-3-(3-[1,2,3]triazol-1-yl-phenyl)-propionylamino]-4-trifluoromethyl-phenyl}-carbamic acid tert-butyl ester (Example M124) (0.44 g, 0.77 mmol) by treatment with TFA in CH$_2$Cl$_2$ according to the general procedure N. Obtained as a light brown solid (170 mg, 49%).

MS (ISP) 457.5 [(M+H)$^+$]; mp 202° C.

Example 177

4-(3-Imidazol-1-yl-phenyl)-7-isobutylamino-8-trifluoromethyl-1,3-dihydro-benzo[b][1,4]diazepin-2-one The title compound was prepared from {2-[3-(3-imidazol-1-yl-phenyl)-3-oxo-propionylamino]-5-isobutylamino-4-trifluoromethyl-phenyl}-carbamic acid tert-butyl ester (Example M125) (0.43 g, 0.77 mmol) by treatment with TFA in CH$_2$Cl$_2$ according to the general procedure N. Obtained as a light yellow solid (260 mg, 76%).

MS (ISP) 442.4 [(M+H)$^+$]; mp 221° C.

Example 178

8-Chloro-4-(3-imidazol-1-yl-phenyl)-7-isobutylamino-1,3-dihydro-benzo[b][1,4]diazepin-2-one The title compound was prepared from {4-chloro-2-[3-(3-imidazol-1-yl-phenyl)-3-oxo-propionylamino]-5-isobutylamino-phenyl}-carbamic acid tert-butyl ester (Example M126) (0.33 g, 0.63 mmol) by treatment with TFA in CH$_2$Cl$_2$ according to the general procedure N. Obtained as a light yellow solid (240 mg, 94%).

MS (ISP) 408.4 [(M+H)$^+$]; mp 212° C.

Example 179

8-Chloro-7-(isobutyl-amino)-4-(3-[1,2,3]triazol-1-yl-phenyl)-1,3-dihydro-benzo[b][1,4]diazepin-2-one The title compound was prepared from {4-chloro-5-(isobutyl-amino)-2-[3-oxo-3-(3-[1,2,3]triazol-1-yl-phenyl)-propionylamino]-phenyl}-carbamic acid tert-butyl ester (Example M127) (0.22 g, 0.42 mmol) by treatment with TFA in CH$_2$Cl$_2$ according to the general procedure N. Obtained as a light yellow solid (90 mg, 53%).

MS (ISP) 407.3 [(M–H)$^-$]; mp 249° C.

Example 180

7-(Isobutyl-amino)-4-(3-[1,2,3]triazol-1-yl-phenyl)-8-trifluoromethyl-1,3-dihydro-benzo[b][1,4]diazepin-2-one The title compound was prepared from {5-(isobutyl-amino)-2-[3-oxo-3-(3-[1,2,3]triazol-1-yl-phenyl)-propionylamino]-4-trifluoromethyl-phenyl}-carbamic acid tert-butyl ester (Example M128) (0.34 g, 0.61 mmol) by treatment with TFA in CH$_2$Cl$_2$ according to the general procedure N. Obtained as a light brown solid (150 mg, 56%).

MS (ISP) 443.4 [(M+H)$^+$]; mp 212° C.

Example 181

8-Chloro-7-(isobutyl-amino)-4-(3-[1,2,4]triazol-1-yl-phenyl)-1,3-dihydro-benzo[b][1,4]diazepin-2-one The title compound was prepared from {4-chloro-5-(isobutyl-amino)-2-[3-oxo-3-(3-[1,2,4]triazol-1-yl-phenyl)- propionylamino]-phenyl}-carbamic acid tert-butyl ester (Example M129) (0.39 g, 0.74 mmol) by treatment with TFA in CH$_2$Cl$_2$ according to the general procedure N. Obtained as a light orange solid (270 mg, 89%).

MS (ISP) 407.3 [(M−H)$^-$]; mp 222° C.

Example 182

7-(Isobutyl-amino)-4-(3-[1,2,4]triazol-1-yl-phenyl)-8-trifluoromethyl-1,3-dihydro-benzo[b][1,4]diazepin-2-one The title compound was prepared from {5-(isobutyl-amino)-2-[3-oxo-3-(3-[1,2,4]triazol-1-yl-phenyl)-propionylamino]-4-trifluoromethyl-phenyl}-carbamic acid tert-butyl ester (Example M130) (0.43 g, 0.77 mmol) by treatment with TFA in CH$_2$Cl$_2$ according to the general procedure N. Obtained as a light brown solid (270 mg, 61%).

MS (ISP) 441.3 [(M−H)$^-$]; mp 191° C.

Example 183

8-Chloro-7-(ethyl-methyl-amino)-4-[3-(4-hydroxymethyl-thiazol-2-yl)-phenyl]-1,3-dihydro-benzo[b][1,4]diazepin-2-one The title compound was prepared from [2-amino-4-chloro-5-(ethyl-methyl-amino)-phenyl]-carbamic acid tert-butyl ester (0.15 g) (Example J7) and 3-oxo-3-[3-[4-(tetrahydro-pyran-2-yloxymethyl)-thiazol-2-yl]-phenyl]-propionic acid tert-butyl ester (0.23 g) (Example K27) according to the general procedure M. The obtained material was deprotected and cyclized by treatment with TFA in CH$_2$Cl$_2$ according to the general procedure N. Obtained as a yellow solid (0.14 g).

MS (ISN) 439.2 [(M−H)$^-$]; mp 136–137° C.

Example 184

8-Chloro-4-[3-(4-hydroxymethyl-thiazol-2-yl)-phenyl]-7-(methyl-propyl-amino)-1,3-dihydro-benzo[b][1,4]diazepin-2-one The title compound was prepared from [2-amino-4-chloro-5-(methyl-propyl-amino)-phenyl]-carbamic acid tert-butyl ester (0.16 g) (Example J8) and 3-oxo-3-[3-[4-(tetrahydro-pyran-2-yloxymethyl)-thiazol-2-yl]-phenyl]-propionic acid tert-butyl ester (0.23 g) (Example K27) according to the general procedure M. The obtained material was deprotected and cyclized by treatment with TFA in CH$_2$Cl$_2$ according to the general procedure N. Obtained as a yellow solid (0.10 g).

MS (ISN) 453.2 [(M−H)$^-$]; mp 211–213° C.

Example 185

8-Chloro-4-[3-(4-hydroxymethyl-thiazol-2-yl)-phenyl]-7-(isopropyl-methyl-amino)-1,3-dihydro-benzo[b][1,4]diazepin-2-one The title compound was prepared from [2-amino-4-chloro-5-(isopropyl-methyl-amino)-phenyl]-carbamic acid tert-butyl ester (0.17 g) (Example J26) and 3-oxo-3-[3-[4-(tetrahydro-pyran-2-yloxymethyl)-thiazol-2-yl]-phenyl]-propionic acid tert-butyl ester (Example K27) (0.23 g) according to the general procedure M. The obtained material was deprotected and cyclized by treatment with TFA in CH$_2$Cl$_2$ according to the general procedure N. Obtained as a light-brown solid (0.05 g).

MS (ISP) 455.2 [(M+H)$^+$]; mp 193–195° C.

Example 186

8-Chloro-4-[3-(4-hydroxymethyl-thiazol-2-yl)-phenyl]-7-(isobutyl-methyl-amino)-1,3-dihydro-benzo[b][1,4]diazepin-2-one The title compound was prepared from [2-amino-4-chloro-5-(isobutyl-methyl-amino)-phenyl]-carbamic acid tert-butyl ester (0.23 g) (Example J27) and 3-oxo-3-[3-[4-(tetrahydro-pyran-2-yloxymethyl)-thiazol-2-yl]-phenyl]-propionic acid tert-butyl ester (0.32 g) (Example K27) according to the general procedure M. The obtained material was deprotected and cyclized by treatment with TFA in CH$_2$Cl$_2$ according to the general procedure N. Obtained as a yellow solid (0.06 g).

MS (ISP) 469.1 [(M+H)$^+$]; mp 135–136° C.

Example 187

8-Chloro-7-(ethyl-methyl-amino)-4-[3-(4-hydroxymethyl-oxazol-2-yl)-phenyl]-1,3-dihydro-benzo[b][1,4]diazepin-2-one The title compound was prepared from [2-amino-4-chloro-5-(ethyl-methyl-amino)-phenyl]-carbamic acid tert-butyl ester (0.15 g) (Example J7) and 3-oxo-3-[3-[4-(tetrahydro-pyran-2-yloxymethyl)-oxazol-2-yl]-phenyl]-propionic acid tert-butyl ester (0.22 g) (Example K11) according to the general procedure M. The obtained material was deprotected and cyclized by treatment with TFA in CH$_2$Cl$_2$ according to the general procedure N. Obtained as a yellow solid (0.10 g).

MS (ISN) 423.1 [(M−H)$^-$]; mp 165–166° C.

Example 188

8-Chloro-4-[3-(4-hydroxymethyl-oxazol-2-yl)-phenyl]-7-(methyl-propyl-amino)-1,3-dihydro-benzo[b][1,4]diazepin-2-one The title compound was prepared from [2-amino-4-chloro-5-(methyl-propyl-amino)-phenyl]-carbamic acid tert-butyl ester (0.16 g) (Example J8) and 3-oxo-3-[3-[4-(tetrahydro-pyran-2-yloxymethyl)-oxazol-2-yl]-phenyl]-propionic acid tert-butyl ester (0.22 g) (Example K11) according to the general procedure M. The obtained material was deprotected and cyclized by treatment with TFA in CH$_2$Cl$_2$ according to the general procedure N. Obtained as a yellow solid (0.10 g).

MS (ISP) 437.2 [(M−H)$^-$]; mp 166–167° C.

Example 189

8-Chloro-4-[3-(4-hydroxymethyl-oxazol-2-yl)-phenyl]-7-(isopropyl-methyl-amino)-1,3-dihydro-benzo[b][1,4]diazepin-2-one The title compound was prepared from [2-amino-4-chloro-5-(isopropyl-methyl-amino)-phenyl]-carbamic acid tert-butyl ester (0.17 g) (Example J26) and 3-oxo-3-[3-[4-(tetrahydro-pyran-2-yloxymethyl)-oxazol-2-yl]-phenyl]-propionic acid tert-butyl ester (0.22 g) (Example K11) according to the general procedure M. The obtained material was deprotected and cyclized by treatment with TFA in CH$_2$Cl$_2$ according to the general procedure N. Obtained as a yellow solid (0.05 g).

MS (ISP) 439.3 [(M+H)$^+$]; mp 143–145° C.

Example 190

8-Chloro-4-[3-(4-hydroxymethyl-oxazol-2-yl)-phenyl]-7-(isobutyl-methyl-amino)-1,3-dihydro-benzo[b][1,4]diazepin-2-one The title compound was prepared from [2-amino-4-chloro-5-(isobutyl-methyl-amino)-phenyl]-carbamic acid tert-butyl ester (0.23 g) (Example J27) and 3-oxo-3-[3-[4-(tetrahydro-pyran-2-yloxymethyl)-oxazol-2-yl]-phenyl]-propionic acid tert-butyl ester (0.31 g) (Example K11) according to the general procedure M. The obtained material was deprotected and cyclized by treatment with TFA in $CH_2Cl_2$ according to the general procedure N. Obtained as a yellow solid (0.18 g).

MS (ISP) 453.3 [(M+H)$^+$]; mp 166–167° C.

Example 191

8-Chloro-7-dimethylamino-4-[3-(4-methylaminomethyl-thiazol-2-yl)-phenyl]-1,3-dihydro-benzo[b][1,4]diazepin-2-one 8-Chloro-4-[3-(4-chloromethyl-thiazol-2-yl)-phenyl]-7-dimethylamino-1,3-dihydro-benzo[b][1,4]diazepin-2-one A mixture of 8-chloro-7-dimethylamino-4-[3-(4-hydroxymethyl-thiazol-2-yl)-phenyl]-1,3-dihydro-benzo[b][1,4]diazepin-2-one (0.38 g) (Example 19) and thionyl chloride (0.1 mL) in $CH_2Cl_2$ was heated to 40° C. for 2 h. The heterogeneous mixture was evaporated in vacuum and the residue was triturated with AcOEt to give the title compound (0.44 g) as a light-brown solid, MS (ISP) 445.1 [(M+H)$^+$].

8-Chloro-7-dimethylamino-4-[3-(4-methylaminomethyl-thiazol-2-yl)-phenyl]-1,3-dihydro-benzo[b][1,4]diazepin-2-one A mixture of 8-chloro-4-[3-(4-chloromethyl-thiazol-2-yl)-phenyl]-7-dimethylamino-1,3-dihydro-benzo[b][1,4]diazepin-2-one (89 mg) and KI (3 mg) in a 8M solution of methylamine in EtOH (1 mL) was stirred at 20° C. for 20 h. $H_2O$ (25 mL) was added and the pH of the mixture was set to 11 by addition of 2N NaOH. The precipitate was collected by filtration and purified by chromatography on silica gel using MeOH as eluent. The product was stirred with 20% aqueous MeOH (10 mL) and the solid was isolated by filtration to give the title compound (49 mg) as a yellow powder.

MS (ISP) 440.2 [(M+H)$^+$]; mp 129–130° C.

Example 192

8-Chloro-7-dimethylamino-4-[3-(4-morpholin-4-ylmethyl-thiazol-2-yl)-phenyl]-1,3-dihydro-benzo[b][1,4]diazepin-2-one A mixture of 8-chloro-4-[3-(4-chloromethyl-thiazol-2-yl)-phenyl]-7-dimethylamino-1,3-dihydro-benzo[b][1,4]diazepin-2-one (89 mg) (Example 191a), morpholine (0.17 mL) and KI (3 mg) in EtOH (0.5 mL) was stirred at 60° C. for 3 h. $H_2O$ (25 mL) was added to the cooled solution and the precipitate was collected by filtration and purified by chromatography on silica gel using AcOEt/acetone (1:1) as eluent. The product was stirred with 20% aqueous MeOH (20 mL) The pH of the mixture was set to 11 by addition of 1N NaOH and the solid was subsequently isolated by filtration to give the title compound (55 mg) as yellow powder.

MS (ISP) 496.2 [(M+H)$^+$]; mp 138–143° C.

Example 193

8-Chloro-7-dimethylamino-4-[3-(2-hydroxymethyl-thiazol-4-yl)-phenyl]-1,3-dihydro-benzo[b][1,4]diazepin-2-one 4-(3-Bromoacetyl-phenyl)-8-chloro-7-dimethylamino-1,3-dihydro-benzo[b][1,4]diazepin-2-one A solution of 3-oxo-3-[3-(2-bromo-1,1-dimethoxy-ethyl)-phenyl]-propionic acid tert-butyl ester (2.34 g) (Example K28) and (2-amino-4-chloro-5-dimethylamino-phenyl)-carbamic acid tert.-butyl ester (Example J2) (1.57 g) in toluene (16 mL) was heated to 100° C. for 5 h. The solvent was evaporated in vacuum and the crude product was purified by chromatography on silica gel using $CH_2Cl_2$/AcOEt (1:20) as eluent. A solution of the purified material (2.4 g) in $CH_2Cl_2$/TFA (1:1, 30 mL) was stirred at 20° C. for 15 min and then evaporated. The residual oil was dissolved in AcOEt and the solution was washed with 1N HCl and with brine, dried and evaporated. The residue was crystallized from AcOEt/$Et_2O$ to give 4-(3-bromoacetyl-phenyl)-8-chloro-7-dimethylamino-1,3-dihydro-benzo[b][1,4] diazepin-2-one as light-brown solid.

8-Chloro-7-dimethylamino-4-[3-(2-hydroxymethyl-thiazol-4-yl)-phenyl]-1,3-dihydro-benzo[b][1,4]diazepin-2-one A mixture of 4-(3-bromoacetyl-phenyl)-8-chloro-7-dimethylamino-1,3-dihydro-benzo[b][1,4]diazepin-2-one (0.22 g) and 2-(tert.-butylcarbonyl-oxy)thioacetamide (0.11 g) in EtOH (3 mL) was heated at 80° C. for 0.5 h. The solution was diluted with AcOEt, washed with sat. $NaHCO_3$ solution and with brine, dried and evaporated. The residue was stirred in a mixture of MeOH (8 mL) and 1.5N KOH (8 mL) at 20° C. for 20 min. $H_2O$ (30 ml) was added and the precipitated product collected by filtration to give the title compound (0.9 g) as yellow powder.

MS (ISP) 427.3 [(M+H)$^+$]; mp 176–178° C.

Example 194

4-[3-(2-Amino-thiazol-4-yl)-phenyl]-8-chloro-7-dimethylamino-1,3-dihydro-benzo[b][1,4]diazepin-2-one A mixture of 4-(3-bromoacetyl-phenyl)-8-chloro-7-dimethylamino-1,3-dihydro-benzo[b][1,4]diazepin-2-one (0.73 g) (Example 193a) and thiourea (0.13 g) in THF (10 mL) was heated to 60° C. for 15 min. The mixture was diluted with AcOEt and washed with sat. $NaHCO_3$ solution and with brine. The organic layer was dried and evaporated and the residue was stirred with $CH_2Cl_2$ to give the title compound (0.14 g) as yellow solid.

MS (ISN) 410.2 [(M–H)$^-$]; mp 247–248° C.

Example 195

8-Chloro-7-dimethylamino-4-[3-(2-ethylamino-thiazol-4-yl)-phenyl]-1,3-dihydro-benzo[b][1,4]diazepin-2-one A mixture of 4-(3-bromoacetyl-phenyl)-8-chloro-7-dimethylamino-1,3-dihydro-benzo[b][1,4]diazepin-2-one (130 mg) (Example 193a) and N-ethyl-thiourea (31 mg) in THF (3 mL) was heated at 60° C. for 15 min. The mixture was diluted with AcOEt and washed with sat. NaHCO$_3$ solution and with brine. The organic layer was dried and evaporated and the residue was purified by chromatography on silica gel using AcOEt/hexane (1:1) as eluent. The purified product was triturated with Et$_2$O to give the title compound (24 mg) as yellow solid.

MS (ISP) 440.3 [(M+H)$^+$]; mp 122–123° C.

Example 196

N-{4-[3-(7-Chloro-8-dimethylamino-4-oxo-4,5-dihydro-3H-benzo[b][1,4]diazepin-2-yl)-phenyl]-thiazol-2-yl}-guanidine A mixture of 4-(3-bromoacetyl-phenyl)-8-chloro-7-dimethylamino-1,3-dihydro-benzo[b][1,4]diazepin-2-one (130 mg) (Example 193a) and N-amidino-thiourea (35 mg) in THF (3 mL) was heated at 60° C. for 1 h. The mixture was diluted with AcOEt and washed with sat. NaHCO$_3$ solution and with brine. The organic layer was dried and evaporated and the residue was purified by chromatography on silica gel using AcOEt/MeOH (20:1) as eluent. The purified product was crystallyzed from acetone to give the title compound (22 mg) as yellow solid.

MS (ISP) 454.2 [(M+H)$^+$]; mp 221° C. dec.

Example 197

8-Chloro-7-dimethylamino-4-{3-[2-(pyridin-4-ylamino)-thiazol-4-yl]-phenyl}-1,3-dihydro-benzo[b][1,4]diazepin-2-one A mixture of 4-(3-bromoacetyl-phenyl)-8-chloro-7-dimethylamino-1,3-dihydro-benzo[b][1,4]diazepin-2-one (130 mg) (Example 193a) and 1-(4-pyridyl)-2-thiourea (46 mg) in THF (3 mL) was heated at 60° C. for 45 min. The mixture was diluted with AcOEt and washed with sat. NaHCO$_3$ solution and with brine. The organic layer was dried and evaporated and the residue was triturated with Et$_2$O to give the title compound (55 mg) as yellow solid.

MS (ISP) 489.2 [(M+H)$^+$]; mp 231–234° C.

Example 198

8-Chloro-4-[3-(2-methyl-oxazol-4-yl)-phenyl]-7-(methyl-propyl-amino)-1,3-dihydro-benzo[b][1,4]diazepin-2-one The title compound was prepared from [2-amino-4-chloro-5-(methyl-propyl-amino)-phenyl]-carbamic acid tert-butyl ester (0.16 g) (Example J8) and 3-oxo-3-[3-(2-methyl-oxazol-4-yl)-phenyl]-propionic acid tert-butyl ester (0.17 g) (Example K29) according to the general procedure M. The obtained material was deprotected and cyclized by treatment with TFA in CH$_2$Cl$_2$ according to the general procedure N. Obtained as a yellow solid (0.07 g).

MS (ISP) 423.2 [(M+H)$^+$]; mp 163–164° C.

Example 199

4-[3-(4-Hydroxymethyl-thiazol-2-yl)-phenyl]-8-methyl-7-(methyl-propyl-amino)-1,3-dihydro-benzo[b][1,4]diazepin-2-one The title compound was prepared from [2-amino-4-methyl-5-(methyl-propyl-amino)-phenyl]-carbamic acid tert-butyl ester (0.21 g) (Example J24) and 3-oxo-3-[3-[4-(tetrahydro-pyran-2-yloxymethyl)-thiazol-2-yl]-phenyl]-propionic acid tert-butyl ester (Example K27) (0.31 g) according to the general procedure M. The obtained material was deprotected and cyclized by treatment with TFA in CH$_2$Cl$_2$ according to the general procedure N. Obtained as a yellow solid (0.09 g).

MS (ISP) 435.3 [(M+H)$^+$]; mp 222–224° C.

Example 200

4-[3-(4-Hydroxymethyl-oxazol-2-yl)-phenyl]-8-methyl-7-(methyl-propyl-amino)-1,3-dihydro-benzo[b][1,4]diazepin-2-one The title compound was prepared from [2-amino-4-methyl-5-(methyl-propyl-amino)-phenyl]-carbamic acid tert-butyl ester (0.21 g) (Example J24) and 3-oxo-3-[3-[4-(tetrahydro-pyran-2-yloxymethyl)-oxazol-2-yl]-phenyl]-propionic acid tert-butyl ester (Example K11) (0.31 g) according to the general procedure M. The obtained material was deprotected and cyclized by treatment with TFA in CH$_2$Cl$_2$ according to the general procedure N. Obtained as a yellow solid (0.16 g).

MS (ISP) 419.3 [(M+H)$^+$]; mp 200–202° C.

Example 201

7-Dimethylamino-4-[3-(4-hydroxymethyl-thiazol-2-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-[3-[4-(tetrahydro-pyran-2-yloxymethyl)-thiazol-2-yl]-phenyl]-propionic acid tert-butyl ester (Example K27) (0.23 g) according to the general procedure M. The obtained material was deprotected and cyclized by treatment with TFA in CH$_2$Cl$_2$ according to the general procedure N. Obtained as a yellow solid (0.12 g).

MS (ISP) 461.2 [(M+H)$^+$]; mp 198–199° C.

Example 202

7-Dimethylamino-4-[3-(4-hydroxymethyl-oxazol-2-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-[3-[4-(tetrahydro-pyran-2-yloxymethyl)-oxazol-2-yl]-phenyl]-propionic acid tert-butyl ester (0.22 g) (Example K11) according to the general procedure M. The obtained material was deprotected and cyclized by treatment with TFA in CH$_2$Cl$_2$ according to the general procedure N. Obtained as a yellow solid (0.11 g).

MS (ISP) 445.0 [(M+H)$^+$]; mp 197–198° C.

Example 203

4-[3-(4-Hydroxymethyl-thiazol-2-yl)-phenyl]-7-(methyl-propyl-amino)-8-trifluoromethyl-1,3-dihydro-benzo[b][1,4]diazepin-2-one The title compound was prepared from [2-amino-5-(methyl-propyl-amino)-4-trifluoromethyl-phenyl]-carbamic acid tert-butyl ester (0.17 g) (Example J35) and 3-oxo-3-[3-[4-(tetrahydro-pyran-2-yloxymethyl)-thiazol-2-yl]-phenyl]-propionic acid tert-butyl ester (Example K27) (0.23 g)

according to the general procedure M. The obtained material was deprotected and cyclized by treatment with TFA in CH$_2$Cl$_2$ according to the general procedure N. Obtained as a yellow solid (0.06 g).

MS (ISP) 489.2 [(M+H)$^+$]; mp 177–180° C.

Example 204

7-Dimethylamino-4-[3-(5-hydroxymethyl-[1,3,4] thiadiazol-2-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-{3-[5-(tetrahydro-pyran-2-yloxymethyl)-[1,3,4]thiadiazol-2-yl]-phenyl}-propionic acid tert-butyl ester (0.23 g) (Example K30) according to the general procedure M. The obtained material was deprotected and cyclized by treatment with TFA in CH$_2$Cl$_2$ according to the general procedure N. Obtained as off-white solid (0.06 g).

MS (ISP) 462.1[(M+H)$^+$]; mp 242–246° C.

Example 205

7-Dimethylamino-4-{3-[5-(2-hydroxy-ethyl)-[1,3,4] thiadiazol-2-yl]-phenyl}-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-(3-{5-[2-(tetrahydro-pyran-2-yloxy)-ethyl]-[1,3,4]thiadiazol-2-yl}-phenyl)-propionic acid tert-butyl ester (0.24 g) (Example K31) according to the general procedure M. The obtained material was deprotected and cyclized by treatment with TFA in CH$_2$Cl$_2$ according to the general procedure N. Obtained as a off-white solid (0.06 g).

MS (ISN) 474.2 [(M−H)$^-$]; mp 234–237° C.

Example 206

7-Dimethylamino-4-[3-(5-hydroxymethyl-1,3,4] oxadiazol-2-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (1.44 g) (Example J6) and 3-oxo-3-{3-[5-(tetrahydro-pyran-2-yloxymethyl)-[1,3,4]oxadiazol-2-yl]-phenyl}-propionic acid tert-butyl ester (2.17 g) (Example K32) according to the general procedure M. The obtained material was deprotected and cyclized by treatment with TFA in CH$_2$Cl$_2$ according to the general procedure N. Obtained as off-white solid (0.88 g).

MS (ISP) 463.2 [(M+NH$_4$)$^+$].

Example 207

7-Dimethylamino-4-{3-[5-(2-hydroxy-ethyl)-[1,3,4] oxadiazol-2-yl]-phenyl}-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-(3-{5-[2-(tetrahydro-pyran-2-yloxy)-ethyl]-[1,3,4]oxadiazol-2-yl}-phenyl)-propionic acid tert-butyl ester (0.23 g) (Example K33) according to the general procedure M. The obtained material was deprotected and cyclized by treatment with TFA in CH$_2$Cl$_2$ according to the general procedure N. Obtained as off-white solid (0.88 g).

MS (ISP) 460.2 [(M+H)$^+$]; mp 237° C. dec.

Example 208

7-Dimethylamino-4-(3-oxazol-4-yl-phenyl)-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (96 mg) (Example J6) and 3-(3-oxazol-4-yl-phenyl)-3-oxo-propionic acid tert-butyl ester (103 mg) (Example K34) according to the general procedure M. The obtained material was deprotected and cyclized by treatment with TFA in CH$_2$Cl$_2$ according to the general procedure N. Obtained as yellow solid (50 mg).

MS (ISP) 415.2 [(M+H)$^+$]; mp 218–219° C.

Example 209

7-Dimethylamino-4-(3-thiazol-4-yl-phenyl)-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (96 mg) (Example J6) and 3-oxo-3-(3-thiazol-4-yl-phenyl)-propionic acid tert-butyl ester (109 mg) (Example K35) according to the general procedure M. The obtained material was deprotected and cyclized by treatment with TFA in CH$_2$Cl$_2$ according to the general procedure N. Obtained as off-white solid (61 mg).

MS (ISP) 431.2 [(M+H)$^+$]; mp 200° C. dec.

Example 210

7-Dimethylamino-4-[3-(2-methyl-oxazol-4-yl)-phenyl]-8-trifluoromethyl-1,3-dihydro-benzo[b][1,4] diazepin-2-one The title compound was prepared from (2-amino-5-dimethylamino-4-trifluoro-methyl-phenyl)-carbamic acid tert-butyl ester (0.16 g) (Example J6) and 3-[3-(2-methyl-oxazol-4-yl)-phenyl]-3-oxo-propionic acid tert-butyl ester (0.18 g) (Example K29) according to the general procedure M. The obtained material was deprotected and cyclized by treatment with TFA in CH$_2$Cl$_2$ according to the general procedure N. Obtained as yellow solid (0.04 g).

MS (ISP) 429.3[(M+H)$^+$]; mp 192–193° C.

Example 211

7-Dimethylamino-4-[3-(5-methyl-oxazol-4-yl)-phenyl]-8-trifluoromethyl-1,3-dihydro-benzo[b][1,4] diazepin-2-one The title compound was prepared from (2-amino-5-dimethylamino-4-trifluoro-methyl-phenyl)-carbamic acid tert-butyl ester (0.16 g) (Example J6) and 3-[3-(5-methyl-oxazol-4-yl)-phenyl]-3-oxo-propionic acid tert-butyl ester (0.18 g) (Example K36) according to the general procedure M. The obtained material was deprotected and cyclized by treatment with TFA in CH$_2$Cl$_2$ according to the general procedure N. Obtained as yellow solid (0.13 g).

MS (ISP) 429.3 [(M+H)$^+$]; mp 238–239° C.

Example 212

7-Dimethylamino-4-[3-(2-methyl-5-propyl-oxazol-4-yl)-phenyl]-8-trifluoromethyl-1,3-dihydro-benzo[b] [1,4]diazepin-2-one The title compound was prepared from (2-amino-5-dimethylamino-4-trifluoro-methyl-phenyl)-carbamic acid tert-butyl ester (80 mg) (Example J6) and 3-[3-(2-methyl-5-propyl-oxazol-4-yl)-phenyl]-3-oxo-propionic acid tert-butyl ester (103 mg) (Example K37) according to the general procedure M. The obtained material was deprotected and cyclized by treatment with TFA in $CH_2Cl_2$ according to the general procedure N. Obtained as pale-yellow solid (20 mg).

MS (ISP) 471.2 [(M+H)$^+$]; mp 211–212 ° C.

Example 213

7-Dimethylamino-4-[3-(5-methyl-thiazol-4-yl)-phenyl]-8-trifluoromethyl-1,3-dihydro-benzo[b][1,4]diazepin-2-one The title compound was prepared from (2-amino-5-dimethylamino-4-trifluoro-methyl-thiazol-4-yl)-phenyl]-3-oxo-propionic acid tert-butyl ester (0.19 g) (Example K38) according to the general procedure M. The obtained material was deprotected and cyclized by treatment with TFA in $CH_2Cl_2$ according to the general procedure N. Obtained as yellow solid (0.06 g).

MS (ISP) 445.2 [(M+H)$^+$]; mp 214–215 ° C.

Example 214

7-Dimethylamino-4-[3-(2,5-dimethyl-thiazol-4-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (48 mg) (Example J6) and 3-[3-(2,5-methyl-thiazol-4-yl)-phenyl]-3-oxo-propionic acid tert-butyl ester (50 mg) (Example K39) according to the general procedure M. The obtained material was deprotected and cyclized by treatment with TFA in $CH_2Cl_2$ according to the general procedure N. Obtained as yellow solid (38 mg).

MS (ISP) 459.2 [(M+H)$^+$]; mp 208–209 ° C.

Example 215

7-Dimethylamino-4-[3-(2-hydroxymethyl-thiazol-4-yl)-phenyl]-8-trifluoromethyl-1,3-dihydro-benzo[b][1,4]diazepin-2-one 4-(3-Bromoacetyl-phenyl)-7-dimethylamino-8-trifluoromethyl-1,3-dihydro-benzo[b][1,4]diazepin-2-one A solution of (2-amino-5-dimethylamino-4-trifluoromethyl-phenyl)-carbamic acid tert-butyl ester (Example J6) (0.32 g) and 3-oxo-3-[3-(2-bromo-1,1-dimethoxy-ethyl)-phenyl]-propionic acid tert-butyl ester (0.43 g) (Example K28) in toluene (3 mL) was heated to 100° C. for 2 h. The solvent was evaporated in vacuum and the crude product was purified by chromatography on silica gel using AcOEt/Hexan(1:3) as eluent. A solution of the purified material (0.57 g) in $CH_2Cl_2$/TFA (1:1, 7 mL) was stirred at 20° C. for 15 min and then evaporated. The residual oil was dissolved in AcOEt and the solution was washed with IN HCl and with brine, dried and evaporated to give crude 4-(3-bromoacetyl-phenyl)-7-dimethylamino-8-trifluoromethyl-1,3-dihydro-benzo[b][1,4]diazepin-2-one (0.22 g) as light-brown solid.

7-Dimethylamino-4-[3-(2-hydroxymethyl-thiazol-4-yl)-phenyl]-8-trifluoro-methyl-1,3-dihydro-benzo[b][1,4]diazepin-2-one A mixture of 4-(3-bromoacetyl-phenyl)-7-dimethylamino-8-trifluoromethyl-1,3-dihydro-benzo[b][1,4]diazepin-2-one (0.40 g) and 2-(tert.-butylcarbonyloxy)thio-acetamide (0.21 g) in EtOH (5 mL) was heated at 80° C. for 0.5 h. The solution was diluted with AcOEt, washed with sat. $NaHCO_3$ solution and with brine, dried and evaporated. The residue was stirred in a mixture of MeOH (5 mL) and 1.5N KOH (5 mL) at 20° C. for 20 min. $H_2O$ was added and the precipitated product collected by filtration and purified by chromatography on silica gel using AcOEt as eluent to give the title compound (0.01 g) as yellow solid.

MS (ISP) 461.1 [(M+H)$^+$].

Example 216

7-Dimethylamino-4-[3-(2-hydroxymethyl-5-methyl-thiazol-4-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-{3-[5-methyl-2-(tetrahydro-pyran-2-yloxymethyl)-thiazol-4-yl]-phenyl}-propionic acid tert-butyl ester (0.26 g) (Example K40) according to the general procedure M. The obtained material was deprotected and cyclized by treatment with TFA in $CH_2Cl_2$ according to the general procedure N. Obtained as light-yellow solid (0.11 g).

MS (ISP) 475.2 [(M+H)$^+$]; mp 190–193° C.

Example 217

7-Dimethylamino-4-[3-(2-hydroxymethyl-5-propyl-thiazol-4-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (79 mg) (Example J6) and 3-oxo-3-{3-[-5-propyl-2-(tetrahydro-pyran-2-yloxymethyl)-thiazol-4-yl]-phenyl}-propionic acid tert-butyl ester (138 mg) (Example K41) according to the general procedure M. The obtained material was deprotected and cyclized by treatment with TFA in $CH_2Cl_2$ according to the general procedure N. Obtained as yellow solid (45 mg).

MS (ISP) 503.2 [(M+H)$^+$]; mp 112–114° C.

Example 218

7-Dimethylamino-4-[3-(5-hydroxymethyl-2-methyl-thiazol-4-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-{3-[2-methyl-5-(tetrahydro-pyran-2-yloxymethyl)-thiazol-4-yl]-phenyl}-propionic acid tert-butyl ester (0.26 g) (Example K42) according to the general procedure M. The obtained material was deprotected and cyclized by treatment with TFA in $CH_2Cl_2$ according to the general procedure N. Obtained as yellow solid (0.11 g).

MS (ISN) 473.0 [(M−H)$^-$]; mp 226–227° C.

Example 219

7-Dimethylamino-4-[3-(5-hydroxymethyl-thiazol-4-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.16 g) (Example J6) and 3-oxo-3-{[5-(tetrahydro-pyran-2-yloxymethyl)-thiazol-4-yl]-phenyl}-propionic acid tert-butyl ester (0.25 g) (Example K43) according to the general procedure M. The obtained material was deprotected and cyclized by treatment with TFA in $CH_2Cl_2$ according to the general procedure N. Obtained as off-white solid (0.08 g).

MS (ISN) 459.3 [(M−H)⁻].

Example 220

4-(3-{5-[(Cyclopropylmethyl-amino)-methyl]-thiazol-4-yl}-phenyl)-7-dimethylamino-8-trifluoromethyl-1,3-dihydro-benzo[b][1,4]diazepin-2-one A mixture of 7-dimethylamino-4-[3-(5-hydroxymethyl-thiazol-4-yl)-phenyl]-8-trifluoromethyl-1,3-dihydro-benzo[b][1,4]diazepin-2-one (Example 219) (65 mg) and thionyl chloride (0.015 mL) in $CH_2Cl_2$ (0.3 mL) was stirred at 20° C. for 1 h. The heterogeneous mixture was evaporated in vacuum and the residue was suspended in EtOH (0.5 mL). Aminomethyl-cyclopropane (0.12 mL) and KI (3 mg) were added and the mixture was stirred at 80° C. for 5 h. The mixture was evaporated in vacuum ant the residue was purified by chromatography on silica gel using AcOEt/MeOH (50:1) as eluent. The resulting product was stirred with 20% aqueous MeOH (10 mL), the pH of the mixture being set to 11 by the addition of 1N NaOH, and the solid was isolated by filtration to give the title compound (44 mg) as off-white solid.

MS (ISP) 514.3 [(M+H)⁺]; 157–158° C.

Example 221

7-Dimethylamino-4-[3-(2-isopropyl-1H-imidazol-4-yl)-phenyl]-8-trifluoromethyl-1,3-dihydro-benzo[b][1,4]diazepin-2-one The title compound was prepared from (2-amino-5-dimethylamino-4-trifluoro-methyl-phenyl)-carbamic acid tert-butyl ester (0.13 g) (Example J6) and 3-[3-(2-isopropyl-3H-imidazol-4-yl)-phenyl]-3-oxo-propionic acid tert-butyl ester (0.20 g) (Example K44) according to the general procedure M. The obtained material was deprotected and cyclized by treatment with TFA in $CH_2Cl_2$ according to the general procedure N. Obtained as off-white solid (0.10 g).

MS (ISP) 456.4 [(M+H)⁺]; mp 150° C. dec.

Example 222

4-[3-(5-Hydroxymethyl-[1,3,4]thiadiazol-2-yl)-phenyl]-7-(methyl-propyl-amino)-8-trifluoromethyl-1,3-dihydro-benzo[b][1,4]diazepin-2-one The title compound was prepared from [2-amino-5-(methyl-propyl-amino)-4-trifluoromethyl-phenyl]-carbamic acid tert-butyl ester (0.17 g) (Example J35) and 3-oxo-3-{3-[5-(tetrahydro-pyran-2-yloxymethyl)-[1,3,4]thiadiazol-2-yl]-phenyl}-propionic acid tert-butyl ester (0.23 g) (Example K30) according to the general procedure M. The obtained material was deprotected and cyclized by treatment with TFA in $CH_2Cl_2$ according to the general procedure N. Obtained as a yellow solid (0.02 g).

MS (ISP) 490.2 [(M+H)⁺]; mp 193–194° C.

Example 223

8-Chloro-7-dimethylamino-4-{3-[5-(2-hydroxy-ethyl)-[1,3,4]thiadiazol-2-yl]-phenyl}-1,3-dihydro-benzo[b][1,4]diazepin-2-one The title compound was prepared from (2-amino-4-chloro-5-dimethylamino-phenyl)-carbamic acid tert.-butyl ester (Example J1) (0.15) and crude 3-oxo-3-(3-{5-[2-(tetrahydro-pyran-2-yloxy)-ethyl]-[1,3,4]thiadiazol-2-yl}-phenyl)-propionic acid tert-butyl ester (0.24 g) (Example K30) according to the general procedure M. The obtained material was deprotected and cyclized by treatment with TFA in $CH_2Cl_2$ according to the general procedure N. Obtained as a yellow solid (0.10 g).

MS (ISN) 440.2 [(M−H)⁻]; mp 198–200° C.

Example I

Tablets of the following composition are produced in a conventional manner:

| mg/Tablet | |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

| mg/Tablet | |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

| mg/Capsule | |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compound of formula

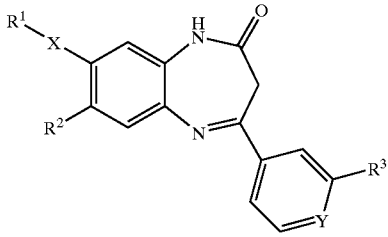

I wherein
X is selected from the group consisting of a single bond and an ethynediyl group; wherein
when X is a single bond,
$R^1$ is selected from the group consisting of cyano,
halogen,
lower alkyl,
$C_3$–$C_6$-cycloalkyl,
lower alkoxy,
fluoro-lower alkoxy,
fluoro-lower alkyl,
unsubstituted pyrrol-1-yl, and pyrrol-1-yl substituted by between one and three substituents selected from the group consisting of
fluoro, chloro, cyano, —(CH$_2$)$_{1-4}$-hydroxy, fluoro-lower alkyl, lower alkyl, —(CH$_2$)$_n$-lower alkoxy, —(CH$_2$)$_n$—C(O)O—R", —(CH$_2$)$_{1-4}$—NR'R", hydroxy-lower alkoxy, —(CH$_2$)$_n$—CONR'R",
unsubstituted phenyl, and phenyl substituted by one or two substituents selected from the group consisting of halogen, lower alkyl, fluoro-lower alkyl, lower alkoxy, fluoro-lower alkoxy and cyano;
when X is an ethynediyl group,
$R^1$ is unsubstituted phenyl, or phenyl substituted by between one and three substituents selected from the group consisting of halogen, lower alkyl, fluoro-lower alkyl,
$C_3$–$C_6$-cycloalkyl, lower alkoxy and fluoro-lower alkoxy;
$R^2$ is selected from the group consisting of NR'R", fluoro-lower alkoxy,
unsubstituted 3-oxo-piperazin-1-yl, pyrrolidin-1-yl or piperidin-1-yl and 3-oxo-piperazin-1-yl, pyrrolidin-1-yl or piperidin-1-yl substituted by R";
R' is selected from the group consisting of hydrogen,
lower alkyl,
$C_3$–$C_6$-cycloalkyl,
fluoro-lower alkyl and
2-lower alkoxy lower alkyl;
R" is selected from the group consisting of hydrogen,
lower alkyl,
$C_3$–$C_6$-cycloalkyl,
fluoro-lower alkyl,
2-lower alkoxy lower alkyl,
—(CH$_2$)$_{2-4}$-di-lower alkylamino,
—(CH$_2$)$_{2-4}$-morpholinyl,
—(CH$_2$)$_{2-4}$-pyrrolidinyl,
—(CH$_2$)$_{2-4}$-piperidinyl and
3-hydroxy-lower alkyl;
Y is selected from the group consisting of —CH= and =N—;
$R^3$ is selected from the group consisting of halogen,
lower alkyl,
fluoro-lower alkyl,
lower alkoxy,
cyano,
—(CH$_2$)$_n$—C(O)—OR",
—(CH$_2$)$_n$—C(O)—NR'R",
unsubstituted five-membered aromatic heterocycle, and a five-membered aromatic heterocycle substituted by a substitutent selected from the group consisting of halogen, fluoro-lower alkyl, fluoro-lower alkoxy, cyano, —(CH$_2$)$_n$—NR'R", —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, unsubstituted lower alkyl and lower alkyl substituted by fluoro, hydroxy, lower alkoxy, cyano or carbamoyloxy; and
n is 0, 1, 2, 3 or 4;
or a pharmaceutically acceptable addition salt thereof.
2. The compound according to claim 1, wherein X is a single bond.
3. The compound according to claim 2, wherein $R^1$ is trifluoromethyl.
4. The compound according to claim 3, wherein $R^3$ is cyano.
5. The compound of claim 4, which is selected from the group consisting of
4-(4-oxo-8-pyrrolidin-1-yl-7-trifluoromethyl-4,5-dihydro-3H-benzo[b][1,4]diazepin-2-yl)-pyridine-2-carbonitrile,
4-[8-(cyclopropylmethyl-methyl-amino)-4-oxo-7-trifluoromethyl-4,5-dihydro-3H-benzo[b][1,4]diazepin-2-yl]-pyridine-2-carbonitrile,
4-[8-(cyclopropylmethyl-amino)-4-oxo-7-trifluoromethyl-4,5-dihydro-3H-benzo[b][1,4]diazepin-2-yl]-pyridine-2-carbonitrile,
4-[4-oxo-8-(2,2,2-trifluoro-ethoxy)-7-trifluoromethyl-4,5-dihydro-3H-benzo[b][1,4]diazepin-2-yl]-pyridine-2-carbonitrile, and
4-[8-(isopropyl-methyl-amino)-4-oxo-7-trifluoromethyl-4,5-dihydro-3H-benzo[b][1,4]diazepin-2-yl]-pyridine-2-carbonitrile.
6. The compound of claim 3, wherein $R^3$ is an unsubstituted five-membered aromatic heterocycle or a five-membered aromatic heterocycle substituted by a substitutent selected from the group consisting of halogen, fluoro-lower alkyl, fluoro-lower alkoxy, cyano, —(CH$_2$)$_n$—NR'R", —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, unsubstituted lower alkyl, and lower alkyl substituted by fluoro, hydroxy, lower alkoxy, cyano or carbamoyloxy.
7. The compound of claim 6, which is selected from the group consisting of
7-dimethylamino-4-[3-(3-methyl-isoxazol-5-yl)-phenyl]-8-trifluoromethyl-1,3-dihydro-benzo[b][1,4]diazepin-2-one,
7-dimethylamino-4-[3-(2-methyl-2H-pyrazol-3-yl)-phenyl]-8-trifluoromethyl-1,3-dihydro-benzo[b][1,4]diazepin-2-one,
7-dimethylamino-4-(3-imidazol-1-yl-phenyl)-8-trifluoromethyl-1,3-dihydro-benzo[b][1,4]diazepin-2-one,
4-[3-(3-methyl-isoxazol-5-yl)-phenyl]-7-(methyl-propyl-amino)-8-trifluoromethyl-1,3-dihydro-benzo[b][1,4]diazepin-2-one,
7-(isobutyl-methyl-amino)-4-[3-(3-methyl-isoxazol-5-yl)-phenyl]-8-trifluoromethyl-1,3-dihydro-benzo[b][1,4]diazepin-2-one, 7-(isopropyl-methyl-amino)-4-[3-(3-methyl-isoxazol-5-yl)-phenyl]-8-trifluoromethyl-1,3-dihydro-benzo[b][1,4]diazepin-2-one, 7-(isobutyl-methyl-amino)-4-(3-{5-[(isopropyl-methyl-amino)-methyl]-[1,2,3]triazol-1-yl}-phenyl)-8-trifluoromethyl-1,3-dihydro-benzo[b][1,4]diazepin-2-one, 7-(isopropyl-methyl-amino)-4-[3-(5-pyrrolidin-1-ylmethyl-[1,2,3]triazol-1-yl)-phenyl]-8-trifluoromethyl-1,3-dihydro-benzo[b][1,4]diazepin-2-one, 7-(methyl-propyl-amino)-4-(3-[1,2,3]triazol-1-yl-phenyl)-8-trifluoromethyl-1,3-dihydro-benzo[b][1,4]diazepin-2-one, 7-(isobutyl-methyl-amino)-4-(3-[1,2,3]triazol-1-yl-phenyl)-8-trifluoromethyl-1,3-dihydro-benzo[b][1,4]diazepin-2-one, 4-(3-imidazol-1-yl-phenyl)-7-isobutylamino-8-trifluoromethyl-1,3-dihydro-benzo[b][1,4]diazepin-2-one, 7-dimethylamino-4-[3-(4-hydroxymethyl-thiazol-2-yl)-phenyl]-8-trifluoromethyl-1,3-dihydro-benzo[b][1,4]diazepin-2-one, 7-dimethylamino-4-[3-(4-hydroxymethyl-oxazol-2-yl)-phenyl]-8-trifluoromethyl-1,3-dihydro-benzo[b][1,4]diazepin-2-one, 4-[3-(4-hydroxymethyl-thiazol-2-yl)-phenyl]-7-(methyl-propyl-amino)-8-trifluoromethyl-1,3-dihydro-benzo[b][1,4]diazepin-2-one, and 4-[3-(5-hydroxymethyl-[1,3,4]thiadiazol-2-yl)-phenyl]-7-(methyl-propyl-amino)-8-trifluoromethyl-1,3-dihydro-benzo[b][1,4]diazepin-2-one.

8. The compound of claim 2, wherein $R^1$ is chloro.

9. The compound of claim 8, which is selected from the group consisting of 8-chloro-7-isobutylamino-4-[3-(3-methyl-isoxazol-5-yl)-phenyl]-1,3-dihydro-benzo[b][1,4]diazepin-2-one, 8-chloro-7-(methyl-propyl-amino)-4-[3-(5-pyrrolidin-1-ylmethyl-[1,2,3]triazol-1-yl)-phenyl]-1,3-dihydro-benzo[b][1,4]diazepin-2-one, 8-chloro-7-(isopropyl-methyl-amino)-4-[3-(5-pyrrolidin-1-ylmethyl-[1,2,3]triazol-1-yl)-phenyl]-1,3-dihydro-benzo[b][1,4]diazepin-2-one, 8-chloro-7-(isobutyl-methyl-amino)-4-[3-(5-pyrrolidin-1-ylmethyl-[1,2,3]triazol-1-yl)-phenyl]-1,3-dihydro-benzo[b][1,4]diazepin-2-one, 8-chloro-4-[3-(5-dimethylaminomethyl-[1,2,3]triazol-1-yl)-phenyl]-7-(isobutyl-methyl-amino)-1,3-dihydro-benzo[b][1,4]diazepin-2-one, 4-[3-(5-azetidin-1-ylmethyl-[1,2,3]triazol-1-yl)-phenyl]-8-chloro-7-(isopropyl-methyl-amino)-1,3-dihydro-benzo[b][1,4]diazepin-2-one, 4-[3-(5-azetidin-1-ylmethyl-[1,2,3]triazol-1-yl)-phenyl]-8-chloro-7-(isobutyl-methyl-amino)-1,3-dihydro-benzo[b][1,4]diazepin-2-one, 8-chloro-7-(isobutyl-methyl-amino)-4-[3-(5-piperidin-1-ylmethyl-[1,2,3]triazol-1-yl)-phenyl]-1,3-dihydro-benzo[b][1,4]diazepin-2-one, 8-chloro-7-(isopropyl-methyl-amino)-4-(3-{5-[(isopropyl-methyl-amino)-methyl]-[1,2,3]triazol-1-yl}-phenyl)-1,3-dihydro-benzo[b][1,4]diazepin-2-one, 8-chloro-4-(3-{5-[(isobutyl-methyl-amino)-methyl]-[1,2,3]triazol-1-yl}-phenyl)-7-(isopropyl-methyl-amino)-1,3-dihydro-benzo[b][1,4]diazepin-2-one, 8-chloro-7-isopropylamino-4-[3-(3-methyl-isoxazol-5-yl)-phenyl]-1,3-dihydro-benzo[b][1,4]diazepin-2-one, 8-chloro-7-(isobutyl-methyl-amino)-4-(3-[1,2,3]triazol-1-yl-phenyl)-1,3-dihydro-benzo[b][1,4]diazepin-2-one, 8-chloro-4-(3-imidazol-1-yl-phenyl)-7-isobutylamino-1,3-dihydro-benzo[b][1,4]diazepin-2-one, 8-chloro-7-(ethyl-methyl-amino)-4-[3-(4-hydroxymethyl-thiazol-2-yl)-phenyl]-1,3-dihydro-benzo[b][1,4]diazepin-2-one 8-chloro-4-[3-(4-hydroxymethyl-thiazol-2-yl)-phenyl]-7-(methyl-propyl-amino)-1,3-dihydro-benzo[b][1,4]diazepin-2-one 8-chloro-4-[3-(4-hydroxymethyl-thiazol-2-yl)-phenyl]-7-(isopropyl-methyl-amino)-1,3-dihydro-benzo[b][1,4]diazepin-2-one 8-chloro-4-[3-(4-hydroxymethyl-thiazol-2-yl)-phenyl]-7-(isobutyl-methyl-amino)-1,3-dihydro-benzo[b][1,4]diazepin-2-one 8-chloro-7-(ethyl-methyl-amino)-4-[3-(4-hydroxymethyl-oxazol-2-yl)-phenyl]-1,3-dihydro-benzo[b][1,4]diazepin-2-one 8-chloro-4-[3-(4-hydroxymethyl-oxazol-2-yl)-phenyl]-7-(methyl-propyl-amino)-1,3-dihydro-benzo[b][1,4]diazepin-2-one 8-chloro-4-[3-(4-hydroxymethyl-oxazol-2-yl)-phenyl]-7-(isopropyl-methyl-amino)-1,3-dihydro-benzo[b][1,4]diazepin-2-one, and 8-chloro-4-[3-(4-hydroxymethyl-oxazol-2-yl)-phenyl]-7-(isobutyl-methyl-amino)-1,3-dihydro-benzo[b][1,4]diazepin-2-one.

10. The compound of claim 2, wherein $R^1$ is cyano.

11. The compound of claim 10, which is selected from the group consisting of 8-diethylamino-2-[3-(3-methyl-isoxazol-5-yl)-phenyl]-4-oxo-4,5-dihydro-3H-benzo[b][1,4]diazepine-7-carbonitrile, and 2-[3-(3-methyl-isoxazol-5-yl)-phenyl]-4-oxo-8-piperidin-1-yl-4,5-dihydro-3H-benzo[b][1,4]diazepine-7-carbonitrile.

12. The compound of claim 1, wherein $R^3$ is an unsubstituted five-membered aromatic heterocycle or a five-membered aromatic heterocycle substituted by a substituent selected from the group consisting of halogen, fluoro-lower alkyl, fluoro-lower alkoxy, cyano, —(CH$_2$)$_n$—NR'R", —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, unsubstituted lower alkyl, and lower alkyl substituted by fluoro, hydroxy, lower alkoxy, cyano or carbamoyloxy.

13. The compound of claim 12, wherein $R^3$ is an unsubstituted five-membered aromatic heterocycle or a five-membered aromatic heterocycle substituted by a substituent selected from the group consisting of thiazolyl, oxazolyl, isoxazolyl, imidazolyl, 2H-pyrazolyl, [1,2,3]triazolyl, [1,2,4]triazolyl, [1,3,4]thiadiazolyl and [1,3,4]oxadiazolyl.

14. The compound of claim 13, which is selected from the group consisting of 7-dimethylamino-8-phenylethynyl-4-(3-[1,2,3]triazol-1-yl-phenyl)-1,3-dihydro-benzo[b][1,4]diazepin-2-one, 8-(2-fluoro-phenyl)-4-(3-[1,2,3]triazol-1-yl-phenyl)-7-(2,2,2-trifluoro-ethoxy)-1,3-dihydro-benzo[b][1,4]diazepin-2-one, 7-(ethyl-methyl-amino)-8-methyl-4-[3-(3-methyl-isoxazol-5-yl)-phenyl]-1,3-dihydro-benzo[b][1,4]diazepin-2-one, 7-dimethylamino-8-methyl-4-[3-(3-methyl-isoxazol-5-yl)-phenyl]-1,3-dihydro-benzo[b][1,4]diazepin-2-one, 7-(isobutyl-methyl-amino)-8-methyl-4-[3-(3-methyl-isoxazol-5-yl)-phenyl]-1,3-dihydro-benzo[b][1,4]diazepin-2-one, 7-(isobutyl-methyl-amino)-8-methyl-4-[3-(5-pyrrolidin-1-ylmethyl-[1,2,3]triazol-1-yl)-phenyl]-1,3-dihydro-benzo[b][1,4]diazepin-2-one, and 4-(3-{5-[(cyclopropylmethyl-amino)-methyl]-[1,2,3]triazol-1-yl}-phenyl)-7-(isobutyl-methyl-amino)-8-methyl-1,3-dihydro-benzo[b][1,4]diazepin-2-one.

15. A pharmaceutical composition comprising at least one compound of formula 1 according to claim 1 or a pharma- 16. A process for preparing a compound of formula I according to claim 1 comprising a) reacting a compound of formula II

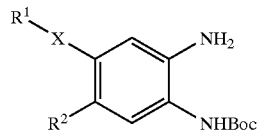

II with a compound of formula IV

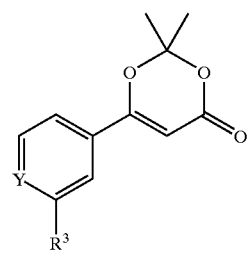

IV wherein R is alkyl, forming a compound of formula III

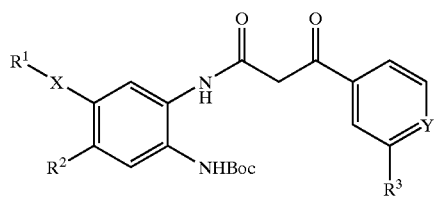

III deprotecting the amino group, and cyclizing, thereby forming a compound of formula

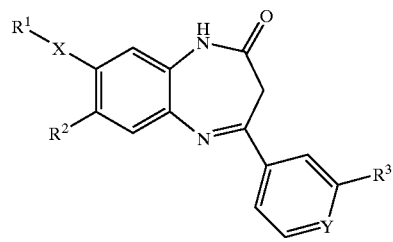

I wherein $R^1$, $R^2$, $R^3$, X and Y are as described.

17. A process for preparing a compound of formula I according to claim 1 comprising a) reacting a compound of formula II

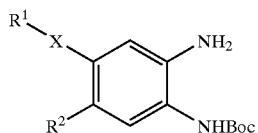

II with a compound of formula IVa

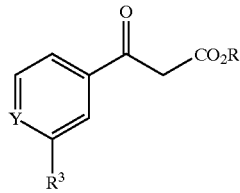

IVa wherein R is alkyl forming a compound of formula III

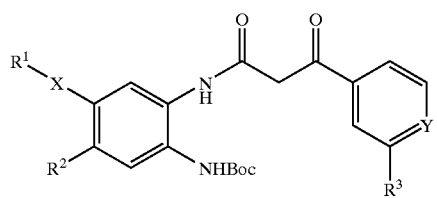

III deprotecting the amino group and cyclizing, thereby forming a compound of formula

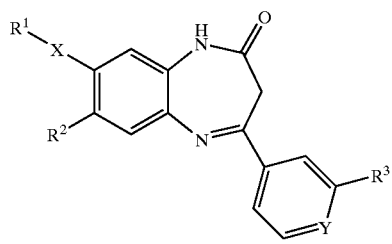

I wherein $R^1$, $R^2$, $R^3$, X and Y are as described.

* * * * *